(12) United States Patent
Tremblay et al.

(10) Patent No.: US 8,741,289 B2
(45) Date of Patent: Jun. 3, 2014

(54) SIGLEC 15 ANTIBODIES IN TREATING BONE LOSS-RELATED DISEASE

(75) Inventors: Gilles Bernard Tremblay, La Prairie (CA); Mario Filion, Longueuil (CA); Matthew Stuible, Montreal (CA)

(73) Assignee: Alethia Biotherapeutics Inc., Montreal, Quebec (CA)

( * ) Notice: Subject to any disclaimer, the term of this patent is extended or adjusted under 35 U.S.C. 154(b) by 0 days.

(21) Appl. No.: 13/499,792

(22) PCT Filed: Oct. 6, 2010

(86) PCT No.: PCT/CA2010/001586
§ 371 (c)(1),
(2), (4) Date: Sep. 18, 2012

(87) PCT Pub. No.: WO2011/041894
PCT Pub. Date: Apr. 14, 2011

(65) Prior Publication Data
US 2013/0039915 A1    Feb. 14, 2013

Related U.S. Application Data

(63) Continuation-in-part of application No. 12/580,943, filed on Oct. 16, 2009, now Pat. No. 8,168,181.

(60) Provisional application No. 61/248,960, filed on Oct. 6, 2009.

(51) Int. Cl.
*A61K 39/395* (2006.01)
*C07K 16/00* (2006.01)

(52) U.S. Cl.
USPC ............. 424/130.1; 424/133.1; 424/134.1; 424/135.1; 424/141.1; 424/142.1; 424/145.1; 424/158.1; 530/387.3; 530/388.1; 530/388.15; 530/388.24; 530/391.1; 530/391.3; 530/391.7

(58) Field of Classification Search
None
See application file for complete search history.

(56) References Cited

U.S. PATENT DOCUMENTS

| | | | |
|---|---|---|---|
| 5,712,127 A | 1/1998 | Malek et al. | |
| 6,057,098 A | 5/2000 | Buechler et al. | |
| 6,451,555 B1 | 9/2002 | Duffy | |
| 6,498,024 B1 | 12/2002 | Malek et al. | |
| 6,617,434 B1 | 9/2003 | Duffy | |
| 7,357,929 B2 | 4/2008 | Carmeliet et al. | |
| 7,402,664 B2 | 7/2008 | Wolfgang et al. | |
| 7,407,940 B2 | 8/2008 | Falla et al. | |
| 7,411,051 B2 | 8/2008 | Rosen et al. | |
| 7,417,112 B2 | 8/2008 | Rathore et al. | |
| 7,425,612 B2 | 9/2008 | Nakamura et al. | |
| 7,432,065 B2 | 10/2008 | Lu et al. | |
| 7,449,320 B2 | 11/2008 | Miller et al. | |
| 7,459,539 B2 | 12/2008 | Challita-Eid et al. | |
| 7,485,327 B2 | 2/2009 | Kim et al. |
| 7,488,590 B2 | 2/2009 | Feige et al. |
| 7,501,391 B2 | 3/2009 | Khan et al. |
| 7,501,557 B1 | 3/2009 | Wagner et al. |
| 7,510,840 B1 | 3/2009 | Challita-Eid et al. |
| 7,514,224 B2 | 4/2009 | Lu et al. |
| 7,514,407 B2 | 4/2009 | Averback |
| 7,517,529 B2 | 4/2009 | Khan et al. |
| 7,524,513 B2 | 4/2009 | Hai-Quan et al. |
| 7,528,232 B2 | 5/2009 | Wagner et al. |
| 7,528,242 B2 | 5/2009 | Anderson et al. |
| 7,534,579 B2 | 5/2009 | Glucksmann et al. |
| 7,541,450 B2 | 6/2009 | Liu et al. |
| 7,547,512 B2 | 6/2009 | Peiris et al. |
| 7,560,433 B2 | 7/2009 | Khan et al. |
| 7,566,685 B2 | 7/2009 | Kinsella |
| 7,569,547 B2 | 8/2009 | Lindberg et al. |
| 7,572,894 B2 | 8/2009 | Jin et al. |
| 7,575,876 B2 | 8/2009 | Zhang |
| 7,585,839 B2 | 9/2009 | Larsen et al. |
| 7,585,849 B2 | 9/2009 | Liu et al. |
| 7,585,937 B2 | 9/2009 | Kungl |
| 7,601,807 B2 | 10/2009 | Kanayama et al. |
| 7,608,704 B2 | 10/2009 | Yue et al. |
| 7,625,996 B2 | 12/2009 | Fischer et al. |
| 7,628,989 B2 | 12/2009 | Jakobovits et al. |
| 7,635,681 B2 | 12/2009 | Bonny |
| 7,635,755 B2 | 12/2009 | Kaplan et al. |
| 7,641,905 B2 | 1/2010 | Jakobovits et al. |

(Continued)

FOREIGN PATENT DOCUMENTS

| EP | 1369479 A1 | 12/2003 |
|---|---|---|
| EP | 1544215 A1 | 6/2005 |

(Continued)

OTHER PUBLICATIONS

Paul, Fundamental Immunology, 3rd Edition, 1993, Raven press, NY, pp. 292-295.*

(Continued)

*Primary Examiner* — Elizabeth C Kemmerer

(74) *Attorney, Agent, or Firm* — Choate, Hall & Stewart LLP; Fangli Chen; Robert N. Sahr

(57) ABSTRACT

Novel antibodies and antigen binding fragments that specifically binds to Siglec-15 are described herein. In some embodiments, the antibodies or antigen binding fragments may block the biological activity of Siglec-15 and are useful in composition for the treatment of bone loss, more particularly in bone diseases that have increased cell surface expression of Siglec-15, such as conditions where there is an increase in the bone degradative activity of osteoclasts. The invention also relates to cells expressing the antibodies or antigen binding fragments such as monoclonal, humanized or chimeric antibodies. Additionally, methods of detecting and treating bone loss, bone-related diseases or cancer using the antibodies and fragments are also disclosed.

21 Claims, 20 Drawing Sheets

(56) References Cited

U.S. PATENT DOCUMENTS

| | | | |
|---|---|---|---|
| 7,662,409 B2 | 2/2010 | Masters | |
| 7,662,776 B2 | 2/2010 | Khan et al. | |
| 7,671,011 B2 | 3/2010 | Shai et al. | |
| 7,691,977 B2 | 4/2010 | Fuh et al. | |
| 7,989,160 B2 | 8/2011 | Sooknanan et al. | |
| 8,168,181 B2 | 5/2012 | Sooknanan et al. | |
| 8,431,126 B2 * | 4/2013 | Sooknanan et al. | 424/134.1 |
| 2003/0118592 A1 | 6/2003 | Ledbetter et al. | |
| 2003/0133939 A1 | 7/2003 | Ledbetter et al. | |
| 2004/0023313 A1 | 2/2004 | Boyle et al. | |
| 2004/0033535 A1 | 2/2004 | Boyle et al. | |
| 2004/0076992 A1 | 4/2004 | Nakamura et al. | |
| 2004/0082508 A1 | 4/2004 | Yue et al. | |
| 2005/0107588 A1 | 5/2005 | Duggan et al. | |
| 2005/0118625 A1 | 6/2005 | Mounts | |
| 2005/0153333 A1 | 7/2005 | Sooknanan | |
| 2005/0170450 A1 | 8/2005 | Durocher et al. | |
| 2006/0153867 A1 | 7/2006 | Li | |
| 2006/0240516 A1 | 10/2006 | Jalinot et al. | |
| 2008/0070232 A1 | 3/2008 | Durocher | |
| 2008/0171094 A1 | 7/2008 | Benner et al. | |
| 2008/0176243 A1 | 7/2008 | Khan et al. | |
| 2008/0176790 A1 | 7/2008 | DeFrees | |
| 2008/0178308 A1 | 7/2008 | Afar et al. | |
| 2008/0194489 A1 | 8/2008 | Khan et al. | |
| 2008/0199939 A1 | 8/2008 | Havenga et al. | |
| 2008/0206239 A1 | 8/2008 | Jones et al. | |
| 2008/0207502 A1 | 8/2008 | Rastelli et al. | |
| 2008/0207522 A1 | 8/2008 | Hancock et al. | |
| 2008/0213268 A1 | 9/2008 | Watts et al. | |
| 2008/0242618 A1 | 10/2008 | Khan et al. | |
| 2008/0242837 A1 | 10/2008 | Khan et al. | |
| 2008/0242847 A1 | 10/2008 | Liu et al. | |
| 2008/0248527 A1 | 10/2008 | Wolfgang et al. | |
| 2008/0254020 A1 | 10/2008 | Walker et al. | |
| 2008/0261819 A1 | 10/2008 | Lorens et al. | |
| 2008/0274979 A1 | 11/2008 | Ellis-Behnke et al. | |
| 2008/0275547 A1 | 11/2008 | Kanamaru et al. | |
| 2008/0279908 A1 | 11/2008 | Bertozzi et al. | |
| 2008/0286808 A1 | 11/2008 | Schellenberger et al. | |
| 2008/0287309 A1 | 11/2008 | Bowdish et al. | |
| 2008/0299111 A1 | 12/2008 | Delacourte et al. | |
| 2008/0299601 A1 | 12/2008 | Fike et al. | |
| 2008/0306001 A1 | 12/2008 | Liik et al. | |
| 2008/0306009 A1 | 12/2008 | Khan et al. | |
| 2008/0318871 A1 | 12/2008 | Khan et al. | |
| 2009/0004210 A1 | 1/2009 | Mattner et al. | |
| 2009/0005257 A1 | 1/2009 | Jespers et al. | |
| 2009/0005266 A1 | 1/2009 | Ostermeier et al. | |
| 2009/0005541 A1 | 1/2009 | Kungl | |
| 2009/0010983 A1 | 1/2009 | Melvik et al. | |
| 2009/0012032 A1 | 1/2009 | Nakamura et al. | |
| 2009/0017460 A1 | 1/2009 | Anderson et al. | |
| 2009/0019605 A1 | 1/2009 | Takagi et al. | |
| 2009/0023648 A1 | 1/2009 | Stredonsky et al. | |
| 2009/0028813 A1 | 1/2009 | Stedronsky et al. | |
| 2009/0028856 A1 | 1/2009 | Chen et al. | |
| 2009/0041671 A1 | 2/2009 | Young et al. | |
| 2009/0042769 A1 | 2/2009 | MacLean | |
| 2009/0047335 A1 | 2/2009 | Rastelli et al. | |
| 2009/0069259 A1 | 3/2009 | Collingwood | |
| 2009/0075377 A1 | 3/2009 | Lu et al. | |
| 2009/0081178 A1 | 3/2009 | Murray et al. | |
| 2009/0081457 A1 | 3/2009 | Nagarajan et al. | |
| 2009/0082551 A1 | 3/2009 | Zuckerman | |
| 2009/0088387 A1 | 4/2009 | Castillo et al. | |
| 2009/0092582 A1 | 4/2009 | Bogin et al. | |
| 2009/0093408 A1 | 4/2009 | Bridon et al. | |
| 2009/0093621 A1 | 4/2009 | Ferrari et al. | |
| 2009/0099031 A1 | 4/2009 | Stemmer et al. | |
| 2009/0099066 A1 | 4/2009 | Moulton et al. | |
| 2009/0117578 A1 | 5/2009 | Metz et al. | |
| 2009/0123412 A1 | 5/2009 | Healy et al. | |
| 2009/0130111 A1 | 5/2009 | Wu et al. | |
| 2009/0131265 A1 | 5/2009 | Zhang | |
| 2009/0136595 A1 | 5/2009 | Shah et al. | |
| 2009/0136912 A1 | 5/2009 | Kurokawa et al. | |
| 2009/0142280 A1 | 6/2009 | Zhang et al. | |
| 2009/0142828 A1 | 6/2009 | Bucciarelli et al. | |
| 2009/0142839 A1 | 6/2009 | Primiano | |
| 2009/0143567 A1 | 6/2009 | Rathore et al. | |
| 2009/0149339 A1 | 6/2009 | Lu et al. | |
| 2009/0169520 A1 | 7/2009 | Soreq et al. | |
| 2009/0170191 A1 | 7/2009 | Jakobovits et al. | |
| 2009/0175821 A1 | 7/2009 | Bridon et al. | |
| 2009/0176664 A1 | 7/2009 | Chu | |
| 2009/0180958 A1 | 7/2009 | Koivistoinen et al. | |
| 2009/0197812 A1 | 8/2009 | Kim et al. | |
| 2009/0214570 A1 | 8/2009 | Mrsny et al. | |
| 2009/0214582 A1 | 8/2009 | Dean | |
| 2009/0215667 A1 | 8/2009 | Wagner et al. | |
| 2009/0221505 A1 | 9/2009 | Kolonin et al. | |
| 2009/0226372 A1 | 9/2009 | Ruoslahti et al. | |
| 2009/0226374 A1 | 9/2009 | Hugli | |
| 2009/0226433 A1 | 9/2009 | Grandea, III et al. | |
| 2009/0227505 A1 | 9/2009 | Khan et al. | |
| 2009/0234026 A1 | 9/2009 | Kaplan et al. | |
| 2009/0252728 A1 | 10/2009 | Jakobovits et al. | |
| 2009/0258017 A1 | 10/2009 | Callahan et al. | |
| 2009/0264372 A1 | 10/2009 | Dal Farra et al. | |
| 2009/0270320 A1 | 10/2009 | Panjwani et al. | |
| 2009/0275050 A1 | 11/2009 | Glucksmann et al. | |
| 2009/0275503 A1 | 11/2009 | Shai et al. | |
| 2009/0281038 A1 | 11/2009 | Wagner et al. | |
| 2009/0298707 A1 | 12/2009 | Yarbrough et al. | |
| 2009/0304746 A1 | 12/2009 | Sette et al. | |
| 2009/0317420 A1 | 12/2009 | Telford et al. | |
| 2010/0004172 A1 | 1/2010 | Khan et al. | |
| 2010/0015664 A1 | 1/2010 | Kanayama et al. | |
| 2010/0016215 A1 | 1/2010 | Moulton et al. | |
| 2010/0016220 A1 | 1/2010 | Nakamura et al. | |
| 2010/0016697 A1 | 1/2010 | Spinale et al. | |
| 2010/0029005 A1 | 2/2010 | Kamiie et al. | |
| 2010/0035817 A1 | 2/2010 | Fischer et al. | |
| 2010/0041614 A1 | 2/2010 | Bussolino et al. | |
| 2010/0047163 A1 | 2/2010 | Forte et al. | |
| 2010/0055438 A1 | 3/2010 | Kaplan et al. | |
| 2010/0056457 A1 | 3/2010 | Barbas, III et al. | |
| 2010/0056459 A1 | 3/2010 | Bonny | |
| 2010/0076173 A1 | 3/2010 | Stephanopoulos et al. | |
| 2010/0080814 A1 | 4/2010 | Desjarlais et al. | |
| 2010/0080824 A1 | 4/2010 | Peiris et al. | |
| 2010/0086532 A1 | 4/2010 | Barbas, III et al. | |
| 2010/0209428 A1 | 8/2010 | Hiruma et al. | |
| 2011/0268733 A1 | 11/2011 | Hiruma et al. | |
| 2011/0311526 A1 | 12/2011 | Sooknanan et al. | |

FOREIGN PATENT DOCUMENTS

| | | |
|---|---|---|
| EP | 1580263 A1 | 9/2005 |
| EP | 1715038 A1 | 10/2006 |
| EP | 1751179 A2 | 2/2007 |
| EP | 1874337 A2 | 1/2008 |
| EP | 1931198 A2 | 6/2008 |
| EP | 1934252 A1 | 6/2008 |
| EP | 1950221 A2 | 7/2008 |
| EP | 1953551 A2 | 8/2008 |
| EP | 1963499 A2 | 9/2008 |
| EP | 1970383 A1 | 9/2008 |
| EP | 1996609 A2 | 12/2008 |
| EP | 2002036 A2 | 12/2008 |
| EP | 2021467 A1 | 2/2009 |
| EP | 2032149 A2 | 3/2009 |
| EP | 2041569 A2 | 4/2009 |
| EP | 2046806 A2 | 4/2009 |
| EP | 2053406 A2 | 4/2009 |
| EP | 2057465 A2 | 5/2009 |
| EP | 2097094 A2 | 9/2009 |
| EP | 2105141 A1 | 9/2009 |
| EP | 2129682 A1 | 12/2009 |
| EP | 2130838 A2 | 12/2009 |
| EP | 2140005 A1 | 1/2010 |
| EP | 2168986 A2 | 3/2010 |
| EP | 2170363 A2 | 4/2010 |

(56) References Cited

FOREIGN PATENT DOCUMENTS

| | | |
|---|---|---|
| JP | 2003169687 A | 6/2003 |
| JP | 2003210166 A | 7/2003 |
| JP | 2004107352 A | 4/2004 |
| JP | 2004189848 A | 7/2004 |
| JP | 2004533803 A | 11/2004 |
| JP | 2004339189 A | 12/2004 |
| JP | 2007020403 A | 2/2007 |
| JP | 2008500267 A | 1/2008 |
| JP | 2008504221 A | 2/2008 |
| JP | 2008094822 A | 4/2008 |
| JP | 2008111841 A | 5/2008 |
| JP | 2008263955 A | 11/2008 |
| JP | 200972081 A | 4/2009 |
| JP | 2009183293 A | 8/2009 |
| JP | 2009528255 A | 8/2009 |
| WO | WO-94/11014 A1 | 5/1994 |
| WO | WO-02/20723 A2 | 3/2002 |
| WO | WO-0220822 A2 | 3/2002 |
| WO | WO-03/048305 A2 | 6/2003 |
| WO | WO-03104275 A2 | 12/2003 |
| WO | WO-2004/064972 A2 | 8/2004 |
| WO | WO-2005/061546 A1 | 7/2005 |
| WO | WO-2005/078087 A1 | 8/2005 |
| WO | WO-2005/081628 A2 | 9/2005 |
| WO | WO-2006/113311 A2 | 10/2006 |
| WO | WO-2007/043059 A1 | 4/2007 |
| WO | WO-2007/062422 A2 | 5/2007 |
| WO | WO-2007/063300 A2 | 6/2007 |
| WO | WO-2007/093042 A1 | 8/2007 |
| WO | WO-2007/100524 A2 | 9/2007 |
| WO | WO-2007/104062 A2 | 9/2007 |
| WO | WO-2007/111952 A2 | 10/2007 |
| WO | WO-2007/128121 A1 | 11/2007 |
| WO | WO-2007/146319 A2 | 12/2007 |
| WO | WO-2008/006028 A2 | 1/2008 |
| WO | WO-2008/024105 A2 | 2/2008 |
| WO | WO-2008/063369 A2 | 5/2008 |
| WO | WO-2008/093982 A1 | 8/2008 |
| WO | WO-2008/101160 A2 | 8/2008 |
| WO | WO-2008/113185 A1 | 9/2008 |
| WO | WO-2008/116468 A2 | 10/2008 |
| WO | WO-2008/134544 A1 | 11/2008 |
| WO | WO-2008/148545 A1 | 12/2008 |
| WO | WO-2009/005793 A2 | 1/2009 |
| WO | WO-2009/008727 A2 | 1/2009 |
| WO | WO-2009/020101 A1 | 2/2009 |
| WO | WO-2009/023125 A1 | 2/2009 |
| WO | WO-2009/031835 A2 | 3/2009 |
| WO | WO-2009/031836 A1 | 3/2009 |
| WO | WO-2009/032158 A2 | 3/2009 |
| WO | WO-2009/038756 A2 | 3/2009 |
| WO | WO-2009/039854 A2 | 4/2009 |
| WO | WO-2009/048072 A1 | 4/2009 |
| WO | WO-2009/050453 A2 | 4/2009 |
| WO | WO-2009/059379 A1 | 5/2009 |
| WO | WO-2009/059972 A2 | 5/2009 |
| WO | WO-2009/061130 A2 | 5/2009 |
| WO | WO-2009/061890 A1 | 5/2009 |
| WO | WO-2009/090651 A2 | 7/2009 |
| WO | WO-2009/106715 A2 | 9/2009 |
| WO | WO-2009/108261 A2 | 9/2009 |
| WO | WO-2009/112645 A1 | 9/2009 |
| WO | WO-2009/132876 A1 | 11/2009 |
| WO | WO-2009/139599 A2 | 11/2009 |
| WO | WO-2009/146179 A1 | 12/2009 |
| WO | WO-2010/000794 A1 | 1/2010 |
| WO | WO-2010/033736 A1 | 3/2010 |
| WO | WO-2010/035504 A1 | 4/2010 |
| WO | WO-2010/037395 A2 | 4/2010 |
| WO | WO-2011/041894 A1 | 4/2011 |
| WO | WO-2012/045481 A2 | 4/2012 |
| WO | PCT/CA2013/000646 | 7/2013 |

OTHER PUBLICATIONS

Casset et al (Biochemical and Biophysical Research Communications, 307:198-205, 2003).*
Hiruma, Yoshiharu et al., Impaired osteoclast differentiation and function and mild osteopetrosis development in Siglec-15-deficient mice, Bone 53, 87-93, (2013).
Agrawal, N., et al., RNA Interference: Biology, Mechanism, and Applications, Microbiology and Molecular Biology Reviews, 67(4):657-685 (2003).
Angata, T. et al., Siglec-15: an immune system Siglec conserved throughout vertebrate evolution, Glycobiology, 17(8):838-846 (2007).
Baron R., Primer on the Metabolic Bone Diseases and Disorders of Mineral Metabolism, Fifth Ed., American Society for Bone and Mineral Research, Washington DC, pp. 1-8 (2003).
Bird, R.E. et al., Single-Chain Antigen-Binding Proteins, Science, 242(4877):423-426 (1988).
Biskobing, D.M. et al., Acid pH increases Carbonic Anhydrase II and Calcitonin Receptor mRNA Expression in Mature Osteoclasts, Calcified Tissue International, 67(2):178-183 (2000).
Blixt, O. et al., Sialoside Specificity of the Siglec Family Assessed Using Novel Multivalent Probes, The Journal of Bilogical Chemistry, 278:31007-31019 (2003).
Boyle, W.J. et al., Osteoclast differentiation and activation, Nature, 423(6937):337-342 (2003).
Brage, M. et al., Different Cysteine Proteinases Involved in Bone Resorption and Osteoclast Formation, Calcified Tissue International, 76(6)439-447 (2005).
Brandenberger, R. et al., Transcriptome characterization elucidates signaling networks that control human ES cell growth and differentiation, Nature Biotechnology, 22(6):707-716 (2004).
Bregni, M. et al., B-Cell restricted saporin immunotoxins: activity against B-cell lines and chronic lymphocytic leukemia cells, Blood, 73:753-762 (1989).
Brummelkamp, T.R. et al., A System for Stable Expression of Short Interfering RNAs in Mammalian Cells, Science, 296(5567):550-553 (2002).
Clackson, T. et al., Making antibody fragments using phage display libraries, Nature, 352:624-628 (1991).
Crocker, P.R. et al., Siglecs and their roles in the immune system, Nature Reviews Immunology, 7(4):255-266 (2007).
Database Geneseq (Online) Derwent; Human Siglec 15, SEQID2, XP002531845, from JP-2007020403-A (Nat. Inst. of Adv. Ind. & Technol.) May 3, 2007.
Database Geneseq [Online], Human protease/osteoarthritis gene-specific probe—SEQ ID 118248, Database accession No. AFV92822, Oct. 18, 2007.
Database Geneseq [Online], Human protease/osteoarthritis gene-specific probe—SEQ ID 72066, Database accession No. AFV46640, Oct. 18, 2007.
De Vernejoul, M.C., Dynamics of Bone Remodeling: Biochemical and Pathophysiological Basis, European Journal of Clinical Chemistry and Clinical Biochemistry, 34:729-734 (1996).
Elbashir, S.M. et al., Duplexes of 21-nucleotide RNAs mediate RNA interference in cultured mammalian cells, Nature, 411(6836):494-498 (2001).
Ellis, G.K. et al., Randomized Trial of Denosumab in Patients Receiving Adjuvant Aromatase Inhibitors for Nonmetastatic Breast Cancer, Journal of Clinical Oncology, 26(30):4875-4882 (2008).
ENSEMBL Protein ID: ENSBTAP00000016659, Jul. 19, 2010.
ENSEMBL Protein ID: ENSBTAP00000022107, Jul. 19, 2010.
ENSEMBL Protein ID: ENSCAFP00000026052, Jul. 19, 2010.
ENSEMBL Protein ID: ENSDNOP00000011608; Jul. 19, 2010.
ENSEMBL Protein ID: ENSECAP00000015632, Jul. 19, 2010.
ENSEMBL Protein ID: ENSFCAP00000009910, Jul. 19, 2010.
ENSEMBL Protein ID: ENSMICP00000015938, Jul. 19, 2010.
ENSEMBL Protein ID: ENSMLUP00000004457, Jul. 19, 2010.
ENSEMBL Protein ID: ENSMMUP00000004742, Jul. 19, 2010.
ENSEMBL Protein ID: ENSMUSP00000112309, Jul. 19, 2010.
ENSEMBL Protein ID: ENSOPRP00000004369, Jul. 19, 2010.
ENSEMBL Protein ID: ENSPPYP00000010254, Jul. 19, 2010.
ENSEMBL Protein ID: ENSPTRP00000042370, Jul. 19, 2010.
ENSEMBL Protein ID: ENSPTRP00000049394, Jul. 19, 2010.

(56) References Cited

OTHER PUBLICATIONS

ENSEMBL Protein ID: ENSRNOP00000041280, Jul. 19, 2010.
ENSEMBL Protein ID: ENSSARP00000011800, Jul. 19, 2010.
ENSEMBL Protein ID: ENSSTOP00000002285, Jul. 19, 2010.
ENSEMBL Protein ID:ENSP00000374125, Jul. 6, 2010.
Frost, H.M., Dynamics of Bone Remodeling. In: Bone Biodynamics, Little and Brown, Boston, MA, USA, pp. 315-333 (1964).
Gee, J.E. et al., Potential Therapeutic Usefulness of Intermolecular Triplex DNA. In: Huber BE Cancer Therapy in the Twenty-First Century, vol. 1: Molecular and Immunologic Approaches, Futura Publishing Co., Inc., Mt. Kisco, N.Y., pp. 163-177 (1994).
GenBank Acc. No. AAY40743, Angata T. et al., J. Glycobiology 17 (8), pp. 838-846 (2007).
GenBank Acc. No. AAY40744, Angata, T. et al., J. Glycobiology, 17(8):838-846 (2007).
GenBank Acc. No. AK172835, GI:47077862, 2004.
GenBank Acc. No. AL357873, GI:16972902, 2008.
GenBank Acc. No. AL645465, GI:18476850, 2008.
GenBank Acc. No. BAD18800, Kawabata, A. et al., Direct Submission, submitted (Apr. 22, 2004), Institute of Medical Science.
GenBank Acc. No. BAF83089, Wakamatsu, A. et al., Direct submission, submitted (Oct. 9, 2007) Reverse Proteomics Research Institute.
GenBank Acc. No. BAF83091, Wakamatsu, A. et al., Direct submission, submitted (Oct. 9, 2007) Reverse Proteomics Research Institute.
GenBank Acc. No. NM_000067, GI:157952216, first referenced 1976, updated 2008.
GenBank Acc. No. NM_000099, GI:19882253, first referenced 1990, updated 2008.
GenBank Acc. No. NM_000887, GI:34452172, first referenced 1987, updated 2008.
GenBank Acc. No. NM_001014433, GI:62526019, first referenced 2000, updated 2005.
GenBank Acc. No. NM_00104433, first referenced 2000, updated 2009.
GenBank Acc. No. NM_001102, GI:194097348, first referenced 1989, updated 2008.
GenBank Acc. No. NM_001690, GI:19913423, first referenced 1993, updated 2007.
GenBank Acc. No. NM_001935, GI:47078262, first referenced 1991, updated 2008.
GenBank Acc. No. NM_002994, GI:41872613, first referenced 1991, updated 2008.
GenBank Acc. No. NM_003341, Gi:33359692, first referenced 1993, updated 2008.
GenBank Acc. No. NM_004414, GI:44680111, first referenced 1995, updated 2008.
GenBank Acc. No. NM_004763, GI:115527101, first referenced 1997, updated 2007.
GenBank Acc. No. NM_004794, GI:34485717, first referenced 1993, updated 2005.
GenBank Acc. No. NM_005410, GI:62530390, first referenced 1991, updated 2008.
GenBank Acc. No. NM_005765, GI:15011917, first referenced 1998, updated 2007.
GenBank Acc. No. NM_006357, GI:33359695, first referenced 1997, updated 2008.
GenBank Acc. No. NM_006555, GI:34304384, first referenced 1997, updated 2007.
GenBank Acc. No. NM_006660, GI:12597621, first referenced 1999, updated 2008.
GenBank Acc. No. NM_013322, GI:23111022, first referenced 2001, updated 2006.
GenBank Acc. No. NM_014358, GI:90577173, first referenced 1999, updated 2003.
GenBank Acc. No. NM_014656, GI:7657258, 2006.
GenBank Acc. No. NM_015973, GI:88853582, first refenced 1990, updated 2008.
GenBank Acc. No. NM_018252, GI:149158718, 2006.
GenBank Acc. No. NM_018482, GI:46094080, first referenced 1998, updated 2008.
GenBank Acc. No. NM_021181, GI:19923571, first referenced 2001, updated 2008.
GenBank Acc. No. NM_030794, GI:13540575, first referenced 2000, updated 2008.
GenBank Acc. No. NM_032565, GI:141802977, first referenced 2003, updated 2007.
GenBank Acc. No. NM_032569, GI:190358483, first referenced 2005, updated 2006.
GenBank Acc. No. NM_032731, GI:153791420, first referenced 2004, updated 2008.
GenBank Acc. No. NM_054027, GI:170671715, first referenced 1995, updated 2008.
GenBank Acc. No. NM_138461, GI:115511027, 2004.
GenBank Acc. No. NM_145280, GI:188528683, 2004.
GenBank Acc. No. NM_178833, GI:196259823, first referenced 2007, updated 2008.
GenBank Acc. No. NM_182488, GI:209954829, first referenced 1998, updated 2004.
GenBank Acc. No. NM_213602, GI:47106068, 2007.
GenBank Acc. No. XM_884636, GI:149270200, 2007.
GeneBank Acc. No. NM_001771.3, first reference 1990.
GeneBank Acc.No. NM_001772.3, first reference 1988.
Ghetie, M.A. et al., Evaluation of Ricin A Chain-containing Immunotoxins Directed Against CD19 and CD22 Antigens on Normal and Malignant Human B-Cells as Potential Reagents for in Vivo Therapy, Cancer Research, 48:2610-2617 (1988).
Hannon, G.J., RNA interference, Nature, 418(6894):244-251 (2002).
Hashimoto, T. et al., Biochemical Markers in Bone Metastasis, Jpn. J. Cancer Chemother, 31(7):1027-1033 (2004).
Hiruma, Y. et al., Siglec-15, a member of the sialic acid-binding lectin, is a novel regulator for osteoclast differentiation, Biochemical and Biophysical Research Communications, 409(3):424-429 (2011).
Huston, J.S. et al., Protein engineering of antibody binding sites: Recovery of specific activity in an anti-digoxin single-chain Fv analogue produced in *Escherichia coli*, Proceedings of the National Academy of Sciences, 85:5879-5883 (1988).
IPI No: IPI00568858.4, sequence update Oct. 12, 2009.
IPI No: IPI00647937.1, Sep. 4, 2005.
IPI No: IPI00663527.4, sequence update Sep. 10, 2007.
IPI No: IPI00711850.4., sequence update Jun. 9, 2010.
IPI No: IPI00716135.2, 2007.
IPI No: IPI00796217.1, sequence update Oct. 31, 2006.
Ishida, N. et al., Large Scale Gene Expression Analysis of Osteoclastogenesis in Vitro and Elucidation of NFAT2 as a Key Regulator, The Journal of Biological Chemistry, 277(43):41147-41156 (2002).
Ishida-Kitagawa, N. et al., Siglec-15 Protein Regulates Formation of Functional Osteoclasts in Concert with DNAX-activating Protein of 12 kDa (DAP12), The Journal of Biological Chemistry, 287(21):17493-17502 (2012).
Janssen, E. et al., LAB: A new membrane-associated adaptor molecule in B cell activation, Nature Immunology, 4(2):117-123 (2003).
Jilka, R.L. et al., Increased Osteoclast Development After Estrogen Loss: Mediation by Interleukin-6, Science 257:88-91 (1992).
Kawai, J. et al., Functional annotation of a full-length mouse cDNA collection, Nature, 409(6821):685-690 (2001).
Kawaida, R. et al., Jun Dimerization Protein 2 (JDP2), a Member of the AP-1 Family of Transcription Factor, Mediates Osteoclast Differentiation Induced by RANKL, The Journal of Experimental Medicine, 197(8):1029-1035 (2003).
Lacey, D.L. et al., Bench to bedside: elucidation of the OPG-RANK-RANKL pathway and the development of denosumab, Nature Reviews Drug Discovery, 11:401-419 (2012).
Larkin, M.A. et al., Clustal W and Clustal X version 2.0, Bioinformatics, 23(21): 2947-2948 (2007).
Lee, J.S. et al., Stable gene silencing in human monocytic cell lines using lentiviral-delivered small interference RNA. Silencing of the p110α isoform of phosphoinositide 3-kinase reveals differential regulation of adherence induced by 1α,25-dihydroxycholecalciferol and bacterial lipopolysaccharide, The Journal of Biological Chemistry, 279(10):9379-9388 (2004).

(56) References Cited

OTHER PUBLICATIONS

Li, C.H. et al., β-Endorphin omission analogs: Dissociation of immunoreactivity from other biological activities, Proceedings of the National Academy of Sciences, 77(6):3211-3214 (1980).
Malkin, I. et al., Association of ANKH gene polymorphisms with radiographic hand bone size and geometry in a Chuvasha population, Bone, 36(2):365-373 (2005).
McMahon, C. et al. Bone marrow transplantation corrects osteopetrosis in the carbonic anhydrase II deficiency syndrome, Blood, 97(7):1947-1950 (2001).
McMillan, S.J. et al., CD33-related sialic-acid-binding immunoglobulin-like lectins in health and disease, Carbohydrate Research, 343(12):2050-2056 (2008).
Morello, R. et al., cDNA cloning, characterization and chromosome mapping of Crtap encoding the mouse Cartilage Associated Protein, Matrix Biology, 18(3): 319-324 (1999).
NCBI Accession No. XP_889729; Dec. 1, 2005.
NCBI reference sequence: AAY40743.1, 2005.
NCBI reference sequence: EAX01462.1, first reference 2005.
NCBI Reference sequence: NP_001094508, May 28, 2010.
NCBI reference sequence: NP_001094508.1, 2007.
NCBI Reference sequence: NP_998767, Angata, T. et al., J. Glycobiology, 17(8):838-846 (2007).
NCBI Reference sequence: XP_001056537, Apr. 2, 2010.
NCBI Reference sequence: XP_001089000, Jun. 1, 2010.
NCBI reference sequence: XP_001089000.1, 2010.
NCBI Reference sequence: XP_512109, Sep. 16, 2006.
NCBI reference sequence: XP_512109.2, Oct. 25, 2012.
NCBI Reference sequence: XP_574176, Apr. 2, 2010.
NCBI Reference sequence: XP_574176.2, 2006.
NCBI Reference sequence: XP_601064, Jun. 3, 2010.
NCBI Reference sequence: XP_601064.4, 2008.
NCBI Reference sequence: XP_855238, Aug. 30, 2005.
NCBI reference sequence: XP_855238.1, 2005.
Netzel-Arnett, S. et al., Member anchored serine proteases: A rapidly expanding group of cell surface proteolytic enzymes with potential roles in cancer, Cancer and Metastasis Reviews, 22(2-3):237-258 (2003).
Ngo, J.T. et al., Computational Complexity, Protein Structure Prediction, and the Levinthal Paradox in The Protein Folding Problem and Tertiary Structure Prediction, Birkhauser, Boston, pp. 491-495 (1994).
Nishi, T. et al., Expression and Function of the Mouse V-ATPase d Subunit Isoforms, The Journal of Biological Chemistry, 278(47): 46396-46402 (2003).
Nishi, T. et al., The vacuolar (H+)-ATPases-nature's most versatile proton pumps. Nature Reviews Molecular Cell Biology, 3(2):94-103 (2002).
O'Reilly, M.K. et al., Siglecs as targets for therapy in immune cell mediated disease, Trends in Pharmacological Sciences, 30(5):240-248 (2009).
Poli, V. et al., Interleukin-6 deficient mice are protected from bone loss caused by estrogen depletion, The EMBO Journal, 13(5):1189-1196 (1994).
Portolano, S. et al., Lack of Promiscuity in Autoantigen-Specific H and L Chain Combinations as Revealed by Human H and L Chain "Roulette", The Journal of Immunology, 150:880-887 (1993).
Rubinson, D.A. et al., A lentivirus-based system to functionally silence genes in primary mammalian cells, stem cells and transgenic mice by RNA interference, Nature Genetics, 33(3):401-406 (2003).
Shan, J. et al., TSP50, A Possible Protease in Human Testes, Is Activated in Breast Cancer Epithelial Cells, Cancer Research, 62(1):290-294 (2002).
Shankavaram, U.T. et al., Transcript and protein expression profiles of the NCI-60 cancer panel: an integromic microarray study, Molecular Cancer Therapies, 6(3):820-832 (2007).

Smith, A.N. et al., Mutations in ATP6N1B, encoding a new kidney vacuolar proton pump 116-kD subunit, cause recessive distal renal tubular acidosis with preserved hearing, Nature Genetics, 26(1):71-75 (2000).
Smith, A.N., et al. Vacuolar H+-ATPase d2 Subunit: Molecular Characterization, Development Regulation, and Localization to Specialized Proton Pumps in Kidney and Bone, Journal of the American Society of Nephrology, 16(5):1245-1256 (2005).
Sooknanan, R. et al., Identification of Osteoclast-Specific Genes using Subtractive Transcription Amplification of mRNA (STAR), Journal of Bone and Mineral Research, 19:S415 (2004).
Sordillo, E.M. et al., Rank-FC: A Therapeutic Antagonist for Rank-L in Myeloma, Skeletal Complications of Malignancy, Cancer Supplement, 97(3):802-812 (2003).
Srivastava, S. et al., Estrogen Blocks M-CSF Gene Expression and Osteoclast Formation by Regulating Phosphorylation of Egr-1 and Its Interaction with Sp-1, The Journal of Clinical Investigation, 102(10):1850-1859 (1998).
Stehberger, P.A. et al., Localization and Regulation of the ATP6V0A4 (a4) Vacuolar H+-ATPase Subunit Defective in an Inherited Form of Distal Renal Tubular Acidosis, Journal of the American Society of Nephrology,14(12):3027-3038 (2003).
Strausberg, R.L. et al., Generation and initial analysis of more than 15,000 full-length human and mouse cDNA sequences, Proceedings of the National Academy of Sciences, 99(26):16899-16903 (2002).
Stuible, M. et al., Abstract of Oral Presentation No. 1187, Targeting of the DAP12-associated, Osteoclast-specific, Receptor Siglec-15 by Antibody 25E9 inhibits Differentiation and Resorption Activity, The American Society for Bone and Mineral Research, San Diego Convention Center, Sep. 19, 2011.
Sugawara, K. et al., A Useful Method to Evaluate Bone Resorption Inhibitors, Using Osteoclast-like Multinucleated Cells, Analytical Biochemistry, 255:204-210 (1998).
Supplementary European Search Report for EP07710624.3, 13 pages (Jul. 10, 2009).
Susa, M. et al., Human primary osteoclasts: in vitro generation and application as pharmacological and clinical assay, Journal of Translational Medicine, 2(6):1-12 (2004).
Takahata, M. et al., Sialylation of cell surface glycoconjugates is essential for osteoclastogenesis, Bone, 41(1):77-86 (2007).
Tatusova, T. et al., Blast 2 sequences, a new tool for comparing protein and nucleotide sequences, FEMS Microbiology Letters, 174:247-250 (1999).
Tonachini, L. et al., cDNA cloning, characterization and chromosome mapping of the gene encoding human cartilage associated protein (CRTAP), Cytogenetics and Cell Genetics, 87(3-4):191-194 (1999).
Tremblay, G.B. et al., Functional Validation of Osteoclast-Specific Genes in RAW264.7 Cells by RNA Interference, Journal of Bone and Mineral Research, 19:S414 (2004).
UniProtKB/Swiss-Prot A8K2Y5_HUMAN, Jul. 13, 2010.
UniProtKB/Swiss-Prot Q6ZMC9 (SIG15_HUMAN), Jun. 15, 2010.
UniProtKB/TrEMBL A7E1W7_HUMAN, Mar. 2, 2010.
UniProtKB/TrEMBL A7E1W8_MOUSE, Sep. 11, 2007.
Van Der Velden, V.H.J. et al., Targeting of the CD33-calicheamicin immunoconjugate Mylotarg (CMA-676) in acute myeloid leukemia: in vivo saturation and internalization by leuikemic and normal myeloid cells, Blood, 97:3197-3204 (2001).
Ward, E.S. et al., Binding activities of a repertoire of single immunoglobulin variable domains secreted from Escherichia coli, Nature, 341:544-546 (1989).
Wells, J.A., Additivity of Mutational Effects in Proteins, Biochemistry, 29(37):8509-8517 (1990).
Williams, E.L. et al., Development and characterization of monoclonal antibodies specific for the murine inhibitory FcγRIIB (CD32B), European Journal of Immunology, 42:2109-2120 (2012).
Yuan, L. et al., Isolation of a Novel Gene, TSP50, by a Hypomethylated DNA Fragment in Human Breast Cancer, Cancer Research, 59(13):3215-3221 (1999).

* cited by examiner

ELISA with biotinylated Fc-SIGLEC-15$_{20-259}$

|   | 1 | 2 | 3 | 4 | 5 | 6 | 7 | 8 | 9 | 10 | 11 | 12 |
|---|---|---|---|---|---|---|---|---|---|---|---|---|
| A | 0.793 | 0.828 | 1.076 | 0.151 | 0.508 | 0.125 | 0.133 | 0.133 | 0.136 | 0.15 | 0.782 | 0.384 |
| B | 0.603 | 0.158 | 0.147 | 1.001 | 0.143 | 1.13 | 0.141 | 0.613 | 0.716 | 0.156 | 0.457 | 1.052 |
| C | 0.473 | 0.155 | 0.443 | 0.134 | 0.118 | 1.005 | 0.163 | 0.517 | 1.055 | 1.93 | 1.059 | 0.151 |
| D | 0.152 | 0.17 | 1.315 | 1.118 | 1.177 | 1.084 | 0.161 | 0.908 | 0.155 | 0.979 | 0.158 | 0.148 |
| E | 0.354 | 0.167 | 0.952 | 0.169 | 0.312 | 0.436 | 1.318 | 0.963 | 0.401 | 0.13 | 0.169 | 1.018 |
| F | 0.142 | 1.131 | 1.111 | 1.027 | 0.873 | 0.751 | 0.818 | 0.15 | 1.844 | 1.315 | 0.785 | 0.907 |
| G | 0.153 | 0.162 | 1.105 | 0.804 | 0.508 | 0.246 | 1.732 | 1.869 | 0.39 | 0.847 | 0.356 | 0.221 |
| H | 0.944 | 1.254 | 0.18 | 1.31 | 1.192 | 1.219 | 0.905 | 1.068 | 0.248 | 1.318 | 0.879 | 1.115 |

B

ELISA with biotinylated Fc

|   | 1 | 2 | 3 | 4 | 5 | 6 | 7 | 8 | 9 | 10 | 11 | 12 |
|---|---|---|---|---|---|---|---|---|---|---|---|---|
| A | 0.118 | 1.879 | 0.112 | 0.119 | 0.119 | 0.113 | 0.102 | 1.002 | 0.123 | 0.101 | 0.133 | 1.603 |
| B | 1.811 | 0.129 | 0.123 | 0.12 | 0.124 | 0.134 | 0.231 | 0.151 | 1.072 | 0.185 | 0.124 | 0.152 |
| C | 0.168 | 0.185 | 1.585 | 0.13 | 0.161 | 0.122 | 0.138 | 1.771 | 0.167 | 0.16 | 1.946 | 0.261 |
| D | 0.117 | 0.173 | 0.134 | 0.12 | 0.133 | 0.128 | 0.133 | 0.137 | 0.152 | 0.209 | 0.219 | 0.255 |
| E | 1.284 | 0.126 | 1.883 | 0.138 | 0.132 | 0.135 | 0.135 | 0.12 | 0.143 | 0.151 | 0.139 | 0.148 |
| F | 0.116 | 0.146 | 0.14 | 1.805 | 0.197 | 0.145 | 0.144 | 0.132 | 0.158 | 0.152 | 0.13 | 0.14 |
| G | 0.128 | 0.13 | 0.138 | 0.128 | 0.137 | 0.134 | 0.126 | 0.125 | 0.135 | 0.134 | 0.132 | 0.146 |
| H | 0.128 | 0.139 | 0.13 | 0.124 | 0.141 | 0.147 | 0.136 | 0.138 | 0.131 | 0.127 | 0.134 | 1.982 |

FIGURE 10A

| CDRL1-alignment1 | CDRL1-alignment2 | CDRL1-alignment3 | CDRL1-alignment4 |
|---|---|---|---|
| RSSKSLLHSNGITYLY 16 | SASSSVSYMY 10 | KASQSVSNAVA 11 | RASGNIHNYLA 11 |
| RSSKSLLHSNGITYLY 16 | SASSSVSYMY 10 |  | RASGNIHNYLA 11 |
| RSSKSLLHSNGITYLY 16 | *.******* |  | RASENIYSYLA 11 |
| RSSKSLLHSNGITYLY 16 |  |  | *.:.*** |
| RSSKSLLHSNGITYLY 16 |  |  |  |
| RSSKSLLHSNGITYLY 16 |  |  |  |
| RSSKSLLHSNCITYLY 16 |  |  |  |
| RSSKSLLHSNCITYLY 16 |  |  |  |
| RSSKSLLHSNGITYLY 16 |  |  |  |
| RSSKSLLHSNGITYLY 16 |  |  |  |
| RSSKSLLHSNGITYLY 16 |  |  |  |
| RSSKSLLHSNGITYLY 16 |  |  |  |
| RSSKSLLHSNGITYLY 16 |  |  |  |
| RSSKSLLHSNGITYLY 16 |  |  |  |
| RSSKSLLHSNGITYLY 16 |  |  |  |
| RSSKSLLHSNGITYLY 16 |  |  |  |
| RSSKSLLHSNGITYLY 16 |  |  |  |
| RSSKSLLHSNGITYLY 16 |  |  |  |
| RSSKSLLHSNGITYLY 16 |  |  |  |
| RSSKSLLHSNGITYLY 16 |  |  |  |
| RSSKSLLHSNGITYLY 16 |  |  |  |
| RSSKSLLHSNGITYLY 16 |  |  |  |
| RSSKSLLHSNGITYLY 16 |  |  |  |
| RSSKSLLHSNGITYLY 16 |  |  |  |
| RSSKSLLHSSGITYLY 16 |  |  |  |
| RSSKSLLASNGITYLY 16 |  |  |  |
| RSSKSLLHSNGITYLY 16 |  |  |  |
| RSSKSLLHSNGVTYLY 16 |  |  |  |
| RSTKSLLHSNGVTYLY 16 |  |  |  |
| RSTKSLLHSNGNTYLY 16 |  |  |  |
| RSSKSLLHSNGNTYLY 16 |  |  |  |
| RSSKSLLHSNGNTYLY 16 |  |  |  |
| :.**.** |  |  |  |

FIGURE 10B

| CDRL2-alignment1 | CDRL2-alignment2 | CDRL2-alignment3 | CDRL2-alignment4 | CDRL2-alignment5 |
|---|---|---|---|---|
| QMSNLAS 7 | QMSNLAS 7 | RMSNLAS 7 | YTSNRYT 7 | NAKTIPE 7 |
| QMSNLAS 7 | QMSNLAS 7 | RMSNLAS 7 | | NAKTIPE 7 |
| QMSNLAS 7 | QMSNLAS 7 | RMSNLAS 7 | | NAKTIAD 7 |
| QMSNLAS 7 | QMSNLAS 7 | RMSNLAS 7 | | *****:: |
| QMSNLAS 7 | QMSNLAS 7 | RMSNLAS 7 | | |
| QMSNLAS 7 | QMSNLAS 7 | RTSNLAS 7 | | |
| QMSNLAS 7 | QMSNLAS 7 | RTSNLVS 7 | | |
| QMSNLAS 7 | QMSNLAS 7 | *:***.* | | |
| QMSNLAS 7 | QMSNLAS 7 | | | |
| QMSNLAS 7 | QMSNLAS 7 | | | |
| QMSNLAS 7 | QMSNLAS 7 | | | |
| QMSNLAS 7 | QMSNLAS 7 | | | |
| QMSNLAS 7 | QMSNLAS 7 | | | |
| QMSNLAS 7 | QMSNLAS 7 | | | |
| QMSNLAS 7 | QMSNLAS 7 | | | |
| QMSNLAS 7 | QMSNLAS 7 | | | |
| QMSNLAS 7 | QMSNLAS 7 | | | |
| QMSNLAS 7 | QMSNLAS 7 | | | |
| QMSNLAS 7 | QMSNLAS 7 | | | |
| QMSNLAS 7 | QMSNLAS 7 | | | |
| QMSNLAS 7 | QMSNLAS 7 | | | |
| QMSNLAS 7 | QMSNLAS 7 | | | |
| QMSNLAS 7 | QMSNLAS 7 | | | |
| QMSNLAS 7 | QMSNLAS 7 | | | |
| QMSNLAS 7 | QMSNLAS 7 | | | |
| QMSNLAS 7 | RMSNLAS 7 | | | |
| QMSNLAS 7 | RMSNLAS 7 | | | |
| QMSNLAS 7 | RMSNLAS 7 | | | |
| QMSNLAS 7 | RMSNLAS 7 | | | |
| QMSNLAS 7 | RMSNLAS 7 | | | |
| ******* | :****** | | | |

| CDRL3-alignment1 | CDRL3-alignment2 | CDRL3-alignment3 | CDRL3-alignment4 |
|---|---|---|---|
| MQHLEYPYT 9 | QQWSSNPLT 9 | QQDYTSPWT 9 | QHHYGVPLT 9 |
| MQHLEYPYT 9 | QQWSSNPPT 9 | | QHHYGVPLT 9 |
| MQHLEYPYT 9 | ********:* | | QHHYGAPLT 9 |
| MQHLEYPYT 9 | | | ***.* |
| MQHLEYPYT 9 | | | |
| MQHLEYPYT 9 | | | |
| MQHLEYPYT 9 | | | |
| MQHLEYPYT 9 | | | |
| MQHLEYPYT 9 | | | |
| MQHLEYPYT 9 | | | |
| MQHLEYPYT 9 | | | |
| MQHLEYPYT 9 | | | |
| MQHLEYPYT 9 | | | |
| MQHLEYPYT 9 | | | |
| MQHLEYPYT 9 | | | |
| MQHLEYPYT 9 | | | |
| MQHLEYPYT 9 | | | |
| MQHLEYPYT 9 | | | |
| MQHLEYPFT 9 | | | |
| MQHLEYPFT 9 | | | |
| MQHLEYPFT 9 | | | |
| MQHLEYPFT 9 | | | |
| AQNLEYPYT 9 | | | |
| AQNLEYPYT 9 | | | |
| AQNLEYPYT 9 | | | |
| AQNLEYPYT 9 | | | |
| AQNLEYPYT 9 | | | |
| AQNLEYPYT 9 | | | |
| AQNLEYPYT 9 | | | |
| AQNLEYPYT 9 | | | |
| AQNLEYPYT 9 | | | |
| AQNLEYPYT 9 | | | |
| *:** .:** | | | |

FIGURE 10C

| CDRH1 alignment | CDRH1-alignment 2 | CDRH1-alignment3 | CDRH1-alignment4 |
|---|---|---|---|
| GYTFTDYDMH 10<br>GYTFTDYDMH 10<br>GYTFTDYDMH 10<br>GYTFTDYDMH 10<br>GYTFTDYDMH 10<br>GYTFTDYEMH 10<br>GYTFTSYWMF 10<br>GYTFTSYWMF 10<br>GYTFTSYWME 10<br>GYTFTSYWME 10<br>GYTFTSYWME 10<br>GYTFTSYWMH 10<br>GYTFTSYWMH 10<br>GYTFTSYWMH 10<br>GYTFTSYWMH 10<br>GYTFTSYWMH 10<br>GYTFTSYWMH 10<br>GYTFTSYWMH 10<br>GYTFTSYWMH 10<br>GYTFTSYWMH 10<br>GYTFTSYWMH 10<br>GYTFTSYWMH 10<br>GYTFTSYWMH 10<br>GYTFTSYWMH 10<br>GYTFTSYWMH 10<br>GYTFTSYWMH 10<br>GYTFTSYWMH 10<br>GYTFTSYWMH 10<br>GYTFTSYWMH 10<br>GYTFTSYWMH 10<br>GYTFFSYWMH 10<br>GYTFFSYWMH 10<br>GYTFFSYWMH 10<br>GYTFFSYWMH 10<br>GYTFFSYWMH 10<br>GYTFFRYWMD 10<br>GYTFTTYWMH 10<br>GYTFTTYWMH 10<br>GYTFTTYWMH 10<br>GYTFNTYNHY 10<br>*: . : + | GYTFTDYDMH<br>GYTFTDYDMH<br>GYTFTDYDMH<br>GYTFTDYDMH<br>GYTFTDYEMH<br>****: | GFDFSKDWMS 10 | GYTFTRNWIQ 10<br>GYTFTRNWIQ 10<br>GYTFTRNWIQ 10<br>********** |

| CDRH2-alignment1 | CDRH2-alignment2 | CDRH2-alignment3 | CDRH2-alignment4 | CDRH2-alignment5 |
|---|---|---|---|---|
| LINPTNGRTN 10 | TIDPETGGTA 10 | EIDPSDSYTN 10 | GIDPSNGDTK 10 | AIYPGNGDSR |
| LINPTNGRTN 10 | TIDPETGGTA 10 | EINPDSSTIN 10 | | AIYPGNGDSR |
| LINPTNGKTN 10 | TIDPETGGTA 10 | **:*...* * | | AVYPGNGDSR |
| LINPTNGRTN 10 | TIDPETGCTA 10 | | | *:******* |
| LINPTNGRTN 10 | AIDPFTGGTA 10 | | | |
| LINPTNGRTN 10 | :********* | | | |
| LINPTNGRTN 10 | | | | |
| LINPTNGRTN 10 | | | | |
| LINPTNGRTN 10 | | | | |
| LINPTNGRTN 10 | | | | |
| LINPTNGRTN 10 | | | | |
| LINPTNGRTN 10 | | | | |
| LINPTNGRTN 10 | | | | |
| LINPTNGRTN 10 | | | | |
| LINPTNGRTN 10 | | | | |
| LINPTNGRTN 10 | | | | |
| LINPTNGRTN 10 | | | | |
| LINPTNGRTN 10 | | | | |
| LINPTNGRTN 10 | | | | |
| LINPTNGRTN 10 | | | | |
| LINPTNGRTN 10 | | | | |
| LINPTNGRTN 10 | | | | |
| LINPTNGRTN 10 | | | | |
| LINPTNGRTN 10 | | | | |
| LINPSNARTN 10 | | | | |
| LINPSNARTN 10 | | | | |
| LINPSNARTN 10 | | | | |
| LINPSNARTN 10 | | | | |
| LINPSNARTN 10 | | | | |
| LINPSNGRPN 10 | | | | |
| ****:*:* * | | | | |

FIGURE 11C

| CDRH3-alignment1 | CDRH3-alignment2 | CDRH3-alignment3 | CDRH3-alignment4 | CDRH3-alignment5 | CDRH3-alignment6 |
|---|---|---|---|---|---|
| ARGGDGDYFDY 11<br>ARGGDGDYFDY 11<br>ARGGDGDYFDY 11<br>ARGGDGDYFDY 11<br>ARGGDGDYFDY 11<br>ARGGDGDYFDY 11<br>ARGHGDYFDY 11<br>ARGHGDYFDY 11<br>ARGGDGDYFDY 11<br>ARGGDCDYFDY 11<br>ARGGDGDYFDY 11<br>ARGGDGDYFDY 11<br>ARGGLCDYFDY 11<br>ARGGDGDYFDY 11<br>ARGGDGDYFDY 11<br>ARGGDGDYFDY 11<br>ARGGDGDYFDY 11<br>ARCCDCDYFDY 11<br>ARGGDGDYFDY 11<br>ARGHKGDYFDY 11<br>ARGGDGDYFDY 11<br>ARGGDGDYFDY 11<br>ARGGDCDYFDY 11<br>ARGGDGDYFDY 11<br>ARGGDGDYFDY 11<br>ARGHGDYFDY 11<br>ARGGDGDYFDY 11<br>ARGGDGDYFDY 11<br>ARGGDGDYFDY 11<br>ARGGDGDYFDY 11<br>ARGCCDYFDY 11<br>\*\*\*\*\*\*\*\*\*\*\* | TSFYYTYSNYDVGFAY 16<br>TSFYYTYSNYDVGFAY 16<br>TSFYYTYSNYDVGFAY 16<br>TSFYYTYNYDVGFAY 16<br>TTFYYSHNYDVGFAY 16<br>\*:\*\*\*\*: \*\*\*\*\*\*\*\* | ARSGAYSSDYSYDGFAY 17 | SRLEDYEDWYFDV 13 | TSHTY 5 | ARLAGNYAYYFDY 13<br>ARLAGNYAYYFDY 13<br>ARLAGNYAYYFDY 13<br>\*\*\*\*\*\*\*\*\*\*\*\*\* |

SEQUENCE LISTING

<160> NUMBER OF SEQ ID NOS: 223

<210> SEQ ID NO 1
<211> LENGTH: 987
<212> TYPE: DNA
<213> ORGANISM: Homo sapiens

<400> SEQUENCE: 1

```
atggaaaagt ccatctggct gctggcctgc ttggcgtggg ttctcccgac aggctcattt      60
gtgagaacta aaatagatac tacgagaaac ttgctcaaca cagaggtgca cagctcgcca     120
gcgcagcgct ggtccatgca ggtgccaccc gaggtgagcg cggaggcagg cgacgcggca     180
gtgctgccct gcaccttcac gcacccgcac cgccactacg acgggccgct gacggccatc     240
tggcgcgcgg gcgagcccta tgcgggcccg caggtgttcc gctgcgctgc ggcgcggggc     300
agcgagctct gccagacggc gctgagcctg acggccgct tccggctgct gggcaacccg     360
cgccgcaacg acctctcgct gcgcgtcgag cgcctcgccc tggctgacga ccgccgctac     420
ttctgccgcg tcgagttcgc cggcgacgtc catgaccgct acgagagccg ccacggcgtc     480
cggctgcacg tgacagccgc gccgcggatc gtcaacatct cggtgctgcc cagtccggct     540
cacgccttcc gcgcgctctg cactgccgaa ggggagccgc cgcccgccct cgcctggtcc     600
ggcccggccc tgggcaacag cttggcagcc gtgcggagcc cgcgtgaggg tcacggccac     660
```

-continued

```
ctagtgaccg ccgaactgcc cgcactgacc catgacggcc gctacacgtg tacggccgcc       720
aacagcctgg gccgctccga ggccagcgtc tacctgttcc gcttccatgg cgccagcggg       780
gcctcgacgg tcgccctcct gctcggcgct ctcggcttca aggcgctgct gctgctcggg       840
gtcctggccg cccgcgctgc ccgccgccgc ccagagcatc tggacacccc ggacacccca       900
ccacggtccc aggcccagga gtccaattat gaaaatttga gccagatgaa cccccggagc       960
ccaccagcca ccatgtgctc accgtga                                            987
```

<210> SEQ ID NO 2
<211> LENGTH: 328
<212> TYPE: PRT
<213> ORGANISM: Homo sapiens

<400> SEQUENCE: 2

```
Met Glu Lys Ser Ile Trp Leu Leu Ala Cys Leu Ala Trp Val Leu Pro
1               5                   10                  15

Thr Gly Ser Phe Val Arg Thr Lys Ile Asp Thr Glu Asn Leu Leu
            20                  25                  30

Asn Thr Glu Val His Ser Ser Pro Ala Gln Arg Trp Ser Met Gln Val
        35                  40                  45

Pro Pro Glu Val Ser Ala Glu Ala Gly Asp Ala Val Leu Pro Cys
    50                  55                  60

Thr Phe Thr His Pro His Arg His Tyr Asp Gly Pro Leu Thr Ala Ile
65                  70                  75                  80

Trp Arg Ala Gly Glu Pro Tyr Ala Gly Pro Gln Val Phe Arg Cys Ala
                85                  90                  95

Ala Ala Arg Gly Ser Glu Leu Cys Gln Thr Ala Leu Ser Leu His Gly
            100                 105                 110

Arg Phe Arg Leu Leu Gly Asn Pro Arg Arg Asn Asp Leu Ser Leu Arg
        115                 120                 125

Val Glu Arg Leu Ala Leu Ala Asp Asp Arg Arg Tyr Phe Cys Arg Val
    130                 135                 140

Glu Phe Ala Gly Asp Val His Asp Arg Tyr Glu Ser Arg His Gly Val
145                 150                 155                 160

Arg Leu His Val Thr Ala Ala Pro Arg Ile Val Asn Ile Ser Val Leu
                165                 170                 175

Pro Ser Pro Ala His Ala Phe Arg Ala Leu Cys Thr Ala Glu Gly Glu
            180                 185                 190

Pro Pro Pro Ala Leu Ala Trp Ser Gly Pro Ala Leu Gly Asn Ser Leu
        195                 200                 205

Ala Ala Val Arg Ser Pro Arg Glu Gly His Gly His Leu Val Thr Ala
    210                 215                 220

Glu Leu Pro Ala Leu Thr His Asp Gly Arg Tyr Thr Cys Thr Ala Ala
225                 230                 235                 240

Asn Ser Leu Gly Arg Ser Glu Ala Ser Val Tyr Leu Phe Arg Phe His
                245                 250                 255

Gly Ala Ser Gly Ala Ser Thr Val Ala Leu Leu Leu Gly Ala Leu Gly
            260                 265                 270

Phe Lys Ala Leu Leu Leu Leu Gly Val Leu Ala Ala Arg Ala Ala Arg
        275                 280                 285

Arg Arg Pro Glu His Leu Asp Thr Pro Asp Thr Pro Arg Ser Gln
    290                 295                 300

Ala Gln Glu Ser Asn Tyr Glu Asn Leu Ser Gln Met Asn Pro Arg Ser
305                 310                 315                 320
```

Pro Pro Ala Thr Met Cys Ser Pro
              325

<210> SEQ ID NO 3
<211> LENGTH: 1029
<212> TYPE: DNA
<213> ORGANISM: Mus musculus

<400> SEQUENCE: 3

```
atggagggt ccctccaact cctggcctgc ttggcctgtg tgctccagat gggatccctt    60
gtgaaaacta aagagacgc ttcgggggat ctgctcaaca cagaggcgca cagtgccccg   120
gcgcagcgct ggtccatgca ggtgcccgcg gaggtgaacg cggaggctgg cgacgcggcg   180
gtgctgccct gcaccttcac gcacccgcac cgccactacg acgggccgct gacggccatc   240
tggcgctcgg gcgagccgta cgcgggcccg caggtgttcc gctgcaccgc ggcgccgggc   300
agcgagctgt gccagacggc gctgagcctg cacggccgct ccgcctgct gggcaacccg   360
cgccgcaacg acctgtccct gcgcgtcgag cgcctcgccc tggcggacag cggccgctac   420
ttctgccgcg tggagttcac cggcgacgcc acgatcgct atgagagtcg ccatggggtc   480
cgtctgcgcg tgactgcagc tgcgccgcgg atcgtcaaca tctcggtgct gccgggcccc   540
gcgcacgcct ccgcgcgct ctgcaccgcc gaggggagc cccgcccgc cctcgcctgg   600
tcgggtcccg ccccaggcaa cagctccgct gccctgcagg gccagggtca cggctaccag   660
gtgaccgccg agttgcccgc gctgaccgcc gacggccgct acacgtgcac ggcggccaat   720
agcctgggcc gcgccgaggc cagcgtctac ctgttccgct ccacggcgc ccccggaacc   780
tcgaccctag cgctcctgct gggcgcgctg ggcctcaagg ccttgctgct gcttggcatt   840
ctgggagcgc gtgccacccg acgccgacta gatcacctgg tccccagga cacccctcca   900
cggtctcagg ctcaggagtc caattatgaa aatttgagcc agatgagtcc tccaggccac   960
cagctgccac gtgtttgctg tgaggaactc ctcagccatc accatctagt cattcaccat  1020
gagaaataa                                                          1029
```

<210> SEQ ID NO 4
<211> LENGTH: 342
<212> TYPE: PRT
<213> ORGANISM: Mus musculus

<400> SEQUENCE: 4

Met Glu Gly Ser Leu Gln Leu Leu Ala Cys Leu Ala Cys Val Leu Gln
1               5                   10                  15

Met Gly Ser Leu Val Lys Thr Arg Arg Asp Ala Ser Gly Asp Leu Leu
            20                  25                  30

Asn Thr Glu Ala His Ser Ala Pro Ala Gln Arg Trp Ser Met Gln Val
        35                  40                  45

Pro Ala Glu Val Asn Ala Glu Ala Gly Asp Ala Ala Val Leu Pro Cys
    50                  55                  60

Thr Phe Thr His Pro His Arg His Tyr Asp Gly Pro Leu Thr Ala Ile
65                  70                  75                  80

Trp Arg Ser Gly Glu Pro Tyr Ala Gly Pro Gln Val Phe Arg Cys Thr
                85                  90                  95

Ala Ala Pro Gly Ser Glu Leu Cys Gln Thr Ala Leu Ser Leu His Gly
            100                 105                 110

Arg Phe Arg Leu Leu Gly Asn Pro Arg Arg Asn Asp Leu Ser Leu Arg
        115                 120                 125

```
Val Glu Arg Leu Ala Leu Ala Asp Ser Gly Arg Tyr Phe Cys Arg Val
    130                 135                 140
Glu Phe Thr Gly Asp Ala His Asp Arg Tyr Glu Ser Arg His Gly Val
145                 150                 155                 160
Arg Leu Arg Val Thr Ala Ala Pro Arg Ile Val Asn Ile Ser Val
                165                 170                 175
Leu Pro Gly Pro Ala His Ala Phe Arg Ala Leu Cys Thr Ala Glu Gly
                180                 185                 190
Glu Pro Pro Pro Ala Leu Ala Trp Ser Gly Pro Ala Pro Gly Asn Ser
                195                 200                 205
Ser Ala Ala Leu Gln Gly Gln Gly His Gly Tyr Gln Val Thr Ala Glu
    210                 215                 220
Leu Pro Ala Leu Thr Arg Asp Gly Arg Tyr Thr Cys Thr Ala Ala Asn
225                 230                 235                 240
Ser Leu Gly Arg Ala Glu Ala Ser Val Tyr Leu Phe Arg Phe His Gly
                245                 250                 255
Ala Pro Gly Thr Ser Thr Leu Ala Leu Leu Gly Ala Leu Gly Leu
                260                 265                 270
Lys Ala Leu Leu Leu Gly Ile Leu Gly Ala Arg Ala Thr Arg Arg
    275                 280                 285
Arg Leu Asp His Leu Val Pro Gln Asp Thr Pro Pro Arg Ser Gln Ala
    290                 295                 300
Gln Glu Ser Asn Tyr Glu Asn Leu Ser Gln Met Ser Pro Gly His
305                 310                 315                 320
Gln Leu Pro Arg Val Cys Cys Glu Glu Leu Leu Ser His His His Leu
                325                 330                 335
Val Ile His His Glu Lys
                340

<210> SEQ ID NO 5
<211> LENGTH: 642
<212> TYPE: DNA
<213> ORGANISM: Artificial Sequence
<220> FEATURE:
<223> OTHER INFORMATION: 25A1 light chain

<400> SEQUENCE: 5
gaaaatgtgc tcacccagtc tccagcaatc atgtctgcat ctccagggga gaaggtcacc    60
atatcctgca gtgccagctc aagtgtaagt tacatgtact ggtaccagca gaagccagga   120
tcctccccca aaccctggat ttatcgcaca tccaacctgg cttctggagt ccctgctcgc   180
ttcagtggca gtgggtctgg gacctcttac tctctcacaa tcagcagcat ggaggctgaa   240
gatgctgcca cttattactg ccagcagtgg agtagtaacc cactcacgtt cggtgctggg   300
accaagctgg agctgaaacg ggctgtggct gcaccatctg tcttcatctt cccgccatct   360
gatgagcagt tgaaatctgg aactgcctct gttgtgtgcc tgctgaataa cttctatccc   420
agagaggcca agtacagtg gaaggtggat aacgccctcc aatcgggtaa ctcccaggag   480
agtgtcacag agcaggacag caaggacagc acctacagcc tcagcagcac cctgacgctg   540
agcaaagcag actacgagaa acacaaagtc tacgcctgcg aagtcaccca tcagggcctg   600
agctcgcccg tcacaaagag cttcaacagg ggagagtgtt ag                      642

<210> SEQ ID NO 6
<211> LENGTH: 211
<212> TYPE: PRT
<213> ORGANISM: Artificial Sequence
<220> FEATURE:
```

<223> OTHER INFORMATION: 25A1 light chain

<400> SEQUENCE: 6

```
Glu Asn Val Leu Thr Gln Ser Pro Ala Ile Met Ser Ala Ser Pro Gly
1               5                   10                  15

Glu Lys Val Thr Ile Ser Cys Ser Ala Ser Ser Val Ser Tyr Met
            20                  25                  30

Tyr Trp Tyr Gln Gln Lys Pro Gly Ser Ser Pro Lys Pro Trp Ile Tyr
        35                  40                  45

Arg Thr Ser Asn Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Asn Pro Leu Thr
                85                  90                  95

Phe Gly Ala Gly Thr Lys Leu Glu Leu Lys Val Ala Ala Pro Ser Val
            100                 105                 110

Phe Ile Phe Pro Pro Ser Asp Glu Gln Leu Lys Ser Gly Thr Ala Ser
        115                 120                 125

Val Val Cys Leu Leu Asn Asn Phe Tyr Pro Arg Glu Ala Lys Val Gln
    130                 135                 140

Trp Lys Val Asp Asn Ala Leu Gln Ser Gly Asn Ser Gln Glu Ser Val
145                 150                 155                 160

Thr Glu Gln Asp Ser Lys Asp Ser Thr Tyr Ser Leu Ser Ser Thr Leu
                165                 170                 175

Thr Leu Ser Lys Ala Asp Tyr Glu Lys His Lys Val Tyr Ala Cys Glu
            180                 185                 190

Val Thr His Gln Gly Leu Ser Ser Pro Val Thr Lys Ser Phe Asn Arg
        195                 200                 205

Gly Glu Cys
    210
```

<210> SEQ ID NO 7
<211> LENGTH: 1353
<212> TYPE: DNA
<213> ORGANISM: Artificial Sequence
<220> FEATURE:
<223> OTHER INFORMATION: 25A1 heavy chain

<400> SEQUENCE: 7

```
gaggtccagc tgcaacaatc tgggactgag ctggtgaggc ctgggtcctc agtgaagatt      60
tcctgcaagg cttctggcta caccttcacc aggtactgga tggactgggt gaagcagagg     120
cctggacaag gccttgagtg gatcggagag attgatcctt ctgatagtta tactaactac     180
aatcaaaagt tcaagggcaa ggccacattg actgtagata attctccag aacagcctat      240 atggaactca gcagcctgac atctgaggac tctgcggtct attactgtgc aagatcgggg     300
gcctactcta gtgactatag ttacgacggg tttgcttact ggggccaagg gactctggtc     360
actgtctctg cagcctcaac gaagggccca tcggtcttcc ccctggcgcc ctgctccagg     420
agcacctccg agagcacagc cgccctgggc tgcctggtca aggactactt ccccgaaccg     480
gtgacggtgt cgtggaactc aggcgctctg accagcggcg tgcacacctt cccagctgtc     540
ctacagtcct caggactcta ctccctcagc agcgtggtga ccgtgccctc agcaacttc      600 ggcacccaga cctacacctg caacgtagat cacaagccca gcaacaccaa ggtggacaag     660
acagttgagc gcaaatgttg tgtcgagtgc ccaccgtgcc cagcaccacc tgtggcagga     720
```

```
ccgtcagtct tccgcttccc cccaaaaccc aaggacaccc gcatgatctc ccggacccct      780
gaggtcacgt gcgtggtggt ggatgtgagc cacgaagacc ccgaggtcca gttcaactgg      840
tacgtggacg gcgtggaggt gcataatgcc aagacaaagc cacgggagga gcagttcaac      900
agcacgttcc gtgtggtcag cgtcctcacc gttgtgcacc aggactggct gaacggcaag      960
gagtacaagt gcaaggtctc caacaaaggc ctcccagccc ccatcgagaa aaccatctcc     1020
aaaaccaaag ggcagcccg agaaccacag gtgtacaccc tgcccccatc ccggaggag       1080 atgaccaaga accaggtcag cctgacctgc ctggtcaaag gcttctaccc cagcgacatc     1140
gccgtggagt gggagagcaa tgggcagccg gagaacaact acaagaccac acctcccatg     1200
ctggactccg acggctcctt cttcctctac agcaagctca ccgtggacaa gagcaggtgg     1260
cagcagggga acgtcttctc atgctccgtg atgcatgagg ctctgcacaa ccactacacg     1320
cagaagagcc tctccctgtc tccgggtaaa tga                                  1353
```

<210> SEQ ID NO 8
<211> LENGTH: 450
<212> TYPE: PRT
<213> ORGANISM: Artificial Sequence
<220> FEATURE:
<223> OTHER INFORMATION: 25A1 heavy chain

<400> SEQUENCE: 8

```
Glu Val Gln Leu Gln Gln Ser Gly Thr Glu Leu Val Arg Pro Gly Ser
1               5                   10                  15

Ser Val Lys Ile Ser Cys Lys Ala Ser Gly Tyr Thr Phe Thr Arg Tyr
            20                  25                  30

Trp Met Asp Trp Val Lys Gln Arg Pro Gly Gln Gly Leu Glu Trp Ile
        35                  40                  45

Gly Glu Ile Asp Pro Ser Asp Ser Tyr Thr Asn Tyr Asn Gln Lys Phe
    50                  55                  60

Lys Gly Lys Ala Thr Leu Thr Val Asp Lys Phe Ser Arg Thr Ala Tyr
65                  70                  75                  80

Met Glu Leu Ser Ser Leu Thr Ser Glu Asp Ser Ala Val Tyr Tyr Cys
                85                  90                  95

Ala Arg Ser Gly Ala Tyr Ser Ser Asp Tyr Tyr Asp Gly Phe Ala
            100                 105                 110

Tyr Trp Gly Gln Gly Thr Leu Val Thr Val Ser Ala Ala Ser Thr Lys
        115                 120                 125

Gly Pro Ser Val Phe Pro Leu Ala Pro Cys Ser Arg Ser Thr Ser Glu
    130                 135                 140

Ser Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Asn Phe Gly Thr Gln Thr Tyr Thr Cys Asn
        195                 200                 205

Val Asp His Lys Pro Ser Asn Thr Lys Val Asp Lys Thr Val Glu Arg
    210                 215                 220

Lys Cys Cys Val Glu Cys Pro Pro Cys Pro Ala Pro Val Ala Gly
225                 230                 235                 240

Pro Ser Val Phe Leu Phe Pro Pro Lys Pro Lys Asp Thr Leu Met Ile
                245                 250                 255
```

```
Ser Arg Thr Pro Glu Val Thr Cys Val Val Val Asp Val Ser His Glu
            260                 265                 270

Asp Pro Glu Val Gln Phe Asn Trp Tyr Val Asp Gly Val Glu Val His
        275                 280                 285

Asn Ala Lys Thr Lys Pro Arg Glu Glu Gln Phe Asn Ser Thr Phe Arg
    290                 295                 300

Val Val Ser Val Leu Thr Val Val His Gln Asp Trp Leu Asn Gly Lys
305                 310                 315                 320

Glu Tyr Lys Cys Lys Val Ser Asn Lys Gly Leu Pro Ala Pro Ile Glu
                325                 330                 335

Lys Thr Ile Ser Lys Thr Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Met
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 9
<211> LENGTH: 660
<212> TYPE: DNA
<213> ORGANISM: Artificial Sequence
<220> FEATURE:
<223> OTHER INFORMATION: 25B4 light chain

<400> SEQUENCE: 9
gatattgtga tgacccaggc tgcattctcc aatccagtca ctcttggaac atcagcttcc      60
atctcctgca ggtctagtaa gagtctccta catagtaatg catcacttat ttgtattgg     120 tatctgcaga agccaggcca gtctcctcag ctcctgattt atcagatgtc caaccttgcc    180
tcaggagtcc cagacaggtt cagtggcagt gggtcaggaa ctgctttcac actgagaatc    240
agtagagtgg aggctgagga tgtgggtgtt tattactgta tgcaacatct agaatatccg    300
tacacgttcg gaggggggac caagctggaa ataaaacggg ctgtggctgc accatctgtc    360
ttcatcttcc cgccatctga tgagcagttg aaatctggaa ctgcctctgt tgtgtgcctg    420
ctgaataact tctatcccag agaggccaaa gtacagtgga aggtggataa cgccctccaa    480
tcgggtaact cccaggagag tgtcacagag caggacagca aggacagcac ctacagcctc    540
agcagcaccc tgacgctgag caaagcagac tacgagaaac acaaagtcta cgcctgcgaa    600
gtcacccatc agggcctgag ctcgcccgtc acaaagagct tcaacagggg agagtgttag    660

<210> SEQ ID NO 10
<211> LENGTH: 217
<212> TYPE: PRT
<213> ORGANISM: Artificial Sequence
<220> FEATURE:
<223> OTHER INFORMATION: 25B4 light chain

<400> SEQUENCE: 10
```

Asp Ile Val Met Thr Gln Ala Ala Phe Ser Asn Pro Val Thr Leu Gly
1               5                   10                  15

Thr Ser Ala Ser Ile Ser Cys Arg Ser Ser Lys Ser Leu Leu His Ser
            20                  25                  30

Asn Gly Ile Thr Tyr Leu Tyr Trp Tyr Leu Gln Lys Pro Gly Gln Ser
        35                  40                  45

Pro Gln Leu Leu Ile Tyr Gln Met Ser Asn Leu Ala Ser Gly Val Pro
    50                  55                  60

Asp Arg Phe Ser Gly Ser Gly Ser Gly Thr Ala Phe Thr Leu Arg Ile
65              70                  75                  80

Ser Arg Val Glu Ala Glu Asp Val Gly Val Tyr Tyr Cys Met Gln His
                85                  90                  95

Leu Glu Tyr Pro Tyr Thr Phe Gly Gly Gly Thr Lys Leu Glu Ile Lys
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215

<210> SEQ ID NO 11
<211> LENGTH: 1335
<212> TYPE: DNA
<213> ORGANISM: Artificial Sequence
<220> FEATURE:
<223> OTHER INFORMATION: 25B4 heavy chain

<400> SEQUENCE: 11
caggtccaag tgcagcagcc tggggctgaa attgtgaggc tggggcttc agtgaagctg     60 tcctgcaagg cttctggcta caccttcacc agctactgga tgcactgggt gaagcagagg    120
cctggacaag gccttgagtg gattggactg attaatccta ccaacggtcg tactaactac    180
aatgagaagt tcaagagcaa ggccacactg actgtagaca atcctccag cacagcctac    240 atgcaactca gcagcctgac atctgaggac tctgcggtct attactgtgc aagagggggg    300 gacgggact actttgacta ctggggccaa ggcaccactc tcacagtctc ctcagcctca    360
acgaagggcc catcggtctt ccccctggcg ccctgctcca ggagcacctc cgagagcaca    420
gccgccctgg gctgcctggt caaggactac ttccccgaac cggtgacggt gtcgtggaac    480
tcaggcgctc tgaccagcgg cgtgcacacc ttcccagctg tcctacagtc ctcaggactc    540
tactccctca gcagcgtggt gaccgtgccc tccagcaact tcggcaccca gacctacacc    600
tgcaacgtag atcacaagcc cagcaacacc aaggtggaca gacagttga gcgcaaatgt    660 tgtgtcgagt gcccaccgtg cccagcacca cctgtggcag gaccgtcagt cttccgcttc    720
cccccaaaac ccaaggacac ccgcatgatc tcccggaccc ctgaggtcac gtgcgtggtg    780
gtggatgtga gccacgaaga ccccgaggtc cagttcaact ggtacgtgga cggcgtggag    840

-continued

```
gtgcataatg ccaagacaaa gccacgggag gagcagttca acagcacgtt ccgtgtggtc    900
agcgtcctca ccgttgtgca ccaggactgg ctgaacggca aggagtacaa gtgcaaggtc    960
tccaacaaag gcctcccagc ccccatcgag aaaaccatct ccaaaaccaa agggcagccc   1020
cgagaaccac aggtgtacac cctgccccca tcccgggagg agatgaccaa gaaccaggtc   1080
agcctgacct gcctggtcaa aggcttctac cccagcgaca tcgccgtgga gtgggagagc   1140
aatgggcagc cggagaacaa ctacaagacc acacctccca tgctggactc cgacggctcc   1200
ttcttcctct acagcaagct caccgtggac aagagcaggt ggcagcaggg gaacgtcttc   1260
tcatgctccg tgatgcatga ggctctgcac aaccactaca cgcagaagag cctctccctg   1320
tctccgggta aatga                                                    1335
```

<210> SEQ ID NO 12
<211> LENGTH: 444
<212> TYPE: PRT
<213> ORGANISM: Artificial Sequence
<220> FEATURE:
<223> OTHER INFORMATION: 25B4 heavy chain

<400> SEQUENCE: 12

```
Gln Val Gln Val Gln Gln Pro Gly Ala Glu Ile Val Arg Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Leu Ile Asn Pro Thr Asn Gly Arg Thr Asn Tyr Asn Glu Lys Phe
    50                  55                  60

Lys Ser Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Gly Gly Asp Gly Asp Tyr Phe Asp Tyr Trp Gly Gln Gly Thr
            100                 105                 110

Thr Leu Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Asn Phe Gly Thr Gln Thr Tyr Thr Cys Asn Val Asp His Lys Pro Ser
        195                 200                 205

Asn Thr Lys Val Asp Lys Thr Val Glu Arg Lys Cys Cys Val Glu Cys
    210                 215                 220

Pro Pro Cys Pro Ala Pro Pro Val Ala Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Gln Phe
            260                 265                 270
```

Asn Trp Tyr Val Asp Gly Val Glu Val His Asn Ala Lys Thr Lys Pro
            275                 280                 285

Arg Glu Glu Gln Phe Asn Ser Thr Phe Arg Val Val Ser Val Leu Thr
    290                 295                 300

Val Val His Gln Asp Trp Leu Asn Gly Lys Glu Tyr Lys Cys Lys Val
305                 310                 315                 320

Ser Asn Lys Gly Leu Pro Ala Pro Ile Glu Lys Thr Ile Ser Lys Thr
                325                 330                 335

Lys Gly Gln Pro Arg Glu Pro Gln Val Tyr Thr Leu Pro Pro Ser Arg
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
370                 375                 380

Glu Asn Asn Tyr Lys Thr Thr Pro Pro Met Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly Lys
        435                 440

<210> SEQ ID NO 13
<211> LENGTH: 660
<212> TYPE: DNA
<213> ORGANISM: Artificial Sequence
<220> FEATURE:
<223> OTHER INFORMATION: 25B8 light chain

<400> SEQUENCE: 13
gatattgtga tgacccaggc tgcaccctct gtacctgtca ctcctggaga gtcagtatcc      60
atctcctgca ggtctactaa gagtctcctg catagtaatg caacacttta cttgtattgg     120
ttcctgcaga ggccaggcca gtctcctcag ctcctgatat atcggatgtc aaccttgcc      180 tcaggagtcc cagacaggtt cagtggcagt gggtcaggaa ctgctttcac actgagaatc     240
agtagagtgg aggctgagga tgtgggtgtt tattactgta tgcaacatct agaatatcct     300
ttcacgttcg gaggggggac caagctggaa ataaaacggg ctgtggctgc accatctgtc     360
ttcatcttcc cgccatctga tgagcagttg aaatctggaa ctgcctctgt tgtgtgcctg     420
ctgaataact tctatcccag agaggccaaa gtacagtgga aggtggataa cgccctccaa     480
tcgggtaact cccaggagag tgtcacagag caggacagca aggacagcac ctacagcctc     540
agcagcaccc tgacgctgag caaagcagac tacgagaaac acaaagtcta cgcctgcgaa     600
gtcacccatc agggcctgag ctcgcccgtc acaaagagct tcaacagggg agagtgttag     660

<210> SEQ ID NO 14
<211> LENGTH: 217
<212> TYPE: PRT
<213> ORGANISM: Artificial Sequence
<220> FEATURE:
<223> OTHER INFORMATION: 25B8 light chain

<400> SEQUENCE: 14

Asp Ile Val Met Thr Gln Ala Ala Pro Ser Val Pro Val Thr Pro Gly
1               5                   10                  15

Glu Ser Val Ser Ile Ser Cys Arg Ser Thr Lys Ser Leu Leu His Ser
            20                  25                  30

Asn Gly Asn Thr Tyr Leu Tyr Trp Phe Leu Gln Arg Pro Gly Gln Ser
         35                  40                  45

Pro Gln Leu Leu Ile Tyr Arg Met Ser Asn Leu Ala Ser Gly Val Pro
 50                  55                  60

Asp Arg Phe Ser Gly Ser Gly Ser Gly Thr Ala Phe Thr Leu Arg Ile
 65                  70                  75                  80

Ser Arg Val Glu Ala Glu Asp Val Gly Val Tyr Tyr Cys Met Gln His
                 85                  90                  95

Leu Glu Tyr Pro Phe Thr Phe Gly Gly Gly Thr Lys Leu Glu Ile Lys
                100                 105                 110

Val Ala Ala Pro Ser Val Phe Ile Phe Pro Pro Ser Asp Glu Gln Leu
                115                 120                 125

Lys Ser Gly Thr Ala Ser Val Val Cys Leu Leu Asn Asn Phe Tyr Pro
        130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
                180                 185                 190

Lys Val Tyr Ala Cys Glu Val Thr His Gln Gly Leu Ser Ser Pro Val
                195                 200                 205

Thr Lys Ser Phe Asn Arg Gly Glu Cys
        210                 215

<210> SEQ ID NO 15
<211> LENGTH: 1350
<212> TYPE: DNA
<213> ORGANISM: Artificial Sequence
<220> FEATURE:
<223> OTHER INFORMATION: 25B8 heavy chain

<400> SEQUENCE: 15
gagatccagc tgcagcagtc tggagttgag ctggtgaggc ctggggcttc agtgacgctg    60
tcctgcaagg cttcgggcta cacatttact gactatgaca tgcactgggt gaagcagaca   120
cctgttcatg gcctggaatg gattggaact attgatcctg aaactggtgg tactgcctac   180
aatcagaagt tcaagggcaa ggccacactg actgcggaca tcctccacac acagcctac   240 atggagctca gcagcctgac atctgaggac tctgccgtct attactgtac aactttctac   300
tatagtcact ataattacga cgtggggttt gcttactggg gccaagggac tctggtcact   360
gtctctgcag cctcaacgaa gggcccatcg gtcttccccc tggcgccctg ctccaggagc   420
acctccgaga gcacagccgc cctgggctgc ctggtcaagg actacttccc cgaaccggtg   480
acggtgtcgt ggaactcagg cgctctgacc agcggcgtgc acaccttccc agctgtccta   540
cagtcctcag gactctactc cctcagcagc gtggtgaccg tgcctccag caacttcggc   600 acccagacct acacctgcaa cgtagatcac aagcccagca acaccaaggt ggacaagaca   660
gttgagcgca aatgttgtgt cgagtgccca ccgtgcccag caccacctgt ggcaggaccg   720
tcagtcttcc gcttcccccc aaaacccaag gacaccccgca tgatctcccg gaccctgag   780 gtcacgtgcg tggtggtgga tgtgagccac gaagacccccg aggtccagtt caactggtac   840
gtggacggcg tggaggtgca taatgccaag acaaagccac gggaggagca gttcaacagc   900
acgttccgtg tggtcagcgt cctcaccgtt gtgcaccagg actggctgaa cggcaaggag   960
tacaagtgca aggtctccaa caaaggcctc ccagcccccca tcgagaaaac catctccaaa  1020

-continued

```
accaagggc agccccgaga accacaggtg tacaccctgc ccccatcccg ggaggagatg    1080
accaagaacc aggtcagcct gacctgcctg gtcaaaggct tctacccag cgacatcgcc    1140 gtggagtggg agagcaatgg gcagccggag aacaactaca agaccacacc tcccatgctg   1200
gactccgacg gctccttctt cctctacagc aagctcaccg tggacaagag caggtggcag   1260
caggggaacg tcttctcatg ctccgtgatg catgaggctc tgcacaacca ctacacgcag   1320
aagagcctct ccctgtctcc gggtaaatga                                    1350
```

<210> SEQ ID NO 16
<211> LENGTH: 449
<212> TYPE: PRT
<213> ORGANISM: Artificial Sequence
<220> FEATURE:
<223> OTHER INFORMATION: 25B8 heavy chain

<400> SEQUENCE: 16

```
Glu Ile Gln Leu Gln Gln Ser Gly Val Glu Leu Val Arg Pro Gly Ala
1               5                   10                  15

Ser Val Thr Leu Ser Cys Lys Ala Ser Gly Tyr Thr Phe Thr Asp Tyr
            20                  25                  30

Asp Met His Trp Val Lys Gln Thr Pro Val His Gly Leu Glu Trp Ile
        35                  40                  45

Gly Thr Ile Asp Pro Glu Thr Gly Gly Thr Ala Tyr Asn Gln Lys Phe
    50                  55                  60

Lys Gly Lys Ala Thr Leu Thr Ala Asp Arg Ser Ser Thr Thr Ala Tyr
65                  70                  75                  80

Met Glu Leu Ser Ser Leu Thr Ser Glu Asp Ser Ala Val Tyr Tyr Cys
                85                  90                  95

Thr Thr Phe Tyr Tyr Ser His Tyr Asn Tyr Asp Val Gly Phe Ala Tyr
            100                 105                 110

Trp Gly Gln Gly Thr Leu Val Thr Val Ser Ala Ala Ser Thr Lys Gly
        115                 120                 125

Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Asn Phe Gly Thr Gln Thr Tyr Thr Cys Asn Val
        195                 200                 205

Asp His Lys Pro Ser Asn Thr Lys Val Asp Lys Thr Val Glu Arg Lys
    210                 215                 220

Cys Cys Val Glu Cys Pro Pro Cys Pro Ala Pro Pro Val Ala Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Gln Phe Asn Trp Tyr Val Asp Gly Val Glu Val His Asn
        275                 280                 285

Ala Lys Thr Lys Pro Arg Glu Glu Gln Phe Asn Ser Thr Phe Arg Val
    290                 295                 300
```

```
Val Ser Val Leu Thr Val Val His Gln Asp Trp Leu Asn Gly Lys Glu
305                 310                 315                 320

Tyr Lys Cys Lys Val Ser Asn Lys Gly Leu Pro Ala Pro Ile Glu Lys
                325                 330                 335

Thr Ile Ser Lys Thr Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Met Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys
```

<210> SEQ ID NO 17
<211> LENGTH: 660
<212> TYPE: DNA
<213> ORGANISM: Artificial Sequence
<220> FEATURE:
<223> OTHER INFORMATION: 25C1 light chain

<400> SEQUENCE: 17

```
gatattgtga tgacccaggc tgcaccctct gtacctgtca ctcctggaga gtcagtatcc    60
atctcctgca ggtctagtaa gagtctcctg catagtaatg gcaacactta cttgtattgg   120
ttcctgcaga ggccaggcca gtcccctcag ctcctgatat atcggatgtc aaccttgcc    180
tcaggagtcc cagacaggtt cagtggcagt gggtcaggaa ctgctttcac actgagaatc   240
agtagagtgg aggctgagga tgtgggtgtt tattactgta tgcaacatct agaatatcct   300
ttcacgttcg gagggggac caagctggaa ataaaacggg ctgtggctgc accatctgtc   360
ttcatcttcc cgccatctga tgagcagttg aaatctggaa ctgcctctgt tgtgtgcctg   420
ctgaataact tctatcccag agaggccaaa gtacagtgga aggtggataa cgccctccaa   480
tcgggtaact cccaggagag tgtcacagag caggacagca aggacagcac ctacagcctc   540
agcagcaccc tgacgctgag caaagcagac tacgagaaac acaaagtcta cgcctgcgaa   600
gtcacccatc agggcctgag ctcgcccgtc acaaagagct tcaacagggg agagtgttag   660
```

<210> SEQ ID NO 18
<211> LENGTH: 217
<212> TYPE: PRT
<213> ORGANISM: Artificial Sequence
<220> FEATURE:
<223> OTHER INFORMATION: 25C1 light chain

<400> SEQUENCE: 18

```
Asp Ile Val Met Thr Gln Ala Ala Pro Ser Val Pro Val Thr Pro Gly
1               5                   10                  15

Glu Ser Val Ser Ile Ser Cys Arg Ser Ser Lys Ser Leu Leu His Ser
            20                  25                  30

Asn Gly Asn Thr Tyr Leu Tyr Trp Phe Leu Gln Arg Pro Gly Gln Ser
        35                  40                  45
```

```
Pro Gln Leu Leu Ile Tyr Arg Met Ser Asn Leu Ala Ser Gly Val Pro
        50                  55                  60
Asp Arg Phe Ser Gly Ser Gly Ser Gly Thr Ala Phe Thr Leu Arg Ile
 65                  70                  75                  80
Ser Arg Val Glu Ala Glu Asp Val Gly Val Tyr Tyr Cys Met Gln His
                 85                  90                  95
Leu Glu Tyr Pro Phe Thr Phe Gly Gly Gly Thr Lys Leu Glu Ile Lys
            100                 105                 110
Val Ala Ala Pro Ser Val Phe Ile Phe Pro Pro Ser Asp Glu Gln Leu
        115                 120                 125
Lys Ser Gly Thr Ala Ser Val Val Cys Leu Leu Asn Asn Phe Tyr Pro
130                 135                 140
Arg Glu Ala Lys Val Gln Trp Lys Val Asp Asn Ala Leu Gln Ser Gly
145                 150                 155                 160
Asn Ser Gln Glu Ser Val Thr Glu Gln Asp Ser Lys Asp Ser Thr Tyr
                165                 170                 175
Ser Leu Ser Ser Thr Leu Thr Leu Ser Lys Ala Asp Tyr Glu Lys His
            180                 185                 190
Lys Val Tyr Ala Cys Glu Val Thr His Gln Gly Leu Ser Ser Pro Val
        195                 200                 205
Thr Lys Ser Phe Asn Arg Gly Glu Cys
    210                 215

<210> SEQ ID NO 19
<211> LENGTH: 1422
<212> TYPE: DNA
<213> ORGANISM: Artificial Sequence
<220> FEATURE:
<223> OTHER INFORMATION: 25C1 heavy chain

<400> SEQUENCE: 19
gagatccagc tgcagcagtc tggagctgag ctggtgaggc ctggggcttc agtgacgctg      60
tcctgcaagg cttcgggcta cacatttact gactatgaaa tgcactgggt gaagcagaca     120
cctgttcatg gcctggaatg gattggagct attgatcctg aaactggtgg tactgcctac     180
aatcagaagt tcaagggcaa ggccacactg actgcagaca atcctccag cacagcctac      240
atggagctca gcagcctgac atctgaggac tctgccgtct attactgtac aagtttctac     300
tatacttact ataattacga cgtggggttt gcttactggg gccaagggac tctggtcact     360
gtctctgcag cctcaactgg ggcgtcttat tactatgcta tggaccactg ggtcaagga      420
acctcagtca ccgtctcctc agcctcaacg aagggcccat cggtcttccc cctggcgccc     480
tgctccagga gcacctccga gagcacagcg gccctgggct gcctggtcaa ggactacttc     540
cccgaaccgg tgacggtgtc gtggaactca ggcgctctga ccagcggcgt gcacaccttc     600
ccagctgtcc tacagtcctc aggactctac tccctcagca gcgtggtgac cgtgccctcc     660
agcaacttcg gcacccagac ctacacctgc aacgtagatc acaagcccag caacaccaag     720
gtggacaaga cagttgagcg caaatgttgt gtcgagtgcc caccgtgccc agcaccacct     780
gtggcaggac cgtcagtctt ccgcttcccc ccaaaaccca aggacacccg catgatctcc     840
cggacccctg aggtcacgtg cgtggtggtg gatgtgagcc acgaagaccc cgaggtccag     900
ttcaactggt acgtggacgg cgtggaggtg cataatgcca agacaaagcc acgggaggag     960
cagttcaaca gcacgttccg tgtggtcagc gtcctcaccg ttgtgcacca ggactggctg    1020
aacggcaagg agtacaagtg caaggtctcc aacaaaggcc tcccagcccc catcgagaaa    1080
accatctcca aaaccaaagg gcagccccga gaaccacagg tgtacaccct gcccccatcc    1140
```

```
cgggaggaga tgaccaagaa ccaggtcagc ctgacctgcc tggtcaaagg cttctacccc     1200
agcgacatcg ccgtggagtg ggagagcaat gggcagccgg agaacaacta caagaccaca     1260
cctcccatgc tggactccga cggctccttc ttcctctaca gcaagctcac cgtggacaag     1320
agcaggtggc agcaggggaa cgtcttctca tgctccgtga tgcatgaggc tctgcacaac     1380
cactacacgc agaagagcct ctccctgtct ccgggtaaat ga                        1422

<210> SEQ ID NO 20
<211> LENGTH: 449
<212> TYPE: PRT
<213> ORGANISM: Artificial Sequence
<220> FEATURE:
<223> OTHER INFORMATION: 25C1 heavy chain

<400> SEQUENCE: 20

Glu Ile Gln Leu Gln Gln Ser Gly Ala Glu Leu Val Arg Pro Gly Ala
1               5                   10                  15

Ser Val Thr Leu Ser Cys Lys Ala Ser Gly Tyr Thr Phe Thr Asp Tyr
            20                  25                  30

Glu Met His Trp Val Lys Gln Thr Pro Val His Gly Leu Glu Trp Ile
        35                  40                  45

Gly Ala Ile Asp Pro Glu Thr Gly Gly Thr Ala Tyr Asn Gln Lys Phe
    50                  55                  60

Lys Gly Lys Ala Thr Leu Thr Ala Asp Lys Ser Ser Ser Thr Ala Tyr
65                  70                  75                  80

Met Glu Leu Ser Ser Leu Thr Ser Glu Asp Ser Ala Val Tyr Tyr Cys
                85                  90                  95

Thr Ser Phe Tyr Tyr Thr Tyr Tyr Asn Tyr Asp Val Gly Phe Ala Tyr
            100                 105                 110

Trp Gly Gln Gly Thr Leu Val Thr Val Ser Ala Ala Ser Thr Lys Gly
        115                 120                 125

Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Asn Phe Gly Thr Gln Thr Tyr Thr Cys Asn Val
        195                 200                 205

Asp His Lys Pro Ser Asn Thr Lys Val Asp Lys Thr Val Glu Arg Lys
    210                 215                 220

Cys Cys Val Glu Cys Pro Pro Cys Pro Ala Pro Pro Val Ala Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Gln Phe Asn Trp Tyr Val Asp Gly Val Glu Val His Asn
        275                 280                 285

Ala Lys Thr Lys Pro Arg Glu Glu Gln Phe Asn Ser Thr Phe Arg Val
    290                 295                 300

Val Ser Val Leu Thr Val Val His Gln Asp Trp Leu Asn Gly Lys Glu
305                 310                 315                 320
```

Tyr Lys Cys Lys Val Ser Asn Lys Gly Leu Pro Ala Pro Ile Glu Lys
                325                 330                 335

Thr Ile Ser Lys Thr Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Met Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 21
<211> LENGTH: 660
<212> TYPE: DNA
<213> ORGANISM: Artificial Sequence
<220> FEATURE:
<223> OTHER INFORMATION: 25D8 light chain

<400> SEQUENCE: 21
gatattgtga tgacccaggc tgcattctcc aatccagtca ctcttggaac atcagcttcc     60
atctcctgca ggtctagtaa gagtctccta catagtaatg gcatcactta tttgtattgg    120
tatctgcaga agccaggcca gtctcctcag ctcctgattt atcagatgtc caaccttgcc    180
tcaggagtcc cagacaggtt cagtagcagt gggtcaggaa ctgatttcac actgagaatc    240
agcagagtgg aggctgagga tgtgggtgtt tattactgtg ctcaaaatct agaacttccg    300
tacacgttcg gaggggggac caagctggaa ataaaacggg ctgtggctgc accatctgtc    360
ttcatcttcc cgccatctga tgagcagttg aaatctggaa ctgcctctgt tgtgtgcctg    420
ctgaataact tctatcccag agaggccaaa gtacagtgga aggtggataa cgccctccaa    480
tcgggtaact cccaggagag tgtcacagag caggacagca aggacagcac ctacagcctc    540
agcagcaccc tgacgctgag caaagcagac tacgagaaac acaaagtcta cgcctgcgaa    600
gtcacccatc agggcctgag ctcgcccgtc acaaagagct tcaacagggg agagtgttag    660

<210> SEQ ID NO 22
<211> LENGTH: 217
<212> TYPE: PRT
<213> ORGANISM: Artificial Sequence
<220> FEATURE:
<223> OTHER INFORMATION: 25D8 light chain

<400> SEQUENCE: 22

Asp Ile Val Met Thr Gln Ala Ala Phe Ser Asn Pro Val Thr Leu Gly
1               5                   10                  15

Thr Ser Ala Ser Ile Ser Cys Arg Ser Ser Lys Ser Leu Leu His Ser
            20                  25                  30

Asn Gly Ile Thr Tyr Leu Tyr Trp Tyr Leu Gln Lys Pro Gly Gln Ser
        35                  40                  45

Pro Gln Leu Leu Ile Tyr Gln Met Ser Asn Leu Ala Ser Gly Val Pro
    50                  55                  60

```
Asp Arg Phe Ser Ser Ser Gly Ser Gly Thr Asp Phe Thr Leu Arg Ile
 65                  70                  75                  80

Ser Arg Val Glu Ala Glu Asp Val Gly Val Tyr Tyr Cys Ala Gln Asn
             85                  90                  95

Leu Glu Leu Pro Tyr Thr Phe Gly Gly Gly Thr Lys Leu Glu Ile Lys
        100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215

<210> SEQ ID NO 23
<211> LENGTH: 1335
<212> TYPE: DNA
<213> ORGANISM: Artificial Sequence
<220> FEATURE:
<223> OTHER INFORMATION: 25D8 heavy chain

<400> SEQUENCE: 23
caggtccaag tgcagcagcc tggggctgag cttgtgaagc ctggggcttc ggtgaagctg      60
tcctgcaagg cttctggcta caccttcacc agctactgga tgcactgggt gaagcagagg     120
cctggacaag gccttgagtg gattggactg attaatccta gcaacgctcg tactaactac     180
aatgagaagt tcaataccaa ggccacactg actgtagaca atcctccag cacagcctac      240 atgcaactca gcagcctgac atctgaggac tctgcggtct attactgtgc aagagggggg     300
gacggggact actttgacta ctggggccaa ggcaccactc tcacagtctc ctcagcctca     360
acgaagggcc catcggtctt ccccctggcg ccctgctcca ggagcacctc cgagagcaca     420
gccgccctgg gctgcctggt caaggactac ttccccgaac cggtgacggt gtcgtggaac     480
tcaggcgctc tgaccagcgg cgtgcacacc ttcccagctg tcctacagtc ctcaggactc     540
tactccctca gcagcgtggt gaccgtgccc tccagcaact tcggcaccca gacctacacc     600
tgcaacgtag atcacaagcc cagcaacacc aaggtggaca gacagttga gcgcaaatgt      660 tgtgtcgagt gcccaccgtg cccagcacca cctgtggcag gaccgtcagt cttccgcttc     720 ccccccaaaac ccaaggacac ccgcatgatc tcccggaccc ctgaggtcac gtgcgtggtg    780
gtggatgtga gccacgaaga ccccgaggtc cagttcaact ggtacgtgga cggcgtggag     840
gtgcataatg ccaagacaaa gccacgggag gagcagttca acagcacgtt ccgtgtggtc     900
agcgtcctca ccgttgtgca ccaggactgg ctgaacggca aggagtacaa gtgcaaggtc     960
tccaacaaag gcctcccagc ccccatcgag aaaaccatct ccaaaccaa agggcagccc     1020 cgagaaccac aggtgtacac cctgccccca tcccgggagg agatgaccaa gaaccaggtc    1080
agcctgacct gcctggtcaa aggcttctac cccagcgaca tcgccgtgga gtgggagagc    1140
aatgggcagc cggagaacaa ctacaagacc acacctccca tgctggactc cgacggctcc    1200
```

```
ttcttcctct acagcaagct caccgtggac aagagcaggt ggcagcaggg gaacgtcttc   1260
tcatgctccg tgatgcatga ggctctgcac aaccactaca cgcagaagag cctctccctg   1320
tctccgggta aatga                                                   1335
```

<210> SEQ ID NO 24
<211> LENGTH: 444
<212> TYPE: PRT
<213> ORGANISM: Artificial Sequence
<220> FEATURE:
<223> OTHER INFORMATION: 25D8 heavy chain

<400> SEQUENCE: 24

```
Gln Val Gln Val Gln Gln Pro Gly Ala Glu Leu Val Lys Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Leu Ile Asn Pro Ser Asn Ala Arg Thr Asn Tyr Asn Glu Lys Phe
    50                  55                  60

Asn Thr Lys Ala Thr Leu Thr Val Asp Lys Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Gly Gly Asp Gly Asp Tyr Phe Asp Tyr Trp Gly Gln Gly Thr
            100                 105                 110

Thr Leu Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Asn Phe Gly Thr Gln Thr Tyr Thr Cys Asn Val Asp His Lys Pro Ser
        195                 200                 205

Asn Thr Lys Val Asp Lys Thr Val Glu Arg Lys Cys Cys Val Glu Cys
    210                 215                 220

Pro Pro Cys Pro Ala Pro Pro Val Ala Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Phe Arg Val Val Ser Val Leu Thr
    290                 295                 300

Val Val His Gln Asp Trp Leu Asn Gly Lys Glu Tyr Lys Cys Lys Val
305                 310                 315                 320

Ser Asn Lys Gly Leu Pro Ala Pro Ile Glu Lys Thr Ile Ser Lys Thr
                325                 330                 335
```

```
Lys Gly Gln Pro Arg Glu Pro Gln Val Tyr Thr Leu Pro Pro Ser Arg
                340                 345                 350

Glu Glu Met Thr Lys Asn Gln Val Ser Leu Thr Cys Leu Val Lys Gly
            355                 360                 365

Phe Tyr Pro Ser Asp Ile Ala Val Glu Trp Glu Ser Asn Gly Gln Pro
        370                 375                 380

Glu Asn Asn Tyr Lys Thr Thr Pro Pro Met Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly Lys
        435                 440

<210> SEQ ID NO 25
<211> LENGTH: 642
<212> TYPE: DNA
<213> ORGANISM: Artificial Sequence
<220> FEATURE:
<223> OTHER INFORMATION: 25E5 light chain

<400> SEQUENCE: 25
caaattgttc tcacccagtc tccaacactc atgtctgcat ctccagggga gaaggtcacc      60
atgacctgca gtgccagctc aagtgtaagt tacatgtact ggtaccagca gaagccaaga     120
tcctccccca aaccctggat ttatcgcaca tccaacctgg tttctggagt ccctgtacgc     180
ttcagtggca gtgggtctgg gacctcttac tctctcacaa tcagcagcat ggaggctgaa     240
gatgctgcca cttattactg ccagcagtgg agtagtaacc cacccacgtt cggtgctggg     300
accaagctgg agctgaaacg ggctgtggct gcaccatctg tcttcatctt cccgccatct     360
gatgagcagt tgaaatctgg aactgcctct gttgtgtgcc tgctgaataa cttctatccc     420
agagaggcca agtacagtg gaaggtggat aacgccctcc aatcgggtaa ctcccaggag     480
agtgtcacag agcaggacag caaggacagc acctacagcc tcagcagcac cctgacgctg     540
agcaaagcag actacgagaa acacaaagtc tacgcctgcg aagtcaccca tcagggcctg     600
agctcgcccg tcacaaagag cttcaacagg ggagagtgtt ag                        642

<210> SEQ ID NO 26
<211> LENGTH: 211
<212> TYPE: PRT
<213> ORGANISM: Artificial Sequence
<220> FEATURE:
<223> OTHER INFORMATION: 25E5 light chain

<400> SEQUENCE: 26

Gln Ile Val Leu Thr Gln Ser Pro Thr Leu Met Ser Ala Ser Pro Gly
1               5                  10                  15

Glu Lys Val Thr Met Thr Cys Ser Ala Ser Ser Ser Val Ser Tyr Met
            20                  25                  30

Tyr Trp Tyr Gln Gln Lys Pro Arg Ser Ser Pro Lys Pro Trp Ile Tyr
        35                  40                  45

Arg Thr Ser Asn Leu Val Ser Gly Val Pro Val Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Asn Pro Pro Thr
                85                  90                  95
```

```
Phe Gly Ala Gly Thr Lys Leu Glu Leu Lys Val Ala Ala Pro Ser Val
                100                 105                 110

Phe Ile Phe Pro Pro Ser Asp Glu Gln Leu Lys Ser Gly Thr Ala Ser
            115                 120                 125

Val Val Cys Leu Leu Asn Asn Phe Tyr Pro Arg Glu Ala Lys Val Gln
        130                 135                 140

Trp Lys Val Asp Asn Ala Leu Gln Ser Gly Asn Ser Gln Glu Ser Val
145                 150                 155                 160

Thr Glu Gln Asp Ser Lys Asp Ser Thr Tyr Ser Leu Ser Ser Thr Leu
                165                 170                 175

Thr Leu Ser Lys Ala Asp Tyr Glu Lys His Lys Val Tyr Ala Cys Glu
            180                 185                 190

Val Thr His Gln Gly Leu Ser Ser Pro Val Thr Lys Ser Phe Asn Arg
        195                 200                 205

Gly Glu Cys
    210

<210> SEQ ID NO 27
<211> LENGTH: 1341
<212> TYPE: DNA
<213> ORGANISM: Artificial Sequence
<220> FEATURE:
<223> OTHER INFORMATION: 25E5 heavy chain

<400> SEQUENCE: 27
gaagtgaagc ttgaggagtc tggaggtggc ctggtgcagc ctggaggatc cctgaaactc      60
tcctgtgcag cctcaggatt cgatttagt aaagactgga tgagttgggt ccggcaggct     120
ccagggaaag gctagaatg gattggagaa attaatccag atagcagtac gataaactat     180
gcaccatctc ttaaggataa attcatcatc tccagagaga cgccaaaaa tacgctgtac     240 ctgcaaatga gcaaagtgag atctgaggac acagcccttt attactgttc aagactagag     300
gactacgaag actggtactt cgatgtctgg ggcgcaggga ccacggtcac cgtctcctca     360
gcctcaacga agggcccatc ggtcttcccc ctggcgccct gctccaggag cacctccgag     420
agcacagccg ccctgggctg cctggtcaag gactacttcc ccgaaccggt gacggtgtcg     480
tggaactcag cgctctgac cagcggcgtg cacaccttcc cagctgtcct acagtcctca     540
ggactctact ccctcagcag cgtggtgacc gtgccctcca gcaacttcgg cacccagacc     600
tacacctgca acgtagatca caagcccagc aacaccaagg tggacaagac agttgagcgc     660
aaatgttgtg tcgagtgccc accgtgccca gcaccacctg tggcaggacc gtcagtcttc     720
cgcttccccc caaaacccaa ggacaccgc atgatctccc ggaccctga ggtcacgtgc     780 gtggtggtgg atgtgagcca cgaagacccc gaggtccagt tcaactggta cgtggacggc     840
gtggaggtgc ataatgccaa gacaaagcca cgggaggagc agttcaacag cacgttccgt     900
gtggtcagcg tcctcaccgt tgtgcaccag gactggctga acggcaagga gtacaagtgc     960
aaggtctcca acaaaggcct cccagccccc atcgagaaaa ccatctccaa aaccaaaggg    1020
cagccccgag aaccacaggt gtacaccctg cccccatccc gggaggagat gaccaagaac    1080
caggtcagcc tgacctgcct ggtcaaaggc ttctacccca gcgacatcgc cgtggagtgg    1140
gagagcaatg ggcagccgga gaacaactac aagaccacac tcccatgct ggactccgac    1200 ggctccttct tcctctacag caagctcacc gtggacaaga gcaggtggca gcaggggaac    1260
gtcttctcat gctccgtgat gcatgaggct ctgcacaacc actacacgca gaagagcctc    1320
tccctgtctc cgggtaaatg a                                             1341
```

<210> SEQ ID NO 28
<211> LENGTH: 446
<212> TYPE: PRT
<213> ORGANISM: Artificial Sequence
<220> FEATURE:
<223> OTHER INFORMATION: 25E5 heavy chain

<400> SEQUENCE: 28

```
Glu Val Lys Leu Glu Glu Ser Gly Gly Gly Leu Val Gln Pro Gly Gly
1               5                   10                  15

Ser Leu Lys Leu Ser Cys Ala Ala Ser Gly Phe Asp Phe Ser Lys Asp
            20                  25                  30

Trp Met Ser Trp Val Arg Gln Ala Pro Gly Lys Gly Leu Glu Trp Ile
        35                  40                  45

Gly Glu Ile Asn Pro Asp Ser Ser Thr Ile Asn Tyr Ala Pro Ser Leu
    50                  55                  60

Lys Asp Lys Phe Ile Ile Ser Arg Glu Asn Ala Lys Asn Thr Leu Tyr
65                  70                  75                  80

Leu Gln Met Ser Lys Val Arg Ser Glu Asp Thr Ala Leu Tyr Tyr Cys
                85                  90                  95

Ser Arg Leu Glu Asp Tyr Glu Asp Trp Tyr Phe Asp Val Trp Gly Ala
            100                 105                 110

Gly Thr Thr Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Asn Phe Gly Thr Gln Thr Tyr Thr Cys Asn Val Asp His Lys
        195                 200                 205

Pro Ser Asn Thr Lys Val Asp Lys Thr Val Glu Arg Lys Cys Cys Val
    210                 215                 220

Glu Cys Pro Pro Cys Pro Ala Pro Pro Val Ala Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Phe Arg Val Val Ser Val
    290                 295                 300

Leu Thr Val Val His Gln Asp Trp Leu Asn Gly Lys Glu Tyr Lys Cys
305                 310                 315                 320

Lys Val Ser Asn Lys Gly Leu Pro Ala Pro Ile Glu Lys Thr Ile Ser
                325                 330                 335

Lys Thr Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365
```

```
Lys Gly Phe Tyr Pro Ser Asp Ile Ala Val Glu Trp Glu Ser Asn Gly
        370                 375                 380

Gln Pro Glu Asn Asn Tyr Lys Thr Thr Pro Met Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
            435                 440                 445

<210> SEQ ID NO 29
<211> LENGTH: 645
<212> TYPE: DNA
<213> ORGANISM: Artificial Sequence
<220> FEATURE:
<223> OTHER INFORMATION: 25E6 light chain

<400> SEQUENCE: 29
agtattgtga tgacccagac tcccaaattc ctgcttgtat cagcaggaga cagggttacc     60
ataacctgca aggccagtca gagtgtgagt aatgctgtag cttggtacca acagaagcca    120
gggcagtctc ctaaactgct gatatactat acatccaatc gctacactgg agtccctgat    180
cgcttcactg gcagtggata tgggacggat ttcactttca ccatcaccac tgtgcaggct    240
gaagacctgg cagtttattt ctgtcagcag gattatacct ctccgtggac gttcggtgga    300
ggcaccaagc tggaaatcaa acgggctgtg gctgcaccat ctgtcttcat cttcccgcca    360
tctgatgagc agttgaaatc tggaactgcc tctgttgtgt gcctgctgaa taacttctat    420
cccagagagg ccaaagtaca gtggaaggtg gataacgccc tccaatcggg taactcccag    480
gagagtgtca cagagcagga cagcaaggac agcacctaca gcctcagcag caccctgacg    540
ctgagcaaag cagactacga gaaacacaaa gtctacgcct gcgaagtcac ccatcagggc    600
ctgagctcgc ccgtcacaaa gagcttcaac aggggagagt gttag                    645

<210> SEQ ID NO 30
<211> LENGTH: 212
<212> TYPE: PRT
<213> ORGANISM: Artificial Sequence
<220> FEATURE:
<223> OTHER INFORMATION: 25E6 light chain

<400> SEQUENCE: 30

Ser Ile Val Met Thr Gln Thr Pro Lys Phe Leu Leu Val Ser Ala Gly
1               5                   10                  15

Asp Arg Val Thr Ile Thr Cys Lys Ala Ser Gln Ser Val Ser Asn Ala
            20                  25                  30

Val Ala Trp Tyr Gln Gln Lys Pro Gly Gln Ser Pro Lys Leu Leu Ile
        35                  40                  45

Tyr Tyr Thr Ser Asn Arg Tyr Thr Gly Val Pro Asp Arg Phe Thr Gly
    50                  55                  60

Ser Gly Tyr Gly Thr Asp Phe Thr Phe Thr Ile Thr Thr Val Gln Ala
65                  70                  75                  80

Glu Asp Leu Ala Val Tyr Phe Cys Gln Gln Asp Tyr Thr Ser Pro Trp
                85                  90                  95

Thr Phe Gly Gly Gly Thr Lys Leu Glu Ile Lys Val Ala Ala Pro Ser
            100                 105                 110

Val Phe Ile Phe Pro Pro Ser Asp Glu Gln Leu Lys Ser Gly Thr Ala
        115                 120                 125
```

Ser Val Val Cys Leu Leu Asn Asn Phe Tyr Pro Arg Glu Ala Lys Val
        130                 135                 140

Gln Trp Lys Val Asp Asn Ala Leu Gln Ser Gly Asn Ser Gln Glu Ser
145                 150                 155                 160

Val Thr Glu Gln Asp Ser Lys Asp Ser Thr Tyr Ser Leu Ser Ser Thr
                165                 170                 175

Leu Thr Leu Ser Lys Ala Asp Tyr Glu Lys His Lys Val Tyr Ala Cys
            180                 185                 190

Glu Val Thr His Gln Gly Leu Ser Ser Pro Val Thr Lys Ser Phe Asn
        195                 200                 205

Arg Gly Glu Cys
    210

<210> SEQ ID NO 31
<211> LENGTH: 1317
<212> TYPE: DNA
<213> ORGANISM: Artificial Sequence
<220> FEATURE:
<223> OTHER INFORMATION: 25E6 heavy chain

<400> SEQUENCE: 31
caggtccaac tgcagcagcc tggggctgaa ctggcgaagc ctggggcttc agtgaagttg      60
tcctgcaagg cttctggcta cacct tcaac acctataata tgtactggtt gaaacgagg     120
cctgggcaag gccttgagtg gattgggggg attgatccta gcaatggtga tactaaaatc    180
aatgagaagt tcaagaacaa ggccacactg actgttgaca atcctccag tacagcctat     240
atgcaactca gcggcctgac atctgaggac tctgcggtct attactgtac aagccatacg    300
tactggggcc aagggactct ggtcactgtc tctgcagcct caacgaaggg cccatcggtc    360
ttccccctgg cgccctgctc caggagcacc tccgagagca gccgccct gggctgcctg      420
gtcaaggact acttccccga accggtgacg gtgtcgtgga actcaggcgc tctgaccagc    480
ggcgtgcaca ccttcccagc tgtcctacag tcctcaggac tctactccct cagcagcgtg    540
gtgaccgtgc cctccagcaa cttcggcacc cagacctaca cctgcaacgt agatcacaag    600
cccagcaaca ccaaggtgga caagacagtt gagcgcaaat gttgtgtcga gtgcccaccg    660
tgcccagcac cacctgtggc aggaccgtca gtcttccgct tccccccaaa acccaaggac    720
acccgcatga tctcccggac ccctgaggtc acgtgcgtgg tggtggatgt gagccacgaa    780
gaccccgagg tccagttcaa ctggtacgtg gacggcgtgg aggtgcataa tgccaagaca    840
aagccacggg aggagcagtt caacagcacg ttccgtgtgg tcagcgtcct caccgttgtg    900
caccaggact ggctgaacgg caaggagtac aagtgcaagg tctccaacaa aggcctccca    960
gcccccatcg agaaaaccat ctccaaaacc aaagggcagc ccgagaacc acaggtgtac      1020
accctgcccc catcccggga ggagatgacc aagaaccagg tcagcctgac ctgcctggtc    1080
aaaggcttct accccagcga catcgccgtg gagtgggaga gcaatgggca gccggagaac    1140
aactacaaga ccacacctcc catgctggac tccgacggct ccttcttcct ctacagcaag    1200
ctcaccgtgg acaagagcag gtggcagcag gggaacgtct tctcatgctc cgtgatgcat    1260
gaggctctgc acaaccacta cacgcagaag agcctctccc tgtctccggg taaatga       1317

<210> SEQ ID NO 32
<211> LENGTH: 438
<212> TYPE: PRT
<213> ORGANISM: Artificial Sequence
<220> FEATURE:
<223> OTHER INFORMATION: 25E6 heavy chain

<400> SEQUENCE: 32

Gln Val Gln Leu Gln Gln Pro Gly Ala Glu Leu Ala Lys Pro Gly Ala
1               5                   10                  15

Ser Val Lys Leu Ser Cys Lys Ala Ser Gly Tyr Thr Phe Asn Thr Tyr
            20                  25                  30

Asn Met Tyr Trp Leu Lys Gln Arg Pro Gly Gln Gly Leu Glu Trp Ile
        35                  40                  45

Gly Gly Ile Asp Pro Ser Asn Gly Asp Thr Lys Ile Asn Glu Lys Phe
    50                  55                  60

Lys Asn Lys Ala Thr Leu Thr Val Asp Lys Ser Ser Ser Thr Ala Tyr
65                  70                  75                  80

Met Gln Leu Ser Gly Leu Thr Ser Glu Asp Ser Ala Val Tyr Tyr Cys
                85                  90                  95

Thr Ser His Thr Tyr Trp Gly Gln Gly Thr Leu Val Thr Val Ser Ala
            100                 105                 110

Ala Ser Thr Lys Gly Pro Ser Val Phe Pro Leu Ala Pro Cys Ser Arg
        115                 120                 125

Ser Thr Ser Glu Ser Thr Ala Ala Leu Gly Cys Leu Val Lys Asp Tyr
    130                 135                 140

Phe Pro Glu Pro Val Thr Val Ser Trp Asn Ser Gly Ala Leu Thr Ser
145                 150                 155                 160

Gly Val His Thr Phe Pro Ala Val Leu Gln Ser Ser Gly Leu Tyr Ser
                165                 170                 175

Leu Ser Ser Val Val Thr Val Pro Ser Ser Asn Phe Gly Thr Gln Thr
            180                 185                 190

Tyr Thr Cys Asn Val Asp His Lys Pro Ser Asn Thr Lys Val Asp Lys
        195                 200                 205

Thr Val Glu Arg Lys Cys Cys Val Glu Cys Pro Pro Cys Pro Ala Pro
    210                 215                 220

Pro Val Ala Gly Pro Ser Val Phe Leu Phe Pro Pro Lys Pro Lys Asp
225                 230                 235                 240

Thr Leu Met Ile Ser Arg Thr Pro Glu Val Thr Cys Val Val Val Asp
                245                 250                 255

Val Ser His Glu Asp Pro Glu Val Gln Phe Asn Trp Tyr Val Asp Gly
            260                 265                 270

Val Glu Val His Asn Ala Lys Thr Lys Pro Arg Glu Glu Gln Phe Asn
        275                 280                 285

Ser Thr Phe Arg Val Val Ser Val Leu Thr Val Val His Gln Asp Trp
    290                 295                 300

Leu Asn Gly Lys Glu Tyr Lys Cys Lys Val Ser Asn Lys Gly Leu Pro
305                 310                 315                 320

Ala Pro Ile Glu Lys Thr Ile Ser Lys Thr Lys Gly Gln Pro Arg Glu
                325                 330                 335

Pro Gln Val Tyr Thr Leu Pro Pro Ser Arg Glu Glu Met Thr Lys Asn
            340                 345                 350

Gln Val Ser Leu Thr Cys Leu Val Lys Gly Phe Tyr Pro Ser Asp Ile
        355                 360                 365

Ala Val Glu Trp Glu Ser Asn Gly Gln Pro Glu Asn Asn Tyr Lys Thr
    370                 375                 380

Thr Pro Pro Met Leu Asp Ser Asp Gly Ser Phe Phe Leu Tyr Ser Lys
385                 390                 395                 400

Leu Thr Val Asp Lys Ser Arg Trp Gln Gln Gly Asn Val Phe Ser Cys
                405                 410                 415

Ser Val Met His Glu Ala Leu His Asn His Tyr Thr Gln Lys Ser Leu
                420                 425                 430

Ser Leu Ser Pro Gly Lys
        435

<210> SEQ ID NO 33
<211> LENGTH: 660
<212> TYPE: DNA
<213> ORGANISM: Artificial Sequence
<220> FEATURE:
<223> OTHER INFORMATION: 25E9 light chain

<400> SEQUENCE: 33
gatattgtga tgacccaggc tgcaccctct gtacctgtca ctcctggaga gtcagtatcc      60
atctcctgca ggtctactaa gagtctcctg catagtaatg caacactta cttgtattgg     120 ttcctgcaga ggccaggcca gtctcctcag ctcctgatat atcggatgtc aaccttgcc    180 tcaggagtcc cagacaggtt cagtggcagt gggtcaggaa ctgctttcac actgagaatc     240
agtagagtgg aggctgagga tgtgggtgtt tattactgta tgcaacatct agaatatcct     300
ttcacgttcg gagggggac caagctggaa ataaaacggg ctgtggctgc accatctgtc    360
ttcatcttcc cgccatctga tgagcagttg aaatctggaa ctgcctctgt tgtgtgcctg     420
ctgaataact tctatcccag agaggccaaa gtacagtgga aggtggataa cgccctccaa     480
tcgggtaact cccaggagag tgtcacagag caggacagca aggacagcac ctacagcctc     540
agcagcaccc tgacgctgag caaagcagac tacgagaaac acaaagtcta cgcctgcgaa     600
gtcacccatc agggcctgag ctcgcccgtc acaaagagct tcaacagggg agagtgttag    660

<210> SEQ ID NO 34
<211> LENGTH: 217
<212> TYPE: PRT
<213> ORGANISM: Artificial Sequence
<220> FEATURE:
<223> OTHER INFORMATION: 25E9 light chain

<400> SEQUENCE: 34

Asp Ile Val Met Thr Gln Ala Ala Pro Ser Val Pro Val Thr Pro Gly
1               5                   10                  15

Glu Ser Val Ser Ile Ser Cys Arg Ser Thr Lys Ser Leu Leu His Ser
            20                  25                  30

Asn Gly Asn Thr Tyr Leu Tyr Trp Phe Leu Gln Arg Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
                85                  90                  95

Leu Glu Tyr Pro Phe Thr Phe Gly Gly Gly Thr Lys Leu Glu Ile Lys
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr

|  | 165 |  |  | 170 |  |  | 175 |  |
|---|---|---|---|---|---|---|---|---|

Ser Leu Ser Ser Thr Leu Thr Leu Ser Lys Ala Asp Tyr Glu Lys His
        180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
        210                 215

<210> SEQ ID NO 35
<211> LENGTH: 1422
<212> TYPE: DNA
<213> ORGANISM: Artificial Sequence
<220> FEATURE:
<223> OTHER INFORMATION: 25E9 heavy chain

<400> SEQUENCE: 35

```
gagatccagc tgcagcagtc tggagttgag ctggtgaggc ctggggcttc agtgacgctg      60
tcctgcaagg cttcgggcta cacatttact gactatgaca tgcactgggt gaagcagaca     120
cctgttcatg gcctggaatg gattggaact attgatcctg aaactggtgg tactgcctac     180
aatcagaagt tcaagggcaa ggccacactg actgcggaca tcctccacac acagcctac     240
atggagctca gcagcctgac atctgaggac tctgccgtct attactgtac aagtttctac     300
tatacttact ctaattacga cgtgggggttt gcttactggg gccaagggac tctggtcact     360
gtctctgcag cctcaactgg ggcgtcttat tactatgcta tggaccactg ggtcaagga     420
acctcagtca ccgtctcctc agcctcaacg aagggcccat cggtcttccc cctggcgccc     480
tgctccagga gcacctccga gcacagcc gccctgggct gcctggtcaa ggactacttc     540
cccgaaccgg tgacggtgtc gtggaactca ggcgctctga ccagcggcgt gcacaccttc     600
ccagctgtcc tacagtcctc aggactctac tccctcagca gcgtggtgac cgtgccctcc     660
agcaacttcg gcacccagac ctacacctgc aacgtagatc acaagcccag caacaccaag     720
gtggacaaga cagttgagcg caaatgttgt gtcgagtgcc caccgtgccc agcaccacct     780
gtggcaggac cgtcagtctt ccgcttcccc ccaaaaccca aggacaccg catgatctcc     840
cggacccctg aggtcacgtg cgtggtggtg gatgtgagcc acgaagaccc cgaggtccag     900
ttcaactggt acgtggacgg cgtggaggtg cataatgcca agacaaagcc acgggaggag     960
cagttcaaca gcacgttccg tgtggtcagc gtcctcaccg ttgtgcacca ggactggctg    1020
aacggcaagg agtacaagtg caaggtctcc aacaaaggcc tcccagcccc catcgagaaa    1080
accatctcca aaaccaaagg gcagccccga gaaccacagg tgtacaccct gcccccatcc    1140
cgggaggaga tgaccaagaa ccaggtcagc ctgacctgcc tggtcaaagg cttctacccc    1200
agcgacatcg ccgtggagtg ggagagcaat gggcagccgg agaacaacta caagaccaca    1260
cctcccatgc tggactccga cggctccttc ttcctctaca gcaagctcac cgtggacaag    1320
agcaggtggc agcaggggaa cgtcttctca tgctccgtga tgcatgaggc tctgcacaac    1380
cactacacgc agaagagcct ctccctgtct ccgggtaaat ga                        1422
```

<210> SEQ ID NO 36
<211> LENGTH: 449
<212> TYPE: PRT
<213> ORGANISM: Artificial Sequence
<220> FEATURE:
<223> OTHER INFORMATION: 25E9 heavy chain

<400> SEQUENCE: 36

Glu Ile Gln Leu Gln Gln Ser Gly Val Glu Leu Val Arg Pro Gly Ala

-continued

```
1               5                   10                  15
Ser Val Thr Leu Ser Cys Lys Ala Ser Gly Tyr Thr Phe Thr Asp Tyr
                20                  25                  30

Asp Met His Trp Val Lys Gln Thr Pro Val His Gly Leu Glu Trp Ile
            35                  40                  45

Gly Thr Ile Asp Pro Glu Thr Gly Gly Thr Ala Tyr Asn Gln Lys Phe
 50                  55                  60

Lys Gly Lys Ala Thr Leu Thr Ala Asp Arg Ser Thr Thr Ala Tyr
 65                  70                  75                  80

Met Glu Leu Ser Ser Leu Thr Ser Glu Asp Ser Ala Val Tyr Tyr Cys
                85                  90                  95

Thr Ser Phe Tyr Tyr Thr Tyr Ser Asn Tyr Asp Val Gly Phe Ala Tyr
                100                 105                 110

Trp Gly Gln Gly Thr Leu Val Thr Val Ser Ala Ala Ser Thr Lys Gly
                115                 120                 125

Pro Ser Val Phe Pro Leu Ala Pro Cys Ser Arg Ser Thr Ser Glu Ser
        130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
                180                 185                 190

Thr Val Pro Ser Ser Asn Phe Gly Thr Gln Thr Tyr Thr Cys Asn Val
                195                 200                 205

Asp His Lys Pro Ser Asn Thr Lys Val Asp Lys Thr Val Glu Arg Lys
        210                 215                 220

Cys Cys Val Glu Cys Pro Pro Cys Pro Ala Pro Pro Val Ala Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Gln Phe Asn Trp Tyr Val Asp Gly Val Glu Val His Asn
        275                 280                 285

Ala Lys Thr Lys Pro Arg Glu Glu Gln Phe Asn Ser Thr Phe Arg Val
        290                 295                 300

Val Ser Val Leu Thr Val Val His Gln Asp Trp Leu Asn Gly Lys Glu
305                 310                 315                 320

Tyr Lys Cys Lys Val Ser Asn Lys Gly Leu Pro Ala Pro Ile Glu Lys
                325                 330                 335

Thr Ile Ser Lys Thr Lys Gly Gln Pro Arg Glu Pro Gln Val Tyr Thr
                340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Met Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430
```

```
Ala Leu His Asn His Tyr Thr Gln Lys Ser Leu Ser Leu Ser Pro Gly
        435                 440                 445

Lys

<210> SEQ ID NO 37
<211> LENGTH: 318
<212> TYPE: DNA
<213> ORGANISM: Artificial Sequence
<220> FEATURE:
<223> OTHER INFORMATION: 25A1 light chain variable region

<400> SEQUENCE: 37
gaaaatgtgc tcacccagtc tccagcaatc atgtctgcat ctccagggga gaaggtcacc      60
atatcctgca gtgccagctc aagtgtaagt tacatgtact ggtaccagca gaagccagga     120
tcctccccca aaccctggat ttatcgcaca tccaacctgg cttctggagt ccctgctcgc     180
ttcagtggca gtgggtctgg gacctcttac tctctcacaa tcagcagcat ggaggctgaa     240
gatgctgcca cttattactg ccagcagtgg agtagtaacc cactcacgtt cggtgctggg     300
accaagctgg agctgaaa                                                   318

<210> SEQ ID NO 38
<211> LENGTH: 106
<212> TYPE: PRT
<213> ORGANISM: Artificial Sequence
<220> FEATURE:
<223> OTHER INFORMATION: 25A1 light chain variable region

<400> SEQUENCE: 38

Glu Asn Val Leu Thr Gln Ser Pro Ala Ile Met Ser Ala Ser Pro Gly
1               5                   10                  15

Glu Lys Val Thr Ile Ser Cys Ser Ala Ser Ser Val Ser Tyr Met
            20                  25                  30

Tyr Trp Tyr Gln Gln Lys Pro Gly Ser Ser Pro Lys Pro Trp Ile Tyr
        35                  40                  45

Arg Thr Ser Asn Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Asn Pro Leu Thr
                85                  90                  95

Phe Gly Ala Gly Thr Lys Leu Glu Leu Lys
            100                 105

<210> SEQ ID NO 39
<211> LENGTH: 372
<212> TYPE: DNA
<213> ORGANISM: Artificial Sequence
<220> FEATURE:
<223> OTHER INFORMATION: 25A1 heavy chain variable region

<400> SEQUENCE: 39
gaggtccagc tgcaacaatc tgggactgag ctggtgaggc ctgggtcctc agtgaagatt      60
tcctgcaagg cttctggcta caccttcacc aggtactgga tggactgggt gaagcagagg     120
cctggacaag gccttgagtg gatcggagag attgatcctt ctgatagtta tactaactac     180
aatcaaaagt tcaagggcaa ggccacattg actgtagata attctccag  aacagcctat     240 atggaactca gcagcctgac atctgaggac tctgcggtct attactgtgc aagatcgggg     300
gcctactcta gtgactatag ttacgacggg tttgcttact ggggccaagg gactctggtc     360
```
actgtctctg ca                                                         372

<210> SEQ ID NO 40
<211> LENGTH: 124
<212> TYPE: PRT
<213> ORGANISM: Artificial Sequence
<220> FEATURE:
<223> OTHER INFORMATION: 25A1 heavy chain variable region

<400> SEQUENCE: 40

Glu Val Gln Leu Gln Gln Ser Gly Thr Glu Leu Val Arg Pro Gly Ser
1               5                   10                  15

Ser Val Lys Ile Ser Cys Lys Ala Ser Gly Tyr Thr Phe Thr Arg Tyr
            20                  25                  30

Trp Met Asp Trp Val Lys Gln Arg Pro Gly Gln Gly Leu Glu Trp Ile
        35                  40                  45

Gly Glu Ile Asp Pro Ser Asp Ser Tyr Thr Asn Tyr Asn Gln Lys Phe
    50                  55                  60

Lys Gly Lys Ala Thr Leu Thr Val Asp Lys Phe Ser Arg Thr Ala Tyr
65                  70                  75                  80

Met Glu Leu Ser Ser Leu Thr Ser Glu Asp Ser Ala Val Tyr Tyr Cys
                85                  90                  95

Ala Arg Ser Gly Ala Tyr Ser Ser Asp Tyr Ser Tyr Asp Gly Phe Ala
            100                 105                 110

Tyr Trp Gly Gln Gly Thr Leu Val Thr Val Ser Ala
        115                 120

<210> SEQ ID NO 41
<211> LENGTH: 336
<212> TYPE: DNA
<213> ORGANISM: Artificial Sequence
<220> FEATURE:
<223> OTHER INFORMATION: 25B4 light chain variable region

<400> SEQUENCE: 41
gatattgtga tgacccaggc tgcattctcc aatccagtca ctcttggaac atcagcttcc     60
atctcctgca ggtctagtaa gagtctccta catagtaatg gcatcactta tttgtattgg    120
tatctgcaga agccaggcca gtctcctcag ctcctgattt atcagatgtc caaccttgcc    180
tcaggagtcc cagacaggtt cagtggcagt gggtcaggaa ctgctttcac actgagaatc    240
agtagagtgg aggctgagga tgtgggtgtt tattactgta tgcaacatct agaatatccg    300
tacacgttcg gaggggggac caagctggaa ataaaa                              336

<210> SEQ ID NO 42
<211> LENGTH: 112
<212> TYPE: PRT
<213> ORGANISM: Artificial Sequence
<220> FEATURE:
<223> OTHER INFORMATION: 25B4 light chain variable region

<400> SEQUENCE: 42

Asp Ile Val Met Thr Gln Ala Ala Phe Ser Asn Pro Val Thr Leu Gly
1               5                   10                  15

Thr Ser Ala Ser Ile Ser Cys Arg Ser Ser Lys Ser Leu Leu His Ser
            20                  25                  30

Asn Gly Ile Thr Tyr Leu Tyr Trp Tyr Leu Gln Lys Pro Gly Gln Ser
        35                  40                  45

Pro Gln Leu Leu Ile Tyr Gln Met Ser Asn Leu Ala Ser Gly Val Pro
    50                  55                  60

```
Asp Arg Phe Ser Gly Ser Gly Ser Gly Thr Ala Phe Thr Leu Arg Ile
 65                  70                  75                  80

Ser Arg Val Glu Ala Glu Asp Val Gly Val Tyr Tyr Cys Met Gln His
                 85                  90                  95

Leu Glu Tyr Pro Tyr Thr Phe Gly Gly Gly Thr Lys Leu Glu Ile Lys
            100                 105                 110
```

<210> SEQ ID NO 43
<211> LENGTH: 354
<212> TYPE: DNA
<213> ORGANISM: Artificial Sequence
<220> FEATURE:
<223> OTHER INFORMATION: 25B4 heavy chain variable region

<400> SEQUENCE: 43

```
caggtccaag tgcagcagcc tggggctgaa attgtgaggc ctggggcttc agtgaagctg      60
tcctgcaagg cttctggcta caccttcacc agctactgga tgcactgggt gaagcagagg     120
cctggacaag gccttgagtg gattggactg attaatccta ccaacggtcg tactaactac     180
aatgagaagt tcaagagcaa ggccacactg actgtagaca atcctccag cacagcctac      240
atgcaactca gcagcctgac atctgaggac tctgcggtct attactgtgc aagagggggg     300
gacgggggact actttgacta ctggggccaa ggcaccactc tcacagtctc ctca          354
```

<210> SEQ ID NO 44
<211> LENGTH: 118
<212> TYPE: PRT
<213> ORGANISM: Artificial Sequence
<220> FEATURE:
<223> OTHER INFORMATION: 25B4 heavy chain variable region

<400> SEQUENCE: 44

```
Gln Val Gln Val Gln Gln Pro Gly Ala Glu Ile Val Arg Pro Gly Ala
  1               5                  10                  15

Ser Val Lys Leu Ser Cys Lys Ala Ser Gly Tyr Thr Phe Thr Ser Tyr
                 20                  25                  30

Trp Met His Trp Val Lys Gln Arg Pro Gly Gln Gly Leu Glu Trp Ile
             35                  40                  45

Gly Leu Ile Asn Pro Thr Asn Gly Arg Thr Asn Tyr Asn Glu Lys Phe
 50                  55                  60

Lys Ser Lys Ala Thr Leu Thr Val Asp Lys Ser Ser Ser Thr Ala Tyr
 65                  70                  75                  80

Met Gln Leu Ser Ser Leu Thr Ser Glu Asp Ser Ala Val Tyr Tyr Cys
                 85                  90                  95

Ala Arg Gly Gly Asp Gly Asp Tyr Phe Asp Tyr Trp Gly Gln Gly Thr
            100                 105                 110

Thr Leu Thr Val Ser Ser
        115
```

<210> SEQ ID NO 45
<211> LENGTH: 336
<212> TYPE: DNA
<213> ORGANISM: Artificial Sequence
<220> FEATURE:
<223> OTHER INFORMATION: 25B8 light chain variable region

<400> SEQUENCE: 45

```
gatattgtga tgacccaggc tgcaccctct gtacctgtca ctcctggaga gtcagtatcc      60
atctcctgca ggtctactaa gagtctcctg catagtaatg caacactta cttgtattgg     120
ttcctgcaga ggccaggcca gtctcctcag ctcctgatat atcggatgtc caaccttgcc     180
```

```
tcaggagtcc cagacaggtt cagtggcagt gggtcaggaa ctgctttcac actgagaatc    240
agtagagtgg aggctgagga tgtgggtgtt tattactgta tgcaacatct agaatatcct    300
ttcacgttcg agggggggac caagctggaa ataaaa                              336
```

<210> SEQ ID NO 46
<211> LENGTH: 112
<212> TYPE: PRT
<213> ORGANISM: Artificial Sequence
<220> FEATURE:
<223> OTHER INFORMATION: 25B8 light chain variable region

<400> SEQUENCE: 46

```
Asp Ile Val Met Thr Gln Ala Ala Pro Ser Val Pro Val Thr Pro Gly
1               5                   10                  15

Glu Ser Val Ser Ile Ser Cys Arg Ser Thr Lys Ser Leu Leu His Ser
            20                  25                  30

Asn Gly Asn Thr Tyr Leu Tyr Trp Phe Leu Gln Arg Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
                85                  90                  95

Leu Glu Tyr Pro Phe Thr Phe Gly Gly Gly Thr Lys Leu Glu Ile Lys
            100                 105                 110
```

<210> SEQ ID NO 47
<211> LENGTH: 369
<212> TYPE: DNA
<213> ORGANISM: Artificial Sequence
<220> FEATURE:
<223> OTHER INFORMATION: 25B8 heavy chain variable region

<400> SEQUENCE: 47

```
gagatccagc tgcagcagtc tggagttgag ctggtgaggc ctggggcttc agtgacgctg     60
tcctgcaagg cttcgggcta cacatttact gactatgaca tgcactgggt gaagcagaca    120
cctgttcatg gcctggaatg gattggaact attgatcctg aaactggtgg tactgcctac    180
aatcagaagt tcaagggcaa ggccacactg actgcggaca atcctccac cacagcctac     240 atggagctca gcagcctgac atctgaggac tctgccgtct attactgtac aactttctac    300
tatagtcact ataattacga cgtggggttt gcttactggg ccaagggac tctggtcact     360 gtctctgca                                                            369
```

<210> SEQ ID NO 48
<211> LENGTH: 123
<212> TYPE: PRT
<213> ORGANISM: Artificial Sequence
<220> FEATURE:
<223> OTHER INFORMATION: 25B8 heavy chain variable region

<400> SEQUENCE: 48

```
Glu Ile Gln Leu Gln Gln Ser Gly Val Glu Leu Val Arg Pro Gly Ala
1               5                   10                  15

Ser Val Thr Leu Ser Cys Lys Ala Ser Gly Tyr Thr Phe Thr Asp Tyr
            20                  25                  30

Asp Met His Trp Val Lys Gln Thr Pro Val His Gly Leu Glu Trp Ile
        35                  40                  45
```

```
Gly Thr Ile Asp Pro Glu Thr Gly Thr Ala Tyr Asn Gln Lys Phe
        50                  55                  60

Lys Gly Lys Ala Thr Leu Thr Ala Asp Arg Ser Ser Thr Thr Ala Tyr
 65                  70                  75                  80

Met Glu Leu Ser Ser Leu Thr Ser Glu Asp Ser Ala Val Tyr Tyr Cys
                85                  90                  95

Thr Thr Phe Tyr Tyr Ser His Tyr Asn Tyr Asp Val Gly Phe Ala Tyr
            100                 105                 110

Trp Gly Gln Gly Thr Leu Val Thr Val Ser Ala
        115                 120

<210> SEQ ID NO 49
<211> LENGTH: 336
<212> TYPE: DNA
<213> ORGANISM: Artificial Sequence
<220> FEATURE:
<223> OTHER INFORMATION: 25C1 light chain variable region

<400> SEQUENCE: 49
gatattgtga tgacccaggc tgcaccctct gtacctgtca ctcctggaga gtcagtatcc      60
atctcctgca ggtctagtaa gagtctcctg catagtaatg gcaacactta cttgtattgg     120
ttcctgcaga ggccaggcca gtcccctcag ctcctgatat atcggatgtc aaccttgcc     180 tcaggagtcc cagacaggtt cagtggcagt gggtcaggaa ctgctttcac actgagaatc     240
agtagagtgg aggctgagga tgtgggtgtt tattactgta tgcaacatct agaatatcct     300
ttcacgttcg gagggggac caagctggaa ataaaa                                336

<210> SEQ ID NO 50
<211> LENGTH: 112
<212> TYPE: PRT
<213> ORGANISM: Artificial Sequence
<220> FEATURE:
<223> OTHER INFORMATION: 25C1 light chain variable region

<400> SEQUENCE: 50

Asp Ile Val Met Thr Gln Ala Ala Pro Ser Val Pro Val Thr Pro Gly
 1               5                  10                  15

Glu Ser Val Ser Ile Ser Cys Arg Ser Ser Lys Ser Leu Leu His Ser
                20                  25                  30

Asn Gly Asn Thr Tyr Leu Tyr Trp Phe Leu Gln Arg Pro Gly Gln Ser
            35                  40                  45

Pro Gln Leu Leu Ile Tyr Arg Met Ser Asn Leu Ala Ser Gly Val Pro
        50                  55                  60

Asp Arg Phe Ser Gly Ser Gly Ser Gly Thr Ala Phe Thr Leu Arg Ile
 65                  70                  75                  80

Ser Arg Val Glu Ala Glu Asp Val Gly Val Tyr Tyr Cys Met Gln His
                85                  90                  95

Leu Glu Tyr Pro Phe Thr Phe Gly Gly Gly Thr Lys Leu Glu Ile Lys
            100                 105                 110

<210> SEQ ID NO 51
<211> LENGTH: 369
<212> TYPE: DNA
<213> ORGANISM: Artificial Sequence
<220> FEATURE:
<223> OTHER INFORMATION: 25C1 heavy chain variable region

<400> SEQUENCE: 51
gagatccagc tgcagcagtc tggagctgag ctggtgaggc ctggggcttc agtgacgctg      60
```

```
tcctgcaagg cttcgggcta cacatttact gactatgaaa tgcactgggt gaagcagaca    120
cctgttcatg gcctggaatg gattggagct attgatcctg aaactggtgg tactgcctac    180
aatcagaagt tcaagggcaa ggccacactg actgcagaca atcctccag cacagcctac     240 atggagctca gcagcctgac atctgaggac tctgccgtct attactgtac aagtttctac    300
tatacttact ataattacga cgtggggttt gcttactggg gccaagggac tctggtcact    360
gtctctgca                                                            369
```

```
<210> SEQ ID NO 52
<211> LENGTH: 123
<212> TYPE: PRT
<213> ORGANISM: Artificial Sequence
<220> FEATURE:
<223> OTHER INFORMATION: 25C1 heavy chain variable region

<400> SEQUENCE: 52

Glu Ile Gln Leu Gln Gln Ser Gly Ala Glu Leu Val Arg Pro Gly Ala
1               5                   10                  15

Ser Val Thr Leu Ser Cys Lys Ala Ser Gly Tyr Thr Phe Thr Asp Tyr
            20                  25                  30

Glu Met His Trp Val Lys Gln Thr Pro Val His Gly Leu Glu Trp Ile
        35                  40                  45

Gly Ala Ile Asp Pro Glu Thr Gly Gly Thr Ala Tyr Asn Gln Lys Phe
    50                  55                  60

Lys Gly Lys Ala Thr Leu Thr Ala Asp Lys Ser Ser Ser Thr Ala Tyr
65                  70                  75                  80

Met Glu Leu Ser Ser Leu Thr Ser Glu Asp Ser Ala Val Tyr Tyr Cys
                85                  90                  95

Thr Ser Phe Tyr Tyr Thr Tyr Tyr Asn Tyr Asp Val Gly Phe Ala Tyr
            100                 105                 110

Trp Gly Gln Gly Thr Leu Val Thr Val Ser Ala
        115                 120
```

```
<210> SEQ ID NO 53
<211> LENGTH: 336
<212> TYPE: DNA
<213> ORGANISM: Artificial Sequence
<220> FEATURE:
<223> OTHER INFORMATION: 25D8 light chain variable region

<400> SEQUENCE: 53
gatattgtga tgacccaggc tgcattctcc aatccagtca ctcttggaac atcagcttcc     60
atctcctgca ggtctagtaa gagtctccta catagtaatg gcatcactta tttgtattgg    120
tatctgcaga agccaggcca gtctcctcag ctcctgattt atcagatgtc caaccttgcc    180
tcaggagtcc cagacaggtt cagtagcagt gggtcaggaa ctgatttcac actgagaatc    240
agcagagtgg aggctgagga tgtgggtgtt tattactgtc tcaaaatctc tagaacttccg    300 tacacgttcg gaggggggac caagctggaa ataaaa                              336
```

```
<210> SEQ ID NO 54
<211> LENGTH: 112
<212> TYPE: PRT
<213> ORGANISM: Artificial Sequence
<220> FEATURE:
<223> OTHER INFORMATION: 25D8 light chain variable region

<400> SEQUENCE: 54

Asp Ile Val Met Thr Gln Ala Ala Phe Ser Asn Pro Val Thr Leu Gly
```

```
                   1               5                  10                  15
Thr Ser Ala Ser Ile Ser Cys Arg Ser Ser Lys Ser Leu Leu His Ser
                    20                  25                  30

Asn Gly Ile Thr Tyr Leu Tyr Trp Tyr Leu Gln Lys Pro Gly Gln Ser
                    35                  40                  45

Pro Gln Leu Leu Ile Tyr Gln Met Ser Asn Leu Ala Ser Gly Val Pro
                    50                  55                  60

Asp Arg Phe Ser Ser Ser Gly Ser Gly Thr Asp Phe Thr Leu Arg Ile
65                  70                  75                  80

Ser Arg Val Glu Ala Glu Asp Val Gly Val Tyr Tyr Cys Ala Gln Asn
                    85                  90                  95

Leu Glu Leu Pro Tyr Thr Phe Gly Gly Gly Thr Lys Leu Glu Ile Lys
                    100                 105                 110
```

<210> SEQ ID NO 55
<211> LENGTH: 354
<212> TYPE: DNA
<213> ORGANISM: Artificial Sequence
<220> FEATURE:
<223> OTHER INFORMATION: 25D8 heavy chain variable region

<400> SEQUENCE: 55

```
caggtccaag tgcagcagcc tggggctgag cttgtgaagc ctggggcttc ggtgaagctg    60
tcctgcaagg cttctggcta caccttcacc agctactgga tgcactgggt gaagcagagg   120
cctggacaag ccttgagtg gattggactg attaatccta gcaacgctcg tactaactac   180
aatgagaagt tcaataccaa ggccacactg actgtagaca atcctccag cacagcctac   240
atgcaactca gcagcctgac atctgaggac tctgcggtct attactgtgc aagagggggg   300
gacgggact actttgacta ctggggccaa ggcaccactc tcacagtctc ctca          354
```

<210> SEQ ID NO 56
<211> LENGTH: 118
<212> TYPE: PRT
<213> ORGANISM: Artificial Sequence
<220> FEATURE:
<223> OTHER INFORMATION: 25D8 heavy chain variable region

<400> SEQUENCE: 56

```
Gln Val Gln Val Gln Gln Pro Gly Ala Glu Leu Val Lys Pro Gly Ala
1               5                   10                  15

Ser Val Lys Leu Ser Cys Lys Ala Ser Gly Tyr Thr Phe Thr Ser Tyr
                    20                  25                  30

Trp Met His Trp Val Lys Gln Arg Pro Gly Gln Gly Leu Glu Trp Ile
                    35                  40                  45

Gly Leu Ile Asn Pro Ser Asn Ala Arg Thr Asn Tyr Asn Glu Lys Phe
                    50                  55                  60

Asn Thr Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Cys
                    85                  90                  95

Ala Arg Gly Gly Asp Gly Asp Tyr Phe Asp Tyr Trp Gly Gln Gly Thr
                    100                 105                 110

Thr Leu Thr Val Ser Ser
                    115
```

<210> SEQ ID NO 57
<211> LENGTH: 318
<212> TYPE: DNA

<213> ORGANISM: Artificial Sequence
<220> FEATURE:
<223> OTHER INFORMATION: 25E5 light chain variable region

<400> SEQUENCE: 57

```
caaattgttc tcacccagtc tccaacactc atgtctgcat ctccagggga gaaggtcacc    60
atgacctgca gtgccagctc aagtgtaagt tacatgtact ggtaccagca gaagccaaga   120
tcctccccca aaccctggat ttatcgcaca tccaacctgg tttctggagt ccctgtacgc   180
ttcagtggca gtgggtctgg gacctcttac tctctcacaa tcagcagcat ggaggctgaa   240
gatgctgccc cttattactg ccagcagtgg agtagtaacc cacccacgtt cggtgctggg   300
accaagctgg agctgaaa                                                  318
```

<210> SEQ ID NO 58
<211> LENGTH: 106
<212> TYPE: PRT
<213> ORGANISM: Artificial Sequence
<220> FEATURE:
<223> OTHER INFORMATION: 25E5 light chain variable region

<400> SEQUENCE: 58

```
Gln Ile Val Leu Thr Gln Ser Pro Thr Leu Met Ser Ala Ser Pro Gly
1               5                   10                  15

Glu Lys Val Thr Met Thr Cys Ser Ala Ser Ser Val Ser Tyr Met
            20                  25                  30

Tyr Trp Tyr Gln Gln Lys Pro Arg Ser Ser Pro Lys Pro Trp Ile Tyr
        35                  40                  45

Arg Thr Ser Asn Leu Val Ser Gly Val Pro Val Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Asn Pro Pro Thr
                85                  90                  95

Phe Gly Ala Gly Thr Lys Leu Glu Leu Lys
            100                 105
```

<210> SEQ ID NO 59
<211> LENGTH: 360
<212> TYPE: DNA
<213> ORGANISM: Artificial Sequence
<220> FEATURE:
<223> OTHER INFORMATION: 25E5 heavy chain variable region

<400> SEQUENCE: 59

```
gaagtgaagc ttgaggagtc tggaggtggc ctggtgcagc ctggaggatc cctgaaactc    60
tcctgtgcag cctcaggatt cgattttagt aaagactgga tgagttgggt ccggcaggct   120
ccagggaaag ggctagaatg gattggagaa attaatccag atagcagtac gataaactat   180
gcaccatctc ttaaggataa attcatcatc tccagagaga acgccaaaaa tacgctgtac   240
ctgcaaatga gcaaagtgag atctgaggac acagcccttt attactgttc aagactagag   300
gactacgaag actggtactt cgatgtctgg ggcgcaggga ccacggtcac cgtctcctca   360
```

<210> SEQ ID NO 60
<211> LENGTH: 120
<212> TYPE: PRT
<213> ORGANISM: Artificial Sequence
<220> FEATURE:
<223> OTHER INFORMATION: 25E5 heavy chain variable region

<400> SEQUENCE: 60

-continued

Glu Val Lys Leu Glu Glu Ser Gly Gly Gly Leu Val Gln Pro Gly Gly
1               5                   10                  15

Ser Leu Lys Leu Ser Cys Ala Ala Ser Gly Phe Asp Phe Ser Lys Asp
            20                  25                  30

Trp Met Ser Trp Val Arg Gln Ala Pro Gly Lys Gly Leu Glu Trp Ile
        35                  40                  45

Gly Glu Ile Asn Pro Asp Ser Ser Thr Ile Asn Tyr Ala Pro Ser Leu
    50                  55                  60

Lys Asp Lys Phe Ile Ile Ser Arg Glu Asn Ala Lys Asn Thr Leu Tyr
65                  70                  75                  80

Leu Gln Met Ser Lys Val Arg Ser Glu Asp Thr Ala Leu Tyr Tyr Cys
                85                  90                  95

Ser Arg Leu Glu Asp Tyr Glu Asp Trp Tyr Phe Asp Val Trp Gly Ala
            100                 105                 110

Gly Thr Thr Val Thr Val Ser Ser
        115                 120

<210> SEQ ID NO 61
<211> LENGTH: 321
<212> TYPE: DNA
<213> ORGANISM: Artificial Sequence
<220> FEATURE:
<223> OTHER INFORMATION: 25E6 light chain variable region

<400> SEQUENCE: 61
agtattgtga tgacccagac tcccaaattc ctgcttgtat cagcaggaga cagggttacc      60
ataacctgca aggccagtca gagtgtgagt aatgctgtag cttggtacca acagaagcca     120
gggcagtctc ctaaactgct gatatactat acatccaatc gctacactgg agtccctgat     180
cgcttcactg gcagtggata tgggacggat ttcactttca ccatcaccac tgtgcaggct     240
gaagacctgg cagtttattt ctgtcagcag gattatacct ctccgtggac gttcggtgga     300
ggcaccaagc tggaaatcaa a                                               321

<210> SEQ ID NO 62
<211> LENGTH: 107
<212> TYPE: PRT
<213> ORGANISM: Artificial Sequence
<220> FEATURE:
<223> OTHER INFORMATION: 25E6 light chain variable region

<400> SEQUENCE: 62

Ser Ile Val Met Thr Gln Thr Pro Lys Phe Leu Leu Val Ser Ala Gly
1               5                   10                  15

Asp Arg Val Thr Ile Thr Cys Lys Ala Ser Gln Ser Val Ser Asn Ala
            20                  25                  30

Val Ala Trp Tyr Gln Gln Lys Pro Gly Gln Ser Pro Lys Leu Leu Ile
        35                  40                  45

Tyr Tyr Thr Ser Asn Arg Tyr Thr Gly Val Pro Asp Arg Phe Thr Gly
    50                  55                  60

Ser Gly Tyr Gly Thr Asp Phe Thr Phe Thr Ile Thr Thr Val Gln Ala
65                  70                  75                  80

Glu Asp Leu Ala Val Tyr Phe Cys Gln Gln Asp Tyr Thr Ser Pro Trp
                85                  90                  95

Thr Phe Gly Gly Gly Thr Lys Leu Glu Ile Lys
            100                 105

<210> SEQ ID NO 63

```
<211> LENGTH: 336
<212> TYPE: DNA
<213> ORGANISM: Artificial Sequence
<220> FEATURE:
<223> OTHER INFORMATION: 25E6 heavy chain variable region

<400> SEQUENCE: 63
caggtccaac tgcagcagcc tggggctgaa ctggcgaagc ctggggcttc agtgaagttg      60
tcctgcaagg cttctggcta caccttcaac acctataata tgtactggtt gaaacagagg     120
cctgggcaag gccttgagtg gattggcggg attgatccta gcaatggtga tactaaaatc     180
aatgagaagt tcaagaacaa ggccacactg actgttgaca aatcctccag tacagcctat     240
atgcaactca gcggcctgac atctgaggac tctgcggtct attactgtac aagccatacg     300
tactggggcc aagggactct ggtcactgtc tctgca                               336

<210> SEQ ID NO 64
<211> LENGTH: 112
<212> TYPE: PRT
<213> ORGANISM: Artificial Sequence
<220> FEATURE:
<223> OTHER INFORMATION: 25E6 heavy chain variable region

<400> SEQUENCE: 64

Gln Val Gln Leu Gln Gln Pro Gly Ala Glu Leu Ala Lys Pro Gly Ala
1               5                   10                  15

Ser Val Lys Leu Ser Cys Lys Ala Ser Gly Tyr Thr Phe Asn Thr Tyr
                20                  25                  30

Asn Met Tyr Trp Leu Lys Gln Arg Pro Gly Gln Gly Leu Glu Trp Ile
            35                  40                  45

Gly Gly Ile Asp Pro Ser Asn Gly Asp Thr Lys Ile Asn Glu Lys Phe
        50                  55                  60

Lys Asn Lys Ala Thr Leu Thr Val Asp Lys Ser Ser Thr Ala Tyr
65                  70                  75                  80

Met Gln Leu Ser Gly Leu Thr Ser Glu Asp Ser Ala Val Tyr Tyr Cys
                85                  90                  95

Thr Ser His Thr Tyr Trp Gly Gln Gly Thr Leu Val Thr Val Ser Ala
            100                 105                 110

<210> SEQ ID NO 65
<211> LENGTH: 336
<212> TYPE: DNA
<213> ORGANISM: Artificial Sequence
<220> FEATURE:
<223> OTHER INFORMATION: 25E9 light chain variable region

<400> SEQUENCE: 65
gatattgtga tgacccaggc tgcaccctct gtacctgtca ctcctggaga gtcagtatcc      60
atctcctgca ggtctactaa gagtctcctg catagtaatg caacactta cttgtattgg     120 ttcctgcaga ggccaggcca gtctcctcag ctcctgatat atcggatgtc caaccttgcc     180
tcaggagtcc cagacaggtt cagtggcagt gggtcaggaa ctgctttcac actgagaatc     240
agtagagtgg aggctgagga tgtgggtgtt tattactgta tgcaacatct agaatatcct     300
ttcacgttcg gaggggggac caagctggaa ataaaa                               336

<210> SEQ ID NO 66
<211> LENGTH: 112
<212> TYPE: PRT
<213> ORGANISM: Artificial Sequence
<220> FEATURE:
<223> OTHER INFORMATION: 25E9 light chain variable region
```

<400> SEQUENCE: 66

Asp Ile Val Met Thr Gln Ala Ala Pro Ser Val Pro Val Thr Pro Gly
1               5                   10                  15

Glu Ser Val Ser Ile Ser Cys Arg Ser Thr Lys Ser Leu Leu His Ser
            20                  25                  30

Asn Gly Asn Thr Tyr Leu Tyr Trp Phe Leu Gln Arg Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
                85                  90                  95

Leu Glu Tyr Pro Phe Thr Phe Gly Gly Gly Thr Lys Leu Glu Ile Lys
            100                 105                 110

<210> SEQ ID NO 67
<211> LENGTH: 369
<212> TYPE: DNA
<213> ORGANISM: Artificial Sequence
<220> FEATURE:
<223> OTHER INFORMATION: 25E9 heavy chain variable region

<400> SEQUENCE: 67
gagatccagc tgcagcagtc tggagttgag ctggtgaggc ctggggcttc agtgacgctg    60
tcctgcaagg cttcgggcta cacatttact gactatgaca tgcactgggt gaagcagaca   120
cctgttcatg gcctggaatg gattggaact attgatcctg aaactggtgg tactgcctac   180
aatcagaagt tcaagggcaa ggccacactg actgcggaca tcctccac acagcctac     240
atggagctca gcagcctgac atctgaggac tctgccgtct attactgtac aagtttctac   300
tatacttact ctaattacga cgtggggttt gcttactggg gccaagggac tctggtcact   360
gtctctgca                                                           369

<210> SEQ ID NO 68
<211> LENGTH: 123
<212> TYPE: PRT
<213> ORGANISM: Artificial Sequence
<220> FEATURE:
<223> OTHER INFORMATION: 25E9 heavy chain variable region

<400> SEQUENCE: 68

Glu Ile Gln Leu Gln Gln Ser Gly Val Glu Leu Val Arg Pro Gly Ala
1               5                   10                  15

Ser Val Thr Leu Ser Cys Lys Ala Ser Gly Tyr Thr Phe Thr Asp Tyr
            20                  25                  30

Asp Met His Trp Val Lys Gln Thr Pro Val His Gly Leu Glu Trp Ile
        35                  40                  45

Gly Thr Ile Asp Pro Glu Thr Gly Gly Thr Ala Tyr Asn Gln Lys Phe
    50                  55                  60

Lys Gly Lys Ala Thr Leu Thr Ala Asp Arg Ser Ser Thr Thr Ala Tyr
65                  70                  75                  80

Met Glu Leu Ser Ser Leu Thr Ser Glu Asp Ser Ala Val Tyr Tyr Cys
                85                  90                  95

Thr Ser Phe Tyr Tyr Tyr Ser Asn Tyr Asp Val Gly Phe Ala Tyr
            100                 105                 110

Trp Gly Gln Gly Thr Leu Val Thr Val Ser Ala

```
<210> SEQ ID NO 69
<211> LENGTH: 10
<212> TYPE: PRT
<213> ORGANISM: Artificial Sequence
<220> FEATURE:
<223> OTHER INFORMATION: 25A1 light chain CDR1

<400> SEQUENCE: 69

Ser Ala Ser Ser Ser Val Ser Tyr Met Tyr
1               5                   10

<210> SEQ ID NO 70
<211> LENGTH: 7
<212> TYPE: PRT
<213> ORGANISM: Artificial Sequence
<220> FEATURE:
<223> OTHER INFORMATION: 25A1 light chain CDR2

<400> SEQUENCE: 70

Arg Thr Ser Asn Leu Ala Ser
1               5

<210> SEQ ID NO 71
<211> LENGTH: 9
<212> TYPE: PRT
<213> ORGANISM: Artificial Sequence
<220> FEATURE:
<223> OTHER INFORMATION: 25A1 light chain CDR3

<400> SEQUENCE: 71

Gln Gln Trp Ser Ser Asn Pro Leu Thr
1               5

<210> SEQ ID NO 72
<211> LENGTH: 10
<212> TYPE: PRT
<213> ORGANISM: Artificial Sequence
<220> FEATURE:
<223> OTHER INFORMATION: 25A1 heavy chain CDR1

<400> SEQUENCE: 72

Gly Tyr Thr Phe Thr Arg Tyr Trp Met Asp
1               5                   10

<210> SEQ ID NO 73
<211> LENGTH: 10
<212> TYPE: PRT
<213> ORGANISM: Artificial Sequence
<220> FEATURE:
<223> OTHER INFORMATION: 25A1 heavy chain CDR2

<400> SEQUENCE: 73

Glu Ile Asp Pro Ser Asp Ser Tyr Thr Asn
1               5                   10

<210> SEQ ID NO 74
<211> LENGTH: 17
<212> TYPE: PRT
<213> ORGANISM: Artificial Sequence
<220> FEATURE:
<223> OTHER INFORMATION: 25A1 heavy chain CDR3

<400> SEQUENCE: 74

Ala Arg Ser Gly Ala Tyr Ser Ser Asp Tyr Ser Tyr Asp Gly Phe Ala
1               5                   10                  15
```

Tyr

<210> SEQ ID NO 75
<211> LENGTH: 16
<212> TYPE: PRT
<213> ORGANISM: Artificial Sequence
<220> FEATURE:
<223> OTHER INFORMATION: 25B4 light chain CDR1

<400> SEQUENCE: 75

Arg Ser Ser Lys Ser Leu Leu His Ser Asn Gly Ile Thr Tyr Leu Tyr
1               5                   10                  15

<210> SEQ ID NO 76
<211> LENGTH: 7
<212> TYPE: PRT
<213> ORGANISM: Artificial Sequence
<220> FEATURE:
<223> OTHER INFORMATION: 25B4 light chain CDR2

<400> SEQUENCE: 76

Gln Met Ser Asn Leu Ala Ser
1               5

<210> SEQ ID NO 77
<211> LENGTH: 9
<212> TYPE: PRT
<213> ORGANISM: Artificial Sequence
<220> FEATURE:
<223> OTHER INFORMATION: 25B4 light chain CDR3

<400> SEQUENCE: 77

Met Gln His Leu Glu Tyr Pro Tyr Thr
1               5

<210> SEQ ID NO 78
<211> LENGTH: 10
<212> TYPE: PRT
<213> ORGANISM: Artificial Sequence
<220> FEATURE:
<223> OTHER INFORMATION: 25B4 heavy chain CDR1

<400> SEQUENCE: 78

Gly Tyr Thr Phe Thr Ser Tyr Trp Met His
1               5                   10

<210> SEQ ID NO 79
<211> LENGTH: 10
<212> TYPE: PRT
<213> ORGANISM: Artificial Sequence
<220> FEATURE:
<223> OTHER INFORMATION: 25B4 heavy chain CDR2

<400> SEQUENCE: 79

Leu Ile Asn Pro Thr Asn Gly Arg Thr Asn
1               5                   10

<210> SEQ ID NO 80
<211> LENGTH: 11
<212> TYPE: PRT
<213> ORGANISM: Artificial Sequence
<220> FEATURE:
<223> OTHER INFORMATION: 25B4 heavy chain CDR3

<400> SEQUENCE: 80

Ala Arg Gly Gly Asp Gly Asp Tyr Phe Asp Tyr
1               5                   10

<210> SEQ ID NO 81
<211> LENGTH: 16
<212> TYPE: PRT
<213> ORGANISM: Artificial Sequence
<220> FEATURE:
<223> OTHER INFORMATION: 25B8 light chain CDR1

<400> SEQUENCE: 81

Arg Ser Thr Lys Ser Leu Leu His Ser Asn Gly Asn Thr Tyr Leu Tyr
1               5                   10                  15

<210> SEQ ID NO 82
<211> LENGTH: 7
<212> TYPE: PRT
<213> ORGANISM: Artificial Sequence
<220> FEATURE:
<223> OTHER INFORMATION: 25B8 light chain CDR2

<400> SEQUENCE: 82

Arg Met Ser Asn Leu Ala Ser
1               5

<210> SEQ ID NO 83
<211> LENGTH: 9
<212> TYPE: PRT
<213> ORGANISM: Artificial Sequence
<220> FEATURE:
<223> OTHER INFORMATION: 25B8 light chain CDR3

<400> SEQUENCE: 83

Met Gln His Leu Glu Tyr Pro Phe Thr
1               5

<210> SEQ ID NO 84
<211> LENGTH: 10
<212> TYPE: PRT
<213> ORGANISM: Artificial Sequence
<220> FEATURE:
<223> OTHER INFORMATION: 25B8 heavy chain CDR1

<400> SEQUENCE: 84

Gly Tyr Thr Phe Thr Asp Tyr Asp Met His
1               5                   10

<210> SEQ ID NO 85
<211> LENGTH: 10
<212> TYPE: PRT
<213> ORGANISM: Artificial Sequence
<220> FEATURE:
<223> OTHER INFORMATION: 25B8 heavy chain CDR2

<400> SEQUENCE: 85

Thr Ile Asp Pro Glu Thr Gly Gly Thr Ala
1               5                   10

<210> SEQ ID NO 86
<211> LENGTH: 16
<212> TYPE: PRT
<213> ORGANISM: Artificial Sequence
<220> FEATURE:
<223> OTHER INFORMATION: 25B8 heavy chain CDR3

<400> SEQUENCE: 86

Thr Thr Phe Tyr Tyr Ser His Tyr Asn Tyr Asp Val Gly Phe Ala Tyr
1               5                   10                  15

<210> SEQ ID NO 87

```
<211> LENGTH: 16
<212> TYPE: PRT
<213> ORGANISM: Artificial Sequence
<220> FEATURE:
<223> OTHER INFORMATION: 25C1 light chain CDR1

<400> SEQUENCE: 87

Arg Ser Ser Lys Ser Leu Leu His Ser Asn Gly Asn Thr Tyr Leu Tyr
1               5                   10                  15

<210> SEQ ID NO 88
<211> LENGTH: 7
<212> TYPE: PRT
<213> ORGANISM: Artificial Sequence
<220> FEATURE:
<223> OTHER INFORMATION: 25C1 light chain CDR2

<400> SEQUENCE: 88

Arg Met Ser Asn Leu Ala Ser
1               5

<210> SEQ ID NO 89
<211> LENGTH: 9
<212> TYPE: PRT
<213> ORGANISM: Artificial Sequence
<220> FEATURE:
<223> OTHER INFORMATION: 25C1 light chain CDR3

<400> SEQUENCE: 89

Met Gln His Leu Glu Tyr Pro Phe Thr
1               5

<210> SEQ ID NO 90
<211> LENGTH: 10
<212> TYPE: PRT
<213> ORGANISM: Artificial Sequence
<220> FEATURE:
<223> OTHER INFORMATION: 25C1 heavy chain CDR1

<400> SEQUENCE: 90

Gly Tyr Thr Phe Thr Asp Tyr Glu Met His
1               5                   10

<210> SEQ ID NO 91
<211> LENGTH: 10
<212> TYPE: PRT
<213> ORGANISM: Artificial Sequence
<220> FEATURE:
<223> OTHER INFORMATION: 25C1 heavy chain CDR2

<400> SEQUENCE: 91

Ala Ile Asp Pro Glu Thr Gly Gly Thr Ala
1               5                   10

<210> SEQ ID NO 92
<211> LENGTH: 16
<212> TYPE: PRT
<213> ORGANISM: Artificial Sequence
<220> FEATURE:
<223> OTHER INFORMATION: 25C1 heavy chain CDR3

<400> SEQUENCE: 92

Thr Ser Phe Tyr Tyr Thr Tyr Tyr Asn Tyr Asp Val Gly Phe Ala Tyr
1               5                   10                  15

<210> SEQ ID NO 93
<211> LENGTH: 16
<212> TYPE: PRT
```

<213> ORGANISM: Artificial Sequence
<220> FEATURE:
<223> OTHER INFORMATION: 25D8 light chain CDR1

<400> SEQUENCE: 93

Arg Ser Ser Lys Ser Leu Leu His Ser Asn Gly Ile Thr Tyr Leu Tyr
1               5                   10                  15

<210> SEQ ID NO 94
<211> LENGTH: 7
<212> TYPE: PRT
<213> ORGANISM: Artificial Sequence
<220> FEATURE:
<223> OTHER INFORMATION: 25D8 light chain CDR2

<400> SEQUENCE: 94

Gln Met Ser Asn Leu Ala Ser
1               5

<210> SEQ ID NO 95
<211> LENGTH: 9
<212> TYPE: PRT
<213> ORGANISM: Artificial Sequence
<220> FEATURE:
<223> OTHER INFORMATION: 25D8 light chain CDR3

<400> SEQUENCE: 95

Ala Gln Asn Leu Glu Leu Pro Tyr Thr
1               5

<210> SEQ ID NO 96
<211> LENGTH: 10
<212> TYPE: PRT
<213> ORGANISM: Artificial Sequence
<220> FEATURE:
<223> OTHER INFORMATION: 25D8 heavy chain CDR1

<400> SEQUENCE: 96

Gly Tyr Thr Phe Thr Ser Tyr Trp Met His
1               5                   10

<210> SEQ ID NO 97
<211> LENGTH: 10
<212> TYPE: PRT
<213> ORGANISM: Artificial Sequence
<220> FEATURE:
<223> OTHER INFORMATION: 25D8 heavy chain CDR2

<400> SEQUENCE: 97

Leu Ile Asn Pro Ser Asn Ala Arg Thr Asn
1               5                   10

<210> SEQ ID NO 98
<211> LENGTH: 11
<212> TYPE: PRT
<213> ORGANISM: Artificial Sequence
<220> FEATURE:
<223> OTHER INFORMATION: 25D8 heavy chain CDR3

<400> SEQUENCE: 98

Ala Arg Gly Gly Asp Gly Asp Tyr Phe Asp Tyr
1               5                   10

<210> SEQ ID NO 99
<211> LENGTH: 10
<212> TYPE: PRT
<213> ORGANISM: Artificial Sequence
<220> FEATURE:

<223> OTHER INFORMATION: 25E5 light chain CDR1

<400> SEQUENCE: 99

Ser Ala Ser Ser Ser Val Ser Tyr Met Tyr
1               5                   10

<210> SEQ ID NO 100
<211> LENGTH: 7
<212> TYPE: PRT
<213> ORGANISM: Artificial Sequence
<220> FEATURE:
<223> OTHER INFORMATION: 25E5 light chain CDR2

<400> SEQUENCE: 100

Arg Thr Ser Asn Leu Val Ser
1               5

<210> SEQ ID NO 101
<211> LENGTH: 9
<212> TYPE: PRT
<213> ORGANISM: Artificial Sequence
<220> FEATURE:
<223> OTHER INFORMATION: 25E5 light chain CDR3

<400> SEQUENCE: 101

Gln Gln Trp Ser Ser Asn Pro Pro Thr
1               5

<210> SEQ ID NO 102
<211> LENGTH: 10
<212> TYPE: PRT
<213> ORGANISM: Artificial Sequence
<220> FEATURE:
<223> OTHER INFORMATION: 25E5 heavy chain CDR1

<400> SEQUENCE: 102

Gly Phe Asp Phe Ser Lys Asp Trp Met Ser
1               5                   10

<210> SEQ ID NO 103
<211> LENGTH: 10
<212> TYPE: PRT
<213> ORGANISM: Artificial Sequence
<220> FEATURE:
<223> OTHER INFORMATION: 25E5 heavy chain CDR2

<400> SEQUENCE: 103

Glu Ile Asn Pro Asp Ser Ser Thr Ile Asn
1               5                   10

<210> SEQ ID NO 104
<211> LENGTH: 13
<212> TYPE: PRT
<213> ORGANISM: Artificial Sequence
<220> FEATURE:
<223> OTHER INFORMATION: 25E5 heavy chain CDR3

<400> SEQUENCE: 104

Ser Arg Leu Glu Asp Tyr Glu Asp Trp Tyr Phe Asp Val
1               5                   10

<210> SEQ ID NO 105
<211> LENGTH: 11
<212> TYPE: PRT
<213> ORGANISM: Artificial Sequence
<220> FEATURE:
<223> OTHER INFORMATION: 25E6 light chain CDR1

```
<400> SEQUENCE: 105

Lys Ala Ser Gln Ser Val Ser Asn Ala Val Ala
 1               5                  10

<210> SEQ ID NO 106
<211> LENGTH: 7
<212> TYPE: PRT
<213> ORGANISM: Artificial Sequence
<220> FEATURE:
<223> OTHER INFORMATION: 25E6 light chain CDR2

<400> SEQUENCE: 106

Tyr Thr Ser Asn Arg Tyr Thr
 1               5

<210> SEQ ID NO 107
<211> LENGTH: 9
<212> TYPE: PRT
<213> ORGANISM: Artificial Sequence
<220> FEATURE:
<223> OTHER INFORMATION: 25E6 light chain CDR3

<400> SEQUENCE: 107

Gln Gln Asp Tyr Thr Ser Pro Trp Thr
 1               5

<210> SEQ ID NO 108
<211> LENGTH: 10
<212> TYPE: PRT
<213> ORGANISM: Artificial Sequence
<220> FEATURE:
<223> OTHER INFORMATION: 25E6 heavy chain CDR1

<400> SEQUENCE: 108

Gly Tyr Thr Phe Asn Thr Tyr Asn Met Tyr
 1               5                  10

<210> SEQ ID NO 109
<211> LENGTH: 10
<212> TYPE: PRT
<213> ORGANISM: Artificial Sequence
<220> FEATURE:
<223> OTHER INFORMATION: 25E6 heavy chain CDR2

<400> SEQUENCE: 109

Gly Ile Asp Pro Ser Asn Gly Asp Thr Lys
 1               5                  10

<210> SEQ ID NO 110
<211> LENGTH: 5
<212> TYPE: PRT
<213> ORGANISM: Artificial Sequence
<220> FEATURE:
<223> OTHER INFORMATION: 25E6 heavy chain CDR3

<400> SEQUENCE: 110

Thr Ser His Thr Tyr
 1               5

<210> SEQ ID NO 111
<211> LENGTH: 16
<212> TYPE: PRT
<213> ORGANISM: Artificial Sequence
<220> FEATURE:
<223> OTHER INFORMATION: 25E9 light chain CDR1

<400> SEQUENCE: 111
```

Arg Ser Thr Lys Ser Leu Leu His Ser Asn Gly Asn Thr Tyr Leu Tyr
1               5                   10                  15

<210> SEQ ID NO 112
<211> LENGTH: 7
<212> TYPE: PRT
<213> ORGANISM: Artificial Sequence
<220> FEATURE:
<223> OTHER INFORMATION: 25E9 light chain CDR2

<400> SEQUENCE: 112

Arg Met Ser Asn Leu Ala Ser
1               5

<210> SEQ ID NO 113
<211> LENGTH: 9
<212> TYPE: PRT
<213> ORGANISM: Artificial Sequence
<220> FEATURE:
<223> OTHER INFORMATION: 25E9 light chain CDR3

<400> SEQUENCE: 113

Met Gln His Leu Glu Tyr Pro Phe Thr
1               5

<210> SEQ ID NO 114
<211> LENGTH: 10
<212> TYPE: PRT
<213> ORGANISM: Artificial Sequence
<220> FEATURE:
<223> OTHER INFORMATION: 25E9 heavy chain CDR1

<400> SEQUENCE: 114

Gly Tyr Thr Phe Thr Asp Tyr Asp Met His
1               5                   10

<210> SEQ ID NO 115
<211> LENGTH: 10
<212> TYPE: PRT
<213> ORGANISM: Artificial Sequence
<220> FEATURE:
<223> OTHER INFORMATION: 25E9 heavy chain CDR2

<400> SEQUENCE: 115

Thr Ile Asp Pro Glu Thr Gly Gly Thr Ala
1               5                   10

<210> SEQ ID NO 116
<211> LENGTH: 16
<212> TYPE: PRT
<213> ORGANISM: Artificial Sequence
<220> FEATURE:
<223> OTHER INFORMATION: 25E9 heavy chain CDR3

<400> SEQUENCE: 116

Thr Ser Phe Tyr Tyr Thr Tyr Ser Asn Tyr Asp Val Gly Phe Ala Tyr
1               5                   10                  15

<210> SEQ ID NO 117
<211> LENGTH: 33
<212> TYPE: DNA
<213> ORGANISM: Artificial Sequence
<220> FEATURE:
<223> OTHER INFORMATION: chemically synthesized oligonucleotide

<400> SEQUENCE: 117
gtaagcaagc ttgctcacgc cttccgcgcg ctc                                    33

<210> SEQ ID NO 118
<211> LENGTH: 35
<212> TYPE: DNA
<213> ORGANISM: Artificial Sequence
<220> FEATURE:
<223> OTHER INFORMATION: chemically synthesized oligonucleotide

<400> SEQUENCE: 118
gtaagcagat ctctggcgcc atggaagcgg aacag                    35

<210> SEQ ID NO 119
<211> LENGTH: 23
<212> TYPE: DNA
<213> ORGANISM: Artificial Sequence
<220> FEATURE:
<223> OTHER INFORMATION: chemically synthesized oligonucleotide

<400> SEQUENCE: 119
cactgggagc tatggaagaa gac                                 23

<210> SEQ ID NO 120
<211> LENGTH: 24
<212> TYPE: DNA
<213> ORGANISM: Artificial Sequence
<220> FEATURE:
<223> OTHER INFORMATION: chemically synthesized oligonucleotide

<400> SEQUENCE: 120
caaaagtgca agaagggaa gaca                                 24

<210> SEQ ID NO 121
<211> LENGTH: 26
<212> TYPE: DNA
<213> ORGANISM: Artificial Sequence
<220> FEATURE:
<223> OTHER INFORMATION: chemically synthesized oligonucleotide

<400> SEQUENCE: 121
tgaaggtcgg agtcaacgga tttggt                              26

<210> SEQ ID NO 122
<211> LENGTH: 24
<212> TYPE: DNA
<213> ORGANISM: Artificial Sequence
<220> FEATURE:
<223> OTHER INFORMATION: chemically synthesized oligonucleotide

<400> SEQUENCE: 122
catgtgggcc atgaggtcca ccac                                24

<210> SEQ ID NO 123
<211> LENGTH: 242
<212> TYPE: PRT
<213> ORGANISM: Artificial Sequence
<220> FEATURE:
<223> OTHER INFORMATION: cDNA encoding amino acids 20 - 259 of SEQ ID
      NO:2

<400> SEQUENCE: 123

Val Arg Thr Lys Ile Asp Thr Thr Glu Asn Leu Leu Asn Thr Glu Val
1               5                   10                  15

His Ser Ser Pro Ala Gln Arg Trp Ser Met Gln Val Pro Pro Glu Val
                20                  25                  30

Ser Ala Glu Ala Gly Asp Ala Ala Val Leu Pro Cys Thr Phe Thr His
        35                  40                  45

```
Pro His Arg His Tyr Asp Gly Pro Leu Thr Ala Ile Trp Arg Ala Gly
     50                  55                  60

Glu Pro Tyr Ala Gly Pro Gln Val Phe Arg Cys Ala Ala Ala Arg Gly
 65                  70                  75                  80

Ser Glu Leu Cys Gln Thr Ala Leu Ser Leu His Gly Arg Phe Arg Leu
                 85                  90                  95

Leu Gly Asn Pro Arg Arg Asn Asp Leu Ser Leu Arg Val Glu Arg Leu
            100                 105                 110

Ala Leu Ala Asp Asp Arg Arg Tyr Phe Cys Arg Val Glu Phe Ala Gly
        115                 120                 125

Asp Val His Asp Arg Tyr Glu Ser Arg His Gly Val Arg Leu His Val
    130                 135                 140

Thr Ala Ala Pro Arg Ile Val Asn Ile Ser Val Leu Pro Ser Pro Ala
145                 150                 155                 160

His Ala Phe Arg Ala Leu Cys Thr Ala Glu Gly Pro Pro Ala
                165                 170                 175

Leu Ala Trp Ser Gly Pro Ala Leu Gly Asn Ser Leu Ala Ala Val Arg
            180                 185                 190

Ser Pro Arg Glu Gly His Gly His Leu Val Thr Ala Glu Leu Pro Ala
        195                 200                 205

Leu Thr His Asp Gly Arg Tyr Thr Cys Thr Ala Ala Asn Ser Leu Gly
    210                 215                 220

Arg Ser Glu Ala Ser Val Tyr Leu Phe Arg Phe His Gly Ala Ser Gly
225                 230                 235                 240

Ala Ser

<210> SEQ ID NO 124
<211> LENGTH: 34
<212> TYPE: DNA
<213> ORGANISM: Artificial Sequence
<220> FEATURE:
<223> OTHER INFORMATION: chemically synthesized oligonucleotide

<400> SEQUENCE: 124
gtaagcggat ccgtgagaac taaaatagat acta                          34

<210> SEQ ID NO 125
<211> LENGTH: 41
<212> TYPE: DNA
<213> ORGANISM: Artificial Sequence
<220> FEATURE:
<223> OTHER INFORMATION: oligonucleotide

<400> SEQUENCE: 125
gtaagcgcgg ccgcgctggc gccatggaag cggaacaggt a                  41

<210> SEQ ID NO 126
<211> LENGTH: 5138
<212> TYPE: DNA
<213> ORGANISM: Artificial Sequence
<220> FEATURE:
<223> OTHER INFORMATION: expression vector pYD5

<400> SEQUENCE: 126
gtacatttat attggctcat gtccaatatg accgccatgt tgacattgat tattgactag    60
ttattaatag taatcaatta cggggtcatt agttcatagc ccatatatgg agttccgcgt   120
tacataactt acggtaaatg gcccgcctgg ctgaccgccc aacgaccccc gcccattgac   180
gtcaataatg acgtatgttc ccatagtaac gccaataggg actttccatt gacgtcaatg   240
```

```
ggtggagtat ttacggtaaa ctgcccactt ggcagtacat caagtgtatc atatgccaag    300 tccgcccct attgacgtca atgacggtaa atggcccgcc tggcattatg cccagtacat     360
gaccttacgg gactttccta cttggcagta catctacgta ttagtcatcg ctattaccat    420
ggtgatgcgg ttttggcagt acaccaatgg gcgtggatag cggtttgact cacggggatt   480
tccaagtctc cacccccattg acgtcaatgg gagtttgttt tggcaccaaa atcaacggga  540
ctttccaaaa tgtcgtaata accccgcccc gttgacgcaa atgggcggta ggcgtgtacg   600
gtgggaggtc tatataagca gagctcgttt agtgaaccgt cagatcctca ctctcttccg   660
catcgctgtc tgcgagggcc agctgttggg ctcgcggttg aggacaaact cttcgcggtc   720
tttccagtac tcttggatcg gaaacccgtc ggcctccgaa cggtactccg ccaccgaggg   780
acctgagcca gtccgcatcg accggatcgg aaaacctctc gagaaaggcg tctaaccagt   840
cacagtcgca aggtaggctg agcaccgtgg cgggcggcag cgggtggcgg tcggggttgt   900
ttctggcgga ggtgctgctg atgatgtaat taaagtaggc ggtcttgagc cggcggatgg   960
tcgaggtgag gtgtggcagg cttgagatcc agctgttggg gtgagtactc cctctcaaaa  1020
gcgggcatga cttctgcgct aagattgtca gtttccaaaa acgaggagga tttgatattc   1080
acctggcccg atctggccat acacttgagt gacaatgaca tccactttgc ctttctctcc   1140
acaggtgtcc actcccaggt ccaagtttgc cgccaccatg gagacagaca cactcctgct   1200
atgggtactg ctgctctggg ttccaggttc cactggcgcc ggatcaactc acacatgccc   1260
accgtgccca gcacctgaac tcctgggggg accgtcagtc ttcctcttcc ccccaaaacc   1320
caaggacacc ctcatgatct cccggacccc tgaggtcaca tgcgtggtgg tggacgtgag   1380
ccacgaagac cctgaggtca gttcaactg gtacgtggac ggcgtggagg tgcataatgc   1440
caagacaaag ccgcgggagg agcagtacaa cagcacgtac cgtgtggtca gcgtcctcac   1500
cgtcctgcac caggactggc tgaatggcaa ggagtacaag tgcaaggtct ccaacaaagc   1560
cctcccagcc cccatcgaga aaaccatctc caaagccaaa gggcagcccc gagaaccaca   1620
ggtgtacacc ctgcccccat cccgggatga gctgaccaag aaccaggtca gcctgacctg   1680
cctggtcaaa ggcttctatc ccagcgacat cgccgtggag tgggagagca atgggcagcc   1740
ggagaacaac tacaagacca cgcctcccgt gttggactcc gacggctcct tcttcctcta   1800
cagcaagctc accgtggaca agagcaggtg gcagcagggg aacgtcttct catgctccgt   1860
gatgcatgag gctctgcaca accactacac gcagaagagc ctctccctgt ctccgggaa    1920 agctagcgga gccggaagca caaccgaaaa cctgtatttt cagggcggat ccgaattcaa   1980
gcttgatatc tgatcccccg acctcgacct ctggctaata aggaaatttt attttcattg   2040
caatagtgtg ttggaatttt ttgtgtctct cactcggaag gacatatggg agggcaaatc   2100
atttggtcga gatccctcgg agatctctag ctagagcccc gccgccggac gaactaaacc   2160 tgactacgg atctctgccc cttcttcgcg ggcagtgca tgtaatccct tcagttggtt     2220
ggtacaactt gccaactgaa ccctaaacgg gtagcatatg cttcccgggt agtagtatat   2280
actatccaga ctaaccctaa ttcaatagca tatgttaccc aacgggaagc atatgctatc   2340
gaattagggt tagtaaaagg gtcctaagga acagcgatgt aggtgggcgg gccaagatag   2400
gggcgcgatt gctgcgatct ggaggacaaa ttacacacac ttgcgcctga cgccaagca    2460 cagggttgtt ggtcctcata ttcacgaggt cgctgagagc acgtgggct aatgttgcca    2520 tgggtagcat atactaccca aatatctgga tagcatatgc tatcctaatc tatatctggg   2580
tagcataggc tatcctaatc tatatctggg tagcatatgc tatcctaatc tatatctggg   2640
```

```
tagtatatgc tatcctaatt tatatctggg tagcataggc tatcctaatc tatatctggg    2700
tagcatatgc tatcctaatc tatatctggg tagtatatgc tatcctaatc tgtatccggg    2760
tagcatatgc tatcctaata gagattaggg tagtatatgc tatcctaatt tatatctggg    2820
tagcatatac tacccaaata tctggatagc atatgctatc ctaatctata tctgggtagc    2880
atatgctatc ctaatctata tctgggtagc ataggctatc ctaatctata tctgggtagc    2940
atatgctatc ctaatctata tctgggtagt atatgctatc ctaatttata tctgggtagc    3000
ataggctatc ctaatctata tctgggtagc atatgctatc ctaatctata tctgggtagt    3060
atatgctatc ctaatctgta tccgggtagc atatgctatc ctcacgatga taagctgtca    3120
aacatgagaa ttaattcttg aagacgaaag ggcctcgtga tacgcctatt tttataggtt    3180
aatgtcatga taataatggt ttcttagacg tcaggtggca cttttcgggg aaatgtgcgc    3240
ggaaccccta tttgtttatt tttctaaata cattcaaata tgtatccgct catgagacaa    3300
taaccctgat aaatgcttca ataatattga aaaaggaaga gtatgagtat tcaacatttc    3360
cgtgtcgccc ttattccctt ttttgcggca ttttgccttc ctgttttgc tcacccagaa    3420 acgctggtga agtaaaaaga tgctgaagat cagttgggtg cacgagtggg ttacatcgaa    3480
ctggatctca acagcggtaa gatccttgag agttttcgcc ccgaagaacg ttttccaatg    3540
atgagcactt ttaaagttct gctatgtggc gcggtattat cccgtgttga cgccgggcaa    3600
gagcaactcg gtcgccgcat acactattct cagaatgact tggttgagta ctcaccagtc    3660
acagaaaagc atcttacgga tggcatgaca gtaagagaat tatgcagtgc tgccataacc    3720
atgagtgata acactgcggc caacttactt ctgacaacga tcggaggacc gaaggagcta    3780
accgcttttt tgcacaacat gggggatcat gtaactcgcc ttgatcgttg gaaccggag    3840 ctgaatgaag ccataccaaa cgacgagcgt gacaccacga tgcctgcagc aatggcaaca    3900
acgttgcgca aactattaac tggcgaacta cttactctag cttcccggca acaattaata    3960
gactggatgg aggcggataa agttgcagga ccacttctgc gctcggccct tccggctggc    4020
tggtttattg ctgataaatc tggagccggt gagcgtgggt ctcgcggtat cattgcagca    4080
ctggggccag atggtaagcc ctcccgtatc gtagttatct acacgacggg gagtcaggca    4140
actatggatg aacgaaatag acagatcgct gagataggtg cctcactgat taagcattgg    4200
taactgtcag accaagttta ctcatatata ctttagattg atttaaaact tcatttttaa    4260
tttaaaagga tctaggtgaa gatccttttt gataatctca tgaccaaaat cccttaacgt    4320
gagttttcgt tccactgagc gtcagacccc gtagaaaaga tcaaaggatc ttcttgagat    4380 ccttttttc tgcgcgtaat ctgctgcttg caaacaaaaa aaccaccgct accagcggtg    4440
gtttgtttgc cggatcaaga gctaccaact ctttttccga aggtaactgg cttcagcaga    4500
gcgcagatac caaatactgt ccttctagtg tagccgtagt taggccacca cttcaagaac    4560
tctgtagcac cgcctacata cctcgctctg ctaatcctgt taccagtggc tgctgccagt    4620
ggcgataagt cgtgtcttac cgggttggac tcaagacgat agttaccgga taaggcgcag    4680
cggtcgggct gaacgggggg ttcgtgcaca cagcccagct tggagcgaac gacctacacc    4740
gaactgagat acctacagcg tgagcattga gaaagcgcca cgcttcccga agggagaaag    4800
gcggacaggt atccggtaag cggcagggtc ggaacaggag agcgcacgag ggagcttcca    4860
gggggaaacg cctggtatct ttatagtcct gtcgggtttc gccacctctg acttgagcgt    4920
cgatttttgt gatgctcgtc aggggggcgg agcctatgga aaaacgccag caacgcggcc    4980
tttttacggt tcctggcctt ttgctggcct tttgctcaca tgttctttcc tgcgttatcc    5040
```

```
cctgattctg tggataaccg tattaccgcc tttgagtgag ctgataccgc tcgccgcagc      5100
cgaacgaccg agcgcagcga gtcagtgagc gaggaagc                              5138
```

<210> SEQ ID NO 127
<211> LENGTH: 50
<212> TYPE: DNA
<213> ORGANISM: Artificial Sequence
<220> FEATURE:
<223> OTHER INFORMATION: chemically synthesized oligonucleotide

<400> SEQUENCE: 127

```
gtaagcgcta gcgcctcaac gaagggccca tctgtctttc cctggcccc                  50
```

<210> SEQ ID NO 128
<211> LENGTH: 37
<212> TYPE: DNA
<213> ORGANISM: Artificial Sequence
<220> FEATURE:
<223> OTHER INFORMATION: chemically synthesized oligonucleotide

<400> SEQUENCE: 128

```
gtaagcgaat tcacaagatt tgggctcaac tttcttg                               37
```

<210> SEQ ID NO 129
<211> LENGTH: 321
<212> TYPE: DNA
<213> ORGANISM: Artificial Sequence
<220> FEATURE:
<223> OTHER INFORMATION: sequence for the human kappa constant region

<400> SEQUENCE: 129

```
gctgtggctg caccatctgt cttcatcttc ccgccatctg atgagcagtt gaaatctgga      60
actgcctctg ttgtgtgcct gctgaataac ttctatccca gagaggccaa agtacagtgg      120
aaggtggata cgccctcca atcgggtaac tcccaggaga gtgtcacaga gcaggacagc       180
aaggacagca cctacagcct cagcagcacc ctgacgctga gcaaagcaga ctacgagaaa      240
cacaaagtct acgcctgcga agtcacccat cagggcctga gctcgcccgt cacaaagagc      300
ttcaacaggg gagagtgtta g                                                321
```

<210> SEQ ID NO 130
<211> LENGTH: 106
<212> TYPE: PRT
<213> ORGANISM: Artificial Sequence
<220> FEATURE:
<223> OTHER INFORMATION: sequence for the human kappa constant region

<400> SEQUENCE: 130

```
Ala Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105
```

<210> SEQ ID NO 131
<211> LENGTH: 6385
<212> TYPE: DNA
<213> ORGANISM: Artificial Sequence
<220> FEATURE:
<223> OTHER INFORMATION: plasmid pTTVK1

<400> SEQUENCE: 131

```
cttgagccgg cggatggtcg aggtgaggtg tggcaggctt gagatccagc tgttggggtg      60
agtactccct ctcaaaagcg ggcattactt ctgcgctaag attgtcagtt tccaaaaacg     120
aggaggattt gatattcacc tggcccgatc tggccataca cttgagtgac aatgacatcc     180
actttgcctt tctctccaca ggtgtccact cccaggtcca gtttaaacg gatctctagc     240
gaattcatga actttctgct gtcttgggtg cattggagcc ttgccttgct gctctacctc     300
caccatgcca gtggtccca ggcttgagac ggagcttaca gcgctgtggc tgcaccatct     360
gtcttcatct tcccgccatc tgatgagcag ttgaaatctg gaactgcctc tgttgtgtgc     420
ctgctgaata acttctatcc cagagaggcc aaagtacagt ggaaggtgga taacgccctc     480
caatcgggta actcccagga gagtgtcaca gagcaggaca gcaaggacag cacctacagc     540
ctcagcagca ccctgacgct gagcaaagca gactacgaga acacaaaagt ctacgcctgc     600
gaagtcaccc atcagggcct gagctcgccc gtcacaaaga gcttcaacag gggagagtgt     660
tagggtaccg cggccgcttc gaatgagatc ccccgacctc gacctctggc taataaagga     720
aatttatttt cattgcaata gtgtgttgga attttttgtg tctctcactc ggaaggacat     780
atgggagggc aaatcatttg gtcgagatcc ctcggagatc tctagctaga gccccgccgc     840
cggacgaact aaacctgact acggcatctc tgccccttct tcgcggggca gtgcatgtaa     900
tcccttcagt tggttggtac aacttgccaa ctgggccctg ttccacatgt gacacgggg     960
gggaccaaac acaaggggt tctctgactg tagttgacat ccttataaat ggatgtgcac    1020
atttgccaac actgagtggc tttcatcctg gagcagactt tgcagtctgt ggactgcaac    1080
acaacattgc ctttatgtgt aactcttggc tgaagctctt acaccaatgc tgggggacat    1140
gtacctccca ggggcccagg aagactacgg gaggctacac caacgtcaat cagaggggcc    1200
tgtgtagcta ccgataagcg gaccctcaag agggcattag caatagtgtt tataaggccc    1260
ccttgttaac cctaaacggg tagcatatgc ttcccgggta gtagtatata ctatccagac    1320
taaccctaat tcaatagcat atgttaccca acgggaagca tatgctatcg aattaggtt    1380
agtaaaaggg tcctaaggaa cagcgatatc tcccacccca tgagctgtca cggtttttatt    1440
tacatgggt caggattcca cgagggtagt gaaccatttt agtcacaagg gcagtggctg    1500
aagatcaagg agcgggcagt gaactctcct gaatcttcgc ctgcttcttc attctccttc    1560
gtttagctaa tagaataact gctgagttgt gaacagtaag gtgtatgtga ggtgctcgaa    1620
aacaaggttt caggtgacgc ccccagaata aaatttggac gggggttca gtggtggcat    1680
tgtgctatga caccaatata acccctcacaa accccttggg caataaatac tagtgtagga    1740
atgaaacatt ctgaatatct ttaacaatag aaatccatgg ggtggggaca agccgtaaag    1800
actggatgtc catctcacac gaatttatgg ctatgggcaa cacataatcc tagtgcaata    1860
tgatactggg gttattaaga tgtgtcccag gcagggacca agacaggtga accatgttgt    1920
tacactctat ttgtaacaag gggaaagaga gtggacgccg acagcagcgg actccactgg    1980
ttgtctctaa caccccgaa aattaaacg ggctccacgc caatgggcc cataaacaaa    2040
gacaagtggc cactcttttt tttgaaattg tggagtgggg gcacgcgtca gccccacac    2100
```

```
gccgccctgc ggttttggac tgtaaaataa gggtgtaata acttggctga ttgtaacccc   2160
gctaaccact gcggtcaaac cacttgccca caaaaccact aatggcaccc cggggaatac   2220
ctgcataagt aggtgggcgg gccaagatag gggcgcgatt gctgcgatct ggaggacaaa   2280
ttacacacac ttgcgcctga gcgccaagca cagggttgtt ggtcctcata ttcacgaggt   2340
cgctgagagc acggtgggct aatgttgcca tgggtagcat atactaccca aatatctgga   2400
tagcatatgc tatcctaatc tatatctggg tagcataggc tatcctaatc tatatctggg   2460
tagcatatgc tatcctaatc tatatctggg tagtatatgc tatcctaatt tatatctggg   2520
tagcataggc tatcctaatc tatatctggg tagcatatgc tatcctaatc tatatctggg   2580
tagtatatgc tatcctaatc tgtatccggg tagcatatgc tatcctaata gagattaggg   2640
tagtatatgc tatcctaatt tatatctggg tagcatatac tacccaaata tctggatagc   2700
atatgctatc ctaatctata tctgggtagc atatgctatc ctaatctata tctgggtagc   2760
ataggctatc ctaatctata tctgggtagc atatgctatc ctaatctata tctgggtagt   2820
atatgctatc ctaatttata tctgggtagc ataggctatc ctaatctata tctgggtagc   2880
atatgctatc ctaatctata tctgggtagt atatgctatc ctaatctgta tccgggtagc   2940
atatgctatc ctcacgatga taagctgtca acatgagaaa ttaattcttg aagacgaaag   3000
ggcctcgtga tacgcctatt tttataggtt aatgtcatga taataatggt tcttagacg    3060 tcaggtggca cttttcgggg aaatgtgcgc ggaaccccta tttgtttatt tttctaaata   3120
cattcaaata tgtatccgct catgagacaa taaccctgat aaatgcttca ataatattga   3180
aaaaggaaga gtatgagtat tcaacatttc cgtgtcgccc ttattcccct ttttgcggca   3240
ttttgccttc ctgtttttgc tcacccagaa acgctggtga agtaaaaga tgctgaagat    3300 cagttgggtg cacgagtggg ttacatcgaa ctggatctca acagcggtaa gatccttgag   3360
agttttcgcc ccgaagaacg ttttccaatg atgagcactt ttaaagttct gctatgtggc   3420
gcggtattat cccgtgttga cgccgggcaa gagcaactcg gtcgccgcat acactattct   3480
cagaatgact tggttgagta ctcaccagtc acagaaaagc atcttacgga tggcatgaca   3540
gtaagagaat tatgcagtgc tgccataacc atgagtgata cactgcggc caacttactt    3600 ctgacaacga tcgaggacc gaaggagcta accgcttttt tgcacaacat ggggatcat     3660 gtaactcgcc ttgatcgttg ggaaccggag ctgaatgaag ccataccaaa cgacgagcgt   3720
gacaccacga tgcctgcagc aatggcaaca acgttgcgca aactattaac tggcgaacta   3780
cttactctag cttcccggca acaattaata gactggatgg aggcggataa agttgcagga   3840
ccacttctgc gctcggccct tccggctggc tggtttattg ctgataaatc tggagccggt   3900
gagcgtgggt ctcgcggtat cattgcagca ctggggccag atggtaagcc ctcccgtatc   3960
gtagttatct acacgacggg gagtcaggca actatggatg aacgaaatag acagatcgct   4020
gagataggtg cctcactgat taagcattgg taactgtcag accaagttta ctcatatata   4080
ctttagattg atttaaaact tcattttaa tttaaaagga tctaggtgaa gatcctttt     4140 gataatctca tgaccaaaat cccttaacgt gagttttcgt tccactgagc gtcagacccc   4200
gtagaaaaga tcaaaggatc ttcttgagat cctttttttc tgcgcgtaat ctgctgcttg   4260
caaacaaaaa aaccaccgct accagcggtg gtttgtttgc cggatcaaga gctaccaact   4320 cttttttccga aggtaactgg cttcagcaga gcgcagatac caaatactgt ccttctagtg   4380
tagccgtagt taggccacca cttcaagaac tctgtagcac cgcctacata cctcgctctg   4440
ctaatcctgt taccagtggc tgctgccagt ggcgataagt cgtgtcttac cgggttggac   4500
```

```
tcaagacgat agttaccgga taaggcgcag cggtcgggct gaacgggggg ttcgtgcaca    4560
cagcccagct tggagcgaac gacctacacc gaactgagat acctacagcg tgagcattga    4620
gaaagcgcca cgcttcccga agggagaaag gcggacaggt atccggtaag cggcagggtc    4680
ggaacaggag agcgcacgag ggagcttcca gggggaaacg cctggtatct ttatagtcct    4740
gtcgggtttc gccacctctg acttgagcgt cgatttttgt gatgctcgtc agggggcgg     4800 agcctatgga aaaacgccag caacgcggcc tttttacggt tcctggcctt ttgctggcct    4860
tttgctcaca tgttctttcc tgcgttatcc cctgattctg tggataaccg tattaccgcc    4920
tttgagtgag ctgataccgc tcgccgcagc cgaacgaccg agcgcagcga gtcagtgagc    4980
gaggaagcgg aagagcgccc aatacgcaaa ccgcctctcc ccgcgcgttg gccgattcat    5040
taatgcagct ggcacgacag gtttcccgac tggaaagcgg gcagtgagcg caacgcaatt    5100
aatgtgagtt agctcactca ttaggcaccc caggctttac actttatgct tccggctcgt    5160
atgttgtgtg gaattgtgag cggataacaa tttcacacag gaaacagcta tgaccatgat    5220
tacgccaagc tctagctaga ggtcgaccaa ttctcatgtt tgacagctta tcatcgcaga    5280
tccgggcaac gttgttgcat tgctgcaggc gcagaactgg taggtatggc agatctatac    5340
attgaatcaa tattggcaat tagccatatt agtcattggt tatatagcat aaatcaatat    5400
tggctattgg ccattgcata cgttgtatct atatcataat atgtacattt atattggctc    5460
atgtccaata tgaccgccat gttgacattg attattgact agttattaat agtaatcaat    5520 tacgggtca ttagttcata gcccatatat ggagttccgc gttacataac ttacggtaaa     5580
tggcccgcct ggctgaccgc ccaacgaccc ccgcccattg acgtcaataa tgacgtatgt    5640
tcccatagta acgccaatag ggactttcca ttgacgtcaa tgggtggagt atttacggta    5700
aactgcccac ttggcagtac atcaagtgta tcatatgcca agtccgcccc ctattgacgt    5760
caatgacggt aaatggcccg cctggcatta tgcccagtac atgaccttac gggactttcc    5820
tacttggcag tacatctacg tattagtcat cgctattacc atggtgatgc ggttttggca    5880
gtacaccaat gggcgtggat agcggtttga ctcacgggga tttccaagtc tccacccccat   5940 tgacgtcaat gggagtttgt tttggcacca aaatcaacgg gactttccaa aatgtcgtaa    6000
taaccccgcc ccgttgacgc aaatgggcgg taggcgtgta cggtgggagg tctatataag    6060
cagagctcgt ttagtgaacc gtcagatcct cactctcttc cgcatcgctg tctgcgaggg    6120
ccagctgttg ggctcgcggt tgaggacaaa ctcttcgcgg tctttccagt actcttggat    6180
cggaaacccg tcggcctccg aacggtactc cgccaccgag ggacctgagc gagtccgcat    6240
cgaccggatc ggaaaacctc tcgagaaagg cgtctaacca gtcacagtcg caaggtaggc    6300
tgagcaccgt ggcgggcggc agcgggtggc ggtcgggggtt gtttctggcg gaggtgctgc    6360
tgatgatgta attaaagtag gcggt                                          6385
```

<210> SEQ ID NO 132
<211> LENGTH: 43
<212> TYPE: DNA
<213> ORGANISM: Artificial Sequence
<220> FEATURE:
<223> OTHER INFORMATION: chemically synthesized oligonucleotide

<400> SEQUENCE: 132

```
atgccaagtg gtcccaggct gaaaatgtgc tcacccagtc tcc                       43
```

<210> SEQ ID NO 133
<211> LENGTH: 43

```
<212> TYPE: DNA
<213> ORGANISM: Artificial Sequence
<220> FEATURE:
<223> OTHER INFORMATION: chemically synthesized oligonucleotide

<400> SEQUENCE: 133
atgccaagtg gtcccaggct gatattgtga tgacccaggc tgc                         43

<210> SEQ ID NO 134
<211> LENGTH: 43
<212> TYPE: DNA
<213> ORGANISM: Artificial Sequence
<220> FEATURE:
<223> OTHER INFORMATION: chemically synthesized oligonucleotide

<400> SEQUENCE: 134
atgccaagtg gtcccaggct caaattgttc tcacccagtc tcc                         43

<210> SEQ ID NO 135
<211> LENGTH: 43
<212> TYPE: DNA
<213> ORGANISM: Artificial Sequence
<220> FEATURE:
<223> OTHER INFORMATION: chemically synthesized oligonucleotide

<400> SEQUENCE: 135
atgccaagtg gtcccaggct agtattgtga tgacccagac tcc                         43

<210> SEQ ID NO 136
<211> LENGTH: 32
<212> TYPE: DNA
<213> ORGANISM: Artificial Sequence
<220> FEATURE:
<223> OTHER INFORMATION: chemically synthesized oligonucleotide

<400> SEQUENCE: 136
gggaagatga agacagatgg tgcagccaca gc                                     32

<210> SEQ ID NO 137
<211> LENGTH: 50
<212> TYPE: DNA
<213> ORGANISM: Artificial Sequence
<220> FEATURE:
<223> OTHER INFORMATION: chemically synthesized oligonucleotide

<400> SEQUENCE: 137
gtaagcgcta gcgcctcaac gaagggccca tctgtctttc ccctggcccc                  50

<210> SEQ ID NO 138
<211> LENGTH: 37
<212> TYPE: DNA
<213> ORGANISM: Artificial Sequence
<220> FEATURE:
<223> OTHER INFORMATION: chemically synthesized oligonucleotide

<400> SEQUENCE: 138
gtaagcgaat tcacaagatt tgggctcaac tttcttg                                37

<210> SEQ ID NO 139
<211> LENGTH: 309
<212> TYPE: DNA
<213> ORGANISM: Artificial Sequence
<220> FEATURE:
<223> OTHER INFORMATION: Human IgG1 CH1 region

<400> SEQUENCE: 139
gcctccacca agggcccatc ggtcttcccc ctggcaccct cctccaagag cacctctggg       60
```

```
ggcacagcag ccctgggctg cctggtcaag gactacttcc ccgaaccggt gacggtgtcg    120
tggaactcag gcgccctgac cagcggcgtg cacaccttcc cggctgtcct acagtcctca    180
ggactctact ccctcagcag cgtggtgacc gtgccctcca gcagcttggg cacccagacc    240
tacatctgca acgtgaatca caagcccagc aacaccaagg tggacaagaa agttgagccc    300
aaatcttgt                                                            309
```

```
<210> SEQ ID NO 140
<211> LENGTH: 103
<212> TYPE: PRT
<213> ORGANISM: Artificial Sequence
<220> FEATURE:
<223> OTHER INFORMATION: Human IgG1 CH1 region

<400> SEQUENCE: 140

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys
            100
```

```
<210> SEQ ID NO 141
<211> LENGTH: 5367
<212> TYPE: DNA
<213> ORGANISM: Artificial Sequence
<220> FEATURE:
<223> OTHER INFORMATION: pYD19 plasmid

<400> SEQUENCE: 141
cttgagccgg cggatggtcg aggtgaggtg tggcaggctt gagatccagc tgttggggtg    60
agtactccct ctcaaaagcg ggcattactt ctgcgctaag attgtcagtt ccaaaaacg    120 aggaggattt gatattcacc tggcccgatc tggccataca cttgagtgac aatgacatcc    180
actttgcctt tctctccaca ggtgtccact cccaggtcca gtttgccgc caccatggag     240 acagacacac tcctgctatg ggtactgctg ctctgggttc caggttccac tggcggagac    300
ggagcttacg ggcccatcgg tcttccccct ggcgccctgc tccaggagca cctccgagag    360
cacagcggcc ctgggctgcc tggtcaagga ctacttcccc gaaccggtga cggtgtcgtg    420
gaactcaggc gctctgacca gcggcgtgca ccttccca gctgtcctac agtcctcagg     480
actctactcc ctcagcagcg tggtgaccgt gccctccagc aacttcggca cccagaccta    540
cacctgcaac gtagatcaca agcccagcaa caccaaggtg gacaagacag ttgagcgcaa    600
atgttgtgtc gagtgcccac cgtgcccagc caccctgtg gcaggaccgt cagtcttcct     660 cttccccca aaacccaagg acaccctcat gatctcccgg acccctgagg tcacgtgcgt    720
ggtggtggac gtgagccacg aagacccga ggtccagttc aactggtacg tggacggcgt     780
ggaggtgcat aatgccaaga caaagccacg ggaggagcag ttcaacagca cgttccgtgt    840
```

```
ggtcagcgtc ctcaccgttg tgcaccagga ctggctgaac ggcaaggagt acaagtgcaa      900
ggtctccaac aaaggcctcc cagcccccat cgagaaaacc atctccaaaa ccaaagggca      960
gccccgagaa ccacaggtgt acaccctgcc cccatcccgg gaggagatga ccaagaacca     1020
ggtcagcctg acctgcctgg tcaaaggctt ctaccccagc gacatcgccg tggagtggga     1080
gagcaatggg cagccggaga caactacaa gaccacacct cccatgctgg actccgacgg     1140
ctccttcttc ctctacagca agctcaccgt ggacaagagc aggtggcagc aggggaacgt     1200
cttctcatgc tccgtgatgc atgaggctct gcacaaccac tacacgcaga gagcctctc      1260
cctgtctccc gggaaatgat cccccgacct cgacctctgg ctaataaagg aaatttattt     1320
tcattgcaat agtgtgttgg aattttttgt gtctctcact cggaaggaca tatgggaggg     1380
caaatcattt ggtcgagatc cctcggagat ctctagctag agccccgccg ccggacgaac     1440
taaacctgac tacggcatct ctgccccttc ttcgcggggc agtgcatgta atcccttcag     1500
ttggttggta caacttgcca actgaaccct aaacgggtag catatgcttc ccgggtagta     1560
gtatatacta tccagactaa ccctaattca atagcatatg ttacccaacg ggaagcatat     1620
gctatcgaat tagggttagt aaaagggtcc taaggaacag cgatgtaggt gggcgggcca     1680
agataggggc gcgattgctg cgatctggag gacaaattac acacacttgc gcctgagcgc     1740
caagcacagg gttgttggtc ctcatattca cgaggtcgct gagagcacgg tgggctaatg     1800
ttgccatggg tagcatatac tacccaaata tctggatagc atatgctatc ctaatctata     1860
tctgggtagc ataggctatc ctaatctata tctgggtagc atatgctatc ctaatctata     1920
tctgggtagt atatgctatc ctaatttata tctgggtagc ataggctatc ctaatctata     1980
tctgggtagc atatgctatc ctaatctata tctgggtagt atatgctatc ctaatctgta     2040
tccgggtagc atatgctatc ctaatagaga ttagggtagt atatgctatc ctaatttata     2100
tctgggtagc atatactacc caaatatctg gatagcatat gctatcctaa tctatatctg     2160
ggtagcatat gctatcctaa tctatatctg ggtagcatag gctatcctaa tctatatctg     2220
ggtagcatat gctatcctaa tctatatctg ggtagtatat gctatcctaa tttatatctg     2280
ggtagcatag gctatcctaa tctatatctg ggtagcatat gctatcctaa tctatatctg     2340
ggtagtatat gctatcctaa tctgtatccg ggtagcatat gctatcctca cgatgataag     2400
ctgtcaaaca tgagaattaa ttcttgaaga cgaaagggcc tcgtgatacg cctattttta     2460
taggttaatg tcatgataat aatggttttct tagacgtcag gtggcacttt tcggggaaat     2520
gtgcgcggaa cccctatttg tttatttttc taaatacatt caaatatgta tccgctcatg     2580
agacaataac cctgataaat gcttcaataa tattgaaaaa ggaagagtat gagtattcaa     2640
catttccgtg tcgcccttat tccctttttt gcggcatttt gccttcctgt ttttgctcac     2700
ccagaaacgc tggtgaaagt aaaagatgct gaagatcagt tgggtgcacg agtgggttac     2760
atcgaactgg atctcaacag cggtaagatc cttgagagtt ttcgccccga agaacgtttt     2820
ccaatgatga gcacttttaa agttctgcta tgtggcgcgg tattatcccg tgttgacgcc     2880
gggcaagagc aactcggtcg ccgcatacac tattctcaga atgacttggt tgagtactca     2940
ccagtcacag aaaagcatct tacggatggc atgacagtaa gagaattatg cagtgctgcc     3000
ataaccatga gtgataacac tgcggccaac ttacttctga caacgatcgg aggaccgaag     3060
gagctaaccg cttttttgca caacatgggg gatcatgtaa ctcgccttga tcgttgggaa     3120
ccggagctga atgaagccat accaaacgac gagcgtgaca ccacgatgcc tgcagcaatg     3180
gcaacaacgt tgcgcaaact attaactggc gaactactta ctctagcttc ccggcaacaa     3240
```

```
ttaatagact ggatggaggc ggataaagtt gcaggaccac ttctgcgctc ggcccttccg    3300
gctggctggt ttattgctga taaatctgga gccggtgagc gtgggtctcg cggtatcatt    3360
gcagcactgg ggccagatgg taagccctcc cgtatcgtag ttatctacac gacggggagt    3420
caggcaacta tggatgaacg aaatagacag atcgctgaga taggtgcctc actgattaag    3480
cattggtaac tgtcagacca agtttactca tatatacttt agattgattt aaaacttcat    3540
tttaattta aaaggatcta ggtgaagatc cttttgata atctcatgac caaatccct      3600
taacgtgagt tttcgttcca ctgagcgtca gaccccgtag aaaagatcaa aggatcttct    3660
tgagatcctt tttttctgcg cgtaatctgc tgcttgcaaa caaaaaaacc accgctacca    3720
gcggtggttt gtttgccgga tcaagagcta ccaactcttt ttccgaaggt aactggcttc    3780
agcagagcgc agataccaaa tactgtcctt ctagtgtagc cgtagttagg ccaccacttc    3840
aagaactctg tagcaccgcc tacatacctc gctctgctaa tcctgttacc agtggctgct    3900
gccagtggcg ataagtcgtg tcttaccggg ttggactcaa gacgatagtt accggataag    3960
gcgcagcggt cgggctgaac ggggggttcg tgcacacagc ccagcttgga gcgaacgacc    4020
tacaccgaac tgagatacct acagcgtgag cattgagaaa gcgccacgct tcccgaaggg    4080
agaaaggcgg acaggtatcc ggtaagcggc agggtcggaa caggagagcg cacgagggag    4140
cttccagggg gaaacgcctg gtatctttat agtcctgtcg ggtttcgcca cctctgactt    4200
gagcgtcgat ttttgtgatg ctcgtcaggg gggcggagcc tatggaaaaa cgccagcaac    4260
gcggcctttt tacggttcct ggccttttgc tggccttttg ctcacatgtt ctttcctgcg    4320
ttatcccctg attctgtgga taaccgtatt accgcctttg agtgagctga taccgctcgc    4380
cgcagccgaa cgaccgagcg cagcgagtca gtgagcgagg aagcgtacat ttatattggc    4440
tcatgtccaa tatgaccgcc atgttgacat tgattattga ctagttatta atagtaatca    4500
attacgggt cattagttca tagcccatat atggagttcc gcgttacata acttacggta    4560
aatggcccgc ctggctgacc gcccaacgac ccccgcccat tgacgtcaat aatgacgtat    4620
gttcccatag taacgccaat agggactttc cattgacgtc aatgggtgga gtatttacgg    4680
taaactgccc acttggcagt acatcaagtg tatcatatgc caagtccgcc cctattgac    4740
gtcaatgacg gtaaatggcc cgcctggcat tatgcccagt acatgacctt acgggacttt    4800
cctacttggc agtacatcta cgtattagtc atcgctatta ccatggtgat gcggttttgg    4860
cagtacacca atgggcgtgg atagcggttt gactcacggg gatttccaag tctccacccc    4920
attgacgtca atgggagttt gttttggcac caaaatcaac gggactttcc aaaatgtcgt    4980
aataaccccg ccccgttgac gcaaatgggc ggtaggcgtg tacggtggga ggtctatata    5040
agcagagctc gtttagtgaa ccgtcagatc ctcactctct tccgcatcgc tgtctgcgag    5100
ggccagctgt tgggctcgcg gttgaggaca aactcttcgc ggtctttcca gtactcttgg    5160
atcggaaacc cgtcggcctc cgaacggtac tccgccaccg agggacctga gcgagtccgc    5220
atcgaccgga tcggaaaacc tctcgagaaa ggcgtctaac cagtcacagt cgcaaggtag    5280
gctgagcacc gtggcgggcg gcagcgggtg cggtcgggg ttgtttctgg cggaggtgct    5340
gctgatgatg taattaaagt aggcggt                                       5367

<210> SEQ ID NO 142
<211> LENGTH: 43
<212> TYPE: DNA
<213> ORGANISM: Artificial Sequence
<220> FEATURE:
<223> OTHER INFORMATION: chemically synthesized oligonucleotide
```

-continued

<400> SEQUENCE: 142
gggttccagg ttccactggc gaggtccagc tgcaacaatc tgg                    43

<210> SEQ ID NO 143
<211> LENGTH: 43
<212> TYPE: DNA
<213> ORGANISM: Artificial Sequence
<220> FEATURE:
<223> OTHER INFORMATION: chemically synthesized oligonucleotide

<400> SEQUENCE: 143
gggttccagg ttccactggc caggtccaag tgcagcagcc tgg                    43

<210> SEQ ID NO 144
<211> LENGTH: 43
<212> TYPE: DNA
<213> ORGANISM: Artificial Sequence
<220> FEATURE:
<223> OTHER INFORMATION: chemically synthesized oligonucleotide

<400> SEQUENCE: 144
gggttccagg ttccactggc gagatccagc tgcagcagtc tgg                    43

<210> SEQ ID NO 145
<211> LENGTH: 43
<212> TYPE: DNA
<213> ORGANISM: Artificial Sequence
<220> FEATURE:
<223> OTHER INFORMATION: chemically synthesized oligonucleotide

<400> SEQUENCE: 145
gggttccagg ttccactggc gaagtgaagc ttgaggagtc tgg                    43

<210> SEQ ID NO 146
<211> LENGTH: 43
<212> TYPE: DNA
<213> ORGANISM: Artificial Sequence
<220> FEATURE:
<223> OTHER INFORMATION: chemically synthesized oligonucleotide

<400> SEQUENCE: 146
gggttccagg ttccactggc caggtccaac tgcagcagcc tgg                    43

<210> SEQ ID NO 147
<211> LENGTH: 38
<212> TYPE: DNA
<213> ORGANISM: Artificial Sequence
<220> FEATURE:
<223> OTHER INFORMATION: chemically synthesized oligonucleotide

<400> SEQUENCE: 147
ggggccaggg gaaagacaga tgggcccttc gttgaggc                          38

<210> SEQ ID NO 148
<211> LENGTH: 16
<212> TYPE: PRT
<213> ORGANISM: Artificial Sequence
<220> FEATURE:
<223> OTHER INFORMATION: CDRL1 consensus
<220> FEATURE:
<221> NAME/KEY: MISC_FEATURE
<222> LOCATION: (3)..(3)
<223> OTHER INFORMATION: Xaa is a neutral hydrophilic amino acid
<220> FEATURE:
<221> NAME/KEY: MISC_FEATURE
<222> LOCATION: (4)..(4)
<223> OTHER INFORMATION: Xaa is lysine or glutamic acid
<220> FEATURE:

```
<221> NAME/KEY: MISC_FEATURE
<222> LOCATION: (12)..(12)
<223> OTHER INFORMATION: Xaa is an hydrophobic amino acid or asparagine

<400> SEQUENCE: 148

Arg Ser Xaa Xaa Ser Leu Leu His Ser Asn Gly Xaa Thr Tyr Leu Tyr
1               5                   10                  15

<210> SEQ ID NO 149
<211> LENGTH: 7
<212> TYPE: PRT
<213> ORGANISM: Artificial Sequence
<220> FEATURE:
<223> OTHER INFORMATION: CDRL2 consensus
<220> FEATURE:
<221> NAME/KEY: MISC_FEATURE
<222> LOCATION: (1)..(1)
<223> OTHER INFORMATION: Xaa is a basic amino acid

<400> SEQUENCE: 149

Xaa Met Ser Asn Leu Ala Ser
1               5

<210> SEQ ID NO 150
<211> LENGTH: 7
<212> TYPE: PRT
<213> ORGANISM: Artificial Sequence
<220> FEATURE:
<223> OTHER INFORMATION: CDRL2 consensus
<220> FEATURE:
<221> NAME/KEY: MISC_FEATURE
<222> LOCATION: (2)..(2)
<223> OTHER INFORMATION: Xaa is methionine or threonine
<220> FEATURE:
<221> NAME/KEY: MISC_FEATURE
<222> LOCATION: (6)..(6)
<223> OTHER INFORMATION: Xaa is an hydrophobic amino acid

<400> SEQUENCE: 150

Arg Xaa Ser Asn Leu Xaa Ser
1               5

<210> SEQ ID NO 151
<211> LENGTH: 9
<212> TYPE: PRT
<213> ORGANISM: Artificial Sequence
<220> FEATURE:
<223> OTHER INFORMATION: CDRL3 consensus
<220> FEATURE:
<221> NAME/KEY: MISC_FEATURE
<222> LOCATION: (1)..(1)
<223> OTHER INFORMATION: Xaa is an hydrophobic amino acid
<220> FEATURE:
<221> NAME/KEY: MISC_FEATURE
<222> LOCATION: (3)..(3)
<223> OTHER INFORMATION: Xaa is a basic amino acid
<220> FEATURE:
<221> NAME/KEY: MISC_FEATURE
<222> LOCATION: (6)..(6)
<223> OTHER INFORMATION: Xaa is tyrosine or leucine
<220> FEATURE:
<221> NAME/KEY: MISC_FEATURE
<222> LOCATION: (8)..(8)
<223> OTHER INFORMATION: Xaa is an aromatic amino acid

<400> SEQUENCE: 151

Xaa Gln Xaa Leu Glu Xaa Pro Xaa Thr
1               5

<210> SEQ ID NO 152
<211> LENGTH: 9
<212> TYPE: PRT
```

```
<213> ORGANISM: Artificial Sequence
<220> FEATURE:
<223> OTHER INFORMATION: CDRL3 consensus
<220> FEATURE:
<221> NAME/KEY: MISC_FEATURE
<222> LOCATION: (8)..(8)
<223> OTHER INFORMATION: Xaa is proline or leucine

<400> SEQUENCE: 152

Gln Gln Trp Ser Ser Asn Pro Xaa Thr
1               5

<210> SEQ ID NO 153
<211> LENGTH: 10
<212> TYPE: PRT
<213> ORGANISM: Artificial Sequence
<220> FEATURE:
<223> OTHER INFORMATION: CDRH1 consensus
<220> FEATURE:
<221> NAME/KEY: MISC_FEATURE
<222> LOCATION: (5)..(5)
<223> OTHER INFORMATION: Xaa is threonine or asparagine
<220> FEATURE:
<221> NAME/KEY: MISC_FEATURE
<222> LOCATION: (6)..(6)
<223> OTHER INFORMATION: Xaa is threonine, arginine, serine or aspartic
      acid
<220> FEATURE:
<221> NAME/KEY: MISC_FEATURE
<222> LOCATION: (8)..(8)
<223> OTHER INFORMATION: Xaa is tryptophan, asparagine, aspartic acid or
      glutamic acid
<220> FEATURE:
<221> NAME/KEY: MISC_FEATURE
<222> LOCATION: (10)..(10)
<223> OTHER INFORMATION: Xaa is tyrosine, histidine or aspartic acid

<400> SEQUENCE: 153

Gly Tyr Thr Phe Xaa Xaa Tyr Xaa Met Xaa
1               5                   10

<210> SEQ ID NO 154
<211> LENGTH: 10
<212> TYPE: PRT
<213> ORGANISM: Artificial Sequence
<220> FEATURE:
<223> OTHER INFORMATION: CDRH1 consensus
<220> FEATURE:
<221> NAME/KEY: MISC_FEATURE
<222> LOCATION: (8)..(8)
<223> OTHER INFORMATION: Xaa is an acidic amino acid

<400> SEQUENCE: 154

Gly Tyr Thr Phe Thr Asp Tyr Xaa Met His
1               5                   10

<210> SEQ ID NO 155
<211> LENGTH: 10
<212> TYPE: PRT
<213> ORGANISM: Artificial Sequence
<220> FEATURE:
<223> OTHER INFORMATION: CDRH2 consensus
<220> FEATURE:
<221> NAME/KEY: MISC_FEATURE
<222> LOCATION: (5)..(5)
<223> OTHER INFORMATION: Xaa is a neutral hydrophilic amino acid
<220> FEATURE:
<221> NAME/KEY: MISC_FEATURE
<222> LOCATION: (7)..(7)
<223> OTHER INFORMATION: Xaa is alanine or glycine
<220> FEATURE:
<221> NAME/KEY: MISC_FEATURE
<222> LOCATION: (9)..(9)
<223> OTHER INFORMATION: Xaa is proline or threonine
```

```
<400> SEQUENCE: 155

Leu Ile Asn Pro Xaa Asn Xaa Arg Xaa Asn
1               5                   10

<210> SEQ ID NO 156
<211> LENGTH: 10
<212> TYPE: PRT
<213> ORGANISM: Artificial Sequence
<220> FEATURE:
<223> OTHER INFORMATION: CDRH2 consensus
<220> FEATURE:
<221> NAME/KEY: MISC_FEATURE
<222> LOCATION: (1)..(1)
<223> OTHER INFORMATION: Xaa is alanine or threonine

<400> SEQUENCE: 156

Xaa Ile Asp Pro Glu Thr Gly Gly Thr Ala
1               5                   10

<210> SEQ ID NO 157
<211> LENGTH: 10
<212> TYPE: PRT
<213> ORGANISM: Artificial Sequence
<220> FEATURE:
<223> OTHER INFORMATION: CDRH2 consensus
<220> FEATURE:
<221> NAME/KEY: MISC_FEATURE
<222> LOCATION: (3)..(3)
<223> OTHER INFORMATION: Xaa is aspartic acid or asparagine
<220> FEATURE:
<221> NAME/KEY: MISC_FEATURE
<222> LOCATION: (5)..(5)
<223> OTHER INFORMATION: Xaa is aspartic acid or serine
<220> FEATURE:
<221> NAME/KEY: MISC_FEATURE
<222> LOCATION: (6)..(6)
<223> OTHER INFORMATION: Xaa is aspartic acid or serine
<220> FEATURE:
<221> NAME/KEY: MISC_FEATURE
<222> LOCATION: (8)..(8)
<223> OTHER INFORMATION: Xaa is tyrosine or threonine
<220> FEATURE:
<221> NAME/KEY: MISC_FEATURE
<222> LOCATION: (9)..(9)
<223> OTHER INFORMATION: Xaa is threonine or isoleucine

<400> SEQUENCE: 157

Glu Ile Xaa Pro Xaa Xaa Ser Xaa Xaa Asn
1               5                   10

<210> SEQ ID NO 158
<211> LENGTH: 16
<212> TYPE: PRT
<213> ORGANISM: Artificial Sequence
<220> FEATURE:
<223> OTHER INFORMATION: CDRH3 consensus
<220> FEATURE:
<221> NAME/KEY: MISC_FEATURE
<222> LOCATION: (2)..(2)
<223> OTHER INFORMATION: Xaa is a neutral hydrophilic amino acid
<220> FEATURE:
<221> NAME/KEY: MISC_FEATURE
<222> LOCATION: (6)..(6)
<223> OTHER INFORMATION: Xaa is a neutral hydrophilic amino acid
<220> FEATURE:
<221> NAME/KEY: MISC_FEATURE
<222> LOCATION: (7)..(7)
<223> OTHER INFORMATION: Xaa is tyrosine or histidine
<220> FEATURE:
<221> NAME/KEY: MISC_FEATURE
<222> LOCATION: (8)..(8)
<223> OTHER INFORMATION: Xaa is tyrosine or serine
```

<400> SEQUENCE: 158

Thr Xaa Phe Tyr Tyr Xaa Xaa Xaa Asn Tyr Asp Val Gly Phe Ala Tyr
1               5                   10                  15

<210> SEQ ID NO 159
<211> LENGTH: 35
<212> TYPE: DNA
<213> ORGANISM: Artificial Sequence
<220> FEATURE:
<223> OTHER INFORMATION: chemically synthesized oligonucleotide

<400> SEQUENCE: 159
gtaagcgaat tcatggtgaa aactagaaga gacgc                             35

<210> SEQ ID NO 160
<211> LENGTH: 34
<212> TYPE: DNA
<213> ORGANISM: Artificial Sequence
<220> FEATURE:
<223> OTHER INFORMATION: chemically synthesized oligonucleotide

<400> SEQUENCE: 160
gtaagcaagc ttttagccgt ggaagcggaa cagg                              34

<210> SEQ ID NO 161
<211> LENGTH: 321
<212> TYPE: DNA
<213> ORGANISM: Artificial Sequence
<220> FEATURE:
<223> OTHER INFORMATION: 25B02 light chain variable region cDNA

<400> SEQUENCE: 161
aacatccaga tgacccagtc tccagcctcc ctatctgcat ctgtgggaga aactgtcacc    60
atcacatgtc gagcaagtga gaatatttac agttatttag catggtatca acagaagcag   120
ggaaaatctc ctcagctcct ggtctataat gcaaaaacct taccagaagg tgtgtcagta   180
aggttcagtg gcagtggatc aggcacacag ttttctctga agatcaacaa cctgcagcct   240
gaagattttg ggagttatca ctgtcaacat cattatggtg ttcctcttac gttcggttct   300
gggaccaagc tggagttgaa a                                            321

<210> SEQ ID NO 162
<211> LENGTH: 107
<212> TYPE: PRT
<213> ORGANISM: Artificial Sequence
<220> FEATURE:
<223> OTHER INFORMATION: 25B02 light chain variable region amino acid
      sequence

<400> SEQUENCE: 162

Asn Ile Gln Met Thr Gln Ser Pro Ala Ser Leu Ser Ala Ser Val Gly
1               5                   10                  15

Glu Thr Val Thr Ile Thr Cys Arg Ala Ser Glu Asn Ile Tyr Ser Tyr
                20                  25                  30

Leu Ala Trp Tyr Gln Gln Lys Gln Gly Lys Ser Pro Gln Leu Leu Val
            35                  40                  45

Tyr Asn Ala Lys Thr Leu Pro Glu Gly Val Ser Val Arg Phe Ser Gly
        50                  55                  60

Ser Gly Ser Gly Thr Gln Phe Ser Leu Lys Ile Asn Asn Leu Gln Pro
65                  70                  75                  80

Glu Asp Phe Gly Ser Tyr His Cys Gln His Tyr Gly Val Pro Leu
                85                  90                  95

Thr Phe Gly Ser Gly Thr Lys Leu Glu Leu Lys
            100                 105

<210> SEQ ID NO 163
<211> LENGTH: 360
<212> TYPE: DNA
<213> ORGANISM: Artificial Sequence
<220> FEATURE:
<223> OTHER INFORMATION: 25B02 heavy chain variable region cDNA

<400> SEQUENCE: 163
caggtgaagc ttcagcagtc cggggctgag ctggcaagac ctggggcttc agtgaagttt     60
tcctgcaagg cttctggcta caccttcact aggaactgga tacagtgggt aaaacagagg    120
cctggacagg gtctggaatg gattggggct atttatcctg gaaatggtga tagtaggtat    180
actcagaagt tcaagggcaa ggccacattg actgcagata atcctcgaa cacagcctac     240 atgcaactca gcggtttggc atctgaggac tctgcggtct attactgtgc aagattggct    300
ggtaactacg cttactactt tgactactgg ggccaaggca ccgctctcac agtctcctca    360

<210> SEQ ID NO 164
<211> LENGTH: 120
<212> TYPE: PRT
<213> ORGANISM: Artificial Sequence
<220> FEATURE:
<223> OTHER INFORMATION: 25B02 heavy chain variable region amino acid
      sequence

<400> SEQUENCE: 164

Gln Val Lys Leu Gln Gln Ser Gly Ala Glu Leu Ala Arg Pro Gly Ala
1               5                   10                  15

Ser Val Lys Phe Ser Cys Lys Ala Ser Gly Tyr Thr Phe Thr Arg Asn
            20                  25                  30

Trp Ile Gln Trp Val Lys Gln Arg Pro Gly Gln Gly Leu Glu Trp Ile
        35                  40                  45

Gly Ala Ile Tyr Pro Gly Asn Gly Asp Ser Arg Tyr Thr Gln Lys Phe
    50                  55                  60

Lys Gly Lys Ala Thr Leu Thr Ala Asp Lys Ser Ser Asn Thr Ala Tyr
65                  70                  75                  80

Met Gln Leu Ser Gly Leu Ala Ser Glu Asp Ser Ala Val Tyr Tyr Cys
                85                  90                  95

Ala Arg Leu Ala Gly Asn Tyr Ala Tyr Tyr Phe Asp Tyr Trp Gly Gln
            100                 105                 110

Gly Thr Ala Leu Thr Val Ser Ser
        115                 120

<210> SEQ ID NO 165
<211> LENGTH: 321
<212> TYPE: DNA
<213> ORGANISM: Artificial Sequence
<220> FEATURE:
<223> OTHER INFORMATION: 25D11 light chain variable region cDNA

<400> SEQUENCE: 165
gacatccaga tgacccagtc tccagcctcc ctatctgcat ctgtgggaga aactgtcacc     60
atcacatgtc gagcaagtgg gaatattcac aattatttag catggtatca acagaagcag    120
ggaaaatctc ctcagctcct ggtctataat gcaaaaacct taccagaagg tgtgtcagta    180
aggttcagtg gcagtggatc aggcacacag ttttctctga agatcaacaa cctgcagcct    240
gaagattttg ggagttatca ctgtcaacat cattatggtg ttcctcttac gttcggttct    300

-continued gggaccaagc tggagttgaa a                                                  321

<210> SEQ ID NO 166
<211> LENGTH: 107
<212> TYPE: PRT
<213> ORGANISM: Artificial Sequence
<220> FEATURE:
<223> OTHER INFORMATION: 25D11 light chain variable region amino acid
      sequence

<400> SEQUENCE: 166

Asp Ile Gln Met Thr Gln Ser Pro Ala Ser Leu Ser Ala Ser Val Gly
1               5                   10                  15

Glu Thr Val Thr Ile Thr Cys Arg Ala Ser Gly Asn Ile His Asn Tyr
            20                  25                  30

Leu Ala Trp Tyr Gln Gln Lys Gln Gly Lys Ser Pro Gln Leu Leu Val
        35                  40                  45

Tyr Asn Ala Lys Thr Leu Pro Glu Gly Val Ser Val Arg Phe Ser Gly
50                  55                  60

Ser Gly Ser Gly Thr Gln Phe Ser Leu Lys Ile Asn Asn Leu Gln Pro
65                  70                  75                  80

Glu Asp Phe Gly Ser Tyr His Cys Gln His His Tyr Gly Val Pro Leu
                85                  90                  95

Thr Phe Gly Ser Gly Thr Lys Leu Glu Leu Lys
            100                 105

<210> SEQ ID NO 167
<211> LENGTH: 360
<212> TYPE: DNA
<213> ORGANISM: Artificial Sequence
<220> FEATURE:
<223> OTHER INFORMATION: 25D11 heavy chain variable region cDNA

<400> SEQUENCE: 167
caggtgaagc ttcagcagtc cggggctgag ctggcaagac ctggggcttc agtgaagttt      60
tcctgcaagg cttctggcta caccttcact aggaactgga tacagtgggt aaaacagagg     120
cctggacagg gtctggaatg gattggggct atttatcctg gaaatggtga tagtaggtat     180
actcagaagt tcaagggcaa ggccacattg actgcagata atcctcgaaa cacagcctac     240
atgcaactca gcggtttggc atctgaggac tctgcggtct attactgtgc aagattggct     300
ggtaactacg cttactactt tgactactgg ggccaaggca ccgctctcac agtctcctca     360

<210> SEQ ID NO 168
<211> LENGTH: 120
<212> TYPE: PRT
<213> ORGANISM: Artificial Sequence
<220> FEATURE:
<223> OTHER INFORMATION: 25D11 heavy chain variable region amino acid
      sequence

<400> SEQUENCE: 168

Gln Val Lys Leu Gln Gln Ser Gly Ala Glu Leu Ala Arg Pro Gly Ala
1               5                   10                  15

Ser Val Lys Phe Ser Cys Lys Ala Ser Gly Tyr Thr Phe Thr Arg Asn
            20                  25                  30

Trp Ile Gln Trp Val Lys Gln Arg Pro Gly Gln Gly Leu Glu Trp Ile
        35                  40                  45

Gly Ala Ile Tyr Pro Gly Asn Gly Asp Ser Arg Tyr Thr Gln Lys Phe
50                  55                  60

Lys Gly Lys Ala Thr Leu Thr Ala Asp Lys Ser Ser Asn Thr Ala Tyr

```
                65                  70                  75                  80
Met Gln Leu Ser Gly Leu Ala Ser Glu Asp Ser Ala Val Tyr Tyr Cys
                    85                  90                  95

Ala Arg Leu Ala Gly Asn Tyr Ala Tyr Tyr Phe Asp Tyr Trp Gly Gln
                    100                 105                 110

Gly Thr Ala Leu Thr Val Ser Ser
                    115                 120

<210> SEQ ID NO 169
<211> LENGTH: 321
<212> TYPE: DNA
<213> ORGANISM: Artificial Sequence
<220> FEATURE:
<223> OTHER INFORMATION: 25E10 light chain variable region cDNA

<400> SEQUENCE: 169
gacatccaga tgacccagtc tccagcctcc ctatctgcat ctgtgggaga aactgtcacc        60
atcacatgtc gagcaagtgg gaatattcac aattatttag catggtatca gcagaaacag      120
ggaaaatctc ctcagctcct ggtctataat gcaaaaaccc tagcagatgg tgtgccatca      180
aggttcagtg gcagtggatc aggaacacaa tattctctca agatcaacag cctgcagcct      240
gaagattttg ggagttatta ctgtcaacat cattacggtg ctcctcttac gttcggtgct      300
gggaccaagg tggagctgaa a                                                 321

<210> SEQ ID NO 170
<211> LENGTH: 107
<212> TYPE: PRT
<213> ORGANISM: Artificial Sequence
<220> FEATURE:
<223> OTHER INFORMATION: 25E10 light chain variable region amino acid
      sequence

<400> SEQUENCE: 170

Asp Ile Gln Met Thr Gln Ser Pro Ala Ser Leu Ser Ala Ser Val Gly
1               5                   10                  15

Glu Thr Val Thr Ile Thr Cys Arg Ala Ser Gly Asn Ile His Asn Tyr
                20                  25                  30

Leu Ala Trp Tyr Gln Gln Lys Gln Gly Lys Ser Pro Gln Leu Leu Val
            35                  40                  45

Tyr Asn Ala Lys Thr Leu Ala Asp Gly Val Pro Ser Arg Phe Ser Gly
        50                  55                  60

Ser Gly Ser Gly Thr Gln Tyr Ser Leu Lys Ile Asn Ser Leu Gln Pro
65                  70                  75                  80

Glu Asp Phe Gly Ser Tyr Tyr Cys Gln His His Tyr Gly Ala Pro Leu
                85                  90                  95

Thr Phe Gly Ala Gly Thr Lys Val Glu Leu Lys
                100                 105

<210> SEQ ID NO 171
<211> LENGTH: 360
<212> TYPE: DNA
<213> ORGANISM: Artificial Sequence
<220> FEATURE:
<223> OTHER INFORMATION: 25E10 heavy chain variable region cDNA

<400> SEQUENCE: 171
gatgtgcagc tgcaacaatc tggggctgag ctggcaagac ctggggcttc agtgaagttt        60
tcctgcaagg cttctggcta cacctttact aggaactgga tacagtgggt taaacagagg      120
cctggacagg gtctggaatg gattggggct gtttatcctg gaaatggtga tagtaggtat      180
```

```
actcagaagt tcaagggcaa ggccacattg actgcagata atcctccag cacagcctac    240 atgcaactca acagtttgtc atctgaggac tctgcggtct attactgcgc aagattggct    300
ggtaactacg cttactactt tgactactgg ggccaaggca ccgctctcac agtctcctca    360
```

<210> SEQ ID NO 172
<211> LENGTH: 120
<212> TYPE: PRT
<213> ORGANISM: Artificial Sequence
<220> FEATURE:
<223> OTHER INFORMATION: 25E10 heavy chain variable region amino acid
      sequence

<400> SEQUENCE: 172

Asp Val Gln Leu Gln Gln Ser Gly Ala Glu Leu Ala Arg Pro Gly Ala
1               5                   10                  15

Ser Val Lys Phe Ser Cys Lys Ala Ser Gly Tyr Thr Phe Thr Arg Asn
            20                  25                  30

Trp Ile Gln Trp Val Lys Gln Arg Pro Gly Gln Gly Leu Glu Trp Ile
        35                  40                  45

Gly Ala Val Tyr Pro Gly Asn Gly Asp Ser Arg Tyr Thr Gln Lys Phe
    50                  55                  60

Lys Gly Lys Ala Thr Leu Thr Ala Asp Lys Ser Ser Ser Thr Ala Tyr
65                  70                  75                  80

Met Gln Leu Asn Ser Leu Ser Ser Glu Asp Ser Ala Val Tyr Tyr Cys
                85                  90                  95

Ala Arg Leu Ala Gly Asn Tyr Ala Tyr Tyr Phe Asp Tyr Trp Gly Gln
            100                 105                 110

Gly Thr Ala Leu Thr Val Ser Ser
        115                 120

<210> SEQ ID NO 173
<211> LENGTH: 11
<212> TYPE: PRT
<213> ORGANISM: Artificial Sequence
<220> FEATURE:
<223> OTHER INFORMATION: 25B02 light chain CDR1

<400> SEQUENCE: 173

Arg Ala Ser Glu Asn Ile Tyr Ser Tyr Leu Ala
1               5                   10

<210> SEQ ID NO 174
<211> LENGTH: 7
<212> TYPE: PRT
<213> ORGANISM: Artificial Sequence
<220> FEATURE:
<223> OTHER INFORMATION: 25B02 light chain CDR2

<400> SEQUENCE: 174

Asn Ala Lys Thr Leu Pro Glu
1               5

<210> SEQ ID NO 175
<211> LENGTH: 9
<212> TYPE: PRT
<213> ORGANISM: Artificial Sequence
<220> FEATURE:
<223> OTHER INFORMATION: 25B02 light chain CDR3

<400> SEQUENCE: 175

Gln His His Tyr Gly Val Pro Leu Thr
1               5

```
<210> SEQ ID NO 176
<211> LENGTH: 10
<212> TYPE: PRT
<213> ORGANISM: Artificial Sequence
<220> FEATURE:
<223> OTHER INFORMATION: 25B02 heavy chain CDR1

<400> SEQUENCE: 176

Gly Tyr Thr Phe Thr Arg Asn Trp Ile Gln
1               5                   10

<210> SEQ ID NO 177
<211> LENGTH: 10
<212> TYPE: PRT
<213> ORGANISM: Artificial Sequence
<220> FEATURE:
<223> OTHER INFORMATION: 25B02 heavy chain CDR2

<400> SEQUENCE: 177

Ala Ile Tyr Pro Gly Asn Gly Asp Ser Arg
1               5                   10

<210> SEQ ID NO 178
<211> LENGTH: 13
<212> TYPE: PRT
<213> ORGANISM: Artificial Sequence
<220> FEATURE:
<223> OTHER INFORMATION: 25B02 heavy chain CDR3

<400> SEQUENCE: 178

Ala Arg Leu Ala Gly Asn Tyr Ala Tyr Tyr Phe Asp Tyr
1               5                   10

<210> SEQ ID NO 179
<211> LENGTH: 11
<212> TYPE: PRT
<213> ORGANISM: Artificial Sequence
<220> FEATURE:
<223> OTHER INFORMATION: 25D11 light chain CDR1

<400> SEQUENCE: 179

Arg Ala Ser Gly Asn Ile His Asn Tyr Leu Ala
1               5                   10

<210> SEQ ID NO 180
<211> LENGTH: 7
<212> TYPE: PRT
<213> ORGANISM: Artificial Sequence
<220> FEATURE:
<223> OTHER INFORMATION: 25D11 light chain CDR2

<400> SEQUENCE: 180

Asn Ala Lys Thr Leu Pro Glu
1               5

<210> SEQ ID NO 181
<211> LENGTH: 9
<212> TYPE: PRT
<213> ORGANISM: Artificial Sequence
<220> FEATURE:
<223> OTHER INFORMATION: 25D11 light chain CDR3

<400> SEQUENCE: 181

Gln His His Tyr Gly Val Pro Leu Thr
1               5
```

```
<210> SEQ ID NO 182
<211> LENGTH: 10
<212> TYPE: PRT
<213> ORGANISM: Artificial Sequence
<220> FEATURE:
<223> OTHER INFORMATION: 25D11 heavy chain CDR1

<400> SEQUENCE: 182

Gly Tyr Thr Phe Thr Arg Asn Trp Ile Gln
1               5                   10

<210> SEQ ID NO 183
<211> LENGTH: 10
<212> TYPE: PRT
<213> ORGANISM: Artificial Sequence
<220> FEATURE:
<223> OTHER INFORMATION: 25D11 heavy chain CDR2

<400> SEQUENCE: 183

Ala Ile Tyr Pro Gly Asn Gly Asp Ser Arg
1               5                   10

<210> SEQ ID NO 184
<211> LENGTH: 13
<212> TYPE: PRT
<213> ORGANISM: Artificial Sequence
<220> FEATURE:
<223> OTHER INFORMATION: 25D11 heavy chain CDR3

<400> SEQUENCE: 184

Ala Arg Leu Ala Gly Asn Tyr Ala Tyr Tyr Phe Asp Tyr
1               5                   10

<210> SEQ ID NO 185
<211> LENGTH: 11
<212> TYPE: PRT
<213> ORGANISM: Artificial Sequence
<220> FEATURE:
<223> OTHER INFORMATION: 25E10 light chain CDR1

<400> SEQUENCE: 185

Arg Ala Ser Gly Asn Ile His Asn Tyr Leu Ala
1               5                   10

<210> SEQ ID NO 186
<211> LENGTH: 7
<212> TYPE: PRT
<213> ORGANISM: Artificial Sequence
<220> FEATURE:
<223> OTHER INFORMATION: 25E10 light chain CDR2

<400> SEQUENCE: 186

Asn Ala Lys Thr Leu Ala Asp
1               5

<210> SEQ ID NO 187
<211> LENGTH: 9
<212> TYPE: PRT
<213> ORGANISM: Artificial Sequence
<220> FEATURE:
<223> OTHER INFORMATION: 25E10 light chain CDR3

<400> SEQUENCE: 187

Gln His His Tyr Gly Ala Pro Leu Thr
1               5

<210> SEQ ID NO 188
<211> LENGTH: 10
```

```
<212> TYPE: PRT
<213> ORGANISM: Artificial Sequence
<220> FEATURE:
<223> OTHER INFORMATION: 25E10 heavy chain CDR1

<400> SEQUENCE: 188

Gly Tyr Thr Phe Thr Arg Asn Trp Ile Gln
1               5                   10

<210> SEQ ID NO 189
<211> LENGTH: 10
<212> TYPE: PRT
<213> ORGANISM: Artificial Sequence
<220> FEATURE:
<223> OTHER INFORMATION: 25E10 heavy chain CDR2

<400> SEQUENCE: 189

Ala Val Tyr Pro Gly Asn Gly Asp Ser Arg
1               5                   10

<210> SEQ ID NO 190
<211> LENGTH: 13
<212> TYPE: PRT
<213> ORGANISM: Artificial Sequence
<220> FEATURE:
<223> OTHER INFORMATION: 25E10 heavy chain CDR3

<400> SEQUENCE: 190

Ala Arg Leu Ala Gly Asn Tyr Ala Tyr Tyr Phe Asp Tyr
1               5                   10

<210> SEQ ID NO 191
<211> LENGTH: 118
<212> TYPE: PRT
<213> ORGANISM: Artificial Sequence
<220> FEATURE:
<223> OTHER INFORMATION: heavy chain variable region consensus
<220> FEATURE:
<221> NAME/KEY: MISC_FEATURE
<222> LOCATION: (1)..(1)
<223> OTHER INFORMATION: Xaa is Q or E
<220> FEATURE:
<221> NAME/KEY: MISC_FEATURE
<222> LOCATION: (2)..(2)
<223> OTHER INFORMATION: Xaa is any amino acid or a hydrophobic amino
      acid such as V or I
<220> FEATURE:
<221> NAME/KEY: MISC_FEATURE
<222> LOCATION: (4)..(4)
<223> OTHER INFORMATION: Xaa is any amino acid or a hydrophobic amino
      acid such as for example V or L
<220> FEATURE:
<221> NAME/KEY: MISC_FEATURE
<222> LOCATION: (7)..(7)
<223> OTHER INFORMATION: Xaa is any amino acid or for example P or S
<220> FEATURE:
<221> NAME/KEY: MISC_FEATURE
<222> LOCATION: (8)..(8)
<223> OTHER INFORMATION: Xaa is any amino acid or for example R or G
<220> FEATURE:
<221> NAME/KEY: MISC_FEATURE
<222> LOCATION: (9)..(9)
<223> OTHER INFORMATION: Xaa is any amino acid or for example A or T
<220> FEATURE:
<221> NAME/KEY: MISC_FEATURE
<222> LOCATION: (11)..(11)
<223> OTHER INFORMATION: Xaa is any amino acid or a hydrophobic amino
      acid such as for example L or I
<220> FEATURE:
<221> NAME/KEY: MISC_FEATURE
<222> LOCATION: (13)..(13)
<223> OTHER INFORMATION: Xaa is any amino acid or a basic amino acid
      such as for example R or K
<220> FEATURE:
```

```
<221> NAME/KEY: MISC_FEATURE
<222> LOCATION: (31)..(31)
<223> OTHER INFORMATION: Xaa is any amino acid or a neutral hydrophilic
      amino acid such as for example for example S or T
<220> FEATURE:
<221> NAME/KEY: MISC_FEATURE
<222> LOCATION: (54)..(54)
<223> OTHER INFORMATION: Xaa is any amino acid or a neutral hydrophilic
      amino acid such as for example T or S
<220> FEATURE:
<221> NAME/KEY: MISC_FEATURE
<222> LOCATION: (56)..(56)
<223> OTHER INFORMATION: Xaa is any amino acid or for example G or A
<220> FEATURE:
<221> NAME/KEY: MISC_FEATURE
<222> LOCATION: (58)..(58)
<223> OTHER INFORMATION: Xaa is any amino acid or for example P or T
<220> FEATURE:
<221> NAME/KEY: MISC_FEATURE
<222> LOCATION: (63)..(63)
<223> OTHER INFORMATION: Xaa is any amino acid or a basic amino acid
      such as for example K or R
<220> FEATURE:
<221> NAME/KEY: MISC_FEATURE
<222> LOCATION: (65)..(65)
<223> OTHER INFORMATION: Xaa is any amino acid or a basic amino acid
      such as for example N or K
<220> FEATURE:
<221> NAME/KEY: MISC_FEATURE
<222> LOCATION: (66)..(66)
<223> OTHER INFORMATION: Xaa is any amino acid or for example N or a
      neutral hydrophilic amino acid such as S or T
<220> FEATURE:
<221> NAME/KEY: MISC_FEATURE
<222> LOCATION: (82)..(82)
<223> OTHER INFORMATION: Xaa is any amino acid or a basic amino acid
      such as for example Q or H

<400> SEQUENCE: 191

Xaa Xaa Gln Xaa Gln Gln Xaa Xaa Xaa Glu Xaa Val Xaa Pro Gly Ala
 1               5                  10                  15

Ser Val Lys Leu Ser Cys Lys Ala Ser Gly Tyr Thr Phe Thr Xaa Tyr
             20                  25                  30

Trp Met His Trp Val Lys Gln Arg Pro Gly Gln Gly Leu Glu Trp Ile
         35                  40                  45

Gly Leu Ile Asn Pro Xaa Asn Xaa Arg Xaa Asn Tyr Asn Glu Xaa Phe
 50                  55                  60

Xaa Xaa Lys Ala Thr Leu Thr Val Asp Lys Ser Ser Ser Thr Ala Tyr
 65                  70                  75                  80

Met Xaa Leu Ser Ser Leu Thr Ser Glu Asp Ser Ala Val Tyr Tyr Cys
             85                  90                  95

Ala Arg Gly Gly Asp Gly Asp Tyr Phe Asp Tyr Trp Gly Gln Gly Thr
            100                 105                 110

Thr Leu Thr Val Ser Ser
            115

<210> SEQ ID NO 192
<211> LENGTH: 120
<212> TYPE: PRT
<213> ORGANISM: Artificial Sequence
<220> FEATURE:
<223> OTHER INFORMATION: heavy chain variable region consensus
<220> FEATURE:
<221> NAME/KEY: MISC_FEATURE
<222> LOCATION: (1)..(1)
<223> OTHER INFORMATION: Xaa is Q or D
<220> FEATURE:
<221> NAME/KEY: MISC_FEATURE
<222> LOCATION: (3)..(3)
<223> OTHER INFORMATION: Xaa is any amino acid or a basic amino acid
      such as for example K or Q
```

```
<220> FEATURE:
<221> NAME/KEY: MISC_FEATURE
<222> LOCATION: (51)..(51)
<223> OTHER INFORMATION: Xaa is any amino acid or a hydrophobic amino
      acid such as for example I or V
<220> FEATURE:
<221> NAME/KEY: MISC_FEATURE
<222> LOCATION: (77)..(77)
<223> OTHER INFORMATION: Xaa is any amino acid or for example S or N
<220> FEATURE:
<221> NAME/KEY: MISC_FEATURE
<222> LOCATION: (84)..(84)
<223> OTHER INFORMATION: Xaa is any amino acid or for example S or N
<220> FEATURE:
<221> NAME/KEY: MISC_FEATURE
<222> LOCATION: (85)..(85)
<223> OTHER INFORMATION: Xaa is any amino acid or for example G or S
<220> FEATURE:
<221> NAME/KEY: MISC_FEATURE
<222> LOCATION: (87)..(87)
<223> OTHER INFORMATION: Xaa is any amino acid or for example A or S

<400> SEQUENCE: 192

Xaa Val Xaa Leu Gln Gln Ser Gly Ala Glu Leu Ala Arg Pro Gly Ala
1               5                   10                  15

Ser Val Lys Phe Ser Cys Lys Ala Ser Gly Tyr Thr Phe Thr Arg Asn
            20                  25                  30

Trp Ile Gln Trp Val Lys Gln Arg Pro Gly Gln Gly Leu Glu Trp Ile
        35                  40                  45

Gly Ala Xaa Tyr Pro Gly Asn Gly Asp Ser Arg Tyr Thr Gln Lys Phe
    50                  55                  60

Lys Gly Lys Ala Thr Leu Thr Ala Asp Lys Ser Ser Xaa Thr Ala Tyr
65                  70                  75                  80

Met Gln Leu Xaa Xaa Leu Xaa Ser Glu Asp Ser Ala Val Tyr Tyr Cys
                85                  90                  95

Ala Arg Leu Ala Gly Asn Tyr Ala Tyr Tyr Phe Asp Tyr Trp Gly Gln
            100                 105                 110

Gly Thr Ala Leu Thr Val Ser Ser
        115                 120

<210> SEQ ID NO 193
<211> LENGTH: 123
<212> TYPE: PRT
<213> ORGANISM: Artificial Sequence
<220> FEATURE:
<223> OTHER INFORMATION: Heavy chain variable region consensus
<220> FEATURE:
<221> NAME/KEY: MISC_FEATURE
<222> LOCATION: (1)..(1)
<223> OTHER INFORMATION: Xaa is E or Q
<220> FEATURE:
<221> NAME/KEY: MISC_FEATURE
<222> LOCATION: (2)..(2)
<223> OTHER INFORMATION: Xaa is any amino acid or a hydrophobic amino
      acid such as for example A or I
<220> FEATURE:
<221> NAME/KEY: MISC_FEATURE
<222> LOCATION: (3)..(3)
<223> OTHER INFORMATION: Xaa is any amino acid or for example Y or Q
<220> FEATURE:
<221> NAME/KEY: MISC_FEATURE
<222> LOCATION: (9)..(9)
<223> OTHER INFORMATION: Xaa is any amino acid or a hydrophobic amino
      acid such as for example A or V
<220> FEATURE:
<221> NAME/KEY: MISC_FEATURE
<222> LOCATION: (33)..(33)
<223> OTHER INFORMATION: Xaa is any amino acid or an acidic amino acid
      such as for example D or E
<220> FEATURE:
<221> NAME/KEY: MISC_FEATURE
```

```
<222> LOCATION: (50)..(50)
<223> OTHER INFORMATION: Xaa is any amino acid or for example A or T
<220> FEATURE:
<221> NAME/KEY: MISC_FEATURE
<222> LOCATION: (74)..(74)
<223> OTHER INFORMATION: Xaa is any amino acid or a basic amino acid
      such as for example K or R
<220> FEATURE:
<221> NAME/KEY: MISC_FEATURE
<222> LOCATION: (77)..(77)
<223> OTHER INFORMATION: Xaa is any amino acid or a neutral hydrophilic
      amino acid such as for example S or T
<220> FEATURE:
<221> NAME/KEY: MISC_FEATURE
<222> LOCATION: (98)..(98)
<223> OTHER INFORMATION: Xaa is any amino acid or a neutral hydrophilic
      amino acid such as for example S or T
<220> FEATURE:
<221> NAME/KEY: MISC_FEATURE
<222> LOCATION: (102)..(102)
<223> OTHER INFORMATION: Xaa is any amino acid or a neutral hydrophilic
      amino acid such as for example T or S
<220> FEATURE:
<221> NAME/KEY: MISC_FEATURE
<222> LOCATION: (103)..(103)
<223> OTHER INFORMATION: Xaa is any amino acid or for example Y or H
<220> FEATURE:
<221> NAME/KEY: MISC_FEATURE
<222> LOCATION: (104)..(104)
<223> OTHER INFORMATION: Xaa is any amino acid or for example S or Y

<400> SEQUENCE: 193

Xaa Xaa Xaa Leu Gln Gln Ser Gly Xaa Glu Leu Val Arg Pro Gly Ala
1               5                   10                  15

Ser Val Thr Leu Ser Cys Lys Ala Ser Gly Tyr Thr Phe Thr Asp Tyr
            20                  25                  30

Xaa Met His Trp Val Lys Gln Thr Pro Val His Gly Leu Glu Trp Ile
        35                  40                  45

Gly Xaa Ile Asp Pro Glu Thr Gly Gly Thr Ala Tyr Asn Gln Lys Phe
    50                  55                  60

Lys Gly Lys Ala Thr Leu Thr Ala Asp Xaa Ser Ser Xaa Thr Ala Tyr
65                  70                  75                  80

Met Glu Leu Ser Ser Leu Thr Ser Glu Asp Ser Ala Val Tyr Tyr Cys
                85                  90                  95

Thr Xaa Phe Tyr Tyr Xaa Xaa Xaa Asn Tyr Asp Val Gly Phe Ala Tyr
            100                 105                 110

Trp Gly Gln Gly Thr Leu Val Thr Val Ser Ala
            115                 120

<210> SEQ ID NO 194
<211> LENGTH: 112
<212> TYPE: PRT
<213> ORGANISM: Artificial Sequence
<220> FEATURE:
<223> OTHER INFORMATION: Light chain variable region consensus
<220> FEATURE:
<221> NAME/KEY: MISC_FEATURE
<222> LOCATION: (6)..(6)
<223> OTHER INFORMATION: Xaa is any amino acid or a basic amino acid
      such as for example Q or H
<220> FEATURE:
<221> NAME/KEY: MISC_FEATURE
<222> LOCATION: (8)..(8)
<223> OTHER INFORMATION: Xaa is any amino acid or a hydrophobic amino
      acid such as for example V or A
<220> FEATURE:
<221> NAME/KEY: MISC_FEATURE
<222> LOCATION: (14)..(14)
<223> OTHER INFORMATION: Xaa is any amino acid or for example T or I
<220> FEATURE:
<221> NAME/KEY: MISC_FEATURE
```

```
<222> LOCATION: (18)..(18)
<223> OTHER INFORMATION: Xaa is any amino acid or for example S or P
<220> FEATURE:
<221> NAME/KEY: MISC_FEATURE
<222> LOCATION: (27)..(27)
<223> OTHER INFORMATION: Xaa is any amino acid or for example E or K
<220> FEATURE:
<221> NAME/KEY: MISC_FEATURE
<222> LOCATION: (35)..(35)
<223> OTHER INFORMATION: Xaa is any amino acid or a hydrophobic amino
      acid such as for example V or I
<220> FEATURE:
<221> NAME/KEY: MISC_FEATURE
<222> LOCATION: (69)..(69)
<223> OTHER INFORMATION: Xaa is any amino acid or for example S or G
<220> FEATURE:
<221> NAME/KEY: MISC_FEATURE
<222> LOCATION: (75)..(75)
<223> OTHER INFORMATION: Xaa is any amino acid or for example D or A
<220> FEATURE:
<221> NAME/KEY: MISC_FEATURE
<222> LOCATION: (94)..(94)
<223> OTHER INFORMATION: Xaa is any amino acid or a hydrophobic amino
      acid such as for example M or A
<220> FEATURE:
<221> NAME/KEY: MISC_FEATURE
<222> LOCATION: (96)..(96)
<223> OTHER INFORMATION: Xaa is any amino acid or a basic amino acid
      such as for example N or H
<220> FEATURE:
<221> NAME/KEY: MISC_FEATURE
<222> LOCATION: (99)..(99)
<223> OTHER INFORMATION: Xaa is any amino acid or for example Y or L
<220> FEATURE:
<221> NAME/KEY: MISC_FEATURE
<222> LOCATION: (105)..(105)
<223> OTHER INFORMATION: Xaa is any amino acid or for example G or S

<400> SEQUENCE: 194

Asp Ile Val Met Thr Xaa Ala Xaa Phe Ser Asn Pro Val Xaa Leu Gly
1               5                   10                  15

Thr Xaa Ala Ser Ile Ser Cys Arg Ser Ser Xaa Ser Leu Leu His Ser
            20                  25                  30

Asn Gly Xaa Thr Tyr Leu Tyr Trp Tyr Leu Gln Lys Pro Gly Gln Ser
        35                  40                  45

Pro Gln Leu Leu Ile Tyr Gln Met Ser Asn Leu Ala Ser Gly Val Pro
    50                  55                  60

Asp Arg Phe Ser Xaa Ser Gly Ser Gly Thr Xaa Phe Thr Leu Arg Ile
65                  70                  75                  80

Ser Arg Val Glu Ala Glu Asp Val Gly Val Tyr Tyr Cys Xaa Gln Xaa
                85                  90                  95

Leu Glu Xaa Pro Tyr Thr Phe Gly Xaa Gly Thr Lys Leu Glu Ile Lys
            100                 105                 110

<210> SEQ ID NO 195
<211> LENGTH: 107
<212> TYPE: PRT
<213> ORGANISM: Artificial Sequence
<220> FEATURE:
<223> OTHER INFORMATION: light chain variable region consensus
<220> FEATURE:
<221> NAME/KEY: MISC_FEATURE
<222> LOCATION: (1)..(1)
<223> OTHER INFORMATION: Xaa is any amino acid or for example D or N
<220> FEATURE:
<221> NAME/KEY: MISC_FEATURE
<222> LOCATION: (27)..(27)
<223> OTHER INFORMATION: Xaa is any amino acid or for example E or G
<220> FEATURE:
<221> NAME/KEY: MISC_FEATURE
<222> LOCATION: (30)..(30)
<223> OTHER INFORMATION: Xaa is any amino acid or for example Y or H
```

```
<220> FEATURE:
<221> NAME/KEY: MISC_FEATURE
<222> LOCATION: (31)..(31)
<223> OTHER INFORMATION: Xaa is any amino acid or for example S or N
<220> FEATURE:
<221> NAME/KEY: MISC_FEATURE
<222> LOCATION: (55)..(55)
<223> OTHER INFORMATION: Xaa is any amino acid or for example P or A
<220> FEATURE:
<221> NAME/KEY: MISC_FEATURE
<222> LOCATION: (56)..(56)
<223> OTHER INFORMATION: Xaa is any amino acid or an acidic amino acid
      such as for example E or D
<220> FEATURE:
<221> NAME/KEY: MISC_FEATURE
<222> LOCATION: (59)..(59)
<223> OTHER INFORMATION: Xaa is any amino acid or for example P or S
<220> FEATURE:
<221> NAME/KEY: MISC_FEATURE
<222> LOCATION: (60)..(60)
<223> OTHER INFORMATION: Xaa is any amino acid or for example V or S
<220> FEATURE:
<221> NAME/KEY: MISC_FEATURE
<222> LOCATION: (71)..(71)
<223> OTHER INFORMATION: Xaa is any amino acid or an aromatic amino acid
      such as for example F or Y
<220> FEATURE:
<221> NAME/KEY: MISC_FEATURE
<222> LOCATION: (77)..(77)
<223> OTHER INFORMATION: Xaa is any amino acid or for example N or S
<220> FEATURE:
<221> NAME/KEY: MISC_FEATURE
<222> LOCATION: (87)..(87)
<223> OTHER INFORMATION: Xaa is any amino acid or for example H or Y
<220> FEATURE:
<221> NAME/KEY: MISC_FEATURE
<222> LOCATION: (94)..(94)
<223> OTHER INFORMATION: Xaa is any amino acid or a hydrophobic amino
      acid such as for example A or V
<220> FEATURE:
<221> NAME/KEY: MISC_FEATURE
<222> LOCATION: (100)..(100)
<223> OTHER INFORMATION: Xaa is any amino acid or for example S or A
<220> FEATURE:
<221> NAME/KEY: MISC_FEATURE
<222> LOCATION: (104)..(104)
<223> OTHER INFORMATION: Xaa is any amino acid or a hydrophobic amino
      acid such as for example V or L

<400> SEQUENCE: 195

Xaa Ile Gln Met Thr Gln Ser Pro Ala Ser Leu Ser Ala Ser Val Gly
1               5                   10                  15

Glu Thr Val Thr Ile Thr Cys Arg Ala Ser Xaa Asn Ile Xaa Xaa Tyr
            20                  25                  30

Leu Ala Trp Tyr Gln Gln Lys Gln Gly Lys Ser Pro Gln Leu Leu Val
        35                  40                  45

Tyr Asn Ala Lys Thr Leu Xaa Xaa Gly Val Xaa Xaa Arg Phe Ser Gly
    50                  55                  60

Ser Gly Ser Gly Thr Gln Xaa Ser Leu Lys Ile Asn Xaa Leu Gln Pro
65                  70                  75                  80

Glu Asp Phe Gly Ser Tyr Xaa Cys Gln His His Tyr Gly Xaa Pro Leu
                85                  90                  95

Thr Phe Gly Xaa Gly Thr Lys Xaa Glu Leu Lys
            100                 105

<210> SEQ ID NO 196
<211> LENGTH: 112
<212> TYPE: PRT
<213> ORGANISM: Artificial Sequence
<220> FEATURE:
<223> OTHER INFORMATION: light chain variable region consensus
<220> FEATURE:
```

```
<221> NAME/KEY: MISC_FEATURE
<222> LOCATION: (26)..(26)
<223> OTHER INFORMATION: Xaa is any amino acid or a neutral hydrophilic
      amino acid such as for example S or T
<220> FEATURE:
<221> NAME/KEY: MISC_FEATURE
<222> LOCATION: (80)..(80)
<223> OTHER INFORMATION: Xaa is any amino acid or a hydrophobic amino
      acid such as for example I or L

<400> SEQUENCE: 196

Asp Ile Val Met Thr Gln Ala Ala Pro Ser Val Pro Val Thr Pro Gly
1               5                   10                  15

Glu Ser Val Ser Ile Ser Cys Arg Ser Xaa Lys Ser Leu Leu His Ser
            20                  25                  30

Asn Gly Asn Thr Tyr Leu Tyr Trp Phe Leu Gln Arg Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Ala Phe Thr Leu Arg Xaa
65                  70                  75                  80

Ser Arg Val Glu Ala Glu Asp Val Gly Val Tyr Tyr Cys Met Gln His
                85                  90                  95

Leu Glu Tyr Pro Phe Thr Phe Gly Gly Gly Thr Lys Leu Glu Ile Lys
            100                 105                 110

<210> SEQ ID NO 197
<211> LENGTH: 11
<212> TYPE: PRT
<213> ORGANISM: Artificial Sequence
<220> FEATURE:
<223> OTHER INFORMATION: CDRL1 consensus
<220> FEATURE:
<221> NAME/KEY: MISC_FEATURE
<222> LOCATION: (4)..(4)
<223> OTHER INFORMATION: Xaa is any amino acid or for example G or E
<220> FEATURE:
<221> NAME/KEY: MISC_FEATURE
<222> LOCATION: (7)..(7)
<223> OTHER INFORMATION: Xaa is any amino acid or for example Y or H
<220> FEATURE:
<221> NAME/KEY: MISC_FEATURE
<222> LOCATION: (8)..(8)
<223> OTHER INFORMATION: Xaa is any amino acid or for example S or N

<400> SEQUENCE: 197

Arg Ala Ser Xaa Asn Ile Xaa Xaa Tyr Leu Ala
1               5                   10

<210> SEQ ID NO 198
<211> LENGTH: 7
<212> TYPE: PRT
<213> ORGANISM: Artificial Sequence
<220> FEATURE:
<223> OTHER INFORMATION: CDRL2 consensus
<220> FEATURE:
<221> NAME/KEY: MISC_FEATURE
<222> LOCATION: (6)..(6)
<223> OTHER INFORMATION: Xaa is any amino acid or for example P or A
<220> FEATURE:
<221> NAME/KEY: MISC_FEATURE
<222> LOCATION: (7)..(7)
<223> OTHER INFORMATION: Xaa is any amino acid or for example an acidic
      amino acid such as E or D

<400> SEQUENCE: 198

Asn Ala Lys Thr Leu Xaa Xaa
1               5
```

```
<210> SEQ ID NO 199
<211> LENGTH: 8
<212> TYPE: PRT
<213> ORGANISM: Artificial Sequence
<220> FEATURE:
<223> OTHER INFORMATION: CDRL3 consensus
<220> FEATURE:
<221> NAME/KEY: MISC_FEATURE
<222> LOCATION: (5)..(5)
<223> OTHER INFORMATION: Xaa is any amino acid or a hydrophobic amino
      acid such as for example A or V

<400> SEQUENCE: 199

Gln His Tyr Gly Xaa Pro Leu Thr
1               5

<210> SEQ ID NO 200
<211> LENGTH: 10
<212> TYPE: PRT
<213> ORGANISM: Artificial Sequence
<220> FEATURE:
<223> OTHER INFORMATION: CDRH2 consensus
<220> FEATURE:
<221> NAME/KEY: MISC_FEATURE
<222> LOCATION: (2)..(2)
<223> OTHER INFORMATION: Xaa is any amino acid or a hydrophobic amino
      acid such as I or V

<400> SEQUENCE: 200

Ala Xaa Tyr Pro Gly Asn Gly Asp Ser Arg
1               5                   10

<210> SEQ ID NO 201
<211> LENGTH: 16
<212> TYPE: PRT
<213> ORGANISM: Artificial Sequence
<220> FEATURE:
<223> OTHER INFORMATION: CDRL1 consensus
<220> FEATURE:
<221> NAME/KEY: MISC_FEATURE
<222> LOCATION: (4)..(4)
<223> OTHER INFORMATION: Xaa is any amino acid or for example E or K
<220> FEATURE:
<221> NAME/KEY: MISC_FEATURE
<222> LOCATION: (12)..(12)
<223> OTHER INFORMATION: Xaa is any amino acid or a hydrophobic amino
      acid such as for example V or I

<400> SEQUENCE: 201

Arg Ser Ser Xaa Ser Leu Leu His Ser Asn Gly Xaa Thr Tyr Leu Tyr
1               5                   10                  15

<210> SEQ ID NO 202
<211> LENGTH: 16
<212> TYPE: PRT
<213> ORGANISM: Artificial Sequence
<220> FEATURE:
<223> OTHER INFORMATION: CDRL1 consensus
<220> FEATURE:
<221> NAME/KEY: MISC_FEATURE
<222> LOCATION: (3)..(3)
<223> OTHER INFORMATION: Xaa is any amino acid or a neutral hydrophilic
      amino acid such as for example S or T

<400> SEQUENCE: 202

Arg Ser Xaa Lys Ser Leu Leu His Ser Asn Gly Asn Thr Tyr Leu Tyr
1               5                   10                  15

<210> SEQ ID NO 203
<211> LENGTH: 9
<212> TYPE: PRT
```

```
<213> ORGANISM: Artificial Sequence
<220> FEATURE:
<223> OTHER INFORMATION: CDRL3 consensus
<220> FEATURE:
<221> NAME/KEY: MISC_FEATURE
<222> LOCATION: (1)..(1)
<223> OTHER INFORMATION: Xaa is any amino acid or a hydrophobic amino
      acid such as for example M or A
<220> FEATURE:
<221> NAME/KEY: MISC_FEATURE
<222> LOCATION: (3)..(3)
<223> OTHER INFORMATION: Xaa is any amino acid or a basic amino acid
      such as for example N or H
<220> FEATURE:
<221> NAME/KEY: MISC_FEATURE
<222> LOCATION: (6)..(6)
<223> OTHER INFORMATION: Xaa is any amino acid or for example Y or L

<400> SEQUENCE: 203

Xaa Gln Xaa Leu Glu Xaa Pro Tyr Thr
1               5

<210> SEQ ID NO 204
<211> LENGTH: 9
<212> TYPE: PRT
<213> ORGANISM: Artificial Sequence
<220> FEATURE:
<223> OTHER INFORMATION: CDRL3 consensus
<220> FEATURE:
<221> NAME/KEY: MISC_FEATURE
<222> LOCATION: (6)..(6)
<223> OTHER INFORMATION: Xaa is any amino acid or a hydrophobic amino
      acid such as for example A or V

<400> SEQUENCE: 204

Gln His His Tyr Gly Xaa Pro Leu Thr
1               5

<210> SEQ ID NO 205
<211> LENGTH: 10
<212> TYPE: PRT
<213> ORGANISM: Artificial Sequence
<220> FEATURE:
<223> OTHER INFORMATION: CDRH1 consensus
<220> FEATURE:
<221> NAME/KEY: MISC_FEATURE
<222> LOCATION: (6)..(6)
<223> OTHER INFORMATION: Xaa is any amino acid or a neutral hydrophilic
      amino acid such as for example for example S or T

<400> SEQUENCE: 205

Gly Tyr Thr Phe Thr Xaa Tyr Trp Met His
1               5                   10

<210> SEQ ID NO 206
<211> LENGTH: 10
<212> TYPE: PRT
<213> ORGANISM: Artificial Sequence
<220> FEATURE:
<223> OTHER INFORMATION: CDRH2 consensus
<220> FEATURE:
<221> NAME/KEY: MISC_FEATURE
<222> LOCATION: (1)..(1)
<223> OTHER INFORMATION: Xaa is any amino acid or for example A or T

<400> SEQUENCE: 206

Xaa Ile Asp Pro Glu Thr Gly Gly Thr Ala
1               5                   10

<210> SEQ ID NO 207
<211> LENGTH: 10
<212> TYPE: PRT
```

```
<213> ORGANISM: Artificial Sequence
<220> FEATURE:
<223> OTHER INFORMATION: CDRH2 consensus
<220> FEATURE:
<221> NAME/KEY: MISC_FEATURE
<222> LOCATION: (5)..(5)
<223> OTHER INFORMATION: Xaa is any amino acid or a neutral hydrophilic
      amino acid such as for example T or S
<220> FEATURE:
<221> NAME/KEY: MISC_FEATURE
<222> LOCATION: (7)..(7)
<223> OTHER INFORMATION: Xaa is any amino acid or for example G or A
<220> FEATURE:
<221> NAME/KEY: MISC_FEATURE
<222> LOCATION: (9)..(9)
<223> OTHER INFORMATION: Xaa is any amino acid or for example P or T

<400> SEQUENCE: 207

Leu Ile Asn Pro Xaa Asn Xaa Arg Xaa Asn
1               5                   10

<210> SEQ ID NO 208
<211> LENGTH: 10
<212> TYPE: PRT
<213> ORGANISM: Artificial Sequence
<220> FEATURE:
<223> OTHER INFORMATION: CDRH1 consensus
<220> FEATURE:
<221> NAME/KEY: MISC_FEATURE
<222> LOCATION: (8)..(8)
<223> OTHER INFORMATION: Xaa is any amino acid or an acidic amino acid
      such as for example D or E

<400> SEQUENCE: 208

Gly Tyr Thr Phe Thr Asp Tyr Xaa Met His
1               5                   10

<210> SEQ ID NO 209
<211> LENGTH: 10
<212> TYPE: PRT
<213> ORGANISM: Artificial Sequence
<220> FEATURE:
<223> OTHER INFORMATION: CDRH2 consensus
<220> FEATURE:
<221> NAME/KEY: MISC_FEATURE
<222> LOCATION: (1)..(1)
<223> OTHER INFORMATION: Xaa is any amino acid or for example A or T

<400> SEQUENCE: 209

Xaa Ile Asp Pro Glu Thr Gly Gly Thr Ala
1               5                   10

<210> SEQ ID NO 210
<211> LENGTH: 16
<212> TYPE: PRT
<213> ORGANISM: Artificial Sequence
<220> FEATURE:
<223> OTHER INFORMATION: CDRH3 consensus
<220> FEATURE:
<221> NAME/KEY: MISC_FEATURE
<222> LOCATION: (2)..(2)
<223> OTHER INFORMATION: Xaa is any amino acid or a neutral hydrophilic
      amino acid such as for example S or T
<220> FEATURE:
<221> NAME/KEY: MISC_FEATURE
<222> LOCATION: (6)..(6)
<223> OTHER INFORMATION: Xaa is any amino acid or a neutral hydrophilic
      amino acid such as for example T or S
<220> FEATURE:
<221> NAME/KEY: MISC_FEATURE
<222> LOCATION: (7)..(7)
<223> OTHER INFORMATION: Xaa is any amino acid or for example Y or H
<220> FEATURE:
<221> NAME/KEY: MISC_FEATURE
```

```
<222> LOCATION: (8)..(8)
<223> OTHER INFORMATION: Xaa is any amino acid or for example S or Y

<400> SEQUENCE: 210

Thr Xaa Phe Tyr Tyr Xaa Xaa Xaa Asn Tyr Asp Val Gly Phe Ala Tyr
1               5                   10                  15

<210> SEQ ID NO 211
<211> LENGTH: 118
<212> TYPE: PRT
<213> ORGANISM: Artificial Sequence
<220> FEATURE:
<223> OTHER INFORMATION: heavy chain variable region sequence

<400> SEQUENCE: 211

Gln Val Gln Leu Gln Gln Ser Arg Ala Glu Leu Val Lys Pro Gly Ala
1               5                   10                  15

Ser Val Lys Leu Ser Cys Lys Ala Ser Gly Tyr Thr Phe Thr Ser Tyr
                20                  25                  30

Trp Met His Trp Val Lys Gln Arg Pro Gly Gln Gly Leu Glu Trp Ile
            35                  40                  45

Gly Leu Ile Asn Pro Thr Asn Gly Arg Thr Asn Tyr Asn Glu Lys Phe
    50                  55                  60

Lys Asn Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Gly Gly Asp Gly Asp Tyr Phe Asp Tyr Trp Gly Gln Gly Thr
            100                 105                 110

Thr Leu Thr Val Ser Ser
        115

<210> SEQ ID NO 212
<211> LENGTH: 118
<212> TYPE: PRT
<213> ORGANISM: Artificial Sequence
<220> FEATURE:
<223> OTHER INFORMATION: Heavy chain variable region sequence

<400> SEQUENCE: 212

Gln Val Gln Val Gln Gln Pro Gly Thr Glu Leu Val Lys Pro Gly Ala
1               5                   10                  15

Ser Val Lys Leu Ser Cys Lys Ala Ser Gly Tyr Thr Phe Thr Thr Tyr
                20                  25                  30

Trp Met His Trp Val Lys Gln Arg Pro Gly Gln Gly Leu Glu Trp Ile
            35                  40                  45

Gly Leu Ile Asn Pro Thr Asn Gly Arg Thr Asn Tyr Asn Glu Lys Phe
    50                  55                  60

Lys Ser Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Gly Gly Asp Gly Asp Tyr Phe Asp Tyr Trp Gly Gln Gly Thr
            100                 105                 110

Thr Leu Thr Val Ser Ser
        115

<210> SEQ ID NO 213
<211> LENGTH: 118
<212> TYPE: PRT
```

<213> ORGANISM: Artificial Sequence
<220> FEATURE:
<223> OTHER INFORMATION: Heavy chain variable region sequence

<400> SEQUENCE: 213

Gln Val Gln Val Gln Gln Pro Gly Ala Glu Ile Val Arg Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Leu Ile Asn Pro Thr Asn Gly Arg Thr Asn Tyr Asn Glu Lys Phe
    50                  55                  60

Lys Ser Lys Ala Thr Leu Thr Val Asp Lys Ser Ser Thr Ala Tyr
65                  70                  75                  80

Met His Leu Ser Ser Leu Thr Ser Glu Asp Ser Ala Val Tyr Tyr Cys
                85                  90                  95

Ala Arg Gly Gly Asp Gly Asp Tyr Phe Asp Tyr Trp Gly Gln Gly Thr
            100                 105                 110

Thr Leu Thr Val Ser Ser
        115

<210> SEQ ID NO 214
<211> LENGTH: 118
<212> TYPE: PRT
<213> ORGANISM: Artificial Sequence
<220> FEATURE:
<223> OTHER INFORMATION: Heavy chain variable region sequence

<400> SEQUENCE: 214

Glu Ile Gln Leu Gln Gln Ser Gly Thr Glu Leu Val Lys Pro Gly Ala
1               5                   10                  15

Ser Val Lys Leu Ser Cys Lys Ala Ser Gly Tyr Thr Phe Thr Thr Tyr
            20                  25                  30

Trp Met His Trp Val Lys Gln Arg Pro Gly Gln Gly Leu Glu Trp Ile
        35                  40                  45

Gly Leu Ile Asn Pro Thr Asn Gly Arg Thr Asn Tyr Asn Glu Lys Phe
    50                  55                  60

Lys Ser Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Gly Gly Asp Gly Asp Tyr Phe Asp Tyr Trp Gly Gln Gly Thr
            100                 105                 110

Thr Leu Thr Val Ser Ser
        115

<210> SEQ ID NO 215
<211> LENGTH: 118
<212> TYPE: PRT
<213> ORGANISM: Artificial Sequence
<220> FEATURE:
<223> OTHER INFORMATION: Heavy chain variable region sequence

<400> SEQUENCE: 215

Gln Val Gln Val Gln Gln Pro Gly Ala Glu Ile Val Arg Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
         35                  40                  45

Gly Leu Ile Asn Pro Thr Asn Gly Arg Thr Asn Tyr Asn Glu Lys Phe
 50                  55                  60

Lys Asn Lys Ala Thr Leu Thr Val Asp Lys Ser Ser Thr Ala Tyr
65                  70                  75                  80

Met Gln Leu Ser Ser Leu Thr Ser Glu Asp Ser Ala Val Tyr Tyr Cys
             85                  90                  95

Ala Arg Gly Gly Asp Gly Asp Tyr Phe Asp Tyr Trp Gly Gln Gly Thr
            100                 105                 110

Thr Leu Thr Val Ser Ser
        115

<210> SEQ ID NO 216
<211> LENGTH: 118
<212> TYPE: PRT
<213> ORGANISM: Artificial Sequence
<220> FEATURE:
<223> OTHER INFORMATION: Heavy chain variable region sequence

<400> SEQUENCE: 216

Gln Val Gln Leu Gln Gln Ser Gly Ala Glu Leu Val Lys Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
         35                  40                  45

Gly Leu Ile Asn Pro Ser Asn Gly Arg Pro Asn Tyr Asn Glu Arg Phe
 50                  55                  60

Lys Thr Lys Ala Thr Leu Thr Val Asp Lys Ser Ser Thr Ala Tyr
65                  70                  75                  80

Met His Leu Ser Ser Leu Thr Ser Glu Asp Ser Ala Val Tyr Tyr Cys
             85                  90                  95

Ala Arg Gly Gly Asp Gly Asp Tyr Phe Asp Tyr Trp Gly Gln Gly Thr
            100                 105                 110

Thr Leu Thr Val Ser Ser
        115

<210> SEQ ID NO 217
<211> LENGTH: 123
<212> TYPE: PRT
<213> ORGANISM: Artificial Sequence
<220> FEATURE:
<223> OTHER INFORMATION: Heavy chain variable region sequence

<400> SEQUENCE: 217

Gln Ala Tyr Leu Gln Gln Ser Gly Val Glu Leu Val Arg Pro Gly Ala
1               5                   10                  15

Ser Val Thr Leu Ser Cys Lys Ala Ser Gly Tyr Thr Phe Thr Asp Tyr
            20                  25                  30

Asp Met His Trp Val Lys Gln Thr Pro Val His Gly Leu Glu Trp Ile
         35                  40                  45

Gly Thr Ile Asp Pro Glu Thr Gly Gly Thr Ala Tyr Asn Gln Lys Phe
 50                  55                  60

Lys Gly Lys Ala Thr Leu Thr Ala Asp Arg Ser Ser Thr Thr Ala Tyr
65                  70                  75                  80

Met Glu Leu Ser Ser Leu Thr Ser Glu Asp Ser Ala Val Tyr Tyr Cys
             85                  90                  95

Thr Ser Phe Tyr Tyr Thr Tyr Ser Asn Tyr Asp Val Gly Phe Ala Tyr
            100                 105                 110

Trp Gly Gln Gly Thr Leu Val Thr Val Ser Ala
        115                 120

<210> SEQ ID NO 218
<211> LENGTH: 112
<212> TYPE: PRT
<213> ORGANISM: Artificial Sequence
<220> FEATURE:
<223> OTHER INFORMATION: Light chain variable region sequence

<400> SEQUENCE: 218

Asp Ile Val Met Thr Gln Ala Val Phe Ser Asn Pro Val Ile Leu Gly
1               5                   10                  15

Thr Pro Ala Ser Ile Ser Cys Arg Ser Ser Lys Ser Leu Leu His Ser
            20                  25                  30

Asn Gly Val Thr Tyr Leu Tyr Trp Tyr Leu Gln Lys Pro Gly Gln Ser
        35                  40                  45

Pro Gln Leu Leu Ile Tyr Gln Met Ser Asn Leu Ala Ser Gly Val Pro
    50                  55                  60

Asp Arg Phe Ser Ser Ser Gly Ser Gly Thr Asp Phe Thr Leu Arg Ile
65                  70                  75                  80

Ser Arg Val Glu Ala Glu Asp Val Gly Val Tyr Tyr Cys Met Gln His
                85                  90                  95

Leu Glu Tyr Pro Tyr Thr Phe Gly Gly Gly Thr Lys Leu Glu Ile Lys
            100                 105                 110

<210> SEQ ID NO 219
<211> LENGTH: 112
<212> TYPE: PRT
<213> ORGANISM: Artificial Sequence
<220> FEATURE:
<223> OTHER INFORMATION: Light chain variable region sequence

<400> SEQUENCE: 219

Asp Ile Val Met Thr Gln Ala Ala Phe Ser Asn Pro Val Thr Leu Gly
1               5                   10                  15

Thr Ser Ala Ser Ile Ser Cys Arg Ser Ser Glu Ser Leu Leu His Ser
            20                  25                  30

Asn Gly Ile Thr Tyr Leu Tyr Trp Tyr Leu Gln Lys Pro Gly Gln Ser
        35                  40                  45

Pro Gln Leu Leu Ile Tyr Gln Met Ser Asn Leu Ala Ser Gly Val Pro
    50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
                85                  90                  95

Leu Glu Tyr Pro Tyr Thr Phe Gly Gly Gly Thr Lys Leu Glu Ile Lys
            100                 105                 110

<210> SEQ ID NO 220
<211> LENGTH: 112
<212> TYPE: PRT
<213> ORGANISM: Artificial Sequence
<220> FEATURE:
<223> OTHER INFORMATION: Light chain variable region sequence

<400> SEQUENCE: 220

Asp Ile Val Met Thr His Ala Ala Phe Ser Asn Pro Val Thr Leu Gly
1               5                   10                  15

Thr Ser Ala Ser Ile Ser Cys Arg Ser Ser Lys Ser Leu Leu His Ser
            20                  25                  30

Asn Gly Ile Thr Tyr Leu Tyr Trp Tyr Leu Gln Lys Pro Gly Gln Ser
        35                  40                  45

Pro Gln Leu Leu Ile Tyr Gln Met Ser Asn Leu Ala Ser Gly Val Pro
    50                  55                  60

Asp Arg Phe Ser Ser Ser Gly Ser Gly Thr Asp Phe Thr Leu Arg Ile
65                  70                  75                  80

Ser Arg Val Glu Ala Glu Asp Val Gly Val Tyr Tyr Cys Ala Gln Asn
                85                  90                  95

Leu Glu Leu Pro Tyr Thr Phe Gly Gly Gly Thr Lys Leu Glu Ile Lys
                100                 105                 110

<210> SEQ ID NO 221
<211> LENGTH: 112
<212> TYPE: PRT
<213> ORGANISM: Artificial Sequence
<220> FEATURE:
<223> OTHER INFORMATION: Light chain variable region sequence

<400> SEQUENCE: 221

Asp Ile Val Met Thr Gln Ala Ala Phe Ser Asn Pro Val Thr Leu Gly
1               5                   10                  15

Thr Ser Ala Ser Ile Ser Cys Arg Ser Ser Lys Ser Leu Leu His Ser
            20                  25                  30

Asn Gly Ile Thr Tyr Leu Tyr Trp Tyr Leu Gln Lys Pro Gly Gln Ser
        35                  40                  45

Pro Gln Leu Leu Ile Tyr Gln Met Ser Asn Leu Ala Ser Gly Val Pro
    50                  55                  60

Asp Arg Phe Ser Ser Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
                85                  90                  95

Leu Glu Tyr Pro Tyr Thr Phe Gly Gly Gly Thr Lys Leu Glu Ile Lys
                100                 105                 110

<210> SEQ ID NO 222
<211> LENGTH: 112
<212> TYPE: PRT
<213> ORGANISM: Artificial Sequence
<220> FEATURE:
<223> OTHER INFORMATION: Light chain variable region sequence

<400> SEQUENCE: 222

Asp Ile Val Met Thr Gln Ala Ala Phe Ser Asn Pro Val Thr Leu Gly
1               5                   10                  15

Thr Ser Ala Ser Ile Ser Cys Arg Ser Ser Lys Ser Leu Leu His Ser
            20                  25                  30

Asn Gly Ile Thr Tyr Leu Tyr Trp Tyr Leu Gln Lys Pro Gly Gln Ser
        35                  40                  45

Pro Gln Leu Leu Ile Tyr Gln Met Ser Asn Leu Ala Ser Gly Val Pro
    50                  55                  60

Asp Arg Phe Ser Ser Ser Gly Ser Gly Thr Asp Phe Thr Leu Arg Ile
65                  70                  75                  80

Ser Arg Val Glu Ala Glu Asp Val Gly Val Tyr Tyr Cys Ala Gln Asn
                85                  90                  95

Leu Glu Tyr Pro Tyr Thr Phe Gly Ser Gly Thr Lys Leu Glu Ile Lys
                100                 105                 110

```
<210> SEQ ID NO 223
<211> LENGTH: 112
<212> TYPE: PRT
<213> ORGANISM: Artificial Sequence
<220> FEATURE:
<223> OTHER INFORMATION: Light chain variable region sequence

<400> SEQUENCE: 223

Asp Ile Val Met Thr Gln Ala Ala Pro Ser Val Pro Val Thr Pro Gly
1               5                   10                  15

Glu Ser Val Ser Ile Ser Cys Arg Ser Ser Lys Ser Leu Leu His Ser
                20                  25                  30

Asn Gly Asn Thr Tyr Leu Tyr Trp Phe Leu Gln Arg Pro Gly Gln Ser
            35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Ala Phe Thr Leu Arg Leu
65                  70                  75                  80

Ser Arg Val Glu Ala Glu Asp Val Gly Val Tyr Tyr Cys Met Gln His
                85                  90                  95

Leu Glu Tyr Pro Phe Thr Phe Gly Gly Gly Thr Lys Leu Glu Ile Lys
            100                 105                 110
```

SIGLEC 15 ANTIBODIES IN TREATING BONE LOSS-RELATED DISEASE

PRIORITY CLAIM

This patent application is a national stage filing under 35 U.S.C. §371 of international application No. PCT/CA2010/001586 filed on Oct. 6, 2010, which claimed priority to U.S. provisional application No. 61/248,960 filed Oct. 6, 2009 and to U.S. application Ser. No. 12/580,943 filed on Oct. 16, 2009, now U.S. Pat. No. 8,168,181. The entire contents of each of these priority applications are incorporated herein by reference.

SEQUENCE LISTING

In accordance with 37 C.F.R. §1.52(e)(5), a Sequence Listing in the form of a text file (entitled "Sequence Listing", created on Apr. 2, 2012 and of 205 kilobytes) is incorporated herein by reference in its entirety.

FIELD OF THE INVENTION

The present invention relates to monoclonal antibodies and antigen binding fragments thereof that specifically bind to Siglec-15 and their use for treating certain diseases including diagnosing, preventing and treating cancer or bone loss, such as severe or excessive bone loss associated with bone-related diseases or associated with an increase in osteoclast differentiation or activity. The present invention also relates to the use of these antibodies for diagnosis, prevention and treatment of various other types of diseases where the activity of osteoclasts is increased.

BACKGROUND OF THE INVENTION

Bone is a dynamic connective tissue comprised of functionally distinct cell populations required to support the structural, mechanical and biochemical integrity of bone and the human body's mineral homeostasis. The principal cell types involved include, osteoblasts responsible for bone formation and maintaining bone mass, and osteoclasts responsible for bone resorption. Osteoblasts and osteoclasts function in a dynamic process termed bone remodelling. The development and proliferation of these cells from their progenitors is governed by networks of growth factors and cytokines produced in the bone microenvironment as well as by systemic hormones. Bone remodelling is ongoing throughout the lifetime of the individual and is necessary for the maintenance of healthy bone tissue and mineral homeostasis. The process remains largely in equilibrium and is governed by a complex interplay of systemic hormones, peptides and downstream signalling pathway proteins, local transcription factors, cytokines, growth factors and matrix remodelling genes.

Any interference or imbalance arising in the bone remodelling process can produce skeletal disease, with the most common skeletal disorders characterized by a net decrease in bone mass. A primary cause of this reduction in bone mass is an increase in osteoclast number and/or activity. The most common of such disease, and perhaps the best known, is osteoporosis occurring particularly in women after the onset of menopause. In fact osteoporosis is the most significant underlying cause of skeletal fractures in late middle-aged and elderly women. While estrogen deficiency has been strongly implicated as a factor in postmenopausal osteoporosis, there is longstanding evidence that remodelling is a locally controlled process being that it takes place in discrete packets throughout the skeleton as first described by Frost over forty years ago (Frost H. M. 1964).

Since bone remodelling takes place in discrete packets, locally produced hormones and enzymes may be more important than systemic hormones for the initiation of bone resorption and the normal remodelling process. Such local control is mediated by osteoblasts and osteoclasts in the microenvironment in which they operate. For example, osteoclasts attach to the bone matrix and form a separate compartment between themselves and the bone surface delimited by a sealing zone formed by a ring of actin surrounding the ruffled border. Multiple small vesicles transport enzymes toward the bone matrix and internalize partially digested bone matrix. The microenvironment within the sealing zone is rich with the presence of lysosomal enzymes and is highly acidic compared to the normal physiological pH of the body. The ruffled border membrane also expresses RANK, the receptor for RANKL, and macrophage-colony stimulating factor (M-CSF) receptor, both of which are responsible for osteoclast differentiation, as well as the calcitonin receptor capable of rapidly inactivating the osteoclast (Baron, R. 2003).

In a complex pattern of inhibition and stimulation, growth hormone, insulin-like growth factor-1, the sex steroids, thyroid hormone, calciotrophic hormones such as PTH and prostaglandin E2, various cytokines, such as interleukin-1 beta, interleukin-6, and tumor necrosis factor-alpha, and 1,25-dihydroxyvitamin D (calcitriol) act co-ordinately in the bone remodelling process (Jilka et al. 1992; Poli et al. 1994; Srivastava et al. 1998; de Vemejoul 1996).

Thus, it stands to reason that the unique local environments created by these specialized cells is due to the expression of either unique genetic sequences not expressed in other tissues and/or splice variants of polynucleotides and polypeptides expressed in other tissues. The isolation and identification of polynucleotides, polypeptides and their variants and derivatives specific to osteoclast activity will permit a clearer understanding of the remodelling process and offer tissue specific therapeutic targets for the treatment of disease states related to bone remodelling.

Many diseases linked to bone remodelling are poorly understood, generally untreatable or treatable only to a limited extent. For example, osteoarthritis is difficult to treat as there is no cure and treatment focuses on relieving pain and preventing the affected joint from becoming deformed. Non-steroidal anti-inflammatory drugs (NSAIDs) are generally used to relieve pain.

Another example is osteoporosis where the only current medications approved by the FDA for use in the United States are the anti-resorptive agents that prevent bone breakdown. Estrogen replacement therapy is one example of an anti-resorptive agent. Others include alendronate (Fosamax—a biphosphonate anti-resorptive), risedronate (Actonel—a bis-phosphonate anti-resorptive), raloxifene (Evista—selective estrogen receptor modulator (SERM)), calcitonin (Calcimar—a hormone), and parathyroid hormone/teriparatide (Forteo—a synthetic version of the human hormone, parathyroid hormone, which helps to regulate calcium metabolism).

Bisphosphonates such as alendronate and risedronate bind permanently to the surface of bone and interfere with osteoclast activity. This allows the osteoblasts to outpace the rate of resorption. The most common side effects are nausea, abdominal pain and loose bowel movements. However, alendronate is reported to also cause irritation and inflammation of the esophagus, and in some cases, ulcers of the esophagus. Risedronate is chemically different from alendronate and has less likelihood of causing esophagus irritation. However, certain foods, calcium, iron supplements, vitamins and minerals, or antacids containing calcium, magnesium, or aluminum can reduce the absorption of risedronate, thereby resulting in loss of effectiveness.

The most common side effect of Raloxifen and other SERMS (such as Tamoxifen) are hot flashes. However, Raloxifene and other hormone replacement therapies have been shown to increase the risk of blood clots, including deep vein thrombosis and pulmonary embolism, cardiovascular disease and cancer.

Calcitonin is not as effective in increasing bone density and strengthening bone as estrogen and the other anti-resorptive agents. Common side effects of either injected or nasal spray calcitonin are nausea and flushing. Patients can develop nasal irritations, a runny nose, or nosebleeds. Injectable calcitonin can cause local skin redness at the site of injection, skin rash, and flushing.

A situation demonstrative of the link between several disorders or disease states involving bone remodelling is that of the use of etidronate (Didronel) first approved by the FDA to treat Paget's disease. Paget's disease is a bone disease characterized by a disorderly and accelerated remodelling of the bone, leading to bone weakness and pain. Didronel has been used 'off-label' and in some studies shown to increase bone density in postmenopausal women with established osteoporosis. It has also been found effective in preventing bone loss in patients requiring long-term steroid medications (such as Prednisone or Cortisone). However, high dose or continuous use of Didronel can cause another bone disease called osteomalacia. Like osteoporosis, osteomalacia can lead to weak bones with increased risk of fractures. Because of osteomalacia concerns and lack of enough studies yet regarding reduction in the rate of bone fractures, the United States FDA has not approved Didronel for the treatment of osteoporosis.

Osteoporosis therapy has been largely focused on antiresorptive drugs that reduce the rate of bone loss but emerging therapies show promise in increasing bone mineral density instead of merely maintaining it or slowing its deterioration. The osteoporosis early stage pipeline consists largely of drug candidates in new therapeutic classes, in particular cathepsin K inhibitors, osteoprotegerin and calcilytics as well as novel bisphosphonates. Some of these are examples where novel drugs exploiting genomics programs are being developed based on a deeper understanding of bone biology and have the potential to change the face of treatment of bone disorders in the long term.

The present invention describes the use of antibodies specific for Siglec-15 for the diagnosis, prognosis, and treatment (including prevention) of cancer or bone loss (e.g., severe or excessive bone loss associated with bone-related disease or associated with an increase in osteoclast differentiation or activity). In particular, the present invention relates to the use of anti-Siglec-15 antibodies for inhibiting the differentiation of osteoclasts.

Sialic-acid-binding immunoglobulin-like lectins (Siglecs) are members of the immunoglobulin (Ig) superfamily that have the ability to interact with sialic acids (McMillan and Crocker, 2008; Crocker et al., 2007). There are several Siglec family members that all share specific structural features, in particular, displaying an amino-terminal V-set Ig domain that binds to sialic acid and a variable number of C2-set Ig domains. These membrane receptors are generally expressed in highly specific manners and many of the family members are expressed in hematopoietic cells (McMillan and Crocker, 2008). These proteins are thought to promote cell-cell interactions, mediate signalling, and regulate immune functions through the recognition of glycans (Crocker et al., 2007). Sialic acids are nine-carbon sugars typically located at the ends of complex glycoconjugates on the surface of cells. They can be attached to a wide variety of proteins and lipids (McMillan and Crocker, 2008).

Siglec-15 is one of the most recently described Siglec family members that have a high homology to Siglec-14 (Angata et al., 2007). These authors reported that it preferentially binds to sialyl Tn structure and that it interacts with DAP12 and DAP10. The functional significance of these interactions is not known but it was proposed that Siglec-15 probably harbors an activating function (Angata et al., 2007). Despite these preliminary insights into a potential role in mammals of Siglec-15, important advances in the understanding of the biological function of the protein were contributed when the sequence was identified as part of a screen to discover novel regulators of osteoclast differentiation (Sooknanan et al. 2007). In this patent application, it was revealed that attenuation of the Siglec-15 transcript by RNA interference in a mouse model of osteoclastogenesis resulted in significant reduction of differentiation of precursors in response to RANKL treatment. Similar results were disclosed in human osteoclasts. Furthermore, the studies presented in this disclosure also showed that the localization of Siglec-15 at the cell membrane was necessary for its function in osteoclast differentiation. Furthermore, a recent publication showed that the presence of sialic acid at the end of surface glycoconjugates was required for proper osteoclast differentiation and were probably important for the fusion of osteoclast precursor cells (Takahata et al., 2007). This last observation creates a direct functional link between sialic acid binding and the expression of Siglec-15 in differentiating osteoclasts and strongly suggested that Siglec-15 plays a role in the early differentiation program of osteoclast precursors.

Thus, the expression profile of Siglec-15, its strong inducibility during osteoclast differentiation, its localization at the surface of the membrane, and its structural features all contribute to the feasibility of targeting this protein at the cell surface with monoclonal antibodies. The only other example of monoclonal antibody-based therapy that target osteoclasts is denosumab, a human monoclonal antibody that is specific for RANKL (Ellis et al. 2008). The present invention relates to the use of anti-Siglec-15 antibodies or antigen binding fragments as blockers of osteoclast differentiation in the detection or treatment of bone loss, especially in the context of bone-related diseases or in the context of increased osteoclast differentiation or activity. The present invention also relates to the use of antibodies or antigen binding fragments in the detection or treatment of cancer.

BRIEF DESCRIPTION OF THE DRAWINGS

FIG. 4 shows the results of an Fc-Siglec-15 ELISA of the individual monoclonal antibodies selected from the 96-well plate from Omniclonal library #25 containing anti-Siglec-15 Fabs. The wells indicated by bold numbers contained the exemplary monoclonals 25A1, 25B4, 25B8, 25C1, 25D8, 25E5, 25E6, and 25E9. Also shown is an ELISA on the same plate using the Fc moiety alone to identify those monoclonals that were specific for the Fc portion of the Fc-Siglec-15 fusion protein.

FIGS. 10A, 10B and 10C is a summary of alignment results obtained for selected CDRL1, CDRL2 and CDRL3 sequences (respectively) using the ClustalW2 program; where "*" means that the residues in that column are identical in all sequences in the alignment, ":" means that conserved substitutions have been observed and "." means that semi-conserved substitutions are observed. Consensus CDRs were generated using the ClustalW program (Larkin M. A., et al., (2007) ClustalW and ClustalX version 2. *Bioinformatics* 2007 23(21): 2947-2948).

FIGS. 11A, 11B and 11C is a summary of alignment results obtained for selected CDRH1, CDRH2 and CDRH3 sequences (respectively) using the ClustalW2 program; where "*" means that the residues in that column are identical in all sequences in the alignment, ":" means that conserved substitutions have been observed and "." means that semi-conserved substitutions are observed. Consensus CDRs were generated using the ClustalW program (Larkin M. A., et al., (2007) ClustalW and ClustalX version 2. *Bioinformatics* 2007 23(21): 2947-2948).

SUMMARY OF THE INVENTION

Figure 1:
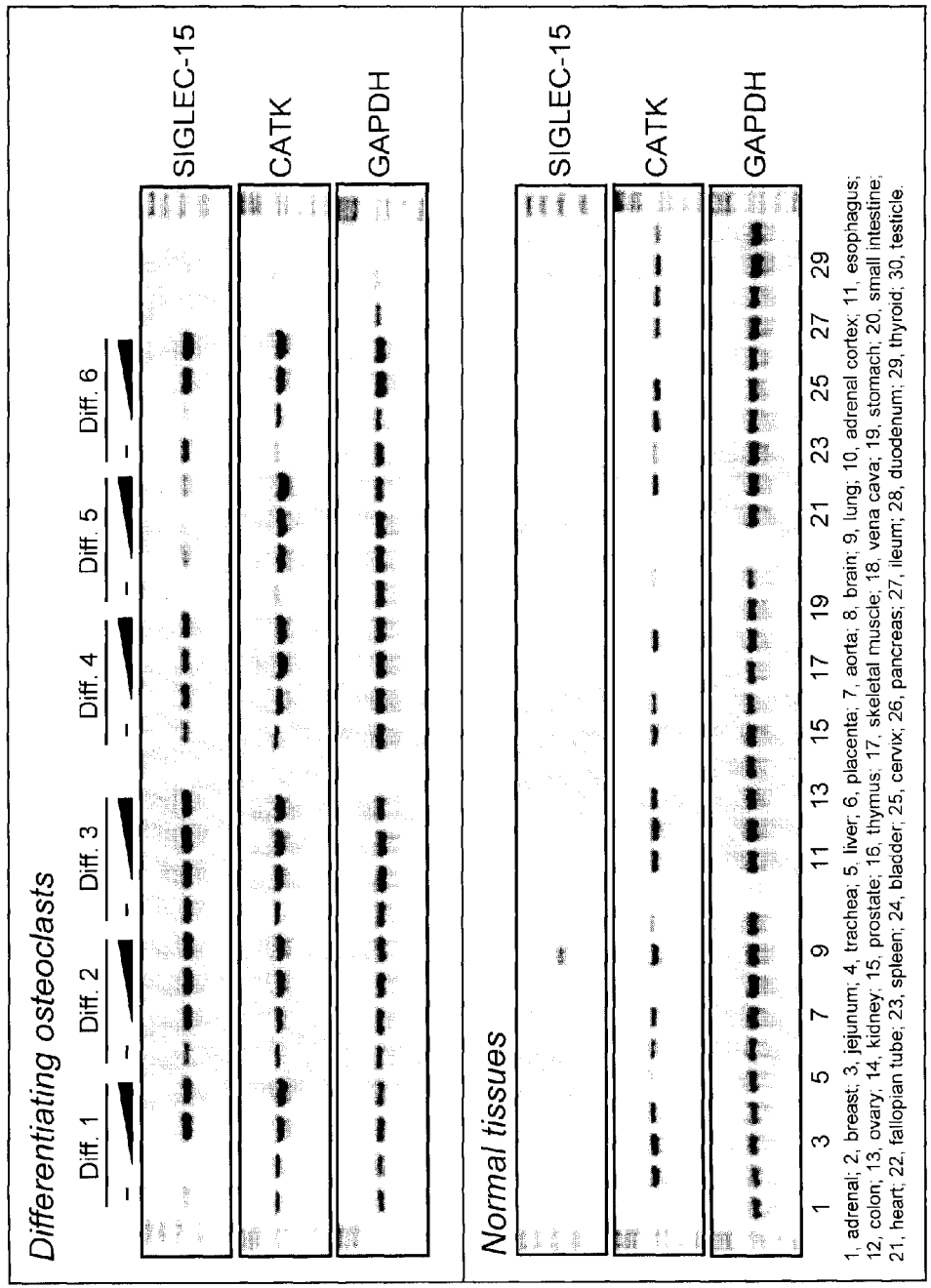
FIG. 1 shows the PCR-based expression profiling of the Siglec-15 mRNA in human differentiating osteoclast samples from six different donors. Also depicted is the expression profiling in RNA samples from 30 human normal tissues. As controls, the Siglec-15 expression pattern was compared to a well-known osteoclast marker, cathepsin K (CATK) and the housekeeping gene glyceraldehyde-3-phosphate dehydrogenase (GAPDH) was included to control for the quantity of RNA in each sample.

This invention relates to antibodies and antigen binding fragments as well as kits useful for the treatment (including prevention), detection and diagnosis of bone loss or cancer. The antibodies and antigen binding fragments may more particularly be useful for detection of differentiated osteoclast, ovarian cancer cells, renal cancer cells, cancer cells of the central nervous system, prostate cancer cells, melanoma cells, breast cancer cells, lung cancer cells or colon cancer cells and diagnosis of bone loss, ovarian cancer, renal cancer, cancer of the central nervous system, prostate cancer, melanoma, breast cancer, lung cancer or colon cancer. The antibodies or antigen binding fragment of the present invention may also be useful for treating bone loss, ovarian cancer, renal cancer, cancer of the central nervous system, prostate cancer, melanoma, breast cancer, lung cancer or colon cancer.

The antibodies or antigen-binding fragment of the present invention may bind to amino acids 20 to 259 of Siglec-15 (SEQ ID NO:2) or to a corresponding region of Siglec-15 variant (e.g., SEQ ID NO:4). More particularly the antibodies or antigen-binding fragment of the present invention may bind to amino acids 49 to 165 of Siglec-15 (SEQ ID NO:2) or to a corresponding region of a Siglec-15 variant (e.g., SEQ ID NO:4).

The present invention more particularly relates to an isolated antibody or antigen binding fragment capable of binding to a polypeptide able to promote osteoclast differentiation and of inhibiting an osteoclast differentiation activity of the polypeptide.

The antibodies or antigen binding fragments of the present invention encompass those which bind to amino acids 20 to 259 of SEQ ID NO:2 or to a variant having at least 80% sequence identity with amino acids 20 to 259 of SEQ ID NO:2.

More particularly, the antibody or antigen binding fragment of the present invention may more particularly bind to amino acids 49 to 165 of SEQ ID NO:2 or to a variant having at least 80% sequence identity with amino acids 49 to 165 of SEQ ID NO:2.

More specifically, antibody or antigen binding fragment of the present invention may more particularly bind to a polypeptide having at least 80% sequence identity with SEQ ID NO:2.

In accordance with the present invention, the antibody or antigen binding fragment may therefore interfere with the ability of the polypeptide to promote osteoclast differentiation or to promote tumor growth.

An antibody or antigen binding fragment capable of binding to the extracellular region of SEQ ID NO:2 or the SEQ ID NO:2 variant is more specifically contemplated.

The present invention therefore provides an isolated antibody or antigen binding fragment capable of binding to a polypeptide able to promote osteoclast differentiation and having at least 80% sequence identity with sEQ ID NO:2 or with amino acids 20 to 259 of SEQ ID NO:2 (or at least 80% identity with amino acids 49-165 of SEQ ID NO:2) of Sialic-acid-binding immunoglobulin-like lectin 15 (Siglec-15; SEQ ID NO:2), wherein said antibody or antigen binging fragment is capable of inhibiting osteoclast differentiation, bone resorption (degradation) or is capable of blocking Siglec-15 from binding to a sialic acid.

The antibody or antigen binding fragment of the present invention may be capable of interfering with (inhibiting) differentiation of an osteoclast precursor cell into a differentiated osteoclast.

In accordance with the present invention, the isolated antibody or antigen binding fragment may be, for example, a polyclonal antibody, a monoclonal antibody, a chimeric antibody, a human antibody or a fragment thereof.

In an exemplary embodiment, the isolated antibody or antigen binding fragment may be chimeric antibody or a human antibody which may comprise amino acids of a constant region of a human antibody or a fragment thereof.

The constant region or fragment thereof may be from an IgG1, IgG2, IgG3, or IgG4. In a more specific embodiment, the constant region may be from an IgG2.

Antigen binding fragments which may be particularly be useful include, for example, a FV (scFv), a Fab, a Fab' or a (Fab')$_2$.

The antibody or antigen binding fragment may be produced in or from an isolated mammalian cell (other than an hybridoma cell) or in an hybridoma cell. An exemplary embodiment of an isolated mammalian cell is a human cell.

Production of a monoclonal antibody, a chimeric antibody, a human antibody or a fragment thereof in an isolated mammalian cell (e.g., human cell) is particularly contemplated. The chimeric antibody or a human antibody thus produced may comprise amino acids of a constant region of a human antibody or a fragment thereof, including, for example, a constant region or fragment thereof from an IgG1, IgG2, IgG3, or IgG4. In a more specific embodiment, the constant region may be from an IgG2.

In an aspect of the invention, the antibody or antigen binding fragment of the present invention may interfere (inhibit) with the differentiation of a human osteoclast precursor cell into a differentiated human osteoclast.

In an exemplary embodiment, the antibody or antigen binding fragment of the present invention may interfere (inhibit) with the differentiation of a primary human osteoclast precursor cell into a differentiated human osteoclast.

Antibodies or antigen binding fragments having such activity may include, for example, a polyclonal antibody, a monoclonal antibody, a chimeric antibody, a human antibody or a fragment thereof.

In a more specific embodiment, antibodies or antigen binding fragments that may be capable of having such activity include, for example, a monoclonal antibody, a chimeric antibody, a human antibody or a fragment thereof.

In an even more specific embodiment, antibodies or antigen binding fragments that may be capable of having such activity include, for example, a chimeric antibody, a human antibody or a fragment thereof that may comprise amino acids of a constant region of a human antibody or a fragment thereof.

The constant region or fragment thereof of the chimeric or human antibody may be from an IgG1, IgG2, IgG3, or IgG4. More particularly, the constant region may be from an IgG2.

The antibodies and antigen binding fragments of the present invention may also be used to generally target cells expressing or overexpressing Siglec-15, including bone cells and breast, colon, lung, ovarian, prostate, and renal cancer cells as well as melanoma cells and cancer cells of the central nervous system.

More particularly, the antibodies and antigen binding fragments may be used to target osteoclasts cells undergoing differentiation.

The present invention provides in one aspect thereof, an isolated or substantially purified antibody or antigen binding fragment which may be capable of specific binding to SEQ ID NO:2.

More specifically and in accordance with an embodiment of the invention, the antibody or antigen binding fragment may bind to a domain located between amino acid 20 and amino acid 259 of SEQ ID NO:2.

In accordance with another embodiment of the invention, the antibody or antigen binding fragment may be capable of binding to an epitope comprised within amino acid 20 and amino acid 259 of SEQ ID NO:2.

As such, the present invention encompasses diagnostic and/or therapeutic antibodies or antigen binding fragments having specificity for SEQ ID NO:2. Also encompassed by the present invention are antibodies or antigen binding fragments having the same epitope specificity as the antibody of the present invention. A candidate antibody may be identified by determining whether it will bind to the epitope to which the antibodies described herein binds and/or by performing competition assays with antibodies or antigen binding fragments known to bind to the epitope.

Therefore, another aspect the present invention provides an isolated antibody or antigen binding fragment capable of competing with the antibody or antigen binding fragment described herein.

In further aspects, the present invention provides method of treatment and method of detection using the antibody or antigen binding fragment of the present invention.

The term "antibody" refers to intact antibody, monoclonal or polyclonal antibodies. The term "antibody" also encompasses, multispecific antibodies such as bispecific antibodies. Human antibodies are usually made of two light chains and two heavy chains each comprising variable regions and constant regions. The light chain variable region comprises 3 CDRs, identified herein as CDRL1, CDRL2 and CDRL3 flanked by framework regions. The heavy chain variable region comprises 3 CDRs, identified herein as CDRH1, CDRH2 and CDRH3 flanked by framework regions.

The term "antigen-binding fragment", as used herein, refers to one or more fragments of an antibody that retain the ability to bind to an antigen (e.g., SEQ ID NO:2 or variants thereof). It has been shown that the antigen-binding function of an antibody can be performed by fragments of an intact antibody. Examples of binding fragments encompassed within the term "antigen-binding fragment" of an antibody include (i) a Fab fragment, a monovalent fragment consisting of the $V_L$, $V_H$, $C_L$ and $C_{H1}$ domains; (ii) a F(ab')$_2$ fragment, a bivalent fragment comprising two Fab fragments linked by a disulfide bridge at the hinge region; (iii) a Fd fragment consisting of the $V_H$ and $C_{H1}$ domains; (iv) a Fv fragment consisting of the $V_L$ and $V_H$ domains of a single arm of an antibody, (v) a dAb fragment (Ward et al., (1989) Nature 341:544-546), which consists of a $V_H$ domain; and (vi) an isolated complementarity determining region (CDR), e.g., $V_H$ CDR3. Furthermore, although the two domains of the Fv fragment, $V_L$ and $V_H$, are coded for by separate genes, they can be joined, using recombinant methods, by a synthetic linker that enables them to be made as a single polypeptide chain in which the $V_L$ and $V_H$ regions pair to form monovalent molecules (known as single chain Fv (scFv); see e.g., Bird et al. (1988) Science 242:423-426; and Huston et al. (1988) Proc. Natl. Acad. Sci. USA 85:5879-5883). Such single chain antibodies are also intended to be encompassed within the term "antigen-binding fragment" of an antibody. Furthermore, the antigen-binding fragments include binding-domain immunoglobulin fusion proteins comprising (i) a binding domain polypeptide (such as a heavy chain variable region, a light chain variable region, or a heavy chain variable region fused to a light chain variable region via a linker peptide) that is fused to an immunoglobulin hinge region polypeptide, (ii) an immunoglobulin heavy chain CH2 constant region fused to the hinge region, and (iii) an immunoglobulin heavy chain CH3 constant region fused to the CH2 constant region. The hinge region may be modified by replacing one or more cysteine residues with serine residues so as to prevent dimerization. Such binding-domain immunoglobulin fusion proteins are further disclosed in US 2003/0118592 and US 2003/0133939. These antibody fragments are obtained using conventional techniques known to those with skill in the art, and the fragments are screened for utility in the same manner as are intact antibodies.

A typical antigen binding site is comprised of the variable regions formed by the pairing of a light chain immunoglobulin and a heavy chain immunoglobulin. The structure of the antibody variable regions is very consistent and exhibits very similar structures. These variable regions are typically comprised of relatively homologous framework regions (FR) interspaced with three hypervariable regions termed Complementarity Determining Regions (CDRs). The overall binding activity of the antigen binding fragment is often dictated by the sequence of the CDRs. The FRs often play a role in the proper positioning and alignment in three dimensions of the CDRs for optimal antigen binding.

Antibodies and/or antigen binding fragments of the present invention may originate, for example, from a mouse, a rat or any other mammal or from other sources such as through recombinant DNA technologies.

Further scope, applicability and advantages of the present invention will become apparent from the non-restrictive detailed description given hereinafter. It should be understood, however, that this detailed description, while indicating exemplary embodiments of the invention, is given by way of example only, with reference to the accompanying drawings.

DETAILED DESCRIPTION OF THE INVENTION

The Expression Profile of Siglec-15 in Osteoclasts and Normal Tissues

The present invention relates to the use of monoclonal antibodies to target osteoclasts found in various bone related disease where severe bone loss is observed due to increased activity of the osteoclasts. In order to direct the antibodies to the osteoclasts, the identification of osteoclast-specific antigens that are expressed at the cell surface of the cells must be carried out. There are several technologies that are available to identify cell-specific antigens and the method that was used to identify Siglec-15 in differentiating osteoclasts that were treated with RANKL, an innovative discovery platform called Subtractive Transcription-based Amplification of mRNA (STAR), is described in the published patent application No. PCT/CA2007/000210.

Analysis of the human osteoclast STAR libraries yielded many genes that encode secreted and cell surface proteins. One of these, termed AB-0326, contained an open reading frame that encoded a polypeptide of 328 amino acids, corresponding to SEQ ID NO:2 that was encoded by a cDNA of 987 base pairs with the nucleotide sequence shown in SEQ ID NO:1. A search of publicly available databases revealed that the AB-0326 nucleotide sequence was identical to that of a human gene called CD33 antigen-like 3 (CD33L3). CD33L3 was later found to be a member of the Siglec family of sialic acid binding proteins and was renamed Siglec-15 based on homology to other Siglecs (Crocker et al., 2007). Based on this information, the mouse orthologue was isolated and sequenced and found to be approximately 85% identical to the human sequence at the amino acid level. SEQ ID NO:3 and SEQ ID NO:4 show the sequences of cDNA and polypeptide of the murine Siglec-15, respectively. Bioinformatic analysis predicted a type I membrane-anchored protein that presents its functional domain to the extracellular compartment. As with other Siglec sequences, an amino-terminal signal peptide (located between amino acids 1 and 19 of SEQ ID NO:2) targets the protein to the membrane of cells and the final processed protein is anchored to the membrane via a single trans-membrane helix located at the carboxy-terminus (located between amino acids 261 and 283 of SEQ ID NO:2). The V-set Ig domain is located between amino acids 49 and 165 of SEQ ID NO:2 whereas the C2-set Ig domain is located between amino acids 178 and 244 of SEQ ID NO:2.

The present invention relates to the function of Siglec-15 during the differentiation of osteoclasts. Previous findings (Sooknanan et al. 2007) established that the transcript encoding human Siglec-15 was significantly upregulated in response to RANKL. This determination was performed on RNA macroarrays that contained spotted total RNA samples from several different human osteoclast differentiation experiments from different human PBMNC donors. Furthermore, these studies (Sooknanan et al. 2007) revealed that the Siglec-15 transcript was expressed in only one normal tissue among a vast panel of 30 human normal tissues indicating a very high osteoclast specificity of the Siglec-15 gene expression. Using more sensitive methods such as semi-quantitative RT-PCR, the expression of the Siglec-15 mRNA was stimulated within one day of RANKL treatment in many osteoclast samples indicating that the gene was expressed early in osteoclast precursor cells, prior to the commencement of cell fusion. Finally, the tissue expression profile of Siglec-15 was assessed by semi-quantitative RT-PCR and found to only be expressed in a single normal human tissue thus validating the macroarray results of Sooknanan et al. Taken together, these expression results underscore the strength of the Applicant's discovery approach in its ability to identify targets, as exemplified by Siglec-15, that are highly restricted to differentiating osteoclasts.

Based on the expression of Siglec-15 in the early stages of differentiation of osteoclasts, its limited expression in normal tissues, and a critical biological role for Siglec-15 in the activity of osteoclasts, Siglec-15 was chosen as a therapeutic target for the development of monoclonal antibodies for the detection, prevention, and treatment of bone-related diseases such as cancer-induced bone loss and osteoporosis.

Therefore, a variety of anti-Siglec-15 antibodies and immunologically functional fragments thereof, such as chimeric and humanized monoclonal antibodies, antibody fragments, single chain antibodies, domain antibodies, and polypeptides with an antigen-binding region, for targeting Siglec-15 are provided.

SEQ ID NO:2 as Antigen and Epitopes Derived from SEQ ID NO:2

In international application No. PCT/CA2007/000210, the Applicant has come to the unexpected discovery that SEQ ID NO:2 is involved in osteoclast differentiation. This antigen may thus be useful for targeting cells expressing the antigen in vitro or in vivo and in the development of detection assays for measuring the antigen in vitro or in vivo.

The present invention therefore provides an antigen useful for generating specific antibodies and/or specific for cells expressing SEQ ID NO:2. The antigen or epitope may comprise a fragment of at least 10 amino acids (and up to the total length) of SEQ ID NO:2 or of a SEQ ID NO:2 variant.

An exemplary antigen is the whole SEQ ID NO:2 protein or a variant form having at least 80% sequence identity with SEQ ID NO:2 or a fragment comprising at least 10 amino acids of SEQ ID NO:2 or of a SEQ ID NO:2 variant.

The antigen or the epitope described herein may be fused with a carrier such as keyhole limpet (KHL), bovine serum albumin (BSA), ovalbumin (OVA) or else in order to generate antibodies and antigen binding fragments.

The present invention also provides an epitope comprised within amino acid 20 to 259 of SEQ ID NO:2 to generate antibodies and antigen binding fragments described herein. The epitope may comprise a fragment of at least 10 amino acids comprised within amino acids 20 to 259 of SEQ ID NO:2 or a corresponding portion of a SEQ ID NO:2 variant.

The present invention further provides a composition for generating antibodies to SEQ ID NO:2 or to a SEQ ID NO:2 variant, the composition may comprise an epitope of SEQ ID NO:2 comprised within amino acids 20 to 259 of SEQ ID NO:2 or a corresponding portion of a SEQ ID NO:2 variant and a carrier.

Exemplary embodiments of compositions are pharmaceutical composition for generating antibodies against SEQ ID NO:2 or against a SEQ ID NO:2 variant. The pharmaceutical composition may comprise an epitope of SEQ ID NO:2 comprised within amino acids 20 to 259 of SEQ ID NO:2 or a corresponding portion of a SEQ ID NO:2 variant and a pharmaceutically acceptable carrier.

In yet a further aspect the invention provides a method for generating antibodies against SEQ ID NO:2 or against a SEQ ID NO:2 variant. The method may comprise administering a polypeptide comprising an epitope of SEQ ID NO:2 comprised within amino acids 20 to 259 of SEQ ID NO:2 or a corresponding portion of a SEQ ID NO:2 variant.

In an additional aspect, the present invention provides the use of an epitope of SEQ ID NO:2 comprised within amino acids 20 to 259 of SEQ ID NO:2 or a corresponding portion of a SEQ ID NO:2 variant for generating antibodies against SEQ ID NO:2 or against a SEQ ID NO:2 variant.

Exemplary embodiments of SEQ ID NO:2 variant having 80% identity with SEQ ID NO:2 include for example and without limitation, SEQ ID NO:4 as well as other analogues that are published in databases under gene bank accession numbers or NCBI reference sequence: AAY40743.1, XP_512109.2, XP_001089000.1, XP_601064.4, NP_001094508.1, XP_855238.1, XP_574176.2 and EAX01462.1.

Antibodies and Antigen Binding Fragments that Binds to SEQ ID NO:2 or to SEQ ID NO:2 Variant Antibodies were initially isolated from Fab libraries for their specificity towards the antigen of interest. Comparison of the amino acid sequences of the light chain variable domains or the heavy chain variable domains of antibodies showing the greatest characteristics allowed us to derive consensus sequences within the CDRs and within the variable regions. The consensus for CDRs are provided in SEQ ID Nos:148-158 and 197-210. The consensus for the variable regions are provided in SEQ ID Nos:191-196.

The variable regions described herein may be fused with constant regions of a desired species thereby allowing recognition of the antibody by effector cells of the desired species. The constant region may originate, for example, from an IgG1, IgG2, IgG3, or IgG4 subtype. Cloning or synthesizing a constant region in frame with a variable region is well within the scope of a person of skill in the art and may be performed, for example, by recombinant DNA technology.

In certain embodiments of the present invention, antibodies that bind to SEQ ID NO:2 may be of the IgG1, IgG2, IgG3, or IgG4 subtype. More specific embodiments of the invention relates to an antibody of the IgG1 subtype. The antibody may be a humanized antibody of the IgG1 subtype that is biologically active in mediating antibody-dependent cellular cytotoxicity (ADCC), complement-mediated cytotoxicity (CMC), or associated with immune complexes. The typical ADCC involves activation of natural killer (NK) cells and is reliant on the recognition of antibody-coated cells by Fc receptors on the surface of the NK cells. The Fc receptors recognize the Fc domain of antibodies such as is present on IgG1, which bind to the surface of a target cell, in particular a bone cell that expresses an antigen, such as SEQ ID NO:2. Once bound to the Fc receptor of IgG the NK cell releases cytokines and cytotoxic granules that enter the target cell and promote cell death by triggering apoptosis.

The present invention described a collection of antibodies that bind to SEQ ID NO:2. In certain embodiments, the antibodies may be selected from the group consisting of polyclonal antibodies, monoclonal antibodies such as chimeric or humanized antibodies, antibody fragments such as antigen binding fragments, single chain antibodies, domain antibodies, and polypeptides with an antigen binding region.

The present invention therefore provides in another aspect thereof, an isolated antibody or antigen binding fragment comprising a light chain variable domain having;

a. a CDRL1 sequence selected from the group consisting of SEQ ID NO:69, SEQ ID NO:75, SEQ ID NO:81, SEQ ID NO:87, SEQ ID NO:93, SEQ ID NO:99, SEQ ID NO:105, SEQ ID NO:111, SEQ ID NO:173, SEQ ID NO:179 and SEQ ID NO:185;

b. a CDRL2 sequence selected from the group consisting of SEQ ID NO:70, SEQ ID NO:76. SEQ ID NO:82, SEQ ID NO:88, SEQ ID NO:94, SEQ ID NO:100, SEQ ID NO:106, SEQ ID NO:112, SEQ ID NO:174, SEQ ID NO:180 and SEQ ID NO:186 and/or;

c. a CDRL3 sequence selected from the group consisting of SEQ ID NO:71, SEQ ID NO:77, SEQ ID NO:83, SEQ ID NO:89, SEQ ID NO:95, SEQ ID NO:101, SEQ ID NO:107, SEQ ID NO:113, SEQ ID NO:175, SEQ ID NO:181 and SEQ ID NO:187.

The isolated antibody or antigen binding fragment may also comprise a heavy chain variable domain having;

a. a CDRH1 sequence selected from the group consisting of SEQ ID NO:72, SEQ ID NO:78, SEQ ID NO:84, SEQ ID NO:90, SEQ ID NO:96, SEQ ID NO:102, SEQ ID NO:108, SEQ ID NO:114, SEQ ID NO:176, SEQ ID NO:182 and SEQ ID NO:188;

b. a CDRH2 sequence selected from the group consisting of SEQ ID NO:73, SEQ ID NO:79, SEQ ID NO:85, SEQ ID NO:91, SEQ ID NO:97, SEQ ID NO:103, SEQ ID NO:109, SEQ ID NO:115, SEQ ID NO:177, SEQ ID NO:183 and SEQ ID NO:189 and/or;

c. a CDRH3 sequence selected from the group consisting of SEQ ID NO:74, SEQ ID NO:80, SEQ ID NO:86, SEQ ID NO:92, SEQ ID NO:98, SEQ ID NO:104, SEQ ID NO:110, SEQ ID NO:116, SEQ ID NO:178, SEQ ID NO:184 and SEQ ID NO:190.

In a further aspect, the present invention provides an isolated antibody or antigen binding fragment which may comprise a light chain variable domain having;
  a) a CDRL1 which may have at least 80% identity with a CDRL1 sequence selected from the group consisting of SEQ ID NO:148, SEQ ID NO:69, SEQ ID NO:75 and SEQ ID NO:105
  b) a CDRL2 which may have at least 80% identity with a CDRL2 sequence selected from the group consisting of SEQ ID NO:149, SEQ ID NO:150, SEQ ID NO:76, SEQ ID NO:82 and SEQ ID NO:106, or;
  c) a CDRL3 which may have at least 80% identity with a CDRL3 sequence selected from the group consisting of SEQ ID NO:151, SEQ ID NO:152, SEQ ID NO:77, SEQ ID NO:83, SEQ ID NO:95, SEQ ID NO:107 and SEQ ID NO:152.

In yet a further aspect, the present invention provides an isolated antibody or antigen binding fragment, wherein the antibody comprises a heavy chain variable domain having;
  a) a CDRH1 which may have at least 80% identity with a CDRH1 sequence selected from the group consisting of SEQ ID NO:153, SEQ ID NO:154, SEQ ID NO:84, SEQ ID NO:96 and SEQ ID NO:102;
  b) a CDRH2 which may have at least 80% identity with a CDRH2 sequence selected from the group consisting of SEQ ID NO:155, SEQ ID NO:156, SEQ ID NO:157, SEQ ID NO:73, SEQ ID NO:79, SEQ ID NO:85, SEQ ID NO:97, SEQ ID NO:103 and SEQ ID NO:109, or;
  c) a CDRH3 which may have at least 80% identity with a CDRH3 sequence selected from the group consisting of SEQ ID NO:158, SEQ ID NO:74, SEQ ID NO:98, SEQ ID NO:104, SEQ ID NO:110 and SEQ ID NO:116.

In an exemplary embodiment, the antibody or antigen binding fragment may comprise any individual CDR or a combination of CDR1, CDR2 and/or CDR3 of the light chain variable region. The CDR3 may more particularly be selected. Combination may include for example, CDRL1 and CDRL3; CDRL1 and CDRL2; CDRL2 and CDRL3 and; CDRL1, CDRL2 and CDRL3.

In another exemplary embodiment, the antibody or antigen binding fragment may comprise any individual CDR or a combination of CDR1, CDR2 and/or CDR3 of the heavy chain variable region. The CDR3 may more particularly be selected. Combination may include for example, CDRH1 and CDRH3; CDRH1 and CDRH2; CDRH2 and CDRH3 and; CDRH1, CDRH2 and CDRH3.

In accordance with the present invention, the antibody or antigen binding fragment may comprise at least two CDRs of a CDRL1, a CDRL2 or a CDRL3.

Also in accordance with the present invention, the antibody or antigen binding fragment may comprise one CDRL1, one CDRL2 and one CDRL3.

Further in accordance with the present invention, the antibody or antigen binding fragment may comprise:
  a. At least two CDRs of a CDRL1, CDRL2 or CDRL3 and;
  b. At least two CDRs of a CDRH1, one CDRH2 or one CDRH3.

The antibody or antigen binding fragment may more preferably comprise one CDRL1, one CDRL2 and one CDRL3.

The antibody or antigen binding fragment may also more preferably comprise one CDRH1, one CDRH2 and one CDRH3.

In another aspect the present invention provides an isolated antibody or antigen binding fragment comprising a heavy chain variable domain having;
  a. a CDRH1 sequence selected from the group consisting of SEQ ID NO:72, SEQ ID NO:78, SEQ ID NO:84, SEQ ID NO:90, SEQ ID NO:96, SEQ ID NO:102, SEQ ID NO:108, SEQ ID NO:114, SEQ ID NO:176, SEQ ID NO:182 and SEQ ID NO:188;
  b. a CDRH2 sequence selected from the group consisting of SEQ ID NO:73, SEQ ID NO:79, SEQ ID NO:85, SEQ ID NO:91, SEQ ID NO:97, SEQ ID NO:103, SEQ ID NO:109, SEQ ID NO:115, SEQ ID NO:177, SEQ ID NO:183 and SEQ ID NO:189 and/or;
  c. a CDRH3 sequence selected from the group consisting of SEQ ID NO:74, SEQ ID NO:80, SEQ ID NO:86, SEQ ID NO:92, SEQ ID NO:98, SEQ ID NO:104, SEQ ID NO:110, SEQ ID NO:116, SEQ ID NO:178, SEQ ID NO:184 and SEQ ID NO:190.

In accordance with the present invention, the antibody or antigen binding fragment may comprise one CDRH1, one CDRH2 or one CDRH3.

In accordance with the present invention, the antibody or antigen binding fragment may also comprise one CDRH1, one CDRH2 and one CDRH3.

When only one of the light chain variable domain or the heavy chain variable domain is available, an antibody or antigen-binding fragment may be reconstituted by screening a library of complementary variable domains using methods known in the art (Portolano et al. The Journal of Immunology (1993) 150:880-887, Clarkson et al., Nature (1991) 352:624-628).

Also encompassed by the present invention are polypeptides or antibodies comprising variable chains having at least one conservative amino acid substitution in at least one of the CDRs described herein.

Also encompassed by the present invention are polypeptides or antibodies comprising variable chains having at least one conservative amino acid substitution in at least two of the CDRs.

Also encompassed by the present invention are polypeptides or antibodies comprising variable chains having at least one conservative amino acid substitution in the 3 CDRs.

Also encompassed by the present invention are polypeptides or antibodies comprising variable chains having at least two conservative amino acid substitution in at least one of the CDRs.

Also encompassed by the present invention are polypeptides or antibodies comprising variable chains having at least two conservative amino acid substitution in at least two of the CDRs.

Also encompassed by the present invention are polypeptides or antibodies comprising variable chains having at least two conservative amino acid substitution in the 3 CDRs.

In another aspect, the present invention relates to a polypeptide, antibody or antigen binding fragment comprising (on a single polypeptide chain or on separate polypeptide chains) at least one complementarity-determining region of a light chain variable domain and at least one complementarity-determining region of a heavy chain variable domain of one of the antibodies or antigen binding fragment described herein.

The present invention relates in another aspect thereof to antibodies that may comprise (on a single polypeptide chain or on separate polypeptide chains) all six complementarity-determining region (CDR) of the antibody or antigen binding fragment described herein.

The antibodies or antigen binding fragment of the present invention may further comprise additional amino acids flanking the amino and/or carboxy region of the CDR(s). Those additional amino acids may be identical to the framework regions of the corresponding antibodies described herein or may include, for example, conservative amino acid substitution.

In accordance with an embodiment of the present invention, the antibody or antigen binding fragment may comprise a CDRL1 sequence comprising or consisting of formula:

RSX$_{1a}$X$_{2a}$SLLHSNGX$_{3a}$TYLY, (SEQ ID NO.: 148)

Wherein X$_{1a}$ may be, for example, a neutral hydrophilic amino acid;
Wherein X$_{2a}$ may be, for example, lysine or glutamic acid
wherein X$_{3a}$ may be, for example, an hydrophobic amino acid or asparagine.
In a more specific embodiment, X$_{1a}$ may be, for example, serine.
In a more specific embodiment, X$_{2a}$ may be, for example, lysine.
More particularly X$_{3a}$ may be, for example, isoleucine or valine.
In a more specific embodiment, X$_{3a}$ may be isoleucine.
In accordance with yet another embodiment of the present invention, the antibody or antigen binding fragment may comprise a CDRL1 sequence comprising or consisting of formula:

RASX$_{a10}$NIX$_{b10}$X$_{c10}$YLA (SEQ ID NO.: 197)

Wherein X$_{a10}$ may be any amino acid or for example G or E;
X$_{b10}$ may be any amino acid or for example Y or H, and;
X$_{c10}$ may be any amino acid or for example S or N.
In accordance with yet another embodiment of the present invention, the antibody or antigen binding fragment may comprise a CDRL1 sequence comprising or consisting of formula: CDRL1 of formula RSSX$_{1x}$SLLHSNGX$_{2x}$TYLY (SEQ ID NO:201) wherein X$_{1x}$ and X$_{2x}$ are as defined herein.
In accordance with yet another embodiment of the present invention, the antibody or antigen binding fragment may comprise a CDRL1 sequence comprising or consisting of formula: CDRL1 of formula RSX$_{a6}$KSLLHSNGNTYLY (SEQ ID NO:202) wherein X$_{a6}$ is as defined herein.
The antibody or antigen binding fragment may also comprise, for example, a CDRL1 sequence selected from those comprising or consisting of SEQ ID NO:75, SEQ ID NO:69, SEQ ID NO:105 and other CDRL1 listed in Table 3 or Table 5B.
In accordance with another embodiment, the antibody or antigen binding fragment may comprise a CDRL2 sequence comprising or consisting of formula:

X$_{1b}$MSNLAS, (SEQ ID NO.: 149)

wherein X$_{1b}$ may be, for example, a basic amino acid.
More particularly, X$_{1b}$ may be, for example, glutamine or asparagine.
In a more specific embodiment, X$_{1b}$ may be glutamine.
In accordance with yet another embodiment, the antibody or antigen binding fragment may comprise a CDRL2 sequence comprising or consisting of formula:

RX$_{1c}$SNLX$_{2c}$S, (SEQ ID NO.: 150)

wherein X$_{1c}$ may be, for example, methionine or threonine and wherein X$_{2c}$ may be, for example, an hydrophobic amino acid.
More particularly, X$_{2c}$ may be, for example, alanine or valine.

In a more specific embodiment, X$_{1c}$ may be, for example, methionine.
In a more specific embodiment, X$_{2c}$ may be, for example, alanine.
In accordance with yet another embodiment of the present invention, the antibody or antigen binding fragment may comprise a CDRL2 sequence comprising or consisting of formula:

NAKTLX$_{a11}$X$_{b11}$ (SEQ ID NO.: 198)

X$_{a11}$ may be any amino acid or for example P or A, and;
X$_{b11}$ may be any amino acid or for example an acidic amino acid such as E or D.
The antibody or antigen binding fragment may also comprise, for example, a CDRL2 sequence selected from those comprising or consisting of SEQ ID NO:76, SEQ ID NO:82, SEQ ID NO:106 and other CDRL2 listed in Table 3 or Table 5B.
In accordance with yet another embodiment, the antibody or antigen binding fragment may comprise a CDRL3 sequence comprising or consisting of formula:

X$_{1d}$QX$_{2d}$LEX$_{3d}$PX$_{4d}$T (SEQ ID NO.: 151)

wherein X$_{1d}$ may be, for example, an hydrophobic amino acid;
wherein X$_{2d}$ may be, for example, a basic amino acid;
wherein X$_{3d}$ may be, for example, tyrosine or leucine, and;
wherein X$_{4d}$ may be, for example, an aromatic amino acid.
More particularly, X$_{1d}$ may be, for example, methionine or alanine, In a more specific embodiment, X$_{1d}$ may be, for example, methionine.
More particularly, X$_{2d}$ may be, for example histidine or asparagine. In a more specific embodiment, X$_{2d}$ may be, for example, histidine.
In a more specific embodiment, X$_{3d}$ may be, for example, tyrosine.
More particularly, X$_{4d}$ may be, for example, tyrosine or phenylalanine. In a more specific embodiment, X$_{4d}$ may be, for example, tyrosine.
In accordance with an additional embodiment, the antibody or antigen binding fragment may comprise a CDRL3 sequence comprising or consisting of formula:

QQWSSNPX$_{1e}$T (SEQ ID NO.: 152)

Wherein X$_{1e}$ is proline or leucine.
In accordance with yet another embodiment of the present invention, the antibody or antigen binding fragment may comprise a CDRL3 sequence comprising or consisting of formula:

QHYGX$_{a12}$PLT (SEQ ID NO.: 199)

X$_{a12}$ may be any amino acid or a hydrophobic amino acid such as for example A or V.
In accordance with a further embodiment of the present invention, the antibody or antigen binding fragment may comprise a CDRL3 sequence comprising or consisting of formula: X$_{a8}$QX$_{b8}$LEX$_{c8}$PYT (SEQ ID NO:203) wherein X$_{a5}$, X$_{b8}$ and X$_{c8}$ are as defined herein.
In accordance with yet a further embodiment of the present invention, the antibody or antigen binding fragment may comprise a CDRL3 sequence comprising or consisting of formula: QHHYGX$_{a4}$PLT (SEQ ID NO:204) wherein X$_{a4}$ is as defined herein.

The antibody or antigen binding fragment may also comprise, for example, a CDRL3 sequence selected from those comprising or consisting of SEQ ID NO:77, SEQ ID NO:83, SEQ ID NO:95, SEQ ID NO:107, SEQ ID NO:152 and other CDRL3 listed in Table 3 or Table 5B.

In accordance with an additional embodiment, the antibody or antigen binding fragment may comprise a CDRH1 sequence comprising or consisting of formula:

GYTFX$_{1f}$X$_{2f}$YX$_{3f}$MX$_{4f}$ (SEQ ID NO.: 153)

wherein X$_{1f}$ may be, for example, threonine or asparagine;
wherein X$_{2f}$ may be, for example, threonine, arginine, serine or aspartic acid;
wherein X$_{3f}$ may be, for example, tryptophan or asparagine, aspartic acid or glutamic acid, and;
wherein X$_{4f}$ may be, for example, tyrosine, histidine or aspartic acid.

In a more specific embodiment, X$_{1f}$ may be, for example, threonine.
In a more specific embodiment, X$_{2f}$ may be, for example, serine.
In a more specific embodiment, X$_{3f}$ may be, for example, tryptophan.
In a more specific embodiment, X$_{4f}$ may be, for example, histidine.

In accordance with yet an additional embodiment, the antibody or antigen binding fragment may comprise a CDRH1 sequence comprising or consisting of formula:

GYTFTDYX$_{5f}$MH (SEQ ID NO.: 154)

Wherein X$_{5f}$ may be, for example, an acidic amino acid.
More particularly, X$_{5f}$ may be, for example, glutamic acid or aspartic acid. In a more specific embodiment, X$_{5f}$ may be, for example, aspartic acid.

In accordance with a further embodiment of the present invention, the antibody or antigen binding fragment may comprise a CDRH1 sequence comprising or consisting of formula: GYTFTX$_{1l}$YWMH (SEQ ID NO:205) wherein X$_{1l}$ is as defined herein.

In accordance with yet a further embodiment of the present invention, the antibody or antigen binding fragment may comprise a CDRH1 sequence comprising or consisting of formula: GYTFTDYX$_{1s}$MH (SEQ ID NO:208) wherein X$_{1s}$ is as defined herein.

The antibody or antigen binding fragment may also comprise, for example, a CDRH1 sequence selected from those comprising or consisting of SEQ ID NO:84, SEQ ID NO:96, SEQ ID NO:102 and other CDRH1 listed in Table 3 or Table 5A.

In accordance with a further embodiment, the antibody or antigen binding fragment may comprise a CDRH2 sequence comprising or consisting of formula:

LINPX$_{1g}$NX$_{2g}$RX$_{3g}$N (SEQ ID NO.: 155)

Wherein X$_{1g}$ may be, for example, a neutral hydrophilic amino acid;
Wherein X$_{2g}$ may be, for example, alanine or glycine; and;
Wherein X$_{3g}$ may be, for example, proline or threonine.

More particularly, X$_{1g}$ may be, for example, serine or threonine. In a more specific embodiment, X$_{1g}$ may be, for example, threonine.
In a more specific embodiment, X$_{2g}$ may be, for example, glycine.
In a more specific embodiment, X$_{3g}$ may be, for example, threonine.

In accordance with yet a further embodiment, the antibody or antigen binding fragment may comprise a CDRH2 sequence comprising or consisting of formula:

X$_{1h}$IDPETGGTA (SEQ ID NO.: 156)

Wherein X$_{1h}$ may be, for example, alanine or threonine.
In accordance with a more specific embodiment, X$_{1h}$ may be, for example, threonine.

In accordance with yet a further embodiment, the antibody or antigen binding fragment may comprise a CDRH2 sequence comprising or consisting of formula:

EIX$_{1i}$PX$_{2i}$X$_{3i}$SX$_{4i}$X$_{5i}$N (SEQ ID NO.: 157)

Wherein X$_{1i}$ may be, for example, aspartic acid or asparagine;
Wherein X$_{2i}$ may be, for example, aspartic acid or serine;
Wherein X$_{3i}$ may be, for example, aspartic acid or serine;
Wherein X$_{4i}$ may be, for example, tyrosine or threonine, and;
Wherein X$_{5i}$ may be, for example, threonine or isoleucine.

In accordance with yet another embodiment of the present invention, the antibody or antigen binding fragment may comprise a CDRH2 sequence comprising or consisting of formula:

AX$_{a13}$YPGNGDSR (SEQ ID NO.: 200)

X$_{a13}$ may be any amino acid or a hydrophobic amino acid such as I or V.

In accordance with an additional embodiment of the present invention, the antibody or antigen binding fragment may comprise a CDRH2 sequence comprising or consisting of formula: X$_{1t}$IDPETGGTA (SEQ ID NO:206) wherein X$_{1t}$ is as defined herein.

In accordance with yet an additional embodiment of the present invention, the antibody or antigen binding fragment may comprise a CDRH2 sequence comprising or consisting of formula: LINPX$_{1m}$NX$_{2m}$RX$_{3m}$N (SEQ ID NO:207) wherein X$_{1m}$, X$_{2m}$ and X$_{3m}$ are as defined herein.

In accordance with a further embodiment of the present invention, the antibody or antigen binding fragment may comprise a CDRH2 sequence comprising or consisting of formula: X$_{1t}$IDPETGGTA (SEQ ID NO:209) wherein X$_{1t}$ is as defined herein.

The antibody or antigen binding fragment may also comprise, for example, a CDRH2 sequence selected from those comprising or consisting of SEQ ID NO:73, SEQ ID NO:79, SEQ ID NO:85, SEQ ID NO:97, SEQ ID NO:103 and SEQ ID NO:109 and other CDRH2 listed in Table 3 or Table 5A.

In accordance with an additional embodiment, the antibody or antigen binding fragment may comprise a CDRH3 sequence comprising or consisting of formula:

TX$_{1j}$FYYX$_{2j}$X$_{3j}$X$_{4j}$NYDVGFAY (SEQ ID NO.: 158)

Wherein $X_{1j}$ may be, for example, a neutral hydrophilic amino acid;

Wherein $X_{2j}$ may be, for example, a neutral hydrophilic amino acid;

Wherein $X_{3j}$ may be, for example, tyrosine or histidine, and;

Wherein $X_{4j}$ may be, for example, tyrosine or serine.

More particularly, $X_{1j}$ may be, for example, serine or threonine. In a more specific embodiment, $X_{1j}$ may be, for example, serine.

More particularly, $X_{2j}$ may be, for example, serine or threonine. In a more specific embodiment, $X_{2j}$ may be, for example, threonine.

In a more specific embodiment, $X_{3j}$ may be, for example, tyrosine. In a more specific embodiment, $X_{4j}$ may be, for example, serine.

In accordance with a further embodiment of the present invention, the antibody or antigen binding fragment may comprise a CDRH3 sequence comprising or consisting of formula: TX$_{1v}$FYYX$_{2v}$X$_{3v}$X$_{4v}$NYDVGFAY (SEQ ID NO:210) wherein $X_{1v}$, $X_{2v}$, $X_{3v}$ and $X_{4v}$ are as defined herein.

The antibody or antigen binding fragment may comprise, for example, a CDRH3 sequence selected from those comprising or consisting of SEQ ID NO:74, SEQ ID NO:98, SEQ ID NO:104, SEQ ID NO:110, SEQ ID NO:116 and other CDRH3 listed in Table 3 or Table 5A.

The framework region of the heavy and/or light chains described herein may be derived from one or more of the framework regions illustrated herein. The antibody or antigen binding fragments may thus comprise one or more of the CDRs described herein (e.g., selected from the specific CDRs or from consensus CDRs SEQ ID NOs:148-158 and 197-210) and framework regions originating from the light or heavy chain variable regions illustrated herein.

In an embodiment of the invention, the antibody or antigen binding fragment of the present invention may comprise a heavy chain variable region (or a fragment) having formula:

(SEQ ID NO.: 191)
X$_{1k}$X$_{2k}$QX$_{3k}$QQX$_{4k}$X$_{5k}$X$_{6k}$EX$_{7k}$VX$_{8k}$PGASVKLSCKASGYTFTX$_{1l}$Y

WMHWVKQRPGQGLEWIGLINPX$_{1m}$NX$_{2m}$RX$_{3m}$NYNEX$_{1n}$FX$_{2n}$X$_{3n}$KATL

TVDKSSSTAYMX$_{4n}$LSSLTSEDSAVYYCARGGDGDYFDYWGQGTTLTVSS

Wherein $X_{1k}$ may be for example Q or E;

$X_{2k}$ may be any amino acid or a hydrophobic amino acid such as for example V or I;

$X_{3k}$ may be any amino acid or a hydrophobic amino acid such as for example V or L;

$X_{4k}$ may be any amino acid or for example P or S;

$X_{5k}$ may be any amino acid or for example R or G;

$X_{6k}$ may be any amino acid or for example A or T;

$X_{7k}$ may be any amino acid or a hydrophobic amino acid such as for example L or I;

$X_{8k}$ may be any amino acid or a basic amino acid such as for example R or K;

$X_{1l}$ may be any amino acid or a neutral hydrophilic amino acid such as for example for example S or T;

$X_{1m}$ may be any amino acid or a neutral hydrophilic amino acid such as for example T or S;

$X_{2m}$ may be any amino acid or for example G or A;

$X_{3m}$ may be any amino acid or for example P or T;

$X_{1n}$ may be any amino acid or a basic amino acid such as for example K or R;

$X_{2n}$ may be any amino acid or a basic amino acid such as for example N or K;

$X_{3n}$ may be any amino acid or for example N or a neutral hydrophilic amino acid such as S or T and;

$X_{4n}$ may be any amino acid or a basic amino acid such as for example Q or H.

In another embodiment of the invention, the antibody or antigen binding fragment of the present invention may comprise a heavy chain variable region (or a fragment) having formula:

(SEQ ID NO.: 192)
X$_{1o}$VX$_{2o}$LQQSGAELARPGASVKFSCKASGYTFTRNWIQWVKQRPGQGLE

WIGAX$_{a13}$YPGNGDSRYTQKFKGKATLTADKSSX$_{1q}$TAYMQLX$_{2q}$X$_{3q}$L

X$_{4q}$SEDSAVYYCARLAGNYAYYFDYWGQGTALTVSS

Wherein $X_{1o}$ may be for example Q or D;

$X_{2o}$ may be any amino acid or a basic amino acid such as for example K or Q;

$X_{a13}$ may be any amino acid or a hydrophobic amino acid such as for example I or V;

$X_{1q}$ may be any amino acid or for example S or N;

$X_{2q}$ may be any amino acid or for example S or N;

$X_{3q}$ may be any amino acid or for example G or S and;

$X_{4q}$ may be any amino acid or for example A or S.

In yet another embodiment of the invention, the antibody or antigen binding fragment of the present invention may comprise a heavy chain variable region (or a fragment) having formula:

(SEQ ID NO.: 193)
X$_{1r}$X$_{2r}$X$_{3r}$LQQSGX$_{4r}$ELVRPGASVTLSCKASGYTFTDYX$_{1s}$MHWVKQT

PVHGLEWIGX$_{1t}$IDPETGGTAYNQKFKGKATLTADX$_{1u}$SSX$_{2u}$TAYMELS

SLTSEDSAVYYCTX$_{1v}$FYYX$_{2v}$X$_{3v}$X$_{4v}$NYDVGFAYWGQGTLVTVSA

Wherein $X_{1r}$ may be for example E or Q;

$X_{2r}$ may be any amino acid or a hydrophobic amino acid such as for example A or I;

$X_{3r}$ may be any amino acid or for example Y or Q;

$X_{4r}$ may be any amino acid or a hydrophobic amino acid such as for example A or V;

$X_{1s}$ may be any amino acid or an acidic amino acid such as for example D or E;

$X_{1t}$ may be any amino acid or for example A or T;

$X_{1u}$ may be any amino acid or a basic amino acid such as for example K or R;

$X_{2u}$ may be any amino acid or a neutral hydrophilic amino acid such as for example S or T;

$X_{1v}$ may be any amino acid or a neutral hydrophilic amino acid such as for example S or T;

$X_{2v}$ may be any amino acid or a neutral hydrophilic amino acid such as for example T or S;

$X_{3v}$ may be any amino acid or for example Y or H and;

$X_{4v}$ may be any amino acid or for example S or Y.

In an additional embodiment, the antibody or antigen binding fragment of the present invention may comprise a light chain variable region (or a fragment) having formula:

(SEQ ID NO.: 194)
DIVMTX$_{1w}$AX$_{2w}$FSNPVX$_{3w}$LGTX$_{4w}$ASISC**RSSX$_{1x}$SLLHSNGX$_{2x}$TYL

YWYLQKPGQSPQLLIYQMSNLAS**GVPDRFSX$_{1y}$SGSGTX$_{2y}$FTLRISRVE

AEDVGVYYCX$_{a8}$QX$_{b8}$LEX$_{c8}$PYTFGX$_{a9}$GTKLEIK

Wherein $X_{1w}$ may be any amino acid or a basic amino acid such as for example Q or H;
$X_{2w}$ may be any amino acid or a hydrophobic amino acid such as for example V or A;
$X_{3w}$ may be any amino acid or for example T or I;
$X_{4w}$ may be any amino acid or for example S or P;
$X_{1x}$ may be any amino acid or for example E or K;
$X_{2x}$ may be any amino acid or a hydrophobic amino acid such as for example V or I;
$X_{1y}$ may be any amino acid or for example S or G;
$X_{2y}$ may be any amino acid or for example D or A;
$X_{a8}$ may be any amino acid or a hydrophobic amino acid such as for example M or A;
$X_{b8}$ may be any amino acid or a basic amino acid such as for example N or H;
$X_{c8}$ may be any amino acid or for example Y or L, and;
$X_{a9}$ may be any amino acid or for example G or S.

In a further embodiment, the antibody or antigen binding fragment of the present invention may comprise a light chain variable region (or a fragment) having formula:

(SEQ ID NO.: 195)
$X_{1z}$IQMTQSPASLSASVGETVTITCRASX$_{a10}$NIX$_{b10}$X$_{c10}$YLAWYQQK

QGKSPQLLVYNAKTLX$_{a1111}$X$_{b11}$GVX$_{a3}$X$_{b3}$RFSGSGSGTQX$_{c3}$SLKINX $_{d3}$LQPEDFGSYX$_{e3}$CQHHYGX$_{a4}$PLTFGX$_{a5}$GTKX$_{b5}$ELK

Wherein $X_{1z}$ may be any amino acid or for example D or N;
$X_{a10}$ may be any amino acid or for example E or G;
$X_{b10}$ may be any amino acid or for example Y or H;
$X_{c10}$ may be any amino acid or for example S or N;
$X_{a1111}$ may be any amino acid or for example P or A;
$X_{b11}$ may be any amino acid or an acidic amino acid such as for example E or D;
$X_{a3}$ may be any amino acid or for example P or S;
$X_{b3}$ may be any amino acid or for example V or S;
$X_{c3}$ may be any amino acid or an aromatic amino acid such as for example F or Y;
$X_{d3}$ may be any amino acid or for example N or S;
$X_{e3}$ may be any amino acid or for example H or Y;
$X_{a4}$ may be any amino acid or a hydrophobic amino acid such as for example A or V;
$X_{a5}$ may be any amino acid or for example S or A, and;
$X_{b5}$ may be any amino acid or a hydrophobic amino acid such as for example V or L.

In yet a further embodiment, the antibody or antigen binding fragment of the present invention may comprise a light chain variable region (or a fragment) having formula:

(SEQ ID NO.: 196)
DIVMTQAAPSVPVTPGESVSISCRSX$_{a6}$KSLLHSNGNTYLYWFLQRPGQS

PQLLIYRMSNLASGVPDRFSGSGSGTAFTLRX$_{a7}$SRVEAEDVGVYYCMQH

LEYPFTFGGGTKLEIK

Wherein $X_{a6}$ may be any amino acid or a neutral hydrophilic amino acid such as for example S or T, and;
$X_{a7}$ may be any amino acid or a hydrophobic amino acid such as for example I or L.

Antibodies that Bind to Siglec-15

In certain embodiments of the present invention, antibodies that bind to Siglec-15 are of the IgG1, IgG2, IgG3, or IgG4 subtype. In the preferred embodiment, the antibody is an antibody of the IgG2 subtype. In the present embodiment, the antibody is a humanized antibody of the IgG2 subtype that is biologically active in blocking the biological activity of normal Siglec-15 function on the surface of osteoclasts. Such blockage, for example, could prevent the association of Siglec-15 with its substrates, its ligands, itself, or other proteins on adjacent cells.

The present invention discloses a collection of antibodies that bind to Siglec-15. In certain embodiments, the antibodies consist of monoclonal antibodies and immunologically functional fragments thereof, such as chimeric and humanized monoclonal antibodies, antibody fragments, single chain antibodies, domain antibodies, and polypeptides with an antigen-binding region.

A typical antigen-binding site is comprised of the variable regions formed by the pairing of a light chain immunoglobulin and a heavy chain immunoglobulin. The structure of the antibody variable regions is very consistent and exhibits very similar structures. These variable regions are typically comprised of relatively homologous framework regions (FR) interspaced with three hypervariable regions termed Complementarity Determining Regions (CDRs). Although the overall binding activity of the antigen binding fragment is dictated by the sequence of the CDRs, the FRs play a critical role in the proper positioning and alignment in three dimensions of the CDRs for optimal antigen binding.

Table 1 discloses the sequences of the nucleotides and the amino acids corresponding to the complete light and heavy chain immunoglobulins of specific examples of anti-Siglec-15 antibodies.

TABLE 1

Complete sequences of light and heavy chain immunoglobulins that bind to Siglec-15

| Antibody designation | Chain type | Nucleotide sequence (SEQ ID NO:) | Amino acid sequence (SEQ ID NO:) |
|---|---|---|---|
| 25A1 | Light (L) | 5 | 6 |
| 25A1 | Heavy (H) | 7 | 8 |
| 25B4 | Light | 9 | 10 |
| 25B4 | Heavy | 11 | 12 |
| 25B8 | Light | 13 | 14 |
| 25B8 | Heavy | 15 | 16 |
| 25C1 | Light | 17 | 18 |
| 25C1 | Heavy | 19 | 20 |
| 25D8 | Light | 21 | 22 |
| 25D8 | Heavy | 23 | 24 |
| 25E5 | Light | 25 | 26 |
| 25E5 | Heavy | 27 | 28 |
| 25E6 | Light | 29 | 30 |
| 25E6 | Heavy | 31 | 32 |
| 25E9 | Light | 33 | 34 |
| 25E9 | Heavy | 35 | 36 |

An antibody that can bind Siglec-15 may comprise any one L chain with any one H chain immunoglobulin that is listed in Table 1. In certain embodiments, the light chain of antibody 25A1 may be combined with the heavy chain of 25A1 or the heavy chain of 25B4 to form a complete antibody with Siglec-15-binding activity. In an exemplary embodiment of the present invention, the 25A1 L chain may be combined with the 25A1 H chain, the 25B4 L chain may be combined with the 25B4 H chain, the 25B8 L chain may be combined with the 25B8 H chain, the 25C1 L chain may be combined with the 25C1 H chain, the 2D8 L chain may be combined with the 25D8 H chain, the 25E5 L chain may be combined with the 25E5 H chain, the 25E6 L chain may be combined with the 25E6 H chain, or the 25E9 L chain may be combined with the 25E9 H chain. Additionally, some examples of antibodies or antigen binding fragment may consist of any combination of two L chains and any two H chains from the list of antibodies listed in Table 1.

The complete nucleotide sequences of the light and heavy immunoglobulin chains of antibody 25A1 are shown in SEQ ID NOS:5 and 7, respectively, and the corresponding amino acid sequences of the light and heavy immunoglobulin chains of antibody 25A1 are shown in SEQ ID NOS:6 and 8, respectively. Thus, in an exemplary embodiment, an antibody that binds to Siglec-15 may comprise the light chain amino acid shown in SEQ ID NO:6 combined with the heavy chain amino acid sequence shown in SEQ ID NO:8. In another embodiment, the antibody may comprise two identical or substantially identical 25A1 light chains comprising SEQ ID NO:6 or a variant thereof and two identical or substantially identical 25A1 heavy chains comprising SEQ ID NO:8 or a variant thereof.

The complete nucleotide sequences of the light and heavy immunoglobulin chains of antibody 25B4 are shown in SEQ ID NOS:9 and 11, respectively, and the corresponding amino acid sequences of the light and heavy immunoglobulin chains of antibody 25B4 are shown in SEQ ID NOS:10 and 12, respectively. Thus, in an exemplary embodiment, an antibody that binds to Siglec-15 may comprise the light chain amino acid shown in SEQ ID NO:10 combined with the heavy chain amino acid sequence shown in SEQ ID NO:12. In another embodiment, the antibody may comprise two identical or substantially identical 25B4 light chains comprising SEQ ID NO:10 or a variant thereof and two identical or substantially identical 25B4 heavy chains comprising SEQ ID NO:12 or a variant thereof.

The complete nucleotide sequences of the light and heavy immunoglobulin chains of antibody 25B8 are shown in SEQ ID NOS:13 and 15, respectively and the corresponding amino acid sequences of the light and heavy immunoglobulin chains of antibody 25B8 are shown in SEQ ID NOS:14 and 16, respectively. Thus, in an exemplary embodiment, an antibody that binds to Siglec-15 may comprise the light chain amino acid shown in SEQ ID NO:14 combined with the heavy chain amino acid sequence shown in SEQ ID NO:16. In another embodiment, the antibody may comprise two identical or substantially identical 25B8 light chains comprising SEQ ID NO:14 or a variant thereof and two identical or substantially identical 25B8 heavy chains comprising SEQ ID NO:16 or a variant thereof.

The complete nucleotide sequences of the light and heavy immunoglobulin chains of antibody 25C1 are shown in SEQ ID NOS:17 and 19, respectively, and the corresponding amino acid sequences of the light and heavy immunoglobulin chains of antibody 25C1 are shown in SEQ ID NOS:18 and 20, respectively. Thus, in an exemplary embodiment, an antibody that binds to Siglec-15 may comprise the light chain amino acid shown in SEQ ID NO:18 combined with the heavy chain amino acid sequence shown in SEQ ID NO:20. In another embodiment, the antibody may comprise two identical or substantially identical 25C1 light chains comprising SEQ ID NO:18 or a variant thereof and two identical or substantially identical 25C1 heavy chains comprising SEQ ID NO:20 or a variant thereof.

The complete nucleotide sequences of the light and heavy immunoglobulin chains of antibody 25D8 are shown in SEQ ID NOS:21 and 23, respectively, and the corresponding amino acid sequences of the light and heavy immunoglobulin chains of antibody 25D8 are shown in SEQ ID NOS:22 and 24, respectively. Thus, in an exemplary embodiment, an antibody that binds to Siglec-15 may comprise the light chain amino acid shown in SEQ ID NO:22 combined with the heavy chain amino acid sequence shown in SEQ ID NO:24. In another embodiment, the antibody may comprise two identical or substantially identical 25D8 light chains comprising of SEQ ID NO:22 or a variant thereof and two identical or substantially identical 25D8 heavy chains comprising SEQ ID NO:24 or a variant thereof.

The complete nucleotide sequences of the light and heavy immunoglobulin chains of antibody 25E5 are shown in SEQ ID NOS:25 and 27, respectively, and the corresponding amino acid sequences of the light and heavy immunoglobulin chains of antibody 25E5 are shown in SEQ ID NOS:26 and 28, respectively. Thus, in an exemplary embodiment, an antibody that binds to Siglec-15 may comprise the light chain amino acid shown in SEQ ID NO:26 combined with the heavy chain amino acid sequence shown in SEQ ID NO:28. In another embodiment, the antibody may comprise two identical or substantially identical 25E5 light chains comprising SEQ ID NO:26 or a variant thereof and two identical or substantially identical 25E5 heavy chains comprising SEQ ID NO:28 or a variant thereof.

The complete nucleotide sequences of the light and heavy immunoglobulin chains of antibody 25E6 are shown in SEQ ID NOS:29 and 31, respectively and the corresponding amino acid sequences of the light and heavy immunoglobulin chains of antibody 25E6 are shown in SEQ ID NOS:30 and 32, respectively. Thus, in an exemplary embodiment, an antibody that binds to Siglec-15 may comprise the light chain amino acid shown in SEQ ID NO:30 combined with the heavy chain amino acid sequence shown in SEQ ID NO:32. In another embodiment, the antibody may comprise two identical or substantially identical 25E6 light chains comprising SEQ ID NO:30 or a variant thereof and two identical or substantially identical 25E6 heavy chains comprising SEQ ID NO:32 or a variant thereof.

The complete nucleotide sequences of the light and heavy immunoglobulin chains of antibody 25E9 are shown in SEQ ID NOS:33 and 35, respectively, and the corresponding amino acid sequences of the light and heavy immunoglobulin chains of antibody 25E9 are shown in SEQ ID NOS:34 and 36, respectively. Thus, in an exemplary embodiment, an antibody that binds to Siglec-15 may comprise the light chain amino acid shown in SEQ ID NO:34 combined with the heavy chain amino acid sequence shown in SEQ ID NO:36. In another embodiment, the antibody may comprise two identical or substantially identical 25E9 light chains comprising SEQ ID NO:34 or a variant thereof and two identical or substantially identical 25E9 heavy chains comprising SEQ ID NO:36 or a variant thereof.

Variants of other anti-Siglec-15 antibodies or antigen binding fragments formed by the combination of light and/or heavy immunoglobulin chains may each independently have at least 80%, 85%, 90%, 95%, 97%, or 99% identity to the amino acid sequences listed in Table 1 are also provided. In certain embodiments, the antibody variants may comprise at least one light chain and one heavy chain. In other instances, the antibody variants may comprise two identical or substantially identical light chains and two identical or substantially identical heavy chains. In accordance with the present invention, the region of variation may be located in the constant region or in the variable region. Also in accordance with the present invention, the region of variation may be located in the framework region.

Also encompassed by the present invention are antibodies comprising a light chain comprising one of the variable region of the light chain sequence listed in Table 1 or a variant thereof and a heavy chain comprising one of the variable region of the heavy chain sequence listed in Table 1 or a variant thereof. The light chain and heavy chain may comprise a constant domain. Combinations of light chains and heavy chains of Table 1 are also encompassed by the present invention.

Antibodies or antigen binding fragments that contain the light chain and heavy chain variable regions are also provided in the present invention. Additionally, certain embodiments include antigen binding fragments, variants, and derivatives of these light and heavy chain variable regions.

Yet other exemplary embodiments of the invention includes an isolated antibody or antigen binding fragment capable of specific binding to SEQ ID NO:2 or to a variant thereof, the antibody comprising:
  a. the light chain variable domain defined in SEQ ID NO:38 and the heavy chain variable domain defined in SEQ ID NO:40;
  b. the light chain variable domain defined in SEQ ID NO:42 and the heavy chain variable domain defined in SEQ ID NO:44;
  c. the light chain variable domain defined in SEQ ID NO:46 and the heavy chain variable domain defined in SEQ ID NO:48;
  d. the light chain variable domain defined in SEQ ID NO:50 and the heavy chain variable domain defined in SEQ ID NO:52;
  e. the light chain variable domain defined in SEQ ID NO:54 and the heavy chain variable domain defined in SEQ ID NO:56,
  f. the light chain variable domain defined in SEQ ID NO:58 and the heavy chain variable domain defined in SEQ ID NO:60;
  g. the light chain variable domain defined in SEQ ID NO:62 and the heavy chain variable domain defined in SEQ ID NO:64;
  h. the light chain variable domain defined in SEQ ID NO:66 and the heavy chain variable domain defined in SEQ ID NO:68;

It is to be understood herein, that the light chain variable region of the specific combination provided above may be changed for any other light chain variable region (especially those of Table 2). Similarly, the heavy chain variable region of the specific combination provided above may be changed for any other heavy chain variable region (especially those of Table 2).

Antibodies that contain the light chain and heavy chain variable regions are also provided in the present invention. Additionally, certain embodiments include antigen binding fragments, variants, and derivatives of these light and heavy chain variable regions. Examples of sequences present in these light and heavy chain variable regions are disclosed in Table 2.

TABLE 2

Sequences of light and heavy chain variable regions that bind to Siglec-15

| Antibody designation | Chain type | Nucleotide sequence (SEQ ID NO:) | Amino acid sequence (SEQ ID NO:) |
| --- | --- | --- | --- |
| 25A1 | Light (L) | 37 | 38 |
| 25A1 | Heavy (H) | 39 | 40 |
| 25B4 | Light | 41 | 42 |
| 25B4 | Heavy | 43 | 44 |
| 25B8 | Light | 45 | 46 |
| 25B8 | Heavy | 47 | 48 |
| 25C1 | Light | 49 | 50 |
| 25C1 | Heavy | 51 | 52 |
| 25D8 | Light | 53 | 54 |
| 25D8 | Heavy | 55 | 56 |
| 25E5 | Light | 57 | 58 |
| 25E5 | Heavy | 59 | 60 |
| 25E6 | Light | 61 | 62 |
| 25E6 | Heavy | 63 | 64 |
| 25E9 | Light | 65 | 66 |
| 25E9 | Heavy | 67 | 68 |
| 25B02 | Light | 161 | 162 |
| 25B02 | Heavy | 163 | 164 |
| 25D11 | Light | 165 | 166 |
| 25D11 | Heavy | 167 | 168 |
| 25E10 | Light | 169 | 170 |
| 25E10 | Heavy | 171 | 172 |

Therefore, antibodies and antigen binding fragments that bind to Siglec-15 may comprise one light chain variable region and one chain heavy variable region of the same designated antibody or in any combinations. For example, in an exemplary embodiment, an anti-Siglec-15 antibody or fragment may comprise the 25A1 light chain variable region (SEQ ID NO:38) and the 25A1 heavy chain variable region (SEQ ID NO:40). In an alternate embodiment, an anti-Siglec-15 antibody or fragment may comprise the 25A1 light chain variable region (SEQ ID NO:38) and the 25B4 heavy chain variable region (SEQ ID NO:44). In another embodiment, the anti-Siglec-15 antibodies may comprise two identical or substantially identical light chain variable regions and two identical or substantially identical heavy chain regions. In yet another embodiment, the anti-Siglec-15 antibodies may comprise two different light chain variable regions and two different heavy chain regions.

Variants of other anti-Siglec-15 antibodies formed by the combination of light and/or heavy chain variable regions that each have at least 70%, 75%, 80%, 85%, 90%, 95%, 97%, or 99% identity to the amino acid sequences listed in Table 2, Tables 5A and 5B are also provided. Those skilled in the art will also recognize that the anti-Siglec-15 antibody variants may include conservative amino acid changes, amino acid substitutions, deletions, or additions in the amino acid sequences of the light and/or heavy chain variable regions listed in Table 2.

TABLE 3

Sequences of the light and heavy chain CDRs

| Antibody designation | Chain type | CDR | SEQ ID NO: | Amino acid sequence |
| --- | --- | --- | --- | --- |
| 25A1 | Light (L) | CDR1 | 69 | SASSSVSYMY |
| 25A1 | Light | CDR2 | 70 | RTSNLAS |
| 25A1 | Light | CDR3 | 71 | QQWSSNPLT |
| 25A1 | Heavy (H) | CDR1 | 72 | GYTFTRYWMD |
| 25A1 | Heavy | CDR2 | 73 | EIDPSDSYTN |
| 25A1 | Heavy | CDR3 | 74 | ARSGAYSSDYSYDGFAY |
| 25B4 | Light | CDR1 | 75 | RSSKSLLHSNGITYLY |
| 25B4 | Light | CDR2 | 76 | QMSNLAS |
| 25B4 | Light | CDR3 | 77 | MQHLEYPYT |
| 25B4 | Heavy | CDR1 | 78 | GYTFTSYWMH |

TABLE 3-continued

Sequences of the light and heavy chain CDRs

| Antibody designation | Chain type | CDR | SEQ ID NO: | Amino acid sequence |
|---|---|---|---|---|
| 25B4 | Heavy | CDR2 | 79 | LINPTNGRTN |
| 25B4 | Heavy | CDR3 | 80 | ARGGDGDYFDY |
| 25B8 | Light | CDR1 | 81 | RSTKSLLHSNGNTYLY |
| 25B8 | Light | CDR2 | 82 | RMSNLAS |
| 25B8 | Light | CDR3 | 83 | MQHLEYPFT |
| 25B8 | Heavy | CDR1 | 84 | GYTFTDYDMH |
| 25B8 | Heavy | CDR2 | 85 | TIDPETGGTA |
| 25B8 | Heavy | CDR3 | 86 | TTFYYSHYNYDVGFAY |
| 25C1 | Light | CDR1 | 87 | RSSKSLLHSNGNTYLY |
| 25C1 | Light | CDR2 | 88 | RMSNLAS |
| 25C1 | Light | CDR3 | 89 | MQHLEYPFT |
| 25C1 | Heavy | CDR1 | 90 | GYTFTDYEMH |
| 25C1 | Heavy | CDR2 | 91 | AIDPETGGTA |
| 25C1 | Heavy | CDR3 | 92 | TSFYYTYYNYDVGFAY |
| 25D8 | Light | CDR1 | 93 | RSSKSLLHSNGITYLY |
| 25D8 | Light | CDR2 | 94 | QMSNLAS |
| 25D8 | Light | CDR3 | 95 | AQNLELPYT |
| 25D8 | Heavy | CDR1 | 96 | GYTFTSYWMH |
| 25D8 | Heavy | CDR2 | 97 | LINPSNARTN |
| 25D8 | Heavy | CDR3 | 98 | ARGGDGDYFDY |
| 25E5 | Light | CDR1 | 99 | SASSSVSYMY |
| 25E5 | Light | CDR2 | 100 | RTSNLVS |
| 25E5 | Light | CDR3 | 101 | QQWSSNPPT |
| 25E5 | Heavy | CDR1 | 102 | GFDFSKDWMS |
| 25E5 | Heavy | CDR2 | 103 | EINPDSSTIN |
| 25E5 | Heavy | CDR3 | 104 | SRLEDYEDWYFDV |
| 25E6 | Light | CDR1 | 105 | KASQSVSNAVA |
| 25E6 | Light | CDR2 | 106 | YTSNRYT |
| 25E6 | Light | CDR3 | 107 | QQDYTSPWT |
| 25E6 | Heavy | CDR1 | 108 | GYTFNTYNMY |
| 25E6 | Heavy | CDR2 | 109 | GIDPSNGDTK |
| 25E6 | Heavy | CDR3 | 110 | TSHTY |
| 25E9 | Light | CDR1 | 111 | RSTKSLLHSNGNTYLY |
| 25E9 | Light | CDR2 | 112 | RMSNLAS |
| 25E9 | Light | CDR3 | 113 | MQHLEYPFT |
| 25E9 | Heavy | CDR1 | 114 | GYTFTDYDMH |
| 25E9 | Heavy | CDR2 | 115 | TIDPETGGTA |
| 25E9 | Heavy | CDR3 | 116 | TSFYYTYSNYDVGFAY |
| 25B02 | Light | CDR1 | 173 | RASENIYSYLA |
| 25B02 | Light | CDR2 | 174 | NAKTLPE |
| 25B02 | Light | CDR3 | 175 | HHYGVPLT |
| 25B02 | Heavy | CDR1 | 176 | GYTFTRNWIQ |
| 25B02 | Heavy | CDR2 | 177 | AIYPGNGDSR |
| 25B02 | Heavy | CDR3 | 178 | ARLAGNYAYYFDY |
| 25D11 | Light | CDR1 | 179 | RASGNIHNYLA |
| 25D11 | Light | CDR2 | 180 | NAKTLPE |
| 25D11 | Light | CDR3 | 181 | QHHYGVPLT |
| 25D11 | Heavy | CDR1 | 182 | GYTFTRNWIQ |
| 25D11 | Heavy | CDR2 | 183 | AIYPGNGDSR |
| 25D11 | Heavy | CDR3 | 184 | ARLAGNYAYYFDY |
| 25E10 | Light | CDR1 | 185 | RASGNIHNYLA |
| 25E10 | Light | CDR2 | 186 | NAKTLAD |
| 25E10 | Light | CDR3 | 187 | QHHYGAPLT |
| 25E10 | Heavy | CDR1 | 188 | GYTFTRNWIQ |
| 25E10 | Heavy | CDR2 | 189 | AVYPGNGDSR |
| 25E10 | Heavy | CDR3 | 190 | ARLAGNYAYYFDY |

In certain embodiments of the present invention, the anti-Siglec-15 antibodies or antigen binding fragments may comprise the CDR sequences shown in Table 3 or have substantial sequence identity to the CDR sequences of Table 3. In an exemplary embodiment, the 25A1 anti-Siglec-15 antibody may comprise a light chain variable region containing CDR1, 2, and 3 that are encoded by SEQ ID NOS:68, 69, and 70, respectively, and/or a heavy chain variable region containing CDR1, 2, and 3 that are encoded by SEQ ID NOS:71, 72, and 73, respectively. In other embodiments the CDR3 region may be sufficient to provide antigen binding. As such polypeptides comprising the CDRL3 or the CDRH3 or both the CDRL3 and the CDRH3 are encompassed by the present invention.

Additionally, the anti-Siglec-15 antibodies or antigen binding fragments may include any combination of the CDRs listed in Table 3. For example, the antibodies or antigen binding fragments may include the light chain CDR3 and the heavy chain CDR3. It is understood that the CDRs that are contained in the anti-Siglec-15 antibodies or antigen binding fragments may be variant CDRs with 80%, 85%, 90%, or 95% sequence identity to the CDR sequences presented in Table 3. Those skilled in the art will also recognize that the variants may include conservative amino acid changes, amino acid substitutions, deletions, or additions in the CDR sequences listed in Table 3.

Other exemplary embodiments of the invention include an isolated antibody or antigen binding fragment capable of specific binding to SEQ ID NO:2 or to a variant thereof (a variant having at least 80% identity with amino acids 20 to 259 or with amino acids 49-165 of SEQ ID NO:2), the antibody comprising:
  a. the 3 CDRs of a light chain variable domain listed in Table 5B and the 3 CDRs of a heavy chain variable listed in Table 5A;
  b. the 3 CDRs of a light chain variable domain defined in SEQ ID NO:194 and the 3 CDRs of a heavy chain variable domain defined in SEQ ID NO:191;
  c. the 3 CDRs of a light chain variable domain defined in SEQ ID NO:195 and the 3 CDRs of a heavy chain variable domain defined in SEQ ID NO:192;
  d. the 3 CDRs of a light chain variable domain defined in SEQ ID NO:196 and the 3 CDRs of a heavy chain variable domain defined in SEQ ID NO:193;
  e. the 3 CDRs of a light chain variable domain defined in SEQ ID NO:38 and the 3 CDRs of a heavy chain variable domain defined in SEQ ID NO:40;
  f. the 3 CDRs of a light chain variable domain defined in SEQ ID NO:42 and the 3 CDRs of a heavy chain variable domain defined in SEQ ID NO:44;
  g. the 3 CDRs of a light chain variable domain defined in SEQ ID NO:46 and the 3 CDRs of a heavy chain variable domain defined in SEQ ID NO:48;
  h. the 3 CDRs of a light chain variable domain defined in SEQ ID NO:50 and the 3 CDRs of a heavy chain variable domain defined in SEQ ID NO:52
  i. the 3 CDRs of a light chain variable domain defined in SEQ ID NO:54 and the 3 CDRs of a heavy chain variable domain defined in SEQ ID NO:56;
  j. the 3 CDRs of a light chain variable domain defined in SEQ ID NO:58 and the 3 CDRs of a heavy chain variable domain defined in SEQ ID NO:60;
  k. the 3 CDRs of a light chain variable domain defined in SEQ ID NO:62 and the 3 CDRs of a heavy chain variable domain defined in SEQ ID NO:64;
  l. the 3 CDRs of a light chain variable domain defined in SEQ ID NO:66 and the 3 CDRs of a heavy chain variable domain defined in SEQ ID NO:68;
  m. the 3 CDRs of a light chain variable domain defined in SEQ ID NO:162 and the 3 CDRs of a heavy chain variable domain defined in SEQ ID NO:164,
  n. the 3 CDRs of a light chain variable domain defined in SEQ ID NO:166 and the 3 CDRs of a heavy chain variable domain defined in SEQ ID NO:168, or;
  o. the 3 CDRs of a light chain variable domain defined in SEQ ID NO:170 and the 3 CDRs of a heavy chain variable domain defined in SEQ ID NO:172.

In an additional aspect, the present invention relates to an isolated antibody or antigen binding fragment capable of specific binding to Siglec-15 or to a variant thereof (a variant having at least 80% identity with amino acids 20 to 259 or with amino acids 49-165 of SEQ ID NO:2), the antibody comprising:
  a) a light chain variable domain having at least 70% (75%, 80%, 85%, 90%, 95%, 100%) sequence identity with the sequence listed in Table 5B and heavy chain variable domain having at least 70% (75%, 80%, 85%, 90%, 95%, 100%) sequence identity with the sequence listed in Table 5A;
  b) a light chain variable domain having at least 70% (75%, 80%, 85%, 90%, 95%, 100%) sequence identity with SEQ ID NO:194 and a heavy chain variable domain having at least 70% (75%, 80%, 85%, 90%, 95%, 100%) sequence identity with SEQ ID NO:191;
  c) a light chain variable domain having at least 70% (75%, 80%, 85%, 90%, 95%, 100%) sequence identity with SEQ ID NO:195 and a heavy chain variable domain having at least 70% (75%, 80%, 85%, 90%, 95%, 100%) sequence identity with SEQ ID NO:192;
  d) a light chain variable domain having at least 70% (75%, 80%, 85%, 90%, 95%, 100%) sequence identity with SEQ ID NO:196 and a heavy chain variable domain having at least 70% (75%, 80%, 85%, 90%, 95%, 100%) sequence identity with SEQ ID NO:193;
  e) a light chain variable domain having at least 70% (75%, 80%, 85%, 90%, 95%, 100%) sequence identity with SEQ ID NO:38 and a heavy chain variable domain having at least 70% (75%, 80%, 85%, 90%, 95%, 100%) sequence identity with SEQ ID NO:40,
  f) a light chain variable domain having at least 70% (75%, 80%, 85%, 90%, 95%, 100%) sequence identity with SEQ ID NO:42 and a heavy chain variable domain having at least 70% (75%, 80%, 85%, 90%, 95%, 100%) sequence identity with SEQ ID NO:44;
  g) a light chain variable domain having at least 70% (75%, 80%, 85%, 90%, 95%, 100%) sequence identity with SEQ ID NO:46 and a heavy chain variable domain having at least 70% (75%, 80%, 85%, 90%, 95%, 100%) sequence identity with SEQ ID NO:48;
  h) a light chain variable domain having at least 70% (75%, 80%, 85%, 90%, 95%, 100%) sequence identity with SEQ ID NO:50 and a heavy chain variable domain having at least 70% (75%, 80%, 85%, 90%, 95%, 100%) sequence identity with SEQ ID NO:52;
  i) a light chain variable domain having at least 70% (75%, 80%, 85%, 90%, 95%, 100%) sequence identity with SEQ ID NO:54 and a heavy chain variable domain having at least 70% (75%, 80%, 85%, 90%, 95%, 100%) sequence identity with SEQ ID NO:56;
  j) a light chain variable domain having at least 70% (75%, 80%, 85%, 90%, 95%, 100%) sequence identity with SEQ ID NO:58 and a heavy chain variable domain having at least 70% (75%, 80%, 85%, 90%, 95%, 100%) sequence identity with SEQ ID NO:60;
  k) a light chain variable domain having at least 70% (75%, 80%, 85%, 90%, 95%, 100%) sequence identity with SEQ ID NO:62 and a heavy chain variable domain having at least 70% (75%, 80%, 85%, 90%, 95%, 100%) sequence identity with SEQ ID NO:64,
  l) a light chain variable domain having at least 70% (75%, 80%, 85%, 90%, 95%, 100%) sequence identity with SEQ ID NO:66 and a heavy chain variable domain having at least 70% (75%, 80%, 85%, 90%, 95%, 100%) sequence identity with SEQ ID NO:68,
  m) a light chain variable domain having at least 70% (75%, 80%, 85%, 90%, 95%, 100%) sequence identity with SEQ ID NO:162 and a heavy chain variable domain having at least 70% (75%, 80%, 85%, 90%, 95%, 100%) sequence identity with SEQ ID NO:164,
  n) a light chain variable domain having at least 70% (75%, 80%, 85%, 90%, 95%, 100%) sequence identity with SEQ ID NO:166 and a heavy chain variable domain having at least 70% (75%, 80%, 85%, 90%, 95%, 100%) sequence identity with SEQ ID NO:168, and;
  o) a light chain variable domain having at least 70% (75%, 80%, 85%, 90%, 95%, 100%) sequence identity with SEQ ID NO:170 and a heavy chain variable domain having at least 70% (75%, 80%, 85%, 90%, 95%, 100%) sequence identity with SEQ ID NO:172.

Again, the light chain variable region of the specific combination provided above may be changed for any other light chain variable region described herein. Similarly, the heavy chain variable region of the specific combination provided above may be changed for any other heavy chain variable region described herein.

Variant Antibody and Antigen Binding Fragments

The present invention also encompasses variants of the antibodies or antigen binding fragments described herein. Variant antibodies or antigen binding fragments included are those having a variation in the amino acid sequence. For example, variant antibodies or antigen binding fragments included are those having at least one variant CDR (two, three, four, five, six and up to twelve variant CDRs), a variant light chain variable domain, a variant heavy chain variable domain, a variant light chain and/or a variant heavy chain. Variant antibodies or antigen binding fragments included in the present invention are those having, for example, similar or improved binding affinity in comparison with the original antibody or antigen binding fragment.

As used herein the term "variant" applies to any of the sequence described herein and includes for example, a variant CDR (either CDRL1, CDRL2, CDRL3, CDRH1, CDRH2 and/or CDRH3), a variant light chain variable domain, a variant heavy chain variable domain, a variant light chain, a variant heavy chain, a variant antibody, a variant antigen binding fragment and a SEQ ID NO:2 variant.

Variant antibodies or antigen binding fragments encompassed by the present invention are those which may comprise an insertion, a deletion or an amino acid substitution (conservative or non-conservative). These variants may have at least one amino acid residue in its amino acid sequence removed and a different residue inserted in its place.

The sites of greatest interest for substitutional mutagenesis include the hypervariable regions (CDRs), but modifications in the framework region or even in the constant region are also contemplated. Conservative substitutions may be made by exchanging an amino acid (of a CDR, variable chain, antibody, etc.) from one of the groups listed below (group 1 to 6) for another amino acid of the same group.

Generally, mutations in the CDRs may have a greater impact on the antigen binding activity of the antibody or antigen binding fragment than mutations in the framework region. Variant antibody or antigen binding fragments that are encompassed by the present invention are those which have a substantially identical antigen binding capacity (including similar, identical, or slightly less) to those presented herein or have a better antigen binding capacity than those presented herein.

Other exemplary embodiment of conservative substitutions are shown in Table 1A under the heading of "preferred substitutions". If such substitutions result in a undesired property, then more substantial changes, denominated "exemplary substitutions" in Table 1A, or as further described below in reference to amino acid classes, may be introduced and the products screened.

It is known in the art that variants may be generated by substitutional mutagenesis and retain the biological activity of the polypeptides of the present invention. These variants have at least one amino acid residue in the amino acid sequence removed and a different residue inserted in its place. For example, one site of interest for substitutional mutagenesis may include a site in which particular residues obtained from various species are identical. Examples of substitutions identified as "conservative substitutions" are shown in Table 1A. If such substitutions result in a change not desired, then other type of substitutions, denominated "exemplary substitutions" in Table 1A, or as further described herein in reference to amino acid classes, are introduced and the products screened.

Substantial modifications in function or immunological identity are accomplished by selecting substitutions that differ significantly in their effect on maintaining (a) the structure of the polypeptide backbone in the area of the substitution, for example, as a sheet or helical conformation. (b) the charge or hydrophobicity of the molecule at the target site, or (c) the bulk of the side chain. Naturally occurring residues are divided into groups based on common side chain properties:

(group 1) hydrophobic: norleucine, methionine (Met), Alanine (Ala), Valine (Val), Leucine (Leu), Isoleucine (Ile)

(group 2) neutral hydrophilic: Cysteine (Cys), Serine (Ser), Threonine (Thr)

(group 3) acidic: Aspartic acid (Asp), Glutamic acid (Glu)

(group 4) basic: Asparagine (Asn), Glutamine (Gln), Histidine (His), Lysine (Lys), Arginine (Arg)

(group 5) residues that influence chain orientation: Glycine (Gly), Proline (Pro); and (group 6) aromatic: Tryptophan (Trp), Tyrosine (Tyr), Phenylalanine (Phe)

Non-conservative substitutions will entail exchanging a member of one of these classes for another.

TABLE 1A

Amino acid substitution

| Original residue | Exemplary substitution | Conservative substitution |
|---|---|---|
| Ala (A) | Val, Leu, Ile | Val |
| Arg (R) | Lys, Gln, Asn | Lys |
| Asn (N) | Gln, His, Lys, Arg, Asp | Gln |
| Asp (D) | Glu, Asn | Glu |
| Cys (C) | Ser, Ala | Ser |
| Gln (Q) | Asn; Glu | Asn |
| Glu (E) | Asp, Gln | Asp |
| Gly (G) | Ala | Ala |
| His (H) | Asn, Gln, Lys, Arg, | Arg |
| Ile (I) | Leu, Val, Met, Ala, Phe, norleucine | Leu |
| Leu (L) | Norleucine, Ile, Val, Met, Ala, Phe | Ile |
| Lys (K) | Arg, Gln, Asn | Arg |
| Met (M) | Leu, Phe, Ile | Leu |
| Phe (F) | Leu, Val, Ile, Ala, Tyr | Tyr |
| Pro (P) | Ala | Ala |
| Ser (S) | Thr | Thr |
| Thr (T) | Ser | Ser |
| Trp (W) | Tyr, Phe | Tyr |
| Tyr (Y) | Trp, Phe, Thr, Ser | Phe |
| Val (V) | Ile, Leu, Met, Phe, Ala, norleucine | Leu |

Variation in the amino acid sequence of the variant antibody or antigen binding fragment may include an amino acid addition, deletion, insertion, substitution etc., one or more modification in the backbone or side-chain of one or more amino acid, or an addition of a group or another molecule to one or more amino acids (side-chains or backbone).

Variant antibody or antigen binding fragment may have substantial sequence similarity and/or sequence identity in its amino acid sequence in comparison with that of the original antibody or antigen binding fragment amino acid sequence. The degree of similarity between two sequences is based upon the percentage of identities (identical amino acids) and of conservative substitution.

Generally, the degree of similarity and identity between variable chains has been determined herein using the Blast2 sequence program (Tatiana A. Tatusova, Thomas L. Madden (1999), "Blast 2 sequences—a new tool for comparing protein and nucleotide sequences", FEMS Microbiol Lett. 174: 247-250) using default settings, i.e., blastp program, BLO- SUM62 matrix (open gap 11 and extension gap penalty 1; gapx dropoff 50, expect 10.0, word size 3) and activated filters.

Percent identity will therefore be indicative of amino acids which are identical in comparison with the original peptide and which may occupy the same or similar position.

Percent similarity will be indicative of amino acids which are identical and those which are replaced with conservative amino acid substitution in comparison with the original peptide at the same or similar position.

Variants (i.e., analogues) of the present invention (including VL variants, VH variants, CDR variants, antibody variants, polypeptide variants, etc.) therefore comprise those which may have at least 70%, 75%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity with an original sequence or a portion of an original sequence.

In accordance with the present invention, a SEQ ID NO:2 variant includes a polypeptide having a region at least 80% identical with amino acids 49-165 or with amino acids 20 to 259 of SEQ ID NO:2. Variants of SEQ ID NO:2 also include polypeptides having at least 80% sequence identity with SEQ ID NO:2.

Other exemplary embodiments of variants are those having at least 90% sequence identity to a sequence described herein and 90%, 91%, 92%, 93%, 94%, 95%, 96%, 97%, 98%, 99% or 100% sequence similarity with an original sequence or a portion of an original sequence.

Additional exemplary embodiments of variants are those having at least 95% sequence identity to a sequence described herein and 95%, 96%, 97%, 98%, 99% or 100% sequence similarity with an original sequence or a portion of an original sequence.

Yet additional exemplary embodiments of variants are those having at least 97% sequence identity to a sequence described herein and 97%, 98%, 99% or 100% sequence similarity with an original sequence or a portion of an original sequence.

For a purpose of concision the applicant provides herein a Table 1B illustrating exemplary embodiments of individual variants encompassed by the present invention and comprising the specified % sequence identity and % sequence similarity. Each "X" is to be construed as defining a given variant.

TABLE 1B

| | | Percent (%) sequence identity | | | | | | | | | | | | | | | | | | | | |
|---|---|---|---|---|---|---|---|---|---|---|---|---|---|---|---|---|---|---|---|---|---|---|
| | | 80 | 81 | 82 | 83 | 84 | 85 | 86 | 87 | 88 | 89 | 90 | 91 | 92 | 93 | 94 | 95 | 96 | 97 | 98 | 99 | 100 |
| Percent (%) sequence similarity | 80 | X | | | | | | | | | | | | | | | | | | | | |
| | 81 | X | X | | | | | | | | | | | | | | | | | | | |
| | 82 | X | X | X | | | | | | | | | | | | | | | | | | |
| | 83 | X | X | X | X | | | | | | | | | | | | | | | | | |
| | 84 | X | X | X | X | X | | | | | | | | | | | | | | | | |
| | 85 | X | X | X | X | X | X | | | | | | | | | | | | | | | |
| | 86 | X | X | X | X | X | X | X | | | | | | | | | | | | | | |
| | 87 | X | X | X | X | X | X | X | X | | | | | | | | | | | | | |
| | 88 | X | X | X | X | X | X | X | X | X | | | | | | | | | | | | |
| | 89 | X | X | X | X | X | X | X | X | X | X | | | | | | | | | | | |
| | 90 | X | X | X | X | X | X | X | X | X | X | X | | | | | | | | | | |
| | 91 | X | X | X | X | X | X | X | X | X | X | X | X | | | | | | | | | |
| | 92 | X | X | X | X | X | X | X | X | X | X | X | X | X | | | | | | | | |
| | 93 | X | X | X | X | X | X | X | X | X | X | X | X | X | X | | | | | | | |
| | 94 | X | X | X | X | X | X | X | X | X | X | X | X | X | X | X | | | | | | |
| | 95 | X | X | X | X | X | X | X | X | X | X | X | X | X | X | X | X | | | | | |
| | 96 | X | X | X | X | X | X | X | X | X | X | X | X | X | X | X | X | X | | | | |
| | 97 | X | X | X | X | X | X | X | X | X | X | X | X | X | X | X | X | X | X | | | |
| | 98 | X | X | X | X | X | X | X | X | X | X | X | X | X | X | X | X | X | X | X | | |
| | 99 | X | X | X | X | X | X | X | X | X | X | X | X | X | X | X | X | X | X | X | X | |
| | 100 | X | X | X | X | X | X | X | X | X | X | X | X | X | X | X | X | X | X | X | X | X |

Exemplary embodiments of variants are those having at least 81% sequence identity to a sequence described herein and 81%, 82%, 83%, 84%, 85%, 86%, 87%, 88%, 89%, 90%, 91%, 92%, 93%, 94%, 95%, 96%, 97%, 98%, 99% or 100% sequence similarity with an original sequence or a portion of an original sequence.

Other exemplary embodiments of variants are those having at least 82% sequence identity to a sequence described herein and 82%, 83%, 84%, 85%, 86%, 87%, 88%, 89%, 90%, 91%, 92%, 93%, 94%, 95%, 96%, 97%, 98%, 99% or 100% sequence similarity with an original sequence or a portion of an original sequence.

Further exemplary embodiments of variants are those having at least 85% sequence identity to a sequence described herein and 85%, 86%, 87%, 88%, 89%, 90%, 91%, 92%, 93%, 94%, 95%, 96%, 97%, 98%, 99% or 100% sequence similarity with an original sequence or a portion of an original sequence.

As used herein, the term "identical" means that a sequence share 100% sequence identity with another sequence.

As used herein, the term "substantially identical" means that a sequence share 70%, 75%, 80%, 81%, 82%, 83%, 84%, 85%, 86%, 87%, 88%, 89%, 90%, 91%, 92%, 93%, 94%, 95%, 96%, 97%, 98%, 99% sequence identity with another sequence or a portion of another sequence.

The present invention encompasses CDRs, light chain variable domains, heavy chain variable domains, light chains, heavy chains, antibodies and/or antigen binding fragments which comprise at least 80% identity with the sequence described herein.

Exemplary embodiments of the antibody or antigen binding fragment of the present invention are those comprising a light chain variable domain comprising a sequence selected from the group consisting of a sequence at least 70% identical (including 80%, 85%, 90%, 95% and 100% identical) to SEQ ID NO:38, a sequence at least 70% identical (including 80%, 85%, 90%, 95% and 100% identical) to SEQ ID NO:42, a sequence at least 70% identical (including 80%, 85%, 90%, 95% and 100% identical) to SEQ ID NO:46, a sequence at least 70% identical (including 80%, 85%, 90%, 95% and 100% identical) to SEQ ID NO:50, a sequence at least 70% identical (including 80%, 85%, 90%, 95% and 100% identical) to SEQ ID NO:54, a sequence at least 70% identical (including 80%, 85%, 90%, 95% and 100%) identical to SEQ ID NO:58, a sequence at least 70% identical (including 80%, 85%, 90%, 95% and 100% identical) to SEQ ID NO:62, a sequence 70% identical (including at least 80%, 85%, 90%, 95% and 100% identical) to SEQ ID NO:66, a sequence 70% identical (including at least 80%, 85%, 90%, 95% and 100% identical) to SEQ ID NO:162, a sequence 70% identical (including at least 80%, 85%, 90%, 95% and 100% identical) to SEQ ID NO:166 and a sequence 70% identical (including at least 80%, 85%, 90%, 95% and 100% identical) to SEQ ID NO:170.

These light chain variable domain may comprise a CDRL1 sequence at least 80% identical to SEQ ID NO:69, a CDRL2 sequence at least 80% identical to SEQ ID NO:70 and a CDRL3 sequence at least 80% identical to SEQ ID NO:71.

In an exemplary embodiment of the present invention, any of the antibodies provided herein may comprise a CDRL1 sequence which may be at least 90% identical to SEQ ID NO:69.

In another exemplary embodiment of the present invention, any of the antibodies provided herein may comprise a CDRL1 sequence which may be 100% identical to SEQ ID NO:69.

In another exemplary embodiment of the present invention, any of the antibodies provided herein may comprise a CDRL2 sequence at least 90% identical to SEQ ID NO:70.

In yet another exemplary embodiment of the present invention, any of the antibodies provided herein may comprise a CDRL2 sequence which may be 100% identical to SEQ ID NO:70.

In another exemplary embodiment of the present invention, any of the antibodies provided herein may comprise a CDRL3 sequence which may be at least 90% identical to SEQ ID NO:71.

In an additional exemplary embodiment of the present invention, any of the antibodies provided herein may comprise a CDRL3 sequence which may be 100% identical to SEQ ID NO:71.

The light chain variable domain listed above may comprise a CDRL1 sequence at least 80% identical to SEQ ID NO:75, a CDRL2 sequence at least 80 identical to SEQ ID NO:76 and a CDRL3 sequence at least 80% identical to SEQ ID NO:77.

In an exemplary embodiment of the present invention, any of the antibodies provided herein may comprise a CDRL1 sequence which may be at least 90% identical to SEQ ID NO:75.

In a further exemplary embodiment of the present invention, any of the antibodies provided herein may comprise a CDRL1 sequence which may be 100% identical to SEQ ID NO:75.

In yet a further exemplary embodiment of the present invention, any of the antibodies provided herein may comprise a the CDRL2 sequence which may be at least 90% identical to SEQ ID NO:76.

In another exemplary embodiment of the present invention, any of the antibodies provided herein may comprise a CDRL2 sequence which may be 100% identical to SEQ ID NO:76.

In another exemplary embodiment of the present invention, any of the antibodies provided herein may comprise a CDRL3 sequence which may be at least 90% identical to SEQ ID NO:77.

In yet another exemplary embodiment of the present invention, any of the antibodies provided herein may comprise a CDRL3 sequence which may be 100% identical to SEQ ID NO:77.

The light chain variable domain listed above may comprise a CDRL1 sequence at least 80% identical to SEQ ID NO:81, a CDRL2 sequence at least 80% identical to SEQ ID NO:82 and a CDRL3 sequence at least 80% identical to SEQ ID NO:83.

In an exemplary embodiment of the present invention, any of the antibodies provided herein may comprise a CDRL1 sequence which may be at least 90% identical to SEQ ID NO:81.

In a further exemplary embodiment of the present invention, any of the antibodies provided herein may comprise a CDRL1 sequence which may be 100% identical to SEQ ID NO:81.

In yet a further exemplary embodiment of the present invention, any of the antibodies provided herein may comprise a the CDRL2 sequence which may be at least 90% identical to SEQ ID NO:82.

In another exemplary embodiment of the present invention, any of the antibodies provided herein may comprise a CDRL2 sequence which may be 100% identical to SEQ ID NO:82.

In another exemplary embodiment of the present invention, any of the antibodies provided herein may comprise a CDRL3 sequence which may be at least 90% identical to SEQ ID NO:83.

In yet another exemplary embodiment of the present invention, any of the antibodies provided herein may comprise a CDRL3 sequence which may be 100% identical to SEQ ID NO:83.

The light chain variable domain listed above may comprise a CDRL1 sequence at least 80% identical to SEQ ID NO:87, a CDRL2 sequence at least 80% identical to SEQ ID NO:88 and a CDRL3 sequence at least 80% identical to SEQ ID NO:89.

In an exemplary embodiment of the present invention, any of the antibodies provided herein may comprise a CDRL1 sequence which may be at least 90% identical to SEQ ID NO:87.

In a further exemplary embodiment of the present invention, any of the antibodies provided herein may comprise a CDRL1 sequence which may be 100% identical to SEQ ID NO:87.

In yet a further exemplary embodiment of the present invention, any of the antibodies provided herein may comprise a the CDRL2 sequence which may be at least 90% identical to SEQ ID NO:88.

In another exemplary embodiment of the present invention, any of the antibodies provided herein may comprise a CDRL2 sequence which may be 100% identical to SEQ ID NO:88.

In another exemplary embodiment of the present invention, any of the antibodies provided herein may comprise a CDRL3 sequence which may be at least 90% identical to SEQ ID NO:89.

In yet another exemplary embodiment of the present invention, any of the antibodies provided herein may comprise a CDRL3 sequence which may be 100% identical to SEQ ID NO:89.

The light chain variable domain listed above may comprise a CDRL1 sequence at least 80% identical to SEQ ID NO:93, a CDRL2 sequence at least 80% identical to SEQ ID NO:94 and a CDRL3 sequence at least 80% identical to SEQ ID NO:95.

In an exemplary embodiment of the present invention, any of the antibodies provided herein may comprise a CDRL1 sequence which may be at least 90% identical to SEQ ID NO:93.

In a further exemplary embodiment of the present invention, any of the antibodies provided herein may comprise a CDRL1 sequence which may be 100% identical to SEQ ID NO:93.

In yet a further exemplary embodiment of the present invention, any of the antibodies provided herein may comprise a the CDRL2 sequence which may be at least 90% identical to SEQ ID NO:94.

In another exemplary embodiment of the present invention, any of the antibodies provided herein may comprise a CDRL2 sequence which may be 100% identical to SEQ ID NO:94.

In another exemplary embodiment of the present invention, any of the antibodies provided herein may comprise a CDRL3 sequence which may be at least 90% identical to SEQ ID NO:95.

In yet another exemplary embodiment of the present invention, any of the antibodies provided herein may comprise a CDRL3 sequence which may be 100% identical to SEQ ID NO:95.

The light chain variable domain listed above may comprise a CDRL1 sequence at least 80% identical to SEQ ID NO:99, a CDRL2 sequence at least 80% identical to SEQ ID NO:100 and a CDRL3 sequence at least 80% identical to SEQ ID NO:101.

In an exemplary embodiment of the present invention, any of the antibodies provided herein may comprise a CDRL1 sequence which may be at least 90% identical to SEQ ID NO:99.

In a further exemplary embodiment of the present invention, any of the antibodies provided herein may comprise a CDRL1 sequence which may be 100% identical to SEQ ID NO:99.

In yet a further exemplary embodiment of the present invention, any of the antibodies provided herein may comprise a the CDRL2 sequence which may be at least 90% identical to SEQ ID NO:100.

In another exemplary embodiment of the present invention, any of the antibodies provided herein may comprise a CDRL2 sequence which may be 100% identical to SEQ ID NO:100.

In another exemplary embodiment of the present invention, any of the antibodies provided herein may comprise a CDRL3 sequence which may be at least 90% identical to SEQ ID NO:101.

In yet another exemplary embodiment of the present invention, any of the antibodies provided herein may comprise a CDRL3 sequence which may be 100% identical to SEQ ID NO:101.

The light chain variable domain listed above may comprise a CDRL1 sequence at least 80% identical to SEQ ID NO:105, a CDRL2 sequence at least 80% identical to SEQ ID NO:106 and a CDRL3 sequence at least 80% identical to SEQ ID NO:107.

In an exemplary embodiment of the present invention, any of the antibodies provided herein may comprise a CDRL1 sequence which may be at least 90% identical to SEQ ID NO:105.

In a further exemplary embodiment of the present invention, any of the antibodies provided herein may comprise a CDRL1 sequence which may be 100% identical to SEQ ID NO:105.

In yet a further exemplary embodiment of the present invention, any of the antibodies provided herein may comprise a CDRL2 sequence which may be at least 90% identical to SEQ ID NO:106.

In another exemplary embodiment of the present invention, any of the antibodies provided herein may comprise a CDRL2 sequence which may be 100% identical to SEQ ID NO:106.

In another exemplary embodiment of the present invention, any of the antibodies provided herein may comprise a CDRL3 sequence which may be at least 90% identical to SEQ ID NO:107.

In yet another exemplary embodiment of the present invention, any of the antibodies provided herein may comprise a CDRL3 sequence which may be 100% identical to SEQ ID NO:107.

The light chain variable domain listed above may comprise a CDRL1 sequence at least 80% identical to SEQ ID NO:111, a CDRL2 sequence at least 80% identical to SEQ ID NO:112 and a CDRL3 sequence at least 80% identical to SEQ ID NO:113.

In an exemplary embodiment of the present invention, any of the antibodies provided herein may comprise a CDRL1 sequence which may be at least 90% identical to SEQ ID NO:111.

In a further exemplary embodiment of the present invention, any of the antibodies provided herein may comprise a CDRL1 sequence which may be 100% identical to SEQ ID NO:111.

In yet a further exemplary embodiment of the present invention, any of the antibodies provided herein may comprise a CDRL2 sequence which may be at least 90% identical to SEQ ID NO:112.

In another exemplary embodiment of the present invention, any of the antibodies provided herein may comprise a CDRL2 sequence which may be 100% identical to SEQ ID NO:112.

In another exemplary embodiment of the present invention, any of the antibodies provided herein may comprise a CDRL3 sequence which may be at least 90% identical to SEQ ID NO:113.

In another exemplary embodiment of the present invention, any of the antibodies provided herein may comprise a CDRL3 sequence which may be at least 100% identical to SEQ ID NO:113.

The light chain variable domain listed above may comprise a CDRL1 sequence at least 80% identical to SEQ ID NO:173, a CDRL2 sequence at least 80% identical to SEQ ID NO:174 and a CDRL3 sequence at least 80% identical to SEQ ID NO:175.

In an exemplary embodiment of the present invention, any of the antibodies provided herein may comprise a CDRL1 sequence which may be at least 90% identical to SEQ ID NO:173.

In a further exemplary embodiment of the present invention, any of the antibodies provided herein may comprise a CDRL1 sequence which may be 100% identical to SEQ ID NO:173.

In yet a further exemplary embodiment of the present invention, any of the antibodies provided herein may comprise a CDRL2 sequence which may be at least 90% identical to SEQ ID NO:174

In another exemplary embodiment of the present invention, any of the antibodies provided herein may comprise a CDRL2 sequence which may be 100% identical to SEQ ID NO:174.

In another exemplary embodiment of the present invention, any of the antibodies provided herein may comprise a CDRL3 sequence which may be at least 90% identical to SEQ ID NO:175.

In another exemplary embodiment of the present invention, any of the antibodies provided herein may comprise a CDRL3 sequence which may be at least 100% identical to SEQ ID NO:175.

The light chain variable domain listed above may comprise a CDRL1 sequence at least 80% identical to SEQ ID NO:179, a CDRL2 sequence at least 80% identical to SEQ ID NO:180 and a CDRL3 sequence at least 80% identical to SEQ ID NO:181.

In an exemplary embodiment of the present invention, any of the antibodies provided herein may comprise a CDRL1 sequence which may be at least 90% identical to SEQ ID NO:179.

In a further exemplary embodiment of the present invention, any of the antibodies provided herein may comprise a CDRL1 sequence which may be 100% identical to SEQ ID NO:179.

In yet a further exemplary embodiment of the present invention, any of the antibodies provided herein may comprise a CDRL2 sequence which may be at least 90% identical to SEQ ID NO:180.

In another exemplary embodiment of the present invention, any of the antibodies provided herein may comprise a CDRL2 sequence which may be 100% identical to SEQ ID NO:180.

In another exemplary embodiment of the present invention, any of the antibodies provided herein may comprise a CDRL3 sequence which may be at least 90% identical to SEQ ID NO:181.

In another exemplary embodiment of the present invention, any of the antibodies provided herein may comprise a CDRL3 sequence which may be at least 100% identical to SEQ ID NO:181.

The light chain variable domain listed above may comprise a CDRL1 sequence at least 80% identical to SEQ ID NO:185, a CDRL2 sequence at least 80% identical to SEQ ID NO:186 and a CDRL3 sequence at least 80% identical to SEQ ID NO:187.

In an exemplary embodiment of the present invention, any of the antibodies provided herein may comprise a CDRL1 sequence which may be at least 90% identical to SEQ ID NO:185.

In a further exemplary embodiment of the present invention, any of the antibodies provided herein may comprise a CDRL1 sequence which may be 100% identical to SEQ ID NO:185.

In yet a further exemplary embodiment of the present invention, any of the antibodies provided herein may comprise a CDRL2 sequence which may be at least 90% identical to SEQ ID NO:186.

In another exemplary embodiment of the present invention, any of the antibodies provided herein may comprise a CDRL2 sequence which may be 100% identical to SEQ ID NO:186.

In another exemplary embodiment of the present invention, any of the antibodies provided herein may comprise a CDRL3 sequence which may be at least 90% identical to SEQ ID NO:187.

In another exemplary embodiment of the present invention, any of the antibodies provided herein may comprise a CDRL3 sequence which may be at least 100% identical to SEQ ID NO:187. In an exemplary embodiment, the antibody or antigen binding fragment may comprise a heavy chain variable domain comprising a sequence selected from the group consisting of a sequence at least 70% identical (including 80%, 85%, 90%, 95%, 100% identical) to SEQ ID NO:40, a sequence at least 70% identical (including 80% identical) to SEQ ID NO:44, a sequence at least 70% identical (including 80%, 85%, 90%, 95%, 100% identical) to SEQ ID NO:48, a sequence at least 70% identical (including 80%, 85%, 90%, 95%, 100% identical) to SEQ ID NO:52, a sequence at least 70% identical (including 80%, 85%, 90%, 95%, 100% identical) to SEQ ID NO:56, a sequence at least 70% identical (including 80%, 85%, 90%, 95%, 100% identical) to SEQ ID NO:60, a sequence at least 70% identical (including 80%, 85%, 90%, 95%, 100%) identical to SEQ ID NO:64, a sequence at least 70% identical (including 80%, 85%, 90%, 95%, 100% identical) to SEQ ID NO:68, a sequence at least 70% identical (including 80%, 85%, 90%, 95%, 100% identical) to SEQ ID NO:164, a sequence at least 70% identical (including 80%, 85%, 90%, 95%, 100% identical) to SEQ ID NO:168 and a sequence at least 70% identical (including 80%, 85%, 90%, 95%, 100% identical) to SEQ ID NO:172.

These heavy chain variable domain may comprise a CDRH1 sequence at least 80% identical to SEQ ID NO:72, a CDRH2 sequence at least 80% identical to SEQ ID NO:73 and a CDRH3 sequence at least 80% identical to SEQ ID NO:74.

In an exemplary embodiment of the present invention, any of the antibodies provided herein may comprise a CDRH1 sequence which may be at least 90% identical to SEQ ID NO:72.

In another exemplary embodiment of the present invention, any of the antibodies provided herein may comprise a CDRH1 sequence which may be 100% identical to SEQ ID NO:72.

In yet another exemplary embodiment of the present invention, any of the antibodies provided herein may comprise a CDRH2 sequence which may be at least 90% identical to SEQ ID NO:73.

In a further exemplary embodiment of the present invention, any of the antibodies provided herein may comprise a CDRH2 sequence which may be 100% identical to SEQ ID NO:73.

In yet a further exemplary embodiment of the present invention, any of the antibodies provided herein may comprise a CDRH3 sequence which may be at least 90% identical to SEQ ID NO:74.

In an additional exemplary embodiment of the present invention, any of the antibodies provided herein may comprise a CDRH3 sequence which may be 100% identical to SEQ ID NO:74.

The heavy chain variable domain listed above may comprise a CDRH1 sequence at least 80% identical to SEQ ID NO:78, a CDRH2 sequence at least 80% identical to SEQ ID NO:79 and a CDRH3 sequence at least 80% identical to SEQ ID NO:80.

In an exemplary embodiment of the present invention, any of the antibodies provided herein may comprise a CDRH1 sequence which may be at least 90% identical to SEQ ID NO:78.

In another exemplary embodiment of the present invention, any of the antibodies provided herein may comprise a CDRH1 sequence which may be 100% identical to SEQ ID NO:78.

In an additional exemplary embodiment of the present invention, any of the antibodies provided herein may comprise a CDRH2 sequence which may be at least 90% identical to SEQ ID NO:79.

In a further exemplary embodiment of the present invention, any of the antibodies provided herein may comprise a CDRH2 sequence which may be 100% identical to SEQ ID NO:79.

In another exemplary embodiment of the present invention, any of the antibodies provided herein may comprise a CDRH3 sequence which may be at least 90% identical to SEQ ID NO:80.

In another exemplary embodiment of the present invention, any of the antibodies provided herein may comprise a CDRH3 sequence which may be 100% identical to SEQ ID NO:80.

The light chain variable domain listed above may comprise a CDRH1 sequence at least 80% identical to SEQ ID NO:84, a CDRH2 sequence at least 80% identical to SEQ ID NO:85 and a CDRH3 sequence at least 80% identical to SEQ ID NO:86.

In an exemplary embodiment of the present invention, any of the antibodies provided herein may comprise a CDRH1 sequence which may be at least 90% identical to SEQ ID NO:84.

In a further exemplary embodiment of the present invention, any of the antibodies provided herein may comprise a CDRH1 sequence which may be 100% identical to SEQ ID NO:84.

In yet a further exemplary embodiment of the present invention, any of the antibodies provided herein may comprise a CDRH2 sequence which may be at least 90% identical to SEQ ID NO:85.

In another exemplary embodiment of the present invention, any of the antibodies provided herein may comprise a CDRH2 sequence which may be 100% identical to SEQ ID NO:85.

In another exemplary embodiment of the present invention, any of the antibodies provided herein may comprise a CDRH3 sequence which may be at least 90% identical to SEQ ID NO:86.

In yet another exemplary embodiment of the present invention, any of the antibodies provided herein may comprise a CDRH3 sequence which may be 100% identical to SEQ ID NO:86.

The light chain variable domain listed above may comprise a CDRH1 sequence at least 80% identical to SEQ ID NO:90, a CDRH2 sequence at least 80% identical to SEQ ID NO:91 and a CDRH3 sequence at least 80% identical to SEQ ID NO:92.

In an exemplary embodiment of the present invention, any of the antibodies provided herein may comprise a CDRH1 sequence which may be at least 90% identical to SEQ ID NO:90.

In a further exemplary embodiment of the present invention, any of the antibodies provided herein may comprise a CDRH1 sequence which may be 100% identical to SEQ ID NO:90.

In yet a further exemplary embodiment of the present invention, any of the antibodies provided herein may comprise a CDRH2 sequence which may be at least 90% identical to SEQ ID NO:91.

In another exemplary embodiment of the present invention, any of the antibodies provided herein may comprise a CDRH2 sequence which may be 100% identical to SEQ ID NO:91.

In another exemplary embodiment of the present invention, any of the antibodies provided herein may comprise a CDRH3 sequence which may be at least 90% identical to SEQ ID NO:92.

In yet another exemplary embodiment of the present invention, any of the antibodies provided herein may comprise a CDRH3 sequence which may be 100% identical to SEQ ID NO:92.

The light chain variable domain listed above may comprise a CDRH1 sequence at least 80% identical to SEQ ID NO:96, a CDRH2 sequence at least 80% identical to SEQ ID NO:97 and a CDRH3 sequence at least 80% identical to SEQ ID NO:98.

In an exemplary embodiment of the present invention, any of the antibodies provided herein may comprise a CDRH1 sequence which may be at least 90% identical to SEQ ID NO:96.

In a further exemplary embodiment of the present invention, any of the antibodies provided herein may comprise a CDRH1 sequence which may be 100% identical to SEQ ID NO:96.

In yet a further exemplary embodiment of the present invention, any of the antibodies provided herein may comprise a CDRH2 sequence which may be at least 90% identical to SEQ ID NO:97.

In another exemplary embodiment of the present invention, any of the antibodies provided herein may comprise a CDRH2 sequence which may be 100% identical to SEQ ID NO:97.

In another exemplary embodiment of the present invention, any of the antibodies provided herein may comprise a CDRH3 sequence which may be at least 90% identical to SEQ ID NO:98.

In yet another exemplary embodiment of the present invention, any of the antibodies provided herein may comprise a CDRH3 sequence which may be 100% identical to SEQ ID NO:98.

The light chain variable domain listed above may comprise a CDRH1 sequence at least 80% identical to SEQ ID NO:102, a CDRH2 sequence at least 80% identical to SEQ ID NO:103 and a CDRH3 sequence at least 80% identical to SEQ ID NO:104.

In an exemplary embodiment of the present invention, any of the antibodies provided herein may comprise a CDRH1 sequence which may be at least 90% identical to SEQ ID NO:102.

In a further exemplary embodiment of the present invention, any of the antibodies provided herein may comprise a CDRH1 sequence which may be 100% identical to SEQ ID NO:102.

In yet a further exemplary embodiment of the present invention, any of the antibodies provided herein may comprise a CDRH2 sequence which may be at least 90% identical to SEQ ID NO:103.

In another exemplary embodiment of the present invention, any of the antibodies provided herein may comprise a CDRH2 sequence which may be 100% identical to SEQ ID NO:103.

In another exemplary embodiment of the present invention, any of the antibodies provided herein may comprise a CDRH3 sequence which may be at least 90% identical to SEQ ID NO:104.

In yet another exemplary embodiment of the present invention, any of the antibodies provided herein may comprise a CDRH3 sequence which may be 100% identical to SEQ ID NO:104.

These heavy chain variable domain may comprise a CDRH1 sequence at least 80% identical to SEQ ID NO:108, a CDRH2 sequence at least 80% identical to SEQ ID NO:109 and a CDRH3 sequence at least 80% identical to SEQ ID NO:110.

In an exemplary embodiment of the present invention, any of the antibodies provided herein may comprise a CDRH1 sequence which may be at least 90% identical to SEQ ID NO:108.

In another exemplary embodiment of the present invention, any of the antibodies provided herein may comprise a CDRH1 sequence which may be 100% identical to SEQ ID NO:108.

In yet another exemplary embodiment of the present invention, any of the antibodies provided herein may comprise a CDRH2 sequence which may be at least 90% identical to SEQ ID NO:109.

In a further exemplary embodiment of the present invention, any of the antibodies provided herein may comprise a CDRH2 sequence which may be 100% identical to SEQ ID NO:109.

In yet a further exemplary embodiment of the present invention, any of the antibodies provided herein may comprise a CDRH3 sequence which may be at least 90% identical to SEQ ID NO:110.

In an additional exemplary embodiment of the present invention, any of the antibodies provided herein may comprise a CDRH3 sequence which may be 100% identical to SEQ ID NO:110.

These heavy chain variable domain may comprise a CDRH1 sequence at least 80% identical to SEQ ID NO:114, a CDRH2 sequence at least 80% identical to SEQ ID NO:115 and a CDRH3 sequence at least 80% identical to SEQ ID NO:116.

In an exemplary embodiment of the present invention, any of the antibodies provided herein may comprise a CDRH1 sequence which may be at least 90% identical to SEQ ID NO:114.

In another exemplary embodiment of the present invention, any of the antibodies provided herein may comprise a CDRH1 sequence which may be 100% identical to SEQ ID NO:114.

In yet another exemplary embodiment of the present invention, any of the antibodies provided herein may comprise a CDRH2 sequence which may be at least 90% identical to SEQ ID NO:115.

In a further exemplary embodiment of the present invention, any of the antibodies provided herein may comprise a CDRH2 sequence which may be 100% identical to SEQ ID NO:115.

In yet a further exemplary embodiment of the present invention, any of the antibodies provided herein may comprise a CDRH3 sequence which may be at least 90% identical to SEQ ID NO:116.

In an additional exemplary embodiment of the present invention, any of the antibodies provided herein may comprise a CDRH3 sequence which may be 100% identical to SEQ ID NO:116.

These heavy chain variable domains may comprise a CDRH1 sequence at least 80% identical to SEQ ID NO:176, a CDRH2 sequence at least 80% identical to SEQ ID NO:177 and a CDRH3 sequence at least 80% identical to SEQ ID NO:178.

In an exemplary embodiment of the present invention, any of the antibodies provided herein may comprise a CDRH1 sequence which may be at least 90% identical to SEQ ID NO:176.

In another exemplary embodiment of the present invention, any of the antibodies provided herein may comprise a CDRH1 sequence which may be 100% identical to SEQ ID NO:176.

In yet another exemplary embodiment of the present invention, any of the antibodies provided herein may comprise a CDRH2 sequence which may be at least 90% identical to SEQ ID NO:177.

In a further exemplary embodiment of the present invention, any of the antibodies provided herein may comprise a CDRH2 sequence which may be 100% identical to SEQ ID NO:177.

In yet a further exemplary embodiment of the present invention, any of the antibodies provided herein may comprise a CDRH3 sequence which may be at least 90% identical to SEQ ID NO:178.

In an additional exemplary embodiment of the present invention, any of the antibodies provided herein may comprise a CDRH3 sequence which may be 100% identical to SEQ ID NO:178.

These heavy chain variable domains may comprise a CDRH1 sequence at least 80% identical to SEQ ID NO:182, a CDRH2 sequence at least 80% identical to SEQ ID NO:183 and a CDRH3 sequence at least 80% identical to SEQ ID NO:184.

In an exemplary embodiment of the present invention, any of the antibodies provided herein may comprise a CDRH1 sequence which may be at least 90% identical to SEQ ID NO:182.

In another exemplary embodiment of the present invention, any of the antibodies provided herein may comprise a CDRH1 sequence which may be 100% identical to SEQ ID NO:182.

In yet another exemplary embodiment of the present invention, any of the antibodies provided herein may comprise a CDRH2 sequence which may be at least 90% identical to SEQ ID NO:183.

In a further exemplary embodiment of the present invention, any of the antibodies provided herein may comprise a CDRH2 sequence which may be 100% identical to SEQ ID NO:183.

In yet a further exemplary embodiment of the present invention, any of the antibodies provided herein may comprise a CDRH3 sequence which may be at least 90% identical to SEQ ID NO:184.

In an additional exemplary embodiment of the present invention, any of the antibodies provided herein may comprise a CDRH3 sequence which may be 100% identical to SEQ ID NO:184.

These heavy chain variable domains may comprise a CDRH1 sequence at least 80% identical to SEQ ID NO:188, a CDRH2 sequence at least 80% identical to SEQ ID NO:189 and a CDRH3 sequence at least 80% identical to SEQ ID NO:190.

In an exemplary embodiment of the present invention, any of the antibodies provided herein may comprise a CDRH1 sequence which may be at least 90% identical to SEQ ID NO:188.

In another exemplary embodiment of the present invention, any of the antibodies provided herein may comprise a CDRH1 sequence which may be 100% identical to SEQ ID NO:188.

In yet another exemplary embodiment of the present invention, any of the antibodies provided herein may comprise a CDRH2 sequence which may be at least 90% identical to SEQ ID NO:189.

In a further exemplary embodiment of the present invention, any of the antibodies provided herein may comprise a CDRH2 sequence which may be 100% identical to SEQ ID NO:189.

In yet a further exemplary embodiment of the present invention, any of the antibodies provided herein may comprise a CDRH3 sequence which may be at least 90% identical to SEQ ID NO:190.

In an additional exemplary embodiment of the present invention, any of the antibodies provided herein may comprise a CDRH3 sequence which may be 100% identical to SEQ ID NO:190.

Production of the Antibodies in Cells

The antibodies that are disclosed herein can be made by a variety of methods familiar to those skilled in the art, such as hybridoma methodology or by recombinant DNA methods.

In an exemplary embodiment of the invention, the antibodies may be produced by the conventional hybridoma technology, where a mouse is immunized with an antigen, spleen cells isolated and fused with myeloma cells lacking HGPRT expression and hybrid cells selected by hypoxanthine, aminopterin and thymine (HAT) containing media.

In an additional exemplary embodiment of the invention, the antibodies may be produced by recombinant DNA methods.

In order to express the antibodies, nucleotide sequences able to encode any one of a light and heavy immunoglobulin chains described herein may be inserted into an expression vector, i.e., a vector that contains the elements for transcriptional and translational control of the inserted coding sequence in a particular host. These elements may include regulatory sequences, such as enhancers, constitutive and inducible promoters, and 5' and 3' un-translated regions. Methods that are well known to those skilled in the art may be used to construct such expression vectors. These methods include in vitro recombinant DNA techniques, synthetic techniques, and in vivo genetic recombination.

A variety of expression vector/host cell systems known to those of skill in the art may be utilized to express a polypeptide or RNA derived from nucleotide sequences able to encode any one of a light and heavy immunoglobulin chains described herein. These include, but are not limited to, microorganisms such as bacteria transformed with recombinant bacteriophage, plasmid, or cosmid DNA expression vectors; yeast transformed with yeast expression vectors; insect cell systems infected with baculovirus vectors; plant cell systems transformed with viral or bacterial expression vectors; or animal cell systems. For long-term production of recombinant proteins in mammalian systems, stable expression in cell lines may be effected. For example, nucleotide sequences able to encode any one of a light and heavy immunoglobulin chains described herein may be transformed into cell lines using expression vectors that may contain viral origins of replication and/or endogenous expression elements and a selectable or visible marker gene on the same or on a separate vector. The invention is not to be limited by the vector or host cell employed. In certain embodiments of the present invention, the nucleotide sequences able to encode any one of a light and heavy immunoglobulin chains described herein may each be ligated into a separate expression vector and each chain expressed separately. In another embodiment, both the light and heavy chains able to encode any one of a light and heavy immunoglobulin chains described herein may be ligated into a single expression vector and expressed simultaneously.

Alternatively, RNA and/or polypeptide may be expressed from a vector comprising nucleotide sequences able to encode any one of a light and heavy immunoglobulin chains described herein using an in vitro transcription system or a coupled in vitro transcription/translation system respectively.

In general, host cells that contain nucleotide sequences able to encode any one of a light and heavy immunoglobulin chains described herein and/or that express a polypeptide encoded by the nucleotide sequences able to encode any one of a light and heavy immunoglobulin chains described herein, or a portion thereof, may be identified by a variety of procedures known to those of skill in the art. These procedures include, but are not limited to, DNA/DNA or DNA/RNA hybridizations, PCR amplification, and protein bioassay or immunoassay techniques that include membrane, solution, or chip based technologies for the detection and/or quantification of nucleic acid or amino acid sequences. Immunological methods for detecting and measuring the expression of polypeptides using either specific polyclonal or monoclonal antibodies are known in the art. Examples of such techniques include enzyme-linked immunosorbent assays (ELISAs), radioimmunoassays (RIAs), and fluorescence activated cell sorting (FACS). Those of skill in the art may readily adapt these methodologies to the present invention.

Host cells comprising nucleotide sequences able to encode any one of a light and heavy immunoglobulin chains described herein may thus be cultured under conditions for the transcription of the corresponding RNA (mRNA, siRNA, shRNA etc.) and/or the expression of the polypeptide from cell culture. The polypeptide produced by a cell may be secreted or may be retained intracellularly depending on the sequence and/or the vector used. In an exemplary embodiment, expression vectors containing nucleotide sequences able to encode any one of a light and heavy immunoglobulin chains described herein may be designed to contain signal sequences that direct secretion of the polypeptide through a prokaryotic or eukaryotic cell membrane.

Due to the inherent degeneracy of the genetic code, other DNA sequences that encode the same, substantially the same or a functionally equivalent amino acid sequence may be produced and used, for example, to express a polypeptide encoded by nucleotide sequences able to encode any one of a light and heavy immunoglobulin chains described herein. The nucleotide sequences of the present invention may be engineered using methods generally known in the art in order to alter the nucleotide sequences for a variety of purposes including, but not limited to, modification of the cloning, processing, and/or expression of the gene product. DNA shuffling by random fragmentation and PCR reassembly of gene fragments and synthetic oligonucleotides may be used to engineer the nucleotide sequences. For example, oligonucleotide-mediated site-directed mutagenesis may be used to introduce mutations that create new restriction sites, alter glycosylation patterns, change codon preference, produce splice variants, and so forth.

In addition, a host cell strain may be chosen for its ability to modulate expression of the inserted sequences or to process the expressed polypeptide in the desired fashion. Such modifications of the polypeptide include, but are not limited to, acetylation, carboxylation, glycosylation, phosphorylation, lipidation, and acylation. In an exemplary embodiment, antibodies that contain particular glycosylation structures or patterns may be desired. Post-translational processing, which cleaves a "prepro" form of the polypeptide, may also be used to specify protein targeting, folding, and/or activity. Different host cells that have specific cellular machinery and characteristic mechanisms for post-translational activities (e.g., CHO, HeLa, MDCK, HEK293, and W138) are available commercially and from the American Type Culture Collection (ATCC) and may be chosen to ensure the correct modification and processing of the expressed polypeptide.

Since hybridoma cells are hybrid mouse cells, they are strictly used to produce murine antibodies. It is clear that the glycosyl side chains of such murine antibodies might significantly differ from the glycosylation pattern observed in human cells. Differences in phosphorylation pattern between human cells and hybridomas might also have an impact on the activity of the antibody. Furthermore, administration of murine antibodies to human usually induces an anti-antibody immune response that could potentially neutralize any of the biological activity that the murine antibody might have.

In order to minimize recognition of murine antibodies by the human immune system or for improving the biological activity of the antibodies in human, murine antibodies are advantageously converted into partially (e.g., chimeric) or fully humanized antibodies. Recombinant form of the light chain and heavy chain of the (partially or fully) humanized antibody may thus be introduced into a mammalian expression system other than hybridoma cells (such as 293 cells, CHO or else). Mammalian expression system may procure the advantage of having a resulting glycosylation pattern that is closer to that of naturally occurring human form of the antibodies.

For example, in the case of lytic IgG1 antibodies, the proper glycosylation of the immunoglobulin chains is necessary for effector functions. These biological functions of IgG1 monoclonal antibodies include antibody-dependent cell cytotoxicity (ADCC) and complement-dependent cytotoxicity (CDC), both of which will be greatly influenced by the type of glycosyl side chains that are grafted to the amino acids during expression in mammalian cells.

In addition, optimized mammalian cell expression systems will often secrete significantly a greater amounts of antibodies compared to hybridomas. Therefore, there is a practical and probably economical reason for adopting human cells for production.

Those of skill in the art will readily appreciate that natural, modified, or recombinant nucleic acid sequences may be ligated to a heterologous sequence resulting in translation of a fusion polypeptide containing heterologous polypeptide moieties in any of the aforementioned host systems. Such heterologous polypeptide moieties may facilitate purification of fusion polypeptides using commercially available affinity matrices. Such moieties include, but are not limited to, glutathione S-transferase (GST), maltose binding protein, thioredoxin, calmodulin binding peptide, 6-His (His), FLAG, c-myc, hemaglutinin (HA), and antibody epitopes such as monoclonal antibody epitopes.

In yet a further aspect, the present invention relates to a polynucleotide which may comprise a nucleotide sequence encoding a fusion protein. The fusion protein may comprise a fusion partner (e.g., HA, Fc, etc.) fused to the polypeptide (e.g., complete light chain, complete heavy chain, variable regions, CDRs etc.) described herein.

Those of skill in the art will also readily recognize that the nucleic acid and polypeptide sequences may be synthesized, in whole or in part, using chemical or enzymatic methods well known in the art. For example, peptide synthesis may be performed using various solid-phase techniques and machines such as the ABI 431A Peptide synthesizer (PE Biosystems) may be used to automate synthesis. If desired, the amino acid sequence may be altered during synthesis and/or combined with sequences from other proteins to produce a variant protein.

Antibody Conjugates

Although it is not always necessary, for detection or therapeutic purposes, the antibody or antigen binding fragment of the present invention may be conjugated with a detectable moiety (i.e., for detection or diagnostic purposes) or with a therapeutic moiety (for therapeutic purposes).

For detection purposes, an unconjugated antibody (primary antibody) may be used for binding to the antigen and a secondary antibody carrying a detectable moiety and capable of binding to the primary antibody may be added. However, as indicated above, the anti-SIGLEC 15 antibody may be conjugated with a detectable label and as such a secondary antibody may not be necessary.

A "detectable moiety" is a moiety detectable by spectroscopic, photochemical, biochemical, immunochemical, chemical and/or other physical means. A detectable moiety may be coupled either directly and/or indirectly (for example via a linkage, such as, without limitation, a DOTA or NHS linkage) to antibodies and antigen binding fragments thereof of the present invention using methods well known in the art. A wide variety of detectable moieties may be used, with the choice depending on the sensitivity required, ease of conjugation, stability requirements and available instrumentation. A suitable detectable moiety include, but is not limited to, a fluorescent label, a radioactive label (for example, without limitation, $^{125}$I, $In^{111}$, $Tc^{99}$, $I^{131}$ and including positron emitting isotopes for PET scanner etc), a nuclear magnetic resonance active label, a luminescent label, a chemiluminescent label, a chromophore label, an enzyme label (for example and without limitation horseradish peroxidase, alkaline phosphatase, etc.), quantum dots and/or a nanoparticle. Detectable moiety may cause and/or produce a detectable signal thereby allowing for a signal from the detectable moiety to be detected.

In another exemplary embodiment of the invention, the antibody or antigen binding fragment thereof may be coupled (modified) with a therapeutic moiety (e.g., drug, cytotoxic moiety).

In some instances, for therapeutic purposes, an unconjugated antibody may by itself be capable of sequestering the antigen, may block an important interaction between the antigen and another binding partner, may recruit effector cells, etc. However, as indicated above, the antibody may be conjugated with a therapeutic moiety.

In an exemplary embodiment, the antibodies and antigen binding fragments may comprise a chemotherapeutic or cytotoxic agent. For example, the antibody and antigen binding fragments may be conjugated to the chemotherapeutic or cytotoxic agent. Such chemotherapeutic or cytotoxic agents include, but are not limited to, Yttrium-90, Scandium-47, Rhenium-186, Iodine-131, Iodine-125, and many others recognized by those skilled in the art (e.g., lutetium (e.g., $Lu^{177}$), bismuth (e.g., $Bi^{213}$), copper (e.g., $Cu^{67}$)). In other instances, the chemotherapeutic or cytotoxic agent may be comprised of, among others known to those skilled in the art, 5-fluorouracil, adriamycin, irinotecan, taxanes, pseudomonas endotoxin, ricin and other toxins.

Alternatively, in order to carry out the methods of the present invention and as known in the art, the antibody or antigen binding fragment of the present invention (conjugated or not) may be used in combination with a second molecule (e.g., a secondary antibody, etc.) which is able to specifically bind to the antibody or antigen binding fragment of the present invention and which may carry a desirable detectable, diagnostic or therapeutic moiety.

Pharmaceutical Compositions of the Antibodies and their Use

Pharmaceutical compositions of the antibodies (conjugated or not) are also encompassed by the present invention. The pharmaceutical composition may comprise an antibody or an antigen binding fragment and may also contain a pharmaceutically acceptable carrier.

Other aspects of the invention relate to a composition which may comprise the antibody or antigen binding fragment described herein and a carrier.

Yet other aspects of the invention relate to the use of the isolated antibody or antigen binding fragment described herein in the treatment or diagnosis of bone diseases or cancer.

In addition to the active ingredients, a pharmaceutical composition may contain pharmaceutically acceptable carriers comprising water, PBS, salt solutions, gelatins, oils, alcohols, and other excipients and auxiliaries that facilitate processing of the active compounds into preparations that may be used pharmaceutically. In other instances, such preparations may be sterilized.

As used herein, "pharmaceutical composition" usually comprises therapeutically effective amounts of the agent together with pharmaceutically acceptable diluents, preservatives, solubilizers, emulsifiers, adjuvant and/or carriers. A "therapeutically effective amount" as used herein refers to that amount which provides a therapeutic effect for a given condition and administration regimen. Such compositions are liquids or lyophilized or otherwise dried formulations and include diluents of various buffer content (e.g., Tris-HCl., acetate, phosphate), pH and ionic strength, additives such as albumin or gelatin to prevent absorption to surfaces, detergents (e.g., Tween 20, Tween 80, Pluronic F68, bile acid salts). Solubilizing agents (e.g., glycerol, polyethylene glycerol), anti-oxidants (e.g., ascorbic acid, sodium metabisulfite), preservatives (e.g., thimerosal, benzyl alcohol, parabens), bulking substances or tonicity modifiers (e.g., lactose, mannitol), covalent attachment of polymers such as polyethylene glycol to the protein, complexation with metal ions, or incorporation of the material into or onto particulate preparations of polymeric compounds such as polylactic acid, polyglycolic acid, hydrogels, etc., or onto liposomes, microemulsions, micelles, unilamellar or multilamellar vesicles, erythrocyte ghosts, or spheroplasts. Such compositions will influence the physical state, solubility, stability, rate of in vivo release, and rate of in vivo clearance. Controlled or sustained release compositions include formulation in lipophilic depots (e.g., fatty acids, waxes, oils). Also comprehended by the invention are particulate compositions coated with polymers (e.g., poloxamers or poloxamines). Other embodiments of the compositions of the invention incorporate particulate forms protective coatings, protease inhibitors or permeation enhancers for various routes of administration, including parenteral, pulmonary, nasal, oral, vaginal, rectal routes. In one embodiment the pharmaceutical composition is administered parenterally, paracancerally, transmucosally, transdermally, intramuscularly, intravenously, intradermally, subcutaneously, intraperitonealy, intraventricularly, intracranially and intratumorally.

Further, as used herein "pharmaceutically acceptable carrier" or "pharmaceutical carrier" are known in the art and include, but are not limited to, 0.01-0.1 M or 0.05 M phosphate buffer or 0.8% saline. Additionally, such pharmaceutically acceptable carriers may be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers such as those based on Ringer's dextrose, and the like. Preservatives and other additives may also be present, such as, for example, antimicrobials, antioxidants, collating agents, inert gases and the like.

For any compound, the therapeutically effective dose may be estimated initially either in cell culture assays or in animal models such as mice, rats, rabbits, dogs, or pigs. An animal model may also be used to determine the concentration range and route of administration. Such information may then be used to determine useful doses and routes for administration in humans. These techniques are well known to one skilled in the art and a therapeutically effective dose refers to that amount of active ingredient that ameliorates the symptoms or condition. Therapeutic efficacy and toxicity may be determined by standard pharmaceutical procedures in cell cultures or with experimental animals, such as by calculating and contrasting the $ED_{50}$ (the dose therapeutically effective in 50% of the population) and $LD_{50}$ (the dose lethal to 50% of the population) statistics. Any of the therapeutic compositions described above may be applied to any subject in need of such therapy, including, but not limited to, mammals such as dogs, cats, cows, horses, rabbits, monkeys, and humans.

The pharmaceutical compositions utilized in this invention may be administered by any number of routes including, but not limited to, oral, intravenous, intramuscular, intra-arterial, intramedullary, intrathecal, intraventricular, transdermal, subcutaneous, intraperitoneal, intranasal, enteral, topical, sublingual, or rectal means.

The term "treatment" for purposes of this disclosure refers to both therapeutic treatment and prophylactic or preventative measures, wherein the object is to prevent or slow down (lessen) the targeted pathologic condition or disorder. Those in need of treatment include those already with the disorder as well as those prone to have the disorder or those in whom the disorder is to be prevented.

The antibodies or antigen binding fragments may have therapeutic uses in the treatment of various bone loss or cancer. In an exemplary embodiment, the antibodies or fragments may have therapeutic uses in bone loss associated with bone diseases such as conditions where there is an increase in the bone degradative activity of osteoclasts. In certain instances, the antibodies or antigen binding fragments may interact with cells that express SEQ ID NO:2 and induce an immunological reaction by mediating ADCC. In other instances, the antibodies and fragments may block the interaction of SEQ ID NO:2 with its protein partners.

The anti-Siglec-15 antibodies or antigen binding fragments may have therapeutic uses in the treatment of bone loss in the context of various bone-related diseases, including but not limited to osteoporosis, osteopenia, osteomalacia, hyperparathyroidism, hypothyroidism, hyperthyroidism, hypogonadism, thyrotoxicosis, systemic mastocytosis, adult hypophosphatasia, hyperadrenocorticism, osteogenesis imperfecta, Paget's disease, Cushing's disease/syndrome, Turner syndrome, Gaucher disease, Ehlers-Danlos syndrome, Marfan's syndrome, Menkes' syndrome, Fanconi's syndrome, multiple myeloma, hypercalcemia, hypocalcemia, arthritides, periodontal disease, rickets (including vitamin D dependent, type I and II, and x-linked hypophosphatemic rickets), fibrogenesis imperfecta ossium, osteosclerotic disorders such as pycnodysostosis and damage caused by macrophage-mediated inflammatory processes. In the preferred embodiment, the antibodies and fragments have therapeutic uses in conditions where severe bone loss prevails, in particular metastatic cancer to the bone. In certain instances, the anti-Siglec-15 antibodies and fragments may interact with cells, such as osteoclasts, that express Siglec-15. In other instances, the anti-Siglec-15 antibodies and fragments may block the interaction of Siglec-15 with its protein partners.

The anti-Siglec-15 antibodies and antigen binding fragments thereof may have therapeutic uses in the treatment of cancer or bone loss caused by or associated with various bone remodelling disorders. In particular, the anti-Siglec-15 antibodies and immunologically functional fragments therein have therapeutic uses in conditions where osteoclasts are hyperactive and contribute to the degradation of the bone surface. In certain instances, the anti-Siglec-15 antibodies and antigen binding fragment thereof may be administered concurrently in combination with other treatments given for the same condition. As such, the antibodies may be administered with anti-resorptives (e.g., bisphosphonates) that are known to those skilled in the art. Additionally, the antibodies may be administered with anti-mitotics (e.g., taxanes), platinum-based agents (e.g., cisplatin), DNA damaging agents (e.g. Doxorubicin), and other cytotoxic therapies that are known to those skilled in the art. In other instances, the anti-Siglec-15 antibodies and immunologically functional fragments therein may be administered with other therapeutic antibodies. These include, but are not limited to, antibodies that target RANKL, EGFR, CD-20, and Her2.

In certain instances, the antibodies and antigen binding fragments therein may be administered concurrently in combination with other treatments given for the same condition. As such, the antibodies may be administered with anti-mitotics (e.g., taxanes), platinum-based agents (e.g., cisplatin), DNA damaging agents (e.g. Doxorubicin), and other anti-cancer therapies that are known to those skilled in the art. In other instances, the antibodies and antigen binding fragments therein may be administered with other therapeutic antibodies. These include, but are not limited to, antibodies that target EGFR, CD-20, and Her2.

The present invention relates in a further aspect thereof to a method for inhibiting the growth of a SEQ ID NO:2-expressing cell or of SEQ ID NO:2 variant-expressing cell, the method which may comprise contacting the cell with an effective amount of the antibody or antigen binding fragment described herein.

The present invention also encompasses method of treating cancer or bone loss or inhibiting the growth of a SEQ ID NO:2 expressing cells or of SEQ ID NO:2 variant-expressing cell in a mammal, the method may comprise administering the antibody or antigen binding fragment described herein to a mammal in need.

The present invention also provides a method for inhibiting the growth of a cancer cell selected from the group consisting of ovarian cancer cells, renal cancer cells, cancer cells of the central nervous system, prostate cancer cells, melanoma cells, breast cancer cells, lung cancer cells or colon cancer cells. The method may comprise providing the cancer cell with a nucleic acid capable of impairing the expression of a polypeptide at least 80% identical to SEQ ID NO:2 or having a region at least 80% identical to amino acids 20 to 259 or to amino acids 49 to 165 of SEQ ID NO:2. The cancer cell may express a polypeptide at least 80% identical to SEQ ID NO:2 or having a region at least 80% identical to amino acids 20 to 259 or to amino acids 49 to 165 of SEQ ID NO:2.

In accordance with the present invention, the nucleic acid may be, for example, a siRNA or an antisense.

The present invention also encompasses method of detecting cancer or bone loss or detecting a SEQ ID NO:2-expressing cell or a SEQ ID NO:2 variant-expressing cell in a mammal, the method may comprise administering the antibody or antigen binding fragment described herein to a mammal in need.

The present invention relates in another aspect thereof to a method for detecting a SEQ ID NO:2-expressing cell or a SEQ ID NO:2 variant-expressing cell, the method may comprise contacting the cell with an antibody or antigen binding fragment described herein and detecting a complex formed by the antibody and the SEQ ID NO:2-expressing cell or the SEQ ID NO:2 variant-expressing cell.

Another aspect of the invention relates to a method for detecting SEQ ID NO:2, a variant having at least 80% sequence identity with amino acids 20-259 or with amino acids 49-165 of SEQ ID NO:2, the method may comprise contacting a cell expressing SEQ ID NO:2 or the variant or a sample (biopsy, serum, plasma, urine etc.) comprising or suspected of comprising SEQ ID NO:2 or the variant with the antibody or antigen binding fragments described herein and measuring binding.

The binding of an antibody to an antigen will cause an increase in the expected molecular weight of the antigen. A physical change therefore occurs upon specific binding of the antibody or antigen binding fragment and the antigen.

Such changes may be detected using, for example, electrophoresis followed by Western blot and coloration of the gel or blot, mass spectrometry, HPLC coupled with a computer or else. Apparatus capable of computing a shift in molecular weight are known in the art and include for example, Phosphorimager™.

When the antibody comprises for example a detectable label, the antigen-antibody complex may be detected by the fluorescence emitted by the label, radiation emission of the label, enzymatic activity of a label provided with its substrate or else.

Detection and/or measurement of binding between an antibody or antigen binding fragment and an antigen may be performed by various methods known in the art. Binding between an antibody or antigen binding fragment and an antigen may be monitored with an apparatus capable of detecting the signal emitted by the detectable label (radiation emission, fluorescence, color change etc.). Such apparatus provides data which indicates that binding as occurred and may also provide indication as to the amount of antibody bound to the antigen. The apparatus (usually coupled with a computer) may also be capable of calculating the difference between a background signal (e.g., signal obtained in the absence of antigen-antibody binding) or background noise and the signal obtained upon specific antibody-antigen binding. Such apparatuses may thus provide the user with indications and conclusions as to whether the antigen has been detected or not.

The sample may originate from a mammal (e.g., a human) which may have cancer or bone disease or may be suspected of having cancer or a bone disease or may experience bone loss or may be subject of experiencing bone loss. The sample may be a tissue sample obtained from the mammal or a cell culture supernatant.

In accordance with the invention the sample may be a serum sample, a plasma sample, a blood sample or ascitic fluid obtained from the mammal. The antibody or antigen binding fragment described herein may advantageously detect SEQ ID NO:2.

The method may comprise quantifying the complex formed by the antibody or antigen binding fragment bound to SEQ ID NO:2 or to the SEQ ID NO:2 variant.

The antibody or antigen binding fragment of the present invention may more particularly be used in the detection, diagnosis or treatment of bone disease or cancer.

Additional aspects of the invention relates to kits which may include one or more container containing one or more antibodies or antigen binding fragments described herein.

Nucleic Acids, Vectors and Cells

Antibodies are usually made in cells allowing expression of the light chain and heavy chain expressed from a vector(s) comprising a nucleic acid sequence encoding the light chain and heavy chain.

The present therefore encompasses nucleic acids capable of encoding any of the CDRs (including CDR variants), light chain variable domains (including light chain variable domain variants), heavy chain variable domains (including heavy chain variable domain variants), light chains (including light chain variants), heavy chains (including heavy chain variants) described herein.

Exemplary embodiments of nucleic acids of the present invention include nucleic acids encoding a light chain variable domain comprising:
- a. a CDRL1 sequence selected from the group consisting of SEQ ID NO:69, SEQ ID NO:75, SEQ ID NO:81, SEQ ID NO:87, SEQ ID NO:93, SEQ ID NO:99, SEQ ID NO:105 and SEQ ID NO:111;
- b. a CDRL2 sequence selected from the group consisting of SEQ ID NO:70, SEQ ID NO:76. SEQ ID NO:82. SEQ ID NO:88. SEQ ID NO:94, SEQ ID NO:100, SEQ ID NO:106 and SEQ ID NO:112, and/or;
- c. a CDRL3 sequence selected from the group consisting of SEQ ID NO:71, SEQ ID NO:77, SEQ ID NO:83, SEQ ID NO:89, SEQ ID NO:95, SEQ ID NO:101, SEQ ID NO:107 and SEQ ID NO:113.

In accordance with the present invention, the nucleic acid may encode a light chain variable domain which may comprise at least two CDRs of a CDRL1, a CDRL2 or a CDRL3.

Also in accordance with the present invention, the nucleic acid may encode a light chain variable domain which may comprise one CDRL1, one CDRL2 and one CDRL3.

The present invention also relates to a nucleic acid encoding a heavy chain variable domain comprising:
- a. a CDRH1 sequence selected from the group consisting of SEQ ID NO:72, SEQ ID NO:78, SEQ ID NO:84, SEQ ID NO:90, SEQ ID NO:96, SEQ ID NO:102, SEQ ID NO:108 and SEQ ID NO:114;
- b. a CDRH2 sequence selected from the group consisting of SEQ ID NO:73, SEQ ID NO:79, SEQ ID NO:85, SEQ ID NO:91, SEQ ID NO:97, SEQ ID NO:103, SEQ ID NO:109 and SEQ ID NO:115, and/or;
- c. a CDRH3 sequence selected from the group consisting of SEQ ID NO:74, SEQ ID NO:80, SEQ ID NO:86, SEQ ID NO:92, SEQ ID NO:98, SEQ ID NO:104, SEQ ID NO:110 and SEQ ID NO:116.

In a further aspect, the present invention provides a nucleic acid encoding a light chain variable domain which may comprise:
- a) a CDRL1 sequence selected from the group consisting of SEQ ID NO:153, SEQ ID NO:154, SEQ ID NO:84, SEQ ID NO:96 and SEQ ID NO:102;
- b) a CDRL2 sequence selected from the group consisting of SEQ ID NO:149, SEQ ID NO:150, SEQ ID NO:76, SEQ ID NO:82 and SEQ ID NO:106, or;
- c) a CDRL3 sequence selected from the group consisting of SEQ ID NO:151, SEQ ID NO:152, SEQ ID NO:77, SEQ ID NO:83, SEQ ID NO:95, SEQ ID NO:107 and SEQ ID NO:152.

In yet a further aspect, the present invention provides a nucleic acid encoding a heavy chain variable domain which may comprise:
- a) a CDRH1 sequence selected from the group consisting of SEQ ID NO:153, SEQ ID NO:154, SEQ ID NO:84, SEQ ID NO:96 and SEQ ID NO:102;
- b) a CDRH2 sequence selected from the group consisting of SEQ ID NO:155, SEQ ID NO:156, SEQ ID NO:157, SEQ ID NO:73, SEQ ID NO:79, SEQ ID NO:85, SEQ ID NO:97, SEQ ID NO:103 and SEQ ID NO:109, or;
- c) a CDRH3 sequence selected from the group consisting of SEQ ID NO:158, SEQ ID NO:74, SEQ ID NO:98, SEQ ID NO:104, SEQ ID NO:110 and SEQ ID NO:116.

In accordance with the present invention, the nucleic acid may encode a heavy chain variable domain which may comprise at least two CDRs of a CDRH1, a CDRH2 or a CDRH3.

In accordance with the present invention, the nucleic acid may encode a heavy chain variable domain which may comprise one CDRH1, one CDRH2 and one CDRH3.

Also encompassed by the present invention are nucleic acids encoding antibody variants having at least one conservative amino acid substitution.

In accordance with the present invention, the nucleic acid may encode a CDR comprising at least one conservative amino acid substitution.

In accordance with the present invention, the nucleic acid may encode a CDR comprising at least one conservative amino acid substitution in at least two of the CDRs.

In accordance with the present invention, the nucleic acid may encode a CDR comprising at least one conservative amino acid substitution in the 3 CDRs.

In accordance with the present invention, the nucleic acid may encode a CDR comprising at least two conservative amino acid substitution in at least one of the CDRs.

In accordance with the present invention, the nucleic acid may encode a CDR comprising at least two conservative amino acid substitution in at least two of the CDRs.

In accordance with the present invention, the nucleic acid may encode a CDR comprising at least two conservative amino acid substitution in the 3 CDRs.

Other aspects of the invention relate to a nucleic acid encoding a light chain variable domain having at least 70% (including at least 80%) sequence identity to a sequence selected from the group consisting of SEQ ID NO:37, SEQ ID NO:41, SEQ ID NO:45, SEQ ID NO:49, SEQ ID NO:53, SEQ ID NO:57, SEQ ID NO:61 and SEQ ID NO:65.

Yet other aspects of the invention relate to a nucleic acid encoding a heavy chain variable domain having at least 70% (including at least 80%) sequence identity to a sequence selected from the group consisting of SEQ ID NO:39, SEQ ID NO:43, SEQ ID NO:47, SEQ ID NO:51, SEQ ID NO:55, SEQ ID NO:59, SEQ ID NO:63 and SEQ ID NO:67.

In yet another aspect, the present invention relates to a vector comprising the nucleic acid described herein.

In accordance with the present invention, the vector may be an expression vector.

Vector that contains the elements for transcriptional and translational control of the inserted coding sequence in a particular host are known in the art. These elements may include regulatory sequences, such as enhancers, constitutive and inducible promoters, and 5' and 3' un-translated regions. Methods that are well known to those skilled in the art may be used to construct such expression vectors. These methods include in vitro recombinant DNA techniques, synthetic techniques, and in vivo genetic recombination.

In another aspect the present invention relates to an isolated cell which may comprise the nucleic acid described herein.

The isolated cell may comprise a nucleic acid encoding a light chain variable domain and a nucleic acid encoding a heavy chain variable domain either on separate vectors or on the same vector. The isolated cell may also comprise a nucleic acid encoding a light chain and a nucleic acid encoding a heavy chain either on separate vectors or on the same vector.

In accordance with the present invention, the cell may be capable of expressing, assembling and/or secreting an antibody or antigen binding fragment thereof.

In another aspect, the present invention provides a cell which may comprise and/or may express the antibody described herein.

In accordance with the invention, the cell may comprise a nucleic acid encoding a light chain variable domain and a nucleic acid encoding a heavy chain variable domain.

The cell may be capable of expressing, assembling and/or secreting an antibody or antigen binding fragment thereof.

The examples below are presented to further outline details of the present invention.

Exemplary Embodiments of Screening Assay

In an additional aspect the present invention provides methods of identifying a compound capable of inhibiting the growth of ovarian cancer cells, renal cancer cells, cancer cells of the central nervous system, prostate cancer cells, melanoma cells, breast cancer cells, lung cancer cells or colon cancer cells. The method may comprise providing a polypeptide comprising a region at least 80% identical to amino acids 20 to 259 of SEQ ID NO:2 or a cell expressing said polypeptide with a candidate compound and measuring the activity or expression of the polypeptide. A reduced activity or expression of the polypeptide may positively identify a suitable inhibitory compound.

In accordance with the present invention, the candidate compound may specifically bind to the polypeptide.

In accordance with the present invention, the candidate compound may be, for example, an antibody or an antigen binding fragment.

In accordance with the present invention, the candidate compound may be, for example, a siRNA or an antisense.

Other types of assay may be carried out without departing from the scope of the invention.

EXAMPLES

Example 1

This example describes the pattern of expression of the Siglec-15 gene in osteoclasts and human tissue RNA samples One of the most promising genes identified was termed AB-0326, which encodes the cell surface type I membrane protein, Siglec-15. This candidate was first isolated from a human osteoclast library and a similar RANKL-dependent upregulation was also confirmed in primary mouse osteoclasts as well as the mouse RAW 264.7 cells compared to precursor cells by RT-PCR (Sooknanan et al. 2007). The tissue expression profile of Siglec-15 was assessed to determine the specificity of expression, a criteria that was imposed on all targets that were chosen for validation. Peripheral blood mononuclear cells (PBMNCs) were obtained from 6 human donors and cultured in osteoclast differentiation medium (MCS-F and RANKL) for at least 14 days. Total RNA was isolated from precursors cells (no RANKL treatment (FIG. 1, top panel, -) or at intermediate time intervals (FIG. 1, top panel, ▲). One microgram of each RNA sample was converted to single-stranded cDNA using Thermoscript reverse transcriptase (Invitrogen, Burlington, ON) according to the manufacturer's instructions, diluted 200-fold, and used in a PCR reaction previously optimized to specifically amplify a fragment of the Siglec-15 transcript. The sequences of the oligonucleotides used in the PCR reaction are shown in SEQ ID NOS: 117 and 118. As shown in FIG. 1 top panel, differentiating osteoclasts), the Siglec-15 transcript was either expressed at much lower level in the precursors cells compared to the differentiating osteoclasts. In addition, the level of Siglec-15 transcript increased as the differentiation progressed. By comparison, a known osteoclast marker gene, cathepsin K (CATK in FIG. 1, differentiating osteoclasts) was also upregulated during osteoclast differentiation. The oligonucleotides used to amplify the CATK message are displayed in SEQ ID NOS: 119 and 120. As a control, PCR reactions were conducted on the same samples with primers that specifically amplify the housekeeping gene glyceraldehyde-3-phosphate dehydrogenase (GAPDH, see lower panel of FIG. 1, differentiating osteoclasts). The sequences of the GAPDH-specific primers used in the PCR reaction are shown in SEQ ID NOS: 121 and 122. This latter reaction demonstrates that an equal amount of starting RNA was present in each sample. Total RNA from human normal tissues was purchased from a commercial vendor (Clontech, Mountain View, Calif.) As shown in FIG. 1 (upper panel, Normal tissues), Siglec-15 was weakly detected in a single tissue (lung, lane 9) and completely absent from all other tissue samples. This underscores the strength of the Applicant's discovery approach in its ability to identify targets that are highly restricted to differentiating osteoclasts. The lane numbers in FIG. 1 correspond to the following tissues: The lanes correspond to the following tissues: lane 1, adrenal; 2, breast; 3, jejunum; 4, trachea; 5, liver; 6, placenta; 7, aorta; 8, brain; 9, lung; 10, adrenal cortex; 11, esophagus; 12, colon; 13, ovary; 14, kidney; 15, prostate; 16, thymus; 17, skeletal muscle; 18, vena cava; 19, stomach; 20, small intestine; 21, heart; 22, fallopian tube; 23, spleen; 24, bladder; 25, cervix; 26, pancreas; 27, ileum; 28, duodenum; 29, thyroid; 30, testicle; the blank lanes between lanes 10 and 11 and lanes 20 and 21 represent negative controls (no cDNA). Our results indicate that Siglec-15 is upregulated in differentiating osteoclasts, absent from virtually all normal human tissues and suggest that an antibody against Siglec-15 would interact significantly less with non-target tissues.

An additional expression profiling study was performed to determine the expression of Siglec-15 in cancer indications. One skilled in the art will recognize that the antibodies described in this invention might have utilities in cancer if it was found that the Siglec-15 gene was expressed in these types of indications. To address this, the PCR-based method was adapted to determine the expression pattern of the Siglec-15 transcript in cancer cell lines isolated from nine types of cancer. The cancer types represented by the cell lines are leukemia, central nervous system, breast, colon, lung, melanoma, ovarian, prostate, and renal cancer (see Table 4). These RNA samples were obtained from the Developmental Therapeutics Program at the NCI/NIH. Using the same RAMP RNA samples that was amplified from the total RNA samples obtained from the NCI, 500 ng of RNA was converted to single-stranded cDNA as described above. The cDNA reaction was diluted so that 1/200 of the reaction was used for each PCR experiment. PCR was conducted in 96-well plates using Hot-Start Taq Polymerase from Qiagen (Mississauga, ON) in a DNA Engine Tetrad from MJ Research. Half of the reaction mixture was loaded on a 1.2% agarose/ethidium bromide gel and the amplicons visualized with UV light. To verify that equal quantities of RNA was used in each reaction, the level of RNA was monitored with GAPDH expression.

TABLE 4

List of cancer cell lines from the NCI-60 panel

| Cell line | Cancer type |
|---|---|
| K-562 | leukemia |
| MOLT-4 | leukemia |
| CCRF-CEM | leukemia |
| RPMI-8226 | leukemia |
| HL-60(TB) | leukemia |
| SR | leukemia |
| SF-268 | CNS |
| SF-295 | CNS |

TABLE 4-continued

List of cancer cell lines from the NCI-60 panel

| Cell line | Cancer type |
|---|---|
| SF-539 | CNS |
| SNB-19 | CNS |
| SNB-75 | CNS |
| U251 | CNS |
| BT-549 | breast |
| HS 578T | breast |
| MCF7 | breast |
| NCI/ADR-RES | breast |
| MDA-MB-231 | breast |
| MDA-MB-435 | breast |
| T-47D | breast |
| COLO 205 | colon |
| HCC-2998 | colon |
| HCT-116 | colon |
| HCT-15 | colon |
| HT29 | colon |
| KM12 | colon |
| SW-620 | colon |
| A549/ATCC | non-small cell lung |
| EKVX | non-small cell lung |
| HOP-62 | non-small cell lung |
| HOP-92 | non-small cell lung |
| NCI-H322M | non-small cell lung |
| NCI-H226 | non-small cell lung |
| NCI-H23 | non-small cell lung |
| NCI-H460 | non-small cell lung |
| NCI-H522 | non-small cell lung |
| LOX IMVI | melanoma |
| M14 | melanoma |
| MALME-3M | melanoma |
| SK-MEL-2 | melanoma |
| SK-MEL-28 | melanoma |
| SK-MEL-5 | melanoma |
| UACC-257 | melanoma |
| UACC-62 | melanoma |
| IGROV-1 | ovarian |
| OVCAR-3 | ovarian |
| OVCAR-4 | ovarian |
| OVCAR-5 | ovarian |
| OVCAR-8 | ovarian |
| SK-OV-3 | ovarian |
| DU-145 | prostate |
| PC-3 | prostate |
| 786-O | renal |
| A498 | renal |
| ACHN | renal |
| CAKI-1 | renal |

Figure 2:
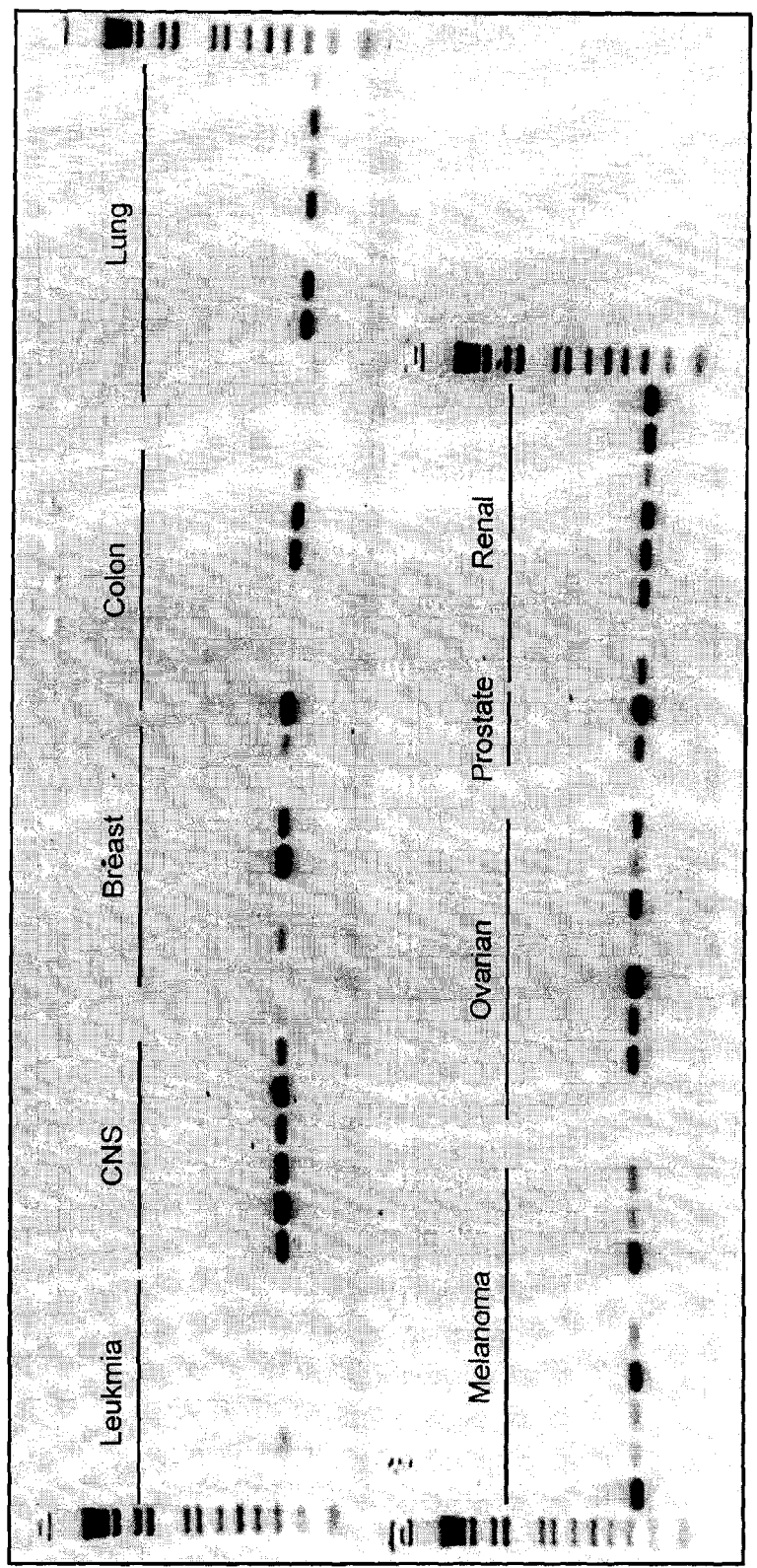
FIG. 2 shows the expression of the Siglec-15 mRNA in samples isolated from the NCI-60 panel of cancer cell lines.

As shown in FIG. 2, Siglec-15 was found to be expressed in several cancer types, in particular ovarian cancer, renal cancer, cancer of the central nervous system, and prostate cancer. In fact, Siglec-15 was detected in almost every cancer indication represented by these samples with the exception of leukemia. This result suggests that antibodies against Siglec-15 might have uses in cancer diseases.

Figure 13:
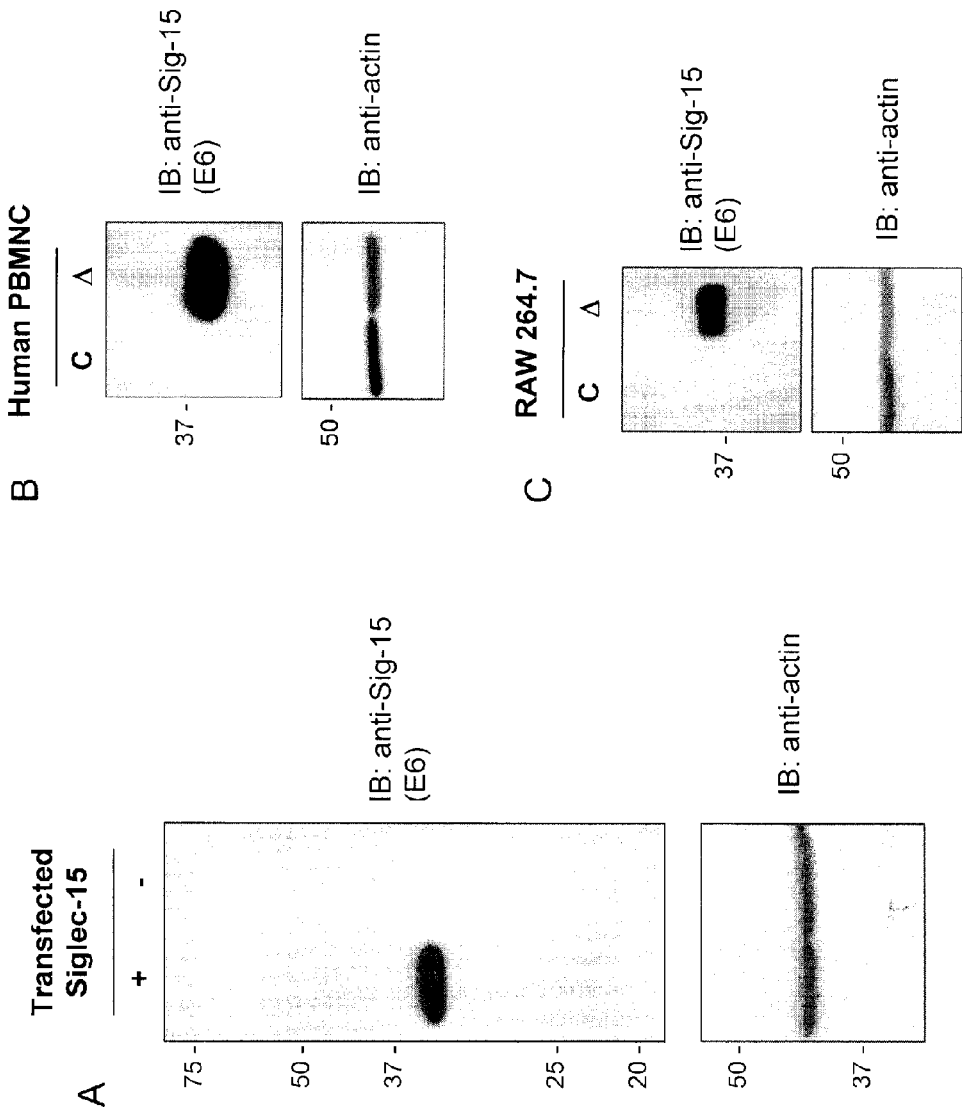
FIGS. 13A, 13B, 13C, 13D and 13E demonstrate that the Siglec-15 antibodies can detect the protein by immunoblotting of lysates prepared from cells overexpressing the Siglec-15 cDNA (13A), in human (13B) and mouse (13C) osteoclasts, and in U87 glioblastoma cells, and by flow cytometry of intact U87 cells.
Figure 13:
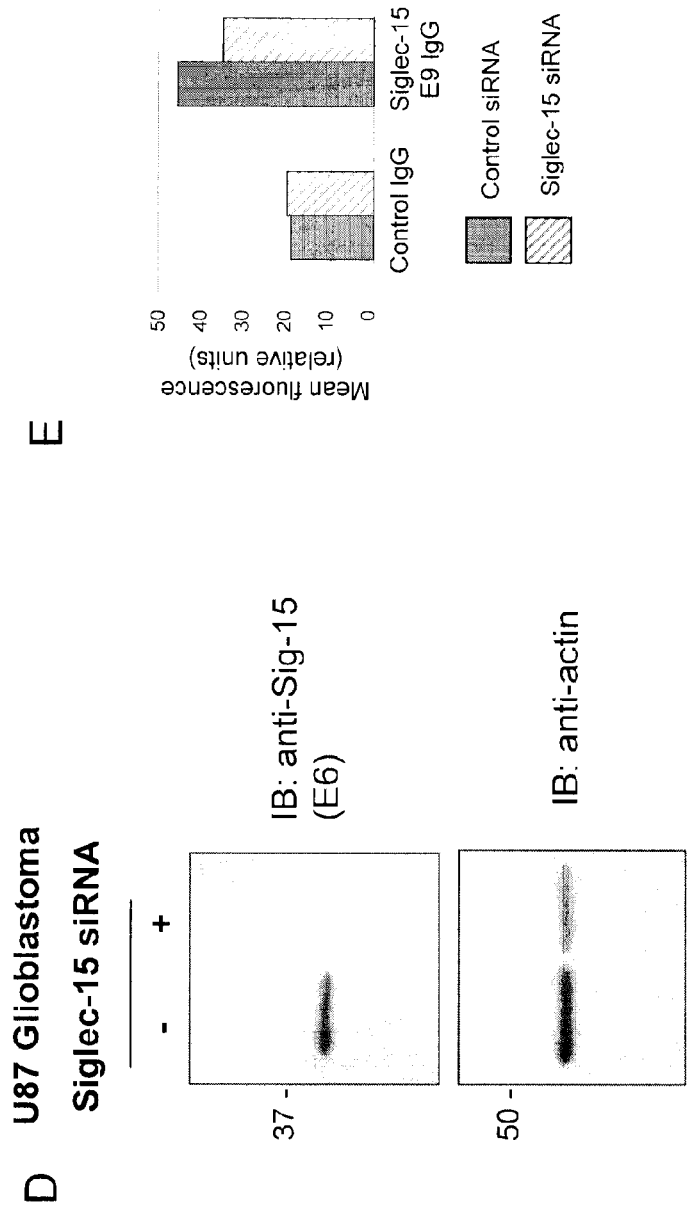

The antibodies described in Example 2 (see below) may also be used for detection of Siglec-15 in cell lysates by immunoblotting. The entire open reading frame of human Siglec-15 cDNA was cloned into a mammalian expression vector downstream of a CMV promoter (pCDNA-Siglec-15). This construct, or a control empty vector which does not encode Siglec-15, were transfected into A375 melanoma cells, which express low endogenous levels of Siglec-15 protein. A pool of stable transfectants was isolated by selection with G418. Cell lysates from Siglec-15-transfected (+) and control (−) A375 cells were analysed by immunoblotting with monoclonal antibody E6. As shown in FIG. 13A, the antibody detects a single band of 35 kDa in the Siglec-15-transfected cells, but not in control cells. This closely matches the predicted molecular weight of Siglec-15 (35.62 kDa), based on the primary amino acid sequence (http://www.bioinformatics.org/sms/prot_mw.html). Lysates were also analyzed by immunoblotting with an anti-β-actin antibody to demonstrate that similar total amounts of lysates were loaded in each lane. This result demonstrates that, by immunoblotting, antibody E6 recognizes, in a highly specific manner, overexpressed Siglec-15 in lysates from cells transfected with cloned Siglec-15 cDNA.

To confirm that the increased Siglec-15 mRNA levels in differentiated human PBMNC (FIG. 1) correspond to an increase in Siglec-15 protein levels, lysates were prepared from human PBMNC treated with MCSF alone (non-differentiated, C) or MCSF and RANKL (differentiated, A) (FIG. 13B). Lysates were also prepared from RAW 264.7 cells left untreated (non-differentiated, C) or treated with RANKL (differentiated, Δ) (FIG. 13C). RAW 264.7 cells were shown previously to upregulate Siglec-15 mRNA levels upon induction of osteoclast differentiation by RANKL (Sooknanan, 2007). Analysis of these lysates by immunoblotting with antibody E9 demonstrates that, as predicted by RT-PCR studies, there is a dramatic increase in Siglec-15 protein levels both in PBMNC and RAW 264.7 cells upon differentiation into osteoclasts (FIGS. 13B and 13C).

RT-PCR analysis of mRNA from the NCI60 panel (FIG. 2) indicated that a particularly high proportion of CNS-derived cancer cell lines express Siglec-15, while a recent microarray study found a small set of cancer cell lines, including the U87 glioblastoma line that is not part of the NCI60 panel, that express very high levels of Siglec-15 mRNA (Shankavaram, 2007). Therefore, we tested whether endogenous expression of Siglec-15 protein could be detected in U87 cells. Indeed, a protein the size of Siglec-15 is detected by immunoblotting of U87 cell lysates. To confirm the identity of this protein, U87 cells were transfected with a pool of small interfering RNAs (siRNAs) targeting Siglec-15 (SIGLEC15 siGENOME SMARTpool, Dharmacon) (+) or with a control, non-targeting siRNA pool (−, FIG. 13D) and allowed to grow for 72 h before cell lysis. Consistent with its identification as Siglec-15, treatment with the targeted siRNA resulted in reduced expression of this protein compared to the non-targeted control (FIG. 13D). To examine whether Siglec-15 is found at the cell surface in cancer cells, we analyzed the siRNA-treated U87 cells by flow cytometry. Living cells were placed on ice and stained with Siglec-15 antibody E9 (see Example 2) or an isotype control antibody, under conditions which allow antibody binding to extracellular but not intracellular antigens. Treatment with the targeted siRNA resulted in reduced binding of antibody E9 but had no effect on binding of the control antibody (FIG. 13E). Together, these results demonstrate that Siglec-15 may be expressed in cancer cells, and that it is accessible for antibody binding at the cell surface.

Example 2

This example provides details pertaining to the family of monoclonal antibodies that bind to Siglec-15.

Figure 3:
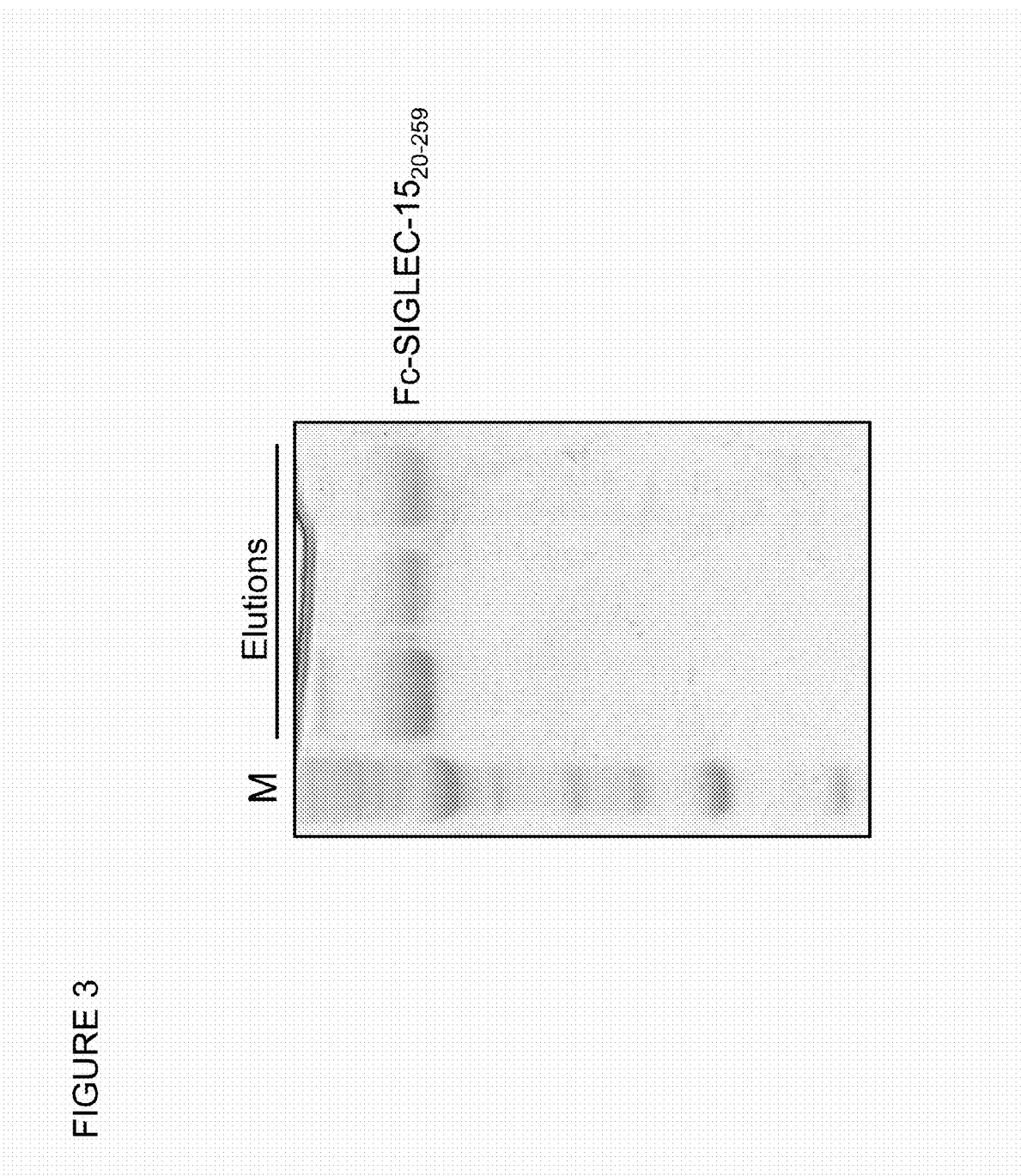
FIG. 3 presents a Coomassie-stained polyacrylamide gel containing a sample of the purified human recombinant Siglec-15 that was expressed as a Fc fusion protein in 293-6E cells. This preparation was used to generate the monoclonal antibodies disclosed in this patent.

To generate monoclonal antibodies, recombinant human Siglec-15 was produced in 293E cells using the large-scale transient transfection technology (Durocher et al., 2002; Durocher, 2004). A cDNA encoding amino acids 20-259 of SEQ ID NO:2 (see SEQ ID NO:123) was amplified by PCR using a forward primer that incorporated a BamHI restriction site (SEQ ID NO:124) and a reverse primer that incorporated a NotI restriction site (SEQ ID NO:125). The resulting PCR product was digested with BamHI and NotI and the fragment was ligated into the expression vector pYD5 (SEQ ID NO:126) that was similarly digested with the same restriction enzymes to create a vector called pYD5-0326. The pYD5 expression plasmid contains the coding sequence for the human Fc domain that allows fusion proteins to be generated as well as the sequence encoding the IgG1 signal peptide to allow the secretion of the fusion protein into the culture medium. For each milliliter of cells, one microgram of the expression vector, called pYD5-0326$_{20-259}$, was transfected in 2936E cells grown in suspension to a density of 1.5-2.0 million cells/ml. The transfection reagent used was polyethylenimine (PEI), (linear, MW 25,000, Cat#23966 Polysciences, Inc., Warrington, Pa.) which was included at a DNA:PEI ratio of 1:3. Growth of the cells was continued for 5 days after which the culture medium was harvested for purification of the recombinant Fc-0326$_{20-259}$ fusion protein. The protein was purified using Protein-A agarose as instructed by the manufacturer (Sigma-Aldrich Canada Ltd., Oakville, ON). A representative polyacrylamide gel showing a sample of the purified Fc-0326$_{20-259}$ (indicated as Fc-Siglec-15$_{20-259}$) is shown in FIG. 3.

The antibodies that bind Siglec-15 were generated using the Biosite phage display technology. A detailed description of the technology and the methods for generating these antibodies can be found in the U.S. Pat. No. 6,057,098. Briefly, the technology utilizes stringent panning of phage libraries that display the antigen binding fragments (Fabs). After a several rounds of panning, a library, termed the Omniclonal, was obtained that was enriched for recombinant Fabs containing light and heavy chain variable regions that bound to Siglec-15 with very high affinity and specificity. From this library, more precisely designated Omniclonal AL0025Z1, 96 individual recombinant monoclonal Fabs were prepared from E. coli and tested for Siglec-15 binding.

To measure the relative binding of each individual monoclonal antibody, recombinant human Fc-Siglec-15$_{20-259}$ was produced in 293E cells using the large-scale transient transfection technology (Durocher et al., 2002; Durocher, 2004). The 96-well master plate of monoclonal preparations contained different concentrations of purified anti-Siglec-15 Fabs in each well. A second stock master plate was prepared by diluting the Fabs to a final concentration of 10 µg/ml from which all subsequent dilutions were performed for ELISA measurements. To carry out the binding of Fc-Siglec-15 to the monoclonal preparations, the Fc-Siglec-15$_{20-259}$ was biotinylated with NHS-biotin (Pierce, Rockford, Ill.) and 10 ng/well was coated in a streptavidin 96-well plate. One nanogram of each Fab monoclonal preparation was added to each well and incubated at room temperature for 30 minutes. Bound antibody was detected with HRP-conjugated mouse anti-kappa light chain antibody in the presence of TMB liquid substrate (Sigma-Aldrich Canada Ltd., Oakville, ON) and readings were conducted at 450 nm in microtiter plate reader. As shown in FIG. 4A, a total of 53 (highlighted dark grey) monoclonal antibodies displayed significant binding in this assay (>0.2 arbitrary OD$_{450}$ units). The antibodies were purposely diluted to 1 ng/well to accentuate the binding of those antibodies with the most affinity for Siglec-15. Since the antibodies were generated using a Fc fusion protein, the monoclonals were also tested in an ELISA using biotinylated Fc domain only. As shown in FIG. 4B, 17 antibodies interacted with the Fc moiety of the Fc-Siglec-15$_{20-259}$ (highlighted light grey). The values presented in bold (see FIG. 4) represent the exemplary antibodies 25A1, 25B4, 25B8, 25C1, 25D8, 25E5, 25E6, and 25E9. These data also revealed that the binding of the antibodies varied from well to well indicating that they exhibited different affinities for Siglec-15.

The applicant noted that the antibody or antigen binding fragment of the present invention may bind efficiently to the antigen, in fact it was found that 1 ng of antibody is capable of binding to less than 500 ng of SEQ ID NO:2.

Figure 14:
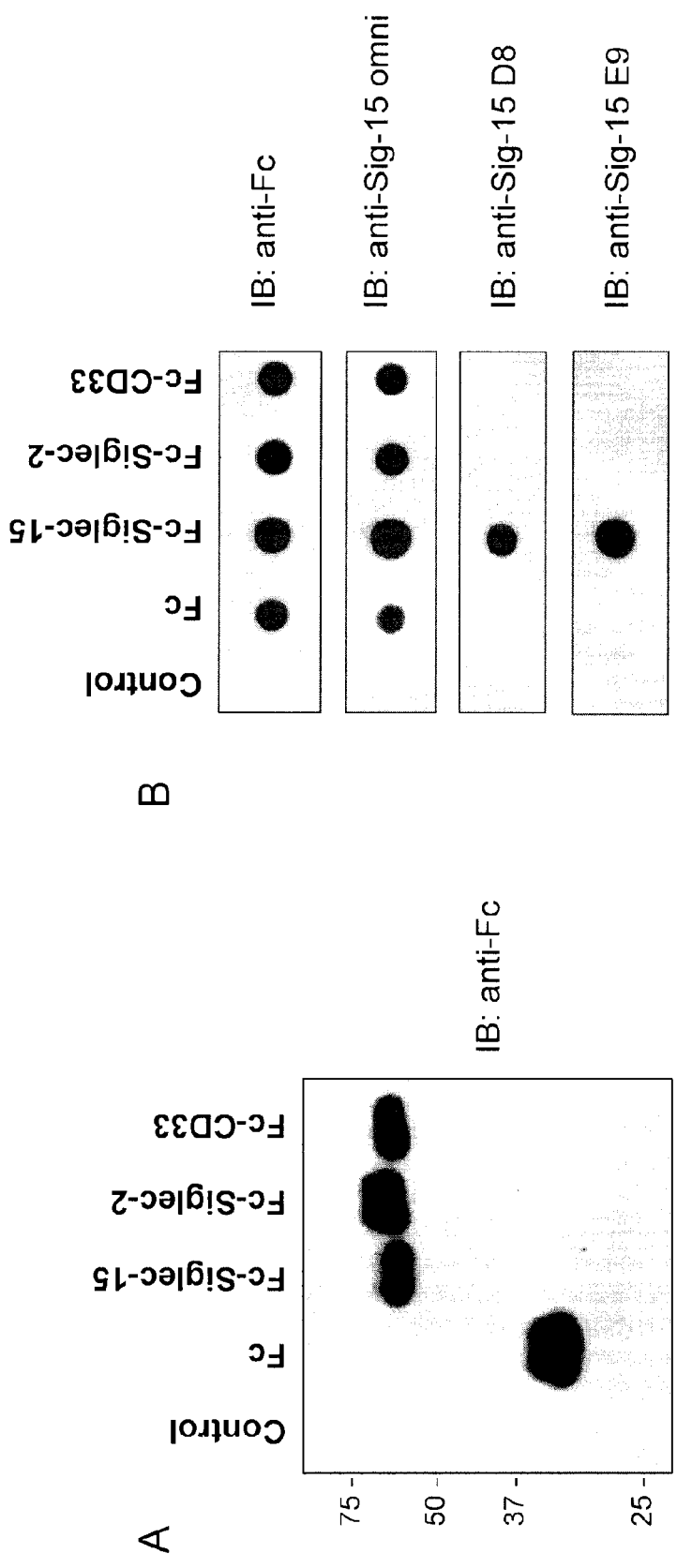
FIGS. 14A and 14B shows that the antibodies generated against Siglec-15 do not bind other related Siglecs including Siglec-2 and CD33.

The specificity of these antibodies for Siglec-15 was assessed by testing their binding to two other members of the Siglec family, CD33 and Siglec-2. CD33 (GeneBank™ accession No. NM__001772.3) is the prototype of the CD33-related family of Siglecs: among human proteins, these Siglecs share the highest amino acid sequence similarity with Siglec-15 (around 29% sequence identity between their two respective N-terminal Ig-like domains). Siglec-2 (GeneBank™ accession No. NM__001771.3) is less similar (23% sequence identity), but like Siglec-15 and unlike most other Siglecs, it has a marked preference for binding α2-6-linked sialic acid conjugates (Angata 2007, Blixt 2003). Sequences comprising the V-set and N-terminal C2-set Ig-like domains of Siglec-2 and CD33 (corresponding to the region of Siglec-15 used as the antigen for antibody production) were cloned from a human PBMNC cDNA library into the pYD5 vector. Supernatants from 293-6E cells transfected with these constructs, as wells as from non-transfected 293-6E cells or those transfected with pYD5-Siglec-15 or pYD5 empty vector, were analyzed by immunoblotting with an anti-Fc antibody to evaluate expression levels (FIG. 14A). Transfection of these constructs resulted in expression of Fc-tagged proteins of the expected size (FIG. 14A). Aliquots of these supernatants were adsorbed onto PVDF by vacuum dot blotting (Bio-dot apparatus, Bio-Rad), and binding of representative Siglec-15 monoclonal antibodies was evaluated (Western blots were not used because many antibodies react only with the native, non-denatured form of Siglec-15). As controls, anti-Fc and anti-Siglec-15 omniclonal antibodies reacted with all four Fc-tagged proteins (FIG. 14B). In contrast, monoclonal antibodies D8 and E9 show no detectable binding to Fc alone, Siglec-2 or CD33, indicating that they are highly specific for Siglec-15.

Example 3

Figure 5:
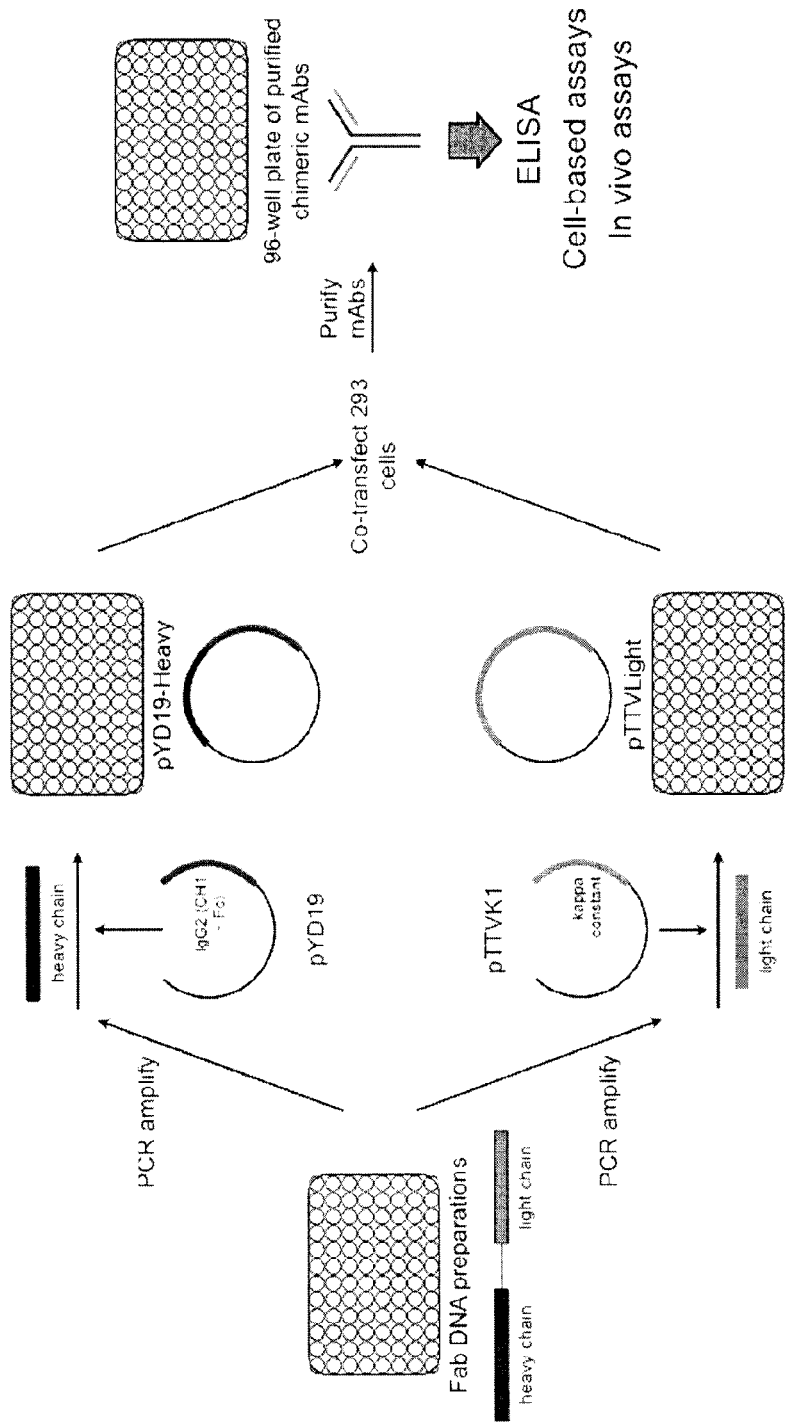
FIG. 5 presents a scheme that illustrates the steps involved to convert the mouse Fabs into IgG2 mouse-human chimeric mAbs.

This example discloses the methods used to convert the Fabs into full IgG2 chimeric monoclonal antibodies. A scheme of the methodology is presented in FIG. 5.

In order to conduct in vitro and in vivo studies to validate the biological function of the antigen the light and heavy chain variable regions contained in the Fabs was transferred to full antibody scaffolds, to generate mouse-human chimeric IgG2s. The expression vectors for both the light and heavy immunoglobulin chains were constructed such that i) the original bacterial signal peptide sequences upstream of the Fab expression vectors were replaced by mammalian signal peptides and ii) the light and heavy chain constant regions in the mouse antibodies were replaced with human constant regions. The methods to accomplish this transfer utilized standard molecular biology techniques that are familiar to those skilled in the art. A brief overview of the methodology is described here (see FIG. 5).

Light chain expression vector—an existing mammalian expression plasmid, called pTTVH8G (Durocher et al., 2002), designed to be used in a 293E transient transfection system was modified to accommodate the mouse light chain variable region. The resulting mouse-human chimeric light chain contained a mouse variable region followed by the human kappa constant domain. The cDNA sequence encoding the human kappa constant domain was amplified by PCR with primers OGS1773 and OGS1774 (SEQ ID NOS:127 and 128, respectively). The nucleotide sequence and the corresponding amino acid sequence for the human kappa constant region are shown in SEQ ID NOS:129 and 130, respectively.

The resulting 321 base pair PCR product was ligated into pTTVH8G immediately downstream of the signal peptide sequence of human VEGF A (NM_003376). This cloning step also positioned unique restriction endonuclease sites that permitted the precise positioning of the cDNAs encoding the mouse light chain variable regions. The sequence of the final expression plasmid, called pTTVK1, is shown in SEQ ID NO:131. Based on the sequences disclosed in Table 2, PCR primers specific for the light chain variable regions of antibodies 25A1, 25B4, 25B8, 25C1, 25D8, 25E5, 25E6, and 25E9 (SEQ ID NOS:37, 41, 45, 49, 53, 57, 61, and 65, respectively) were designed that incorporated, at their 5'-end, a sequence identical to the last 20 base pairs of the VEGF A signal peptide. The sequences of these primers are shown in SEQ ID NO:132 for 25A1; SEQ ID NO:133 for 25B4, 25B8, 25C1, 25D8, and 25E9; SEQ ID NO:134 for 25E5, and SEQ ID NO:135 for 25E6, respectively. The same reverse primer was used to amplify all four light chain variable regions since the extreme 3'-ends were identical. This primer (SEQ ID NO:136) incorporated, at its 3'-end, a sequence identical to the first 20 base pairs of the human kappa constant domain. Both the PCR fragments and the digested pTTVK1 were treated with the 3'-5' exonuclease activity of T4 DNA polymerase resulting in complimentary ends that were joined by annealing. The annealing reactions were transformed into competent E. coli and the expression plasmids were verified by sequencing to ensure that the mouse light chain variable regions were properly inserted into the pTTVK1 expression vector. Those skilled in the art will readily recognize that the method used for construction of the light chain expression plasmids applies to all anti-Siglec-15 antibodies contained in the original Fab library.

Heavy chain expression vector—the expression vector that produced the heavy chain immunoglobulins was designed in a similar manner to the pTTVK1 described above for production of the light chain immunoglobulins. In the case of the chimeric anti-Siglec-15 antibodies, IgG2 isotype was required which is the preferred type for stable, blocking antibodies. To this end, the constant regions (CH1, CH2, and CH3) of the human IgG2 immunoglobulin were amplified and ligated into a pre-existing IgG1 expression vector and the detailed methods are described herein. Plasmid pYD11 (Durocher et al., 2002), which contains the human IgGK signal peptide sequence as well as the CH2 and CH3 regions of the human Fc domain of IgG1, was modified by ligating the cDNA sequence encoding the human constant CH1 region. PCR primers OGS1769 and OGS1770 (SEQ ID NOS:137 and 138), designed to contain unique restriction endonuclease sites, were used to amplify the human IgG1 CH1 region containing the nucleotide sequence and corresponding amino acid sequence shown in SEQ ID NOS:139 and 140. Following ligation of the 309 base pair fragment of human CH1 immediately downstream of the IgGK signal peptide sequence, the resulting plasmid was digested with the restriction enzymes ApaI and NsiI. These enzymes that digest both the constant IgG1 and IgG2 cDNAs in exactly the same positions that permits the IgG1 constant sequence to be replaced by the human IgG2 sequence in the expression vector. The cDNA encoding the human IgG2 constant domains was obtained from a commercially available source (Open Biosystems, Huntsville, Ala.). The final plasmid used to express the IgG2 immunoglobulin heavy chain was designated pYD19 and the sequence is shown in SEQ ID NO:141. When a selected heavy chain variable region is ligated into this vector, the resulting plasmid encodes a full IgG2 heavy chain immunoglobulin with human constant regions. Based on the sequences disclosed in Table 2, PCR primers specific for the heavy chain variable regions of antibodies 25A1, 25B4, 25B8, 25C1, 25D8, 25E5, 25E6, and 25E9 (SEQ ID NOS:39, 43, 47, 51, 55, 59, 63, and 67, respectively) were designed that incorporated, at their 5'-end, a sequence identical to the last 20 base pairs of the IgGK signal peptide. The sequences of these primers are shown in SEQ ID NOS:142 for 25A1; SEQ ID NO:143 for 24B4 and 25D8; SEQ ID NO:144 for 25B8, 25C1, and 25E9; SEQ ID NO:145 for 25E5; and SEQ ID NO:146 for 25E6, respectively. The same reverse primer was used to amplify all four heavy chain variable regions since the extreme 3'-ends were identical. This primer (SEQ ID NO:147) incorporated, at its 3'-end, a sequence identical to the first 20 base pairs of the human CH1 constant domain. Both the PCR fragments and the digested pYD19 were treated with the 3'-5' exonuclease activity of T4 DNA polymerase resulting in complimentary ends that were joined by annealing. The annealing reactions were transformed into competent E. coli and the expression plasmids were verified by sequencing to ensure that the mouse heavy chain variable regions were properly inserted into the pYD19 expression vector. Those skilled in the art will readily recognize that the method used for construction of the heavy chain expression plasmids applies to all anti-Siglec-15 antibodies contained in the original Fab library.

Expression of human IgG2s in 293E cells—The expression vectors prepared above that encoded the light and heavy chain immunoglobulins were expressed in 293E cells using the transient transfection system (Durocher et al., 2002). By virtue of the signal peptides incorporated at the amino-termini of both immunoglobulin chains, the mature IgG2 was harvested from the serum-free culture medium of the cells. The methods used for co-transfecting the light and heavy chain expression vectors were described herein. For each milliliter of cells, one microgram of a combination of both the light and heavy chain expression plasmids was transfected in 293E cells grown in suspension to a density of 1.5-2.0 million cells/ml. The ratio of light to heavy chain plasmid was optimized in order to achieve the most yield of antibody in the tissue culture medium and it was found to be 9:1 (L:H). The transfection reagent used was polyethylenimine (PEI), (linear, MW 25,000, Cat#23966 Polysciences, Inc., Warrington, Pa.) which was included at a DNA:PEI ratio of 1:3. Growth of the cells was continued for 5 days after which the culture medium was harvested for purification of the IgG2 chimeric monoclonal antibodies. The protein was purified using Protein-A agarose as instructed by the manufacturer (Sigma-Aldrich Canada Ltd., Oakville, ON).

Figure 6:
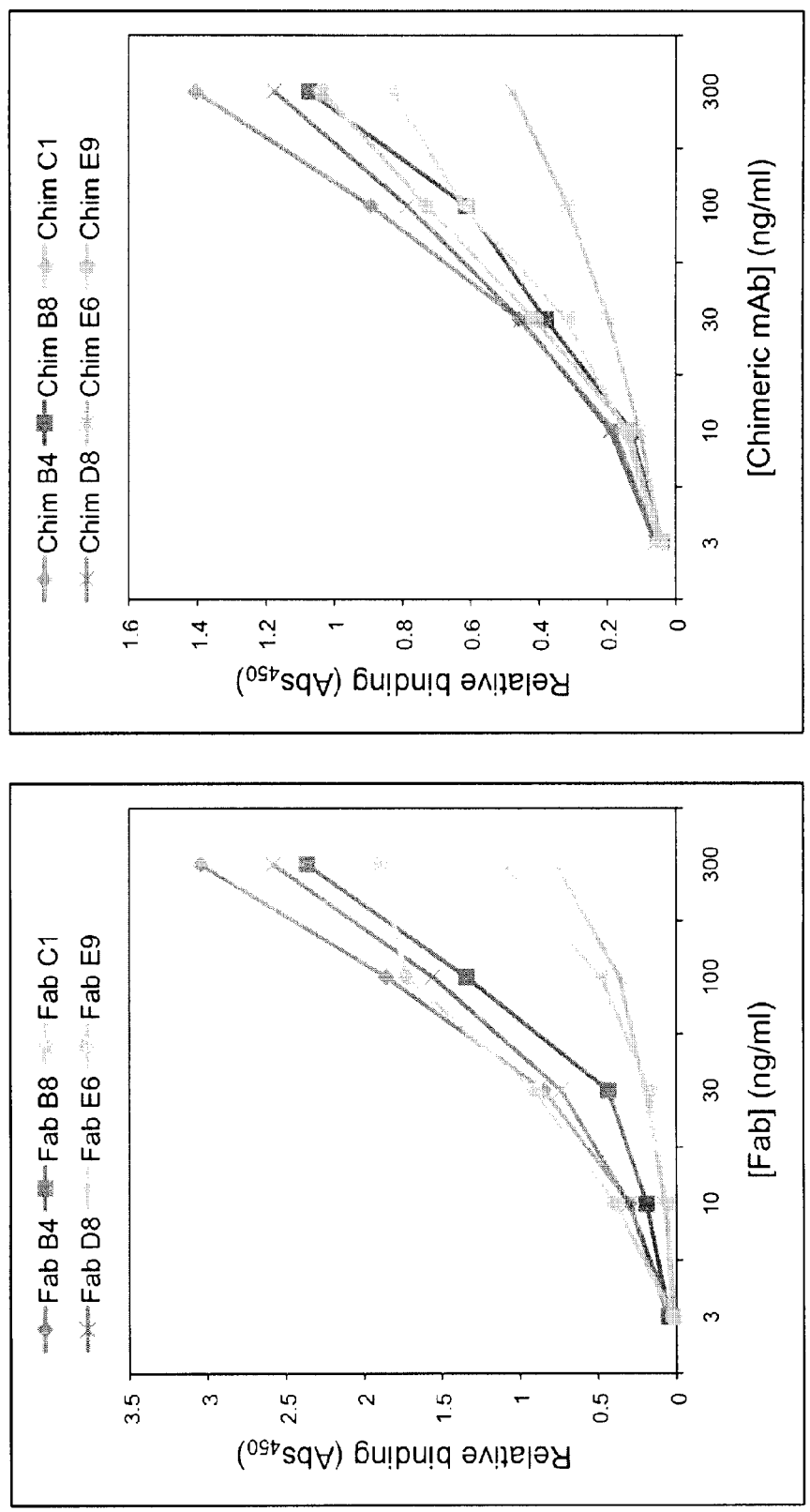
FIG. 6 shows drawings that compare the binding of the mouse anti-Siglec-15 Fabs with the binding of the corresponding IgG2 chimeric monoclonal antibodies for exemplary antibodies 25B4, 25B8, 25C1, 25D8, 25E6, and 25E9. The results indicate that the relative binding of the Fab variable regions was maintained when transferred to a full human IgG2 scaffold.

To determine the relative binding affinity of selected monoclonals more accurately, increasing concentration of the Fabs was incubated with biotinylated Fc-Siglec-15$_{20-259}$. Ten nanograms of biotinylated Fc-Siglec-15$_{20-259}$ was coated in streptavidin microtiter plates and increasing amounts of either Fabs or the chimeric IgG2 monclonals 25B4, 25B8, 25C1, 25D8, 25E6, and 25E9 were added as indicated in FIG. 6. As depicted in FIG. 6, the binding of the 25B4, 25B8, 25C1, 25D8, 25E6, and 25E9 chimeric IgG2 monoclonal antibodies was very similar to the Fabs. This result shows that the transposition of the variable domains from the mouse Fabs into a human IgG2 backbone did not significantly affect the capacity of the light and heavy chain variable regions to confer Siglec-15 binding.

Example 4

This example describes the use of anti-Siglec-15 antibodies for inhibiting the differentiation of osteoclasts.

Figure 7:
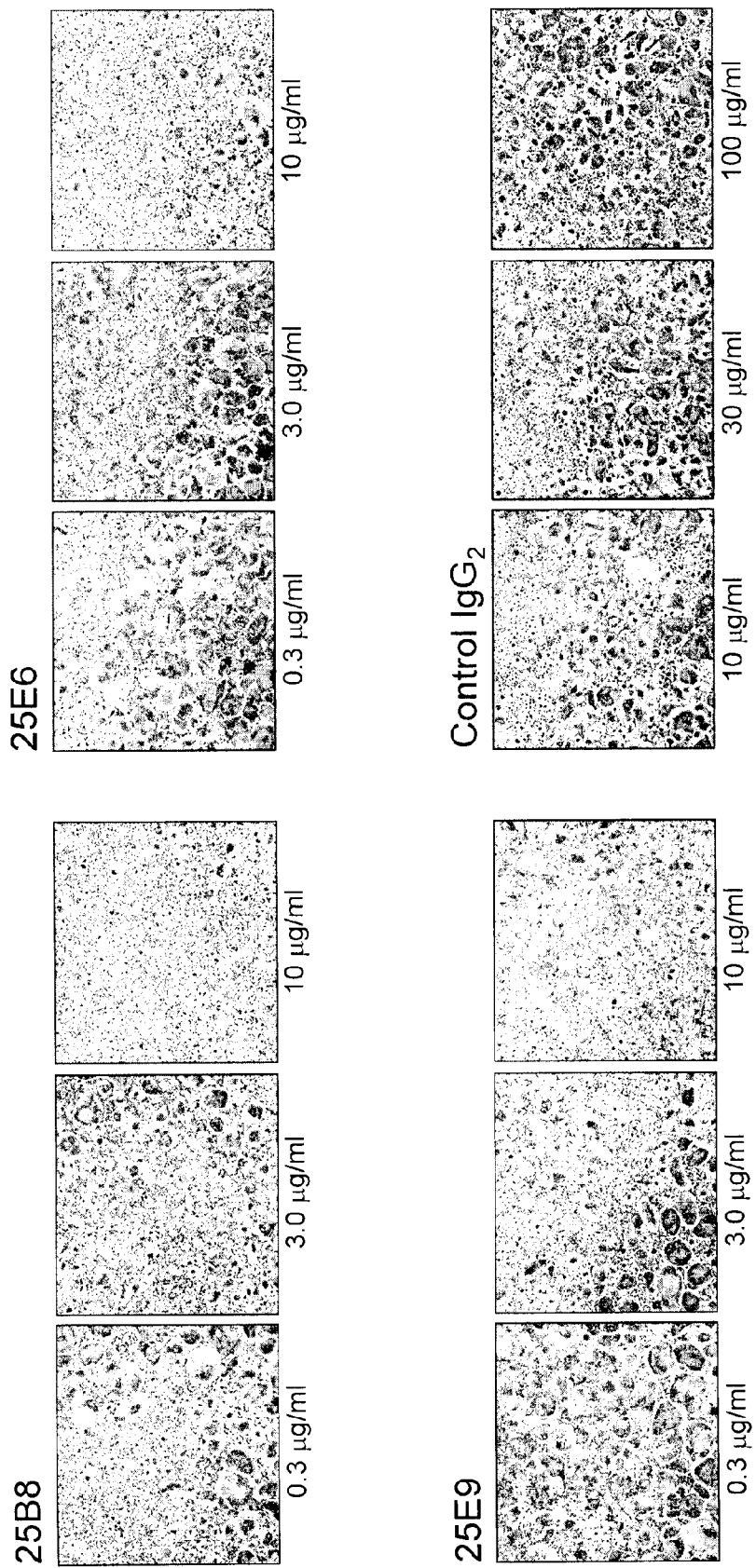
FIG. 7 shows the inhibition of the differentiation of human osteoclasts upon treatment with increasing concentrations of anti-Siglec-15 IgG2 chimeric monoclonal antibodies 25B8, 25E6, and 25E9. After treatment, the osteoclasts were stained for TRAP expression.

Human PBMNCs (AllCells, Emoryville, Calif.) were placed in the appropriate culture medium for 24 h at 37 C in a 5% $CO_2$ atmosphere. The cells were seeded in 96-well plates at a cell density of 100,000 cells/ml and treated with increasing concentration (0.01 µg/ml-100 µg/ml) of anti-Siglec-15 IgG2 chimeric monoclonal antibodies in the presence of 35 ng/ml M-CSF and 30 ng/ml RANKL. Undifferentiated precursor cells were treated only with M-CSF. The control wells were treated with a non-Siglec-15 binding IgG2. The cells were fixed, stained for TRAP, and multinucleated cells counted and photographed (magnification 40×). As depicted in FIG. 7, mAbs targeting Siglec-15 could efficiently inhibit the differentiation of human osteoclasts in a dose-dependent manner. Inhibition of osteoclast differentiation was observed to varying extents with every exemplary Siglec-15 antibody that was tested but the most active monoclonals were 25B8, 25E6, and 25E9. Cells treated with a control chimeric IgG2 were not inhibited (see lower right panels in FIG. 8, Control IgG2). This result is in complete agreement with the experiments disclosed by Sooknanan (Sooknanan et al., 2007) that showed that knockdown of Siglec-15 expression by RNA interference caused inhibition of human osteoclast differentiation.

Figure 12:
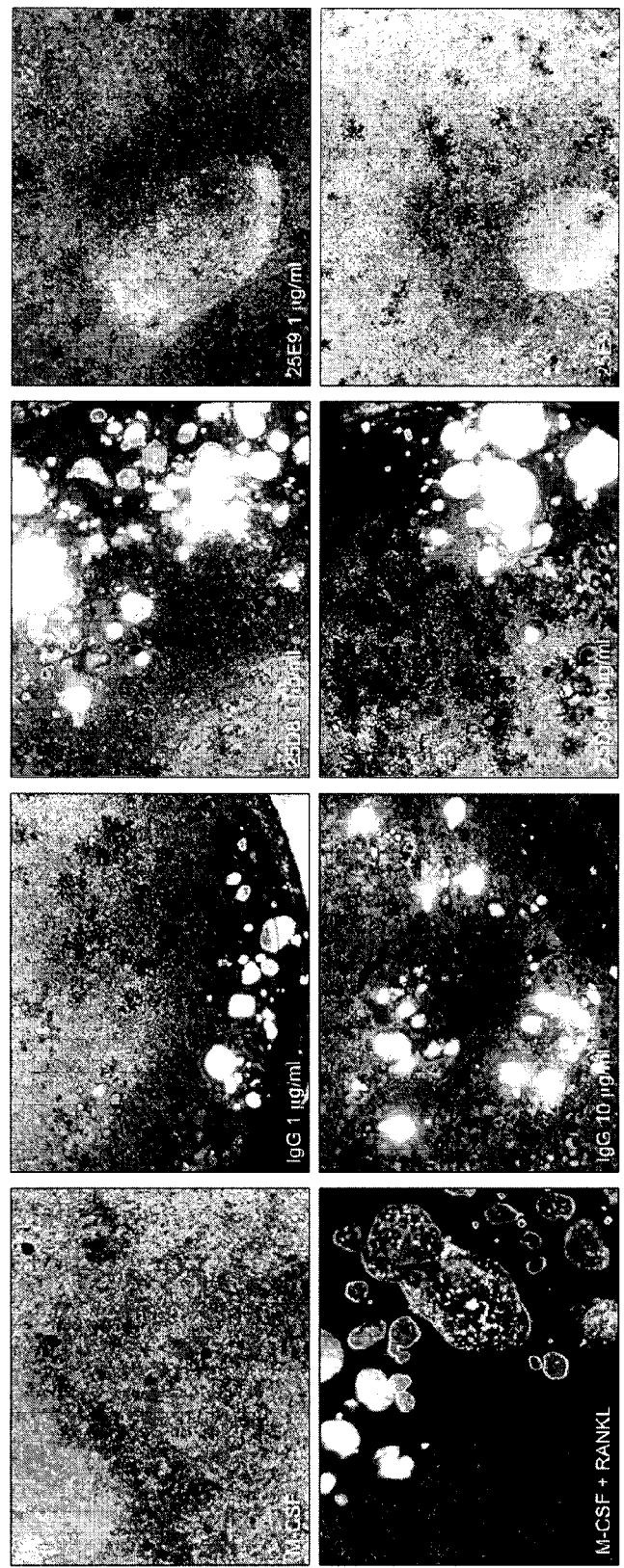
FIG. 12 illustrates the ability of the 25E9 candidate antibody that is specific for Siglec-15 to inhibit the bone resorbing activity of osteoclasts.

The biological function of differentiated osteoclasts is to resorb bone and thus the activity of osteoclasts should also be inhibited by antibodies that target Siglec-15. To test this, human PBMNCs were seeded on synthetic calcium phosphate substrate discs (BD BioCoat™ Osteologic™ MultiTest Slides) and cultured in similar conditions as described above. The precursor cells were treated with M-CSF and RANKL in the presence of either a control isotype IgG or the 25D8 or 25E9 anti-Siglec-15 antibodies. The antibodies were at a concentration of 1 µg/ml or 10 µg/ml. Once fully matured osteoclasts were present in the control untreated wells. The cells were scarped off the discs and the remaining bone substrate was stained using a standard von Kossa stain which renders the calcium mineral brown. As shown in FIG. 12, the wells containing undifferentiated osteoclasts (upper left panel, M-CSF) showed no evidence of degradation of the substrate which appears as white spots on the surface (degradation pits). As expected, the cells treated with RANKL had evidence of significant degradation and the surface contained many pits (lower left panel, M-CSF+RANKL). Similarly, the osteoclasts treated with the control IgG could also degrade the bone substrate which demonstrated that these control antibodies did not inhibit osteoclast activity non-specifically. When the differentiating osteoclasts were treated with the anti-Siglec-15 antibodies, the 25E9 candidate efficiently inhibited bone degradation in this assay (FIG. 12, right panels). By contrast, the 25D8 antibody did not inhibit degradation in this assays (see middle-right panels of FIG. 12). Taken together, these results (FIG. 7 and FIG. 12) demonstrate that antibodies against Siglec-15 inhibit osteoclast differentiation and bone degradation activity.

Figure 8:
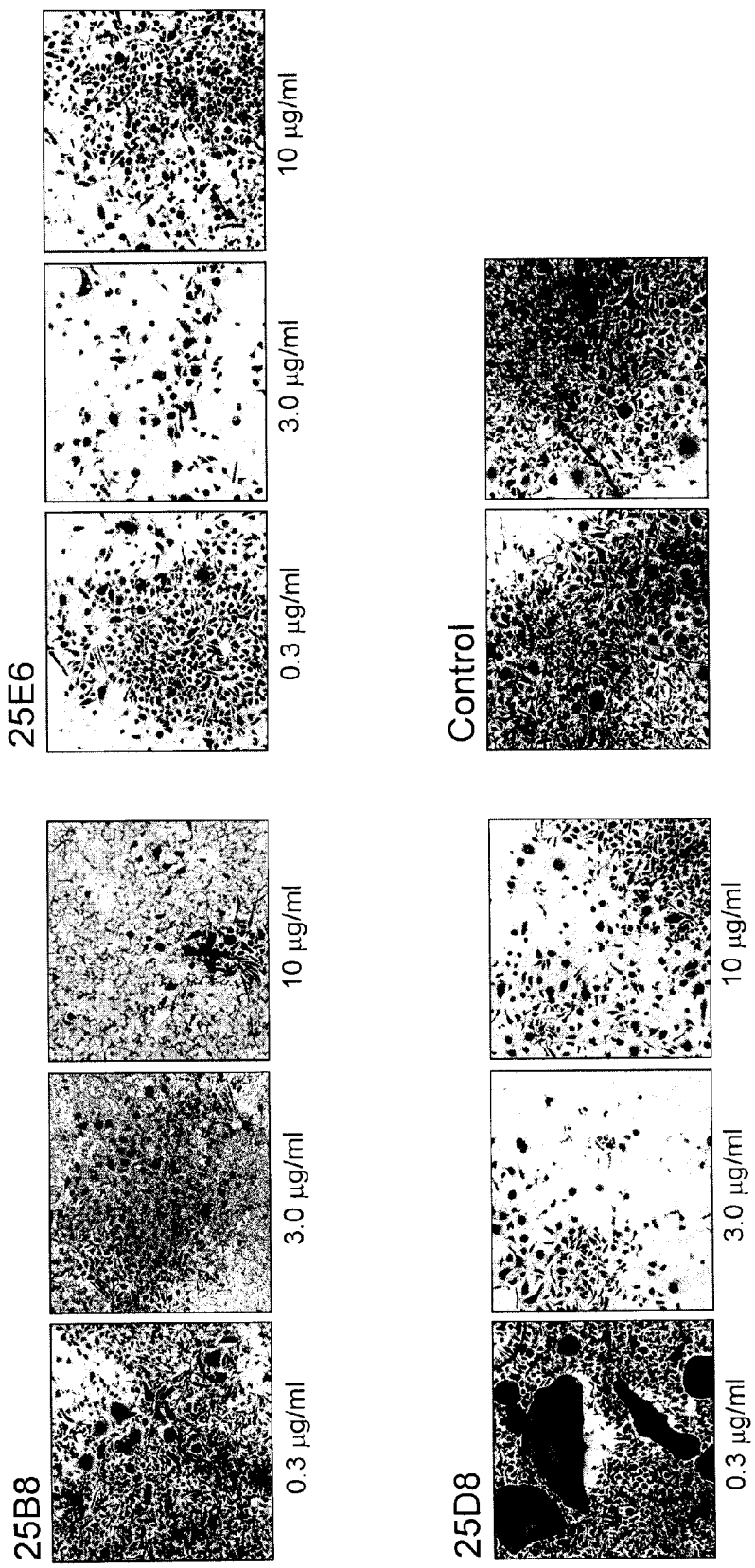
FIG. 8 shows the inhibition of the differentiation of mouse osteoclasts upon treatment with increasing concentrations of anti-Siglec-15 IgG2 chimeric monoclonal antibodies 25B8, 25E6, and 25D8. After treatment, the osteoclasts were stained for TRAP expression.

In a parallel experiment, mouse PBMNCs were treated in a similar manner. As depicted in FIG. 8, anti-Siglec-15 chimeric antibodies could inhibit the differentiation of mouse osteoclasts as exemplified by the chimeric mAbs designated 25B8, 25E6, and 25D8. This result confirms that the monoclonal antibodies that were generated against the human orthologue of Siglec-15 are cross-reactive against the mouse Siglec-15 protein as well. This was experimentally verified using an ELISA. A fragment of the mouse Siglec-15 cDNA was amplified corresponding to amino acids 21-256 using oligonucleotides containing the sequences shown in SEQ ID NOS: 159 and 160. This PCR fragment was ligated into the pYD5 expression vector as was described for the human Siglec-15 fragment for expression in 293-6E cells. The recombinant Fc-mouseSiglec-15 was purified using Protein-A affinity chromatography.

Figure 9:
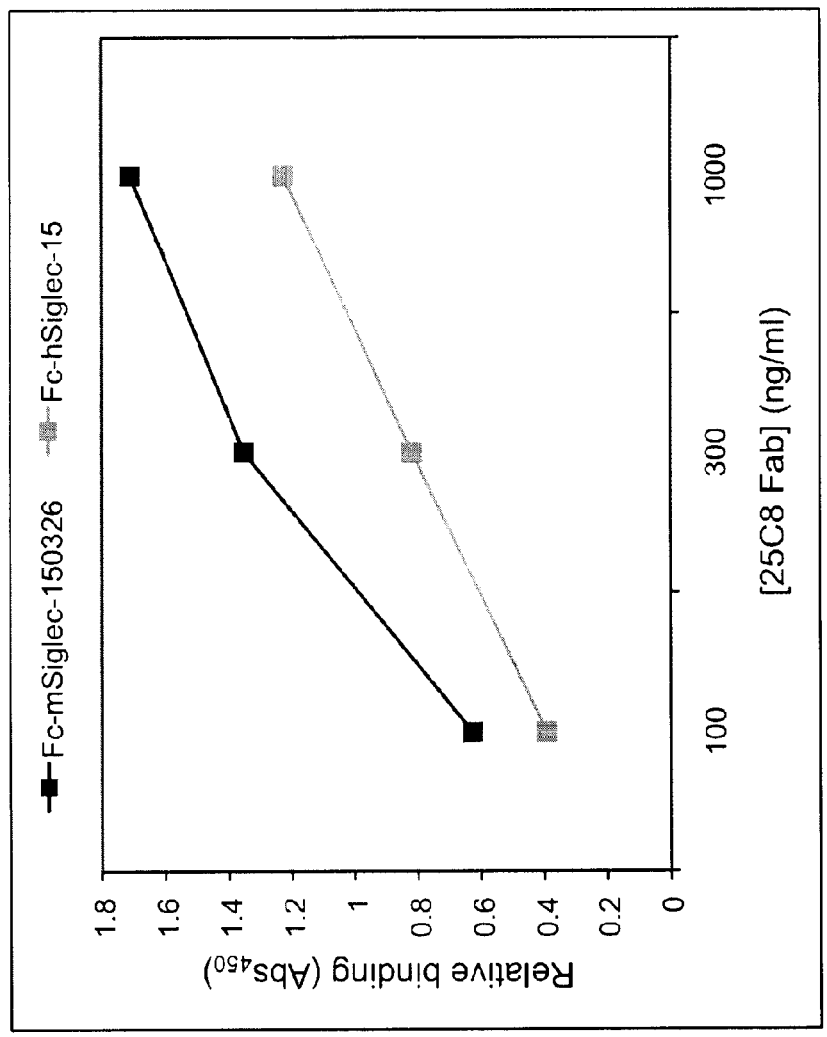
FIG. 9 shows the comparative binding of the human and mouse Siglec-15 in the presence of the exemplary antibody 25C8. The result indicates that the binding of the antibodies generated against the human Siglec-15 also interact with the mouse Siglec-15.

An exemplary anti-Siglec-15 monoclonal Fab designated 25C8 was incubated with either Fc-human(h)Siglec-$15_{20-259}$ or Fc-mouse(m)Siglec-$15_{21-256}$. The results (see FIG. 9) indicate that the binding activity of the antibodies that were generated against the human Siglec-15 also cross-react with the mouse orthologue of Siglec-15.

The results described above clearly demonstrate the importance of Siglec-15 in osteoclastogenesis. Attenuation of Siglec-15 expression in osteoclast precursor cells results in cells that are highly impaired in their ability to form multinucleated mature osteoclasts. Thus, targeting Siglec-15 with an inhibitor, in particular a therapeutic monoclonal antibody, would prove to be a very selective way to target those cells that are directly responsible for bone degradation during acute metastatic bone cancer or chronic osteoporosis.

Example 5

This example pertains to the ability of anti-Siglec-15 antibodies to block binding of Siglec-15 to sialic acid (SA) conjugates.

Figure 15:
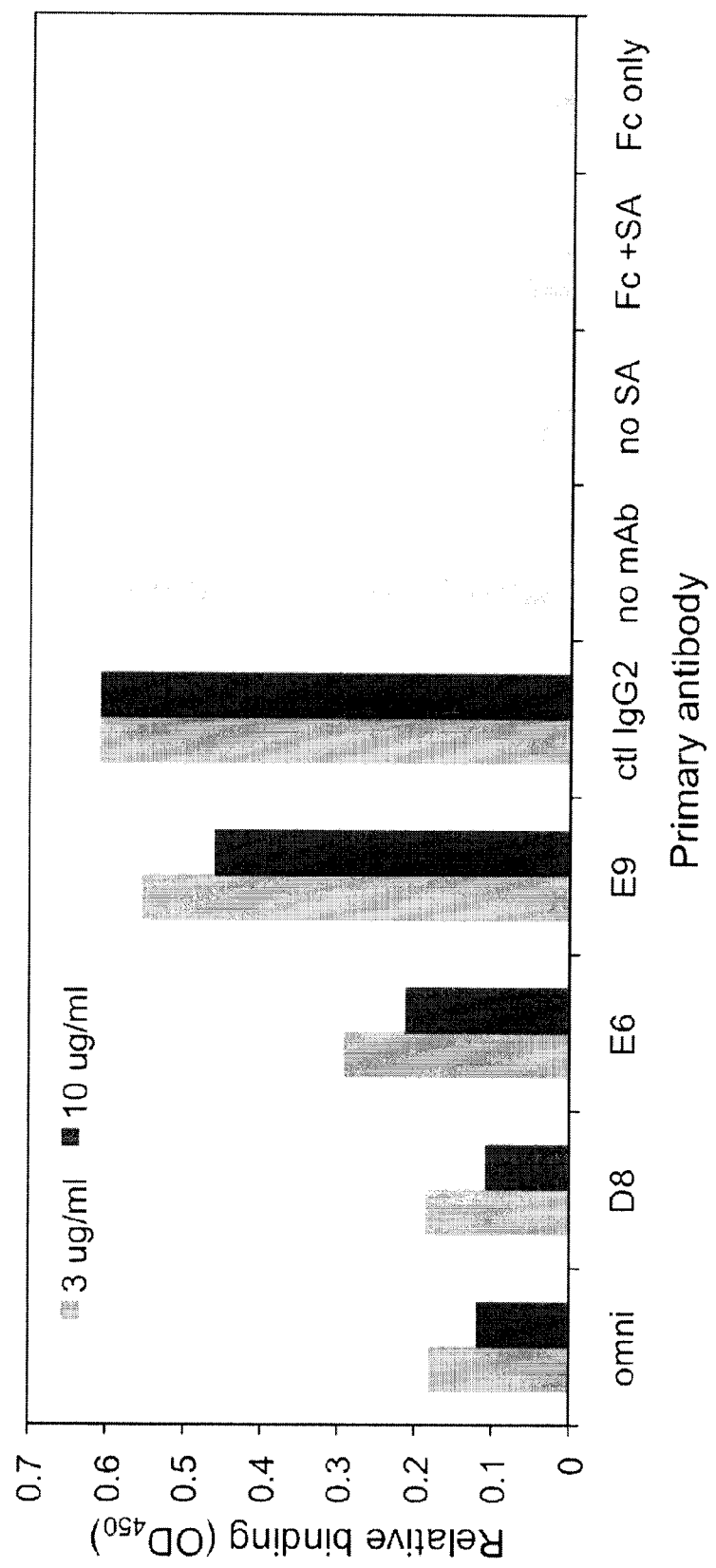
FIG. 15 shows an ELISA that demonstrates that the anti-Siglec-15 antibodies can inhibit the interaction between Siglec-15 and sialic acids.

The formation of sialylated glycoproteins is required for proper osteoclastogenesis (Takahata et al., 2007). Siglec-15 binds sialic acid, and this binding is dependent on the amino acid residue R143 (Angata 2007). One mechanism by which Siglec-15 antibodies inhibit osteoclast formation could involve interference with their target's sialic acid-binding function due to interactions with an epitope encompassing R143. To examine this possibility, we performed an ELISA-based assay to test the ability of Siglec-15 antibodies to block binding of recombinant Fc-Siglec-15 to Neu5Aca2-6-GalNAc-PAA-Biotin (Glycotech, Rockville, Md.), which is a preferred, sialic acid-containing binding partner of Siglec-15 (Angata 2007). Fc-Siglec-15 was immobilized on a Protein A-coated microtiter plate, and different Siglec-15 antibodies were then applied. After incubation and removal of unbound antibody, Neu5Aca2-6-GalNAc-PAA-Biotin was added. This biotinylated probe should form a complex with Siglec-15 only if an antibody is not blocking the sialic acid binding site. The presence of the biotinylated probe was detected using streptavidin-HRP by standard methods. As shown in FIG. 15, anti-Siglec-15 omniclonal and 25D8 antibodies inhibit sialic acid binding compared to a non-targeting, control antibody. Antibody E6 also has a clear, but less pronounced effect. Antibody E9 has little effect, indicating that its epitope does not overlap with the sialic acid binding site. Addition of a control antibody (FIG. 15, see ctl IgG2) did not prevent the binding of sialic acid moiety to Siglec-15. The method was highly dependent on the presence of Siglec-15 since no binding was detected when only the Fc was coated in the plates nor was there any binding when the SA was omitted (FIG. 15, see no SA, Fc+SA, and Fc only). Together, these results demonstrate that the Siglec-15 monoclonal antibodies can interfere, to varying extents, with the sialic acid binding function of Siglec-15 likely due to interactions near R143. This property could be important for their effects on osteoclastogenesis.

CITED REFERENCES

Frost H. M., 1964 Dymanics of Bone Remodelling. In: Bone Biodynamics, Little and Brown, Boston, Mass., USA pp. 315;

Baron, R., Anatomy and Biology of Bone Matrix and Cellular Elements, In: Primer on the Metabolic Bone Diseases and Disorders of Mineral Metabolism, Fifth Edition 2003, American Society for Bone and Mineral Research, Washington D.C., pp. 1-8;

Jilka, R. L. et al., "Increased Osteoclast Development After Estrogen Loss: Mediation by Interleukin-6", Science 257: 88-91 (1992).

Poli, V. et al., "Interleukin-6 deficient mice are protected from bone loss caused by estrogen depletion", EMBO J 13: 1189-1196 (1994).

Srivastava, S. et al., "Estrogen Blocks M-CSF Gene Expression and Osteoclast Formation by Regulating Phosphorylation of Egr-1 and Its Interaction with Sp-1", J Clin Invest 102: 1850-1859 (1998).

de Vernejoul, M. C., "Dynamics of Bone Remodelling: Biochemical and Pathophysiological Basis", Eur J Clin Chem Clin Biochem 34: 729-734 (1996).

McMillan, S. J. and P. R. Crocker, "CD33-related sialic-acid-binding immunoglobulin-like lectins in health and disease", Carbohydr Res, 343(12): p. 2050-6 (2008).

Crocker, P. R., J. C. Paulson, and A. Varki, Siglecs and their roles in the immune system. Nat Rev Immunol, 7(4): p. 255-66 (2007).

Angata, T., et al., Siglec-15: an immune system Siglec conserved throughout vertebrate evolution. Glycobiology, 17(8): p. 838-46 (2007).

Sooknanan, R. R., "Polynucleotides and polypeptide sequences involved in the process of bone remodelling", PCT/CA2007/000210 (2007).

Takahata, M., et al., Sialylation of cell surface glycoconjugates is essential for osteoclastogenesis. Bone, 41(1): p. 77-86 (2007).

Ellis, G. K. et al., "Randomized Trial of Denosumab in Patients Receiving Adjuvant Aromatase Inhibitors for Nonmetastatic Breast Cancer", J Clin Oncol 26: 4875-4882 (2008).

Buechler J, Valkirs G, Gray J. "Polyvalent display libraries." U.S. Pat. No. 6,057,098 (2000).

Durocher Y, Kamen A, Perret S, Pham P L. "Enhanced production of recombinant proteins by transient transfection of suspension-growing mammalian cells." Canadian patent application No. CA 2446185 (2002).

Durocher Y. "Expression vectors for enhanced transient gene expression and mammalian cells expressing them." U.S. patent application No. 60/662,392 (2004).

Shankavaram, U. T. et al., "Transcript and protein expression profiles of the NCI-60 cancer panel: an integromic microarray study", Mol Cancer Ther 6: 820-832 (2007).

Blixt O. et al., "Sialoside specificity of the siglec family assessed using novel multivalent probes", J Biol Chem, 278, 31007-31019.

---

SEQUENCE LISTINGS

```
SEQ ID NO: 1
ATGGAAAAGTCCATCTGGCTGCTGGCCTGCTTGGCGTGGGTTCTCCCGACAGGCTCATTTGT

GAGAACTAAAATAGATACTACGGAGAACTTGCTCAACACAGAGGTGCACAGCTCGCCAGCGC

AGCGCTGGTCCATGCAGGTGCCACCCGAGGTGAGCGCGGAGGCAGGCGACGCGGCAGTGCTG

CCCTGCACCTTCACGCACCCGCACCGCCACTACGACGGGCCGCTGACGGCCATCTGGCGCGC

GGGCGAGCCCTATGCGGGCCCGCAGGTGTTCCGCTGCGCTGCGGCGCGGGGCAGCGAGCTCT

GCCAGACGGCGCTGAGCCTGCACGGCCGCTTCCGGCTGCTGGGCAACCCGCGCCGCAACGAC

CTCTCGCTGCGCGTCGAGCGCCTCGCCCTGGCTGACGACCGCCGCTACTTCTGCCGCGTCGA

GTTCGCCGGCGACGTCCATGACCGCTACGAGAGCCGCCACGGCGTCCGGCTGCACGTGACAG

CCGCGCCGCGGATCGTCAACATCTCGGTGCTGCCCAGTCCGGCTCACGCCTTCCGCGCGCTC

TGCACTGCCGAAGGGGAGCCGCCGCCCGCCCTCGCCTGGTCCGGCCCGGCCCTGGGCAACAG

CTTGGCAGCCGTGCGGAGCCCGCGTGAGGGTCACGGCCACCTAGTGACCGCCGAACTGCCCG

CACTGACCCATGACGGCCGCTACACGTGTACGGCCGCCAACAGCCTGGGCCGCTCCGAGGCC

AGCGTCTACCTGTTCCGCTTCCATGGCGCCAGCGGGGCCTCGACGGTCGCCCTCCTGCTCGG

CGCTCTCGGCTTCAAGGCGCTGCTGCTGCTCGGGGTCCTGGCCGCCCGCGCTGCCCGCCGCC

GCCCAGAGCATCTGGACACCCCGGACACCCCACCACGGTCCCAGGCCCAGGAGTCCAATTAT

GAAAATTTGAGCCAGATGAACCCCCGGAGCCCACCAGCCACCATGTGCTCACCGTGA

SEQ ID NO: 2
MEKSIWLLACLAWVLPTGSFVRTKIDTTENLLNTEVHSSPAQRWSMQVPPEVSAEAGDAAVL

PCTFTHPHRHYDGPLTAIWRAGEPYAGPQVFRCAAARGSELCQTALSLHGRFRLLGNPRRND

LSLRVERLALADDRRYFCRVEFAGDVHDRYESRHGVRLHVTAAPRIVNISVLPSPAHAFRAL

CTAEGEPPPALAWSGPALGNSLAAVRSPREGHGHLVTAELPALTHDGRYTCTAANSLGRSEA
```

SVYLFRFHGASGASTVALLLLGALGFKALLLLGVLAARAARRRPEHLDTPDTPPRSQAQESNY

ENLSQMNPRSPPATMCSP

SEQ ID NO: 3
ATGGAGGGGTCCCTCCAACTCCTGGCCTGCTTGGCCTGTGTGCTCCAGATGGGATCCCTTGT

GAAAACTAGAAGAGACGCTTCGGGGGATCTGCTCAACACAGAGGCGCACAGTGCCCCGGCGC

AGCGCTGGTCCATGCAGGTGCCCGCGGAGGTGAACGCGGAGGCTGGCGACGCGGCGGTGCTG

CCCTGCACCTTCACGCACCCGCACCGCCACTACGACGGGCCGCTGACGGCCATCTGGCGCTC

GGGCGAGCCGTACGCGGGCCCGCAGGTGTTCCGCTGCACCGCGGCGCCGGGCAGCGAGCTGT

GCCAGACGGCGCTGAGCCTGCACGGCCGCTTCCGCCTGCTGGGCAACCCGCGCCGCAACGAC

CTGTCCCTGCGCGTCGAGCGCCTCGCCCTGGCGGACAGCGGCCGCTACTTCTGCCGCGTGGA

GTTCACCGGCGACGCCCACGATCGCTATGAGAGTCGCCATGGGGTCCGTCTGCGCGTGACTG

CAGCTGCGCCGCGGATCGTCAACATCTCGGTGCTGCCGGGCCCCGCGCACGCCTTCCGCGCG

CTCTGCACCGCCGAGGGGGAGCCCCCGCCCGCCCTCGCCTGGTCGGGTCCCGCCCCAGGCAA

CAGCTCCGCTGCCCTGCAGGGCCAGGGTCACGGCTACCAGGTGACCGCCGAGTTGCCCGCGC

TGACCCGCGACGGCCGCTACACGTGCACGGCGGCCAATAGCCTGGGCCGCGCCGAGGCCAGC

GTCTACCTGTTCCGCTTCCACGGCGCCCCCGGAACCTCGACCCTAGCGCTCCTGCTGGGCGC

GCTGGGCCTCAAGGCCTTGCTGCTGCTTGGCATTCTGGGAGCGCGTGCCACCCGACGCCGAC

TAGATCACCTGGTCCCCCAGGACACCCCTCCACGGTCTCAGGCTCAGGAGTCCAATTATGAA

AATTTGAGCCAGATGAGTCCTCCAGGCCACCAGCTGCCACGTGTTTGCTGTGAGGAACTCCT

CAGCCATCACCATCTAGTCATTCACCATGAGAAATAA

SEQ ID NO: 4
MEGSLQLLACLACVLQMGSLVKTRRDASGDLLNTEAHSAPAQRWSMQVPAEVNAEAGDAAVL

PCTFTHPHRHYDGPLTAIWRSGEPYAGPQVFRCTAAPGSELCQTALSLHGRFRLLGNPRRND

LSLRVERLALADSGRYFCRVEFTGDAHDRYESRHGVRLRVTAAAPRIVNISVLPGPAHAFRA

LCTAEGEPPPALAWSGPAPGNSSAALQGQGHGYQVTAELPALTRDGRYTCTAANSLGRAEAS

VYLFRFHGAPGTSTLALLLGALGLKALLLLGILGARATRRRLDHLVPQDTPPRSQAQESNYE

NLSQMSPPGHQLPRVCCEELLSHHHLVIHHEK

SEQ ID NO: 5
GAAAATGTGCTCACCCAGTCTCCAGCAATCATGTCTGCATCTCCAGGGGAGAAGGTCACCAT

ATCCTGCAGTGCCAGCTCAAGTGTAAGTTACATGTACTGGTACCAGCAGAAGCCAGGATCCT

CCCCCAAACCCTGGATTTATCGCACATCCAACCTGGCTTCTGGAGTCCCTGCTCGCTTCAGT

GGCAGTGGGTCTGGGACCTCTTACTCTCTCACAATCAGCAGCATGGAGGCTGAAGATGCTGC

CACTTATTACTGCCAGCAGTGGAGTAGTAACCCACTCACGTTCGGTGCTGGGACCAAGCTGG

AGCTGAAACGGGCTGTGGCTGCACCATCTGTCTTCATCTTCCCGCCATCTGATGAGCAGTTG

AAATCTGGAACTGCCTCTGTTGTGTGCCTGCTGAATAACTTCTATCCCAGAGAGGCCAAAGT

ACAGTGGAAGGTGGATAACGCCCTCCAATCGGGTAACTCCCAGGAGAGTGTCACAGAGCAGG

ACAGCAAGGACAGCACCTACAGCCTCAGCAGCACCCTGACGCTGAGCAAAGCAGACTACGAG

AAACACAAAGTCTACGCCTGCGAAGTCACCCATCAGGGCCTGAGCTCGCCCGTCACAAAGAG

CTTCAACAGGGGAGAGTGTTAG

SEQ ID NO: 6
ENVLTQSPAIMSASPGEKVTISCSASSSVSYMYWYQQKPGSSPKPWIYRTSNLASGVPARFS
GSGSGTSYSLTISSMEAEDAATYYCQQWSSNPLTFGAGTKLELKVAAPSVFIFPPSDEQLKS
GTASVVCLLNNFYPREAKVQWKVDNALQSGNSQESVTEQDSKDSTYSLSSTLTLSKADYEKH
KVYACEVTHQGLSSPVTKSFNRGEC

SEQ ID NO: 7
GAGGTCCAGCTGCAACAATCTGGGACTGAGCTGGTGAGGCCTGGGTCCTCAGTGAAGATTTC
CTGCAAGGCTTCTGGCTACACCTTCACCAGGTACTGGATGGACTGGGTGAAGCAGAGGCCTG
GACAAGGCCTTGAGTGGATCGGAGAGATTGATCCTTCTGATAGTTATACTAACTACAATCAA
AAGTTCAAGGGCAAGGCCACATTGACTGTAGATAAATTCTCCAGAACAGCCTATATGGAACT
CAGCAGCCTGACATCTGAGGACTCTGCGGTCTATTACTGTGCAAGATCGGGGGCCTACTCTA
GTGACTATAGTTACGACGGGTTTGCTTACTGGGGCCAAGGGACTCTGGTCACTGTCTCTGCA
GCCTCAACGAAGGGCCCATCGGTCTTCCCCCTGGCGCCCTGCTCCAGGAGCACCTCCGAGAG
CACAGCCGCCCTGGGCTGCCTGGTCAAGGACTACTTCCCCGAACCGGTGACGGTGTCGTGGA
ACTCAGGCGCTCTGACCAGCGGCGTGCACACCTTCCCAGCTGTCCTACAGTCCTCAGGACTC
TACTCCCTCAGCAGCGTGGTGACCGTGCCCTCCAGCAACTTCGGCACCCAGACCTACACCTG
CAACGTAGATCACAAGCCCAGCAACACCAAGGTGGACAAGACAGTTGAGCGCAAATGTTGTG
TCGAGTGCCCACCGTGCCCAGCACCACCTGTGGCAGGACCGTCAGTCTTCCGCTTCCCCCCA
AAACCCAAGGACACCCGCATGATCTCCCGGACCCCTGAGGTCACGTGCGTGGTGGTGGATGT
GAGCCACGAAGACCCCGAGGTCCAGTTCAACTGGTACGTGGACGGCGTGGAGGTGCATAATG
CCAAGACAAAGCCACGGGAGGAGCAGTTCAACAGCACGTTCCGTGTGGTCAGCGTCCTCACC
GTTGTGCACCAGGACTGGCTGAACGGCAAGGAGTACAAGTGCAAGGTCTCCAACAAAGGCCT
CCCAGCCCCCATCGAGAAAACCATCTCCAAAACCAAAGGGCAGCCCCGAGAACCACAGGTGT
ACACCCTGCCCCCATCCCGGGAGGAGATGACCAAGAACCAGGTCAGCCTGACCTGCCTGGTC
AAAGGCTTCTACCCCAGCGACATCGCCGTGGAGTGGGAGAGCAATGGGCAGCCGGAGAACAA
CTACAAGACCACACCTCCCATGCTGGACTCCGACGGCTCCTTCTTCCTCTACAGCAAGCTCA
CCGTGGACAAGAGCAGGTGGCAGCAGGGGAACGTCTTCTCATGCTCCGTGATGCATGAGGCT
CTGCACAACCACTACACGCAGAAGAGCCTCTCCCTGTCTCCGGGTAAATGA

SEQ ID NO: 8
EVQLQQSGTELVRPGSSVKISCKASGYTFTRYWMDWVKQRPGQGLEWIGEIDPSDSYTNYNQ
KFKGKATLTVDKFSRTAYMELSSLTSEDSAVYYCARSGAYSSDYSYDGFAYWGQGTLVTVSA
ASTKGPSVFPLAPCSRSTSESTAALGCLVKDYFPEPVTVSWNSGALTSGVHTFPAVLQSSGL
YSLSSVVTVPSSNFGTQTYTCNVDHKPSNTKVDKTVERKCCVECPPCPAPPVAGPSVFLFPP
KPKDTLMISRTPEVTCVVVDVSHEDPEVQFNWYVDGVEVHNAKTKPREEQFNSTFRVVSVLT
VVHQDWLNGKEYKCKVSNKGLPAPIEKTISKTKGQPREPQVYTLPPSREEMTKNQVSLTCLV
KGFYPSDIAVEWESNGQPENNYKTTPPMLDSDGSFFLYSKLTVDKSRWQQGNVFSCSVMHEA
LHNHYTQKSLSLSPGK

SEQ ID NO: 9
GATATTGTGATGACCCAGGCTGCATTCTCCAATCCAGTCACTCTTGGAACATCAGCTTCCAT
CTCCTGCAGGTCTAGTAAGAGTCTCCTACATAGTAATGGCATCACTTATTTGTATTGGTATC
TGCAGAAGCCAGGCCAGTCTCCTCAGCTCCTGATTTATCAGATGTCCAACCTTGCCTCAGGA

GTCCCAGACAGGTTCAGTGGCAGTGGGTCAGGAACTGCTTTCACACTGAGAATCAGTAGAGT

GGAGGCTGAGGATGTGGGTGTTTATTACTGTATGCAACATCTAGAATATCCGTACACGTTCG

GAGGGGGGACCAAGCTGGAAATAAAACGGGCTGTGGCTGCACCATCTGTCTTCATCTTCCCG

CCATCTGATGAGCAGTTGAAATCTGGAACTGCCTCTGTTGTGTGCCTGCTGAATAACTTCTA

TCCCAGAGAGGCCAAAGTACAGTGGAAGGTGGATAACGCCCTCCAATCGGGTAACTCCCAGG

AGAGTGTCACAGAGCAGGACAGCAAGGACAGCACCTACAGCCTCAGCAGCACCCTGACGCTG

AGCAAAGCAGACTACGAGAAACACAAAGTCTACGCCTGCGAAGTCACCCATCAGGGCCTGAG

CTCGCCCGTCACAAAGAGCTTCAACAGGGGAGAGTGTTAG

SEQ ID NO: 10
DIVMTQAAFSNPVTLGTSASISCRSSKSLLHSNGITYLYWYLQKPGQSPQLLIYQMSNLASG

VPDRFSGSGSGTAFTLRISRVEAEDVGVYYCMQHLEYPYTFGGGTKLEIKVAAPSVFIFPPS

DEQLKSGTASVVCLLNNFYPREAKVQWKVDNALQSGNSQESVTEQDSKDSTYSLSSTLTLSK

ADYEKHKVYACEVTHQGLSSPVTKSFNRGEC

SEQ ID NO: 11
CAGGTCCAAGTGCAGCAGCCTGGGGCTGAAATTGTGAGGCCTGGGGCTTCAGTGAAGCTGTC

CTGCAAGGCTTCTGGCTACACCTTCACCAGCTACTGGATGCACTGGGTGAAGCAGAGGCCTG

GACAAGGCCTTGAGTGGATTGGACTGATTAATCCTACCAACGGTCGTACTAACTACAATGAG

AAGTTCAAGAGCAAGGCCACACTGACTGTAGACAAATCCTCCAGCACAGCCTACATGCAACT

CAGCAGCCTGACATCTGAGGACTCTGCGGTCTATTACTGTGCAAGAGGGGGGGACGGGGACT

ACTTTGACTACTGGGGCCAAGGCACCACTCTCACAGTCTCCTCAGCCTCAACGAAGGGCCCA

TCGGTCTTCCCCCTGGCGCCCTGCTCCAGGAGCACCTCCGAGAGCACAGCCGCCCTGGGCTG

CCTGGTCAAGGACTACTTCCCCGAACCGGTGACGGTGTCGTGGAACTCAGGCGCTCTGACCA

GCGGCGTGCACACCTTCCCAGCTGTCCTACAGTCCTCAGGACTCTACTCCCTCAGCAGCGTG

GTGACCGTGCCCTCCAGCAACTTCGGCACCCAGACCTACACCTGCAACGTAGATCACAAGCC

CAGCAACACCAAGGTGGACAAGACAGTTGAGCGCAAATGTTGTGTCGAGTGCCCACCGTGCC

CAGCACCACCTGTGGCAGGACCGTCAGTCTTCCGCTTCCCCCCAAAACCCAAGGACACCCGC

ATGATCTCCCGGACCCCTGAGGTCACGTGCGTGGTGGTGGATGTGAGCCACGAAGACCCCGA

GGTCCAGTTCAACTGGTACGTGGACGGCGTGGAGGTGCATAATGCCAAGACAAAGCCACGGG

AGGAGCAGTTCAACAGCACGTTCCGTGTGGTCAGCGTCCTCACCGTTGTGCACCAGGACTGG

CTGAACGGCAAGGAGTACAAGTGCAAGGTCTCCAACAAAGGCCTCCCAGCCCCCATCGAGAA

AACCATCTCCAAAACCAAAGGGCAGCCCCGAGAACCACAGGTGTACACCCTGCCCCCATCCC

GGGAGGAGATGACCAAGAACCAGGTCAGCCTGACCTGCCTGGTCAAAGGCTTCTACCCCAGC

GACATCGCCGTGGAGTGGGAGAGCAATGGGCAGCCGGAGAACAACTACAAGACCACACCTCC

CATGCTGGACTCCGACGGCTCCTTCTTCCTCTACAGCAAGCTCACCGTGGACAAGAGCAGGT

GGCAGCAGGGGAACGTCTTCTCATGCTCCGTGATGCATGAGGCTCTGCACAACCACTACACG

CAGAAGAGCCTCTCCCTGTCTCCGGGTAAATGA

SEQ ID NO: 12
QVQVQQPGAEIVRPGASVKLSCKASGYTFTSYWMHWVKQRPGQGLEWIGLINPTNGRTNYNE

KFKSKATLTVDKSSSTAYMQLSSLTSEDSAVYYCARGGDGDYFDYWGQGTTLTVSSASTKGP

SVFPLAPCSRSTSESTAALGCLVKDYFPEPVTVSWNSGALTSGVHTFPAVLQSSGLYSLSSV

VTVPSSNFGTQTYTCNVDHKPSNTKVDKTVERKCCVECPPCPAPPVAGPSVFLFPPKPKDTL

MISRTPEVTCVVVDVSHEDPEVQFNWYVDGVEVHNAKTKPREEQFNSTFRVVSVLTVVHQDW

LNGKEYKCKVSNKGLPAPIEKTISKTKGQPREPQVYTLPPSREEMTKNQVSLTCLVKGFYPS

DIAVEWESNGQPENNYKTTPPMLDSDGSFFLYSKLTVDKSRWQQGNVFSCSVMHEALHNHYT

QKSLSLSPGK

SEQ ID NO: 13
GATATTGTGATGACCCAGGCTGCACCCTCTGTACCTGTCACTCCTGGAGAGTCAGTATCCAT

CTCCTGCAGGTCTACTAAGAGTCTCCTGCATAGTAATGGCAACACTTACTTGTATTGGTTCC

TGCAGAGGCCAGGCCAGTCTCCTCAGCTCCTGATATATCGGATGTCCAACCTTGCCTCAGGA

GTCCCAGACAGGTTCAGTGGCAGTGGGTCAGGAACTGCTTTCACACTGAGAATCAGTAGAGT

GGAGGCTGAGGATGTGGGTGTTTATTACTGTATGCAACATCTAGAATATCCTTTCACGTTCG

GAGGGGGGACCAAGCTGGAAATAAAACGGGCTGTGGCTGCACCATCTGTCTTCATCTTCCCG

CCATCTGATGAGCAGTTGAAATCTGGAACTGCCTCTGTTGTGTGCCTGCTGAATAACTTCTA

TCCCAGAGAGGCCAAAGTACAGTGGAAGGTGGATAACGCCCTCCAATCGGGTAACTCCCAGG

AGAGTGTCACAGAGCAGGACAGCAAGGACAGCACCTACAGCCTCAGCAGCACCCTGACGCTG

AGCAAAGCAGACTACGAGAAACACAAAGTCTACGCCTGCGAAGTCACCCATCAGGGCCTGAG

CTCGCCCGTCACAAAGAGCTTCAACAGGGGAGAGTGTTAG

SEQ ID NO: 14
DIVMTQAAPSVPVTPGESVSISCRSTKSLLHSNGNTYLYWFLQRPGQSPQLLIYRMSNLASG

VPDRFSGSGSGTAFTLRISRVEAEDVGVYYCMQHLEYPFTFGGGTKLEIKVAAPSVFIFPPS

DEQLKSGTASVVCLLNNFYPREAKVQWKVDNALQSGNSQESVTEQDSKDSTYSLSSTLTLSK

ADYEKHKVYACEVTHQGLSSPVTKSFNRGEC

SEQ ID NO: 15
GAGATCCAGCTGCAGCAGTCTGGAGTTGAGCTGGTGAGGCCTGGGGCTTCAGTGACGCTGTC

CTGCAAGGCTTCGGGCTACACATTTACTGACTATGACATGCACTGGGTGAAGCAGACACCTG

TTCATGGCCTGGAATGGATTGGAACTATTGATCCTGAAACTGGTGGTACTGCCTACAATCAG

AAGTTCAAGGGCAAGGCCACACTGACTGCGGACAGATCCTCCACCACAGCCTACATGGAGCT

CAGCAGCCTGACATCTGAGGACTCTGCCGTCTATTACTGTACAACTTTCTACTATAGTCACT

ATAATTACGACGTGGGGTTTGCTTACTGGGGCCAAGGGACTCTGGTCACTGTCTCTGCAGCC

TCAACGAAGGGCCCATCGGTCTTCCCCCTGGCGCCCTGCTCCAGGAGCACCTCCGAGAGCAC

AGCCGCCCTGGGCTGCCTGGTCAAGGACTACTTCCCCGAACCGGTGACGGTGTCGTGGAACT

CAGGCGCTCTGACCAGCGGCGTGCACACCTTCCCAGCTGTCCTACAGTCCTCAGGACTCTAC

TCCCTCAGCAGCGTGGTGACCGTGCCCTCCAGCAACTTCGGCACCCAGACCTACACCTGCAA

CGTAGATCACAAGCCCAGCAACACCAAGGTGGACAAGACAGTTGAGCGCAAATGTTGTGTCG

AGTGCCCACCGTGCCCAGCACCACCTGTGGCAGGACCGTCAGTCTTCCGCTTCCCCCCAAAA

CCCAAGGACACCCGCATGATCTCCCGGACCCCTGAGGTCACGTGCGTGGTGGTGGATGTGAG

CCACGAAGACCCCGAGGTCCAGTTCAACTGGTACGTGGACGGCGTGGAGGTGCATAATGCCA

AGACAAAGCCACGGGAGGAGCAGTTCAACAGCACGTTCCGTGTGGTCAGCGTCCTCACCGTT

GTGCACCAGGACTGGCTGAACGGCAAGGAGTACAAGTGCAAGGTCTCCAACAAAGGCCTCCC

AGCCCCCATCGAGAAAACCATCTCCAAAACCAAAGGGCAGCCCCGAGAACCACAGGTGTACA

CCCTGCCCCCATCCCGGGAGGAGATGACCAAGAACCAGGTCAGCCTGACCTGCCTGGTCAAA

GGCTTCTACCCCAGCGACATCGCCGTGGAGTGGGAGAGCAATGGGCAGCCGGAGAACAACTA

CAAGACCACACCTCCCATGCTGGACTCCGACGGCTCCTTCTTCCTCTACAGCAAGCTCACCG

TGGACAAGAGCAGGTGGCAGCAGGGGAACGTCTTCTCATGCTCCGTGATGCATGAGGCTCTG

CACAACCACTACACGCAGAAGAGCCTCTCCCTGTCTCCGGGTAAATGA

SEQ ID NO: 16
EIQLQQSGVELVRPGASVTLSCKASGYTFTDYDMHWVKQTPVHGLEWIGTIDPETGGTAYNQ

KFKGKATLTADRSSTTAYMELSSLTSEDSAVYYCTTFYYSHYNYDVGFAYWGQGTLVTVSAA

STKGPSVFPLAPCSRSTSESTAALGCLVKDYFPEPVTVSWNSGALTSGVHTFPAVLQSSGLY

SLSSVVTVPSSNFGTQTYTCNVDHKPSNTKVDKTVERKCCVECPPCPAPPVAGPSVFLFPPK

PKDTLMISRTPEVTCVVVDVSHEDPEVQFNWYVDGVEVHNAKTKPREEQFNSTFRVVSVLTV

VHQDWLNGKEYKCKVSNKGLPAPIEKTISKTKGQPREPQVYTLPPSREEMTKNQVSLTCLVK

GFYPSDIAVEWESNGQPENNYKTTPPMLDSDGSFFLYSKLTVDKSRWQQGNVFSCSVMHEAL

HNHYTQKSLSLSPGK

SEQ ID NO: 17
GATATTGTGATGACCCAGGCTGCACCCTCTGTACCTGTCACTCCTGGAGAGTCAGTATCCAT

CTCCTGCAGGTCTAGTAAGAGTCTCCTGCATAGTAATGGCAACACTTACTTGTATTGGTTCC

TGCAGAGGCCAGGCCAGTCCCCTCAGCTCCTGATATATCGGATGTCCAACCTTGCCTCAGGA

GTCCCAGACAGGTTCAGTGGCAGTGGGTCAGGAACTGCTTTCACACTGAGAATCAGTAGAGT

GGAGGCTGAGGATGTGGGTGTTTATTACTGTATGCAACATCTAGAATATCCTTTCACGTTCG

GAGGGGGGACCAAGCTGGAAATAAAACGGGCTGTGGCTGCACCATCTGTCTTCATCTTCCCG

CCATCTGATGAGCAGTTGAAATCTGGAACTGCCTCTGTTGTGTGCCTGCTGAATAACTTCTA

TCCCAGAGAGGCCAAAGTACAGTGGAAGGTGGATAACGCCCTCCAATCGGGTAACTCCCAGG

AGAGTGTCACAGAGCAGGACAGCAAGGACAGCACCTACAGCCTCAGCAGCACCCTGACGCTG

AGCAAAGCAGACTACGAGAAACACAAAGTCTACGCCTGCGAAGTCACCCATCAGGGCCTGAG

CTCGCCCGTCACAAAGAGCTTCAACAGGGGAGAGTGTTAG

SEQ ID NO: 18
DIVMTQAAPSVPVTPGESVSISCRSSKSLLHSNGNTYLYWFLQRPGQSPQLLIYRMSNLASG

VPDRFSGSGSGTAFTLRISRVEAEDVGVYYCMQHLEYPFTFGGGTKLEIKVAAPSVFIFPPS

DEQLKSGTASVVCLLNNFYPREAKVQWKVDNALQSGNSQESVTEQDSKDSTYSLSSTLTLSK

ADYEKHKVYACEVTHQGLSSPVTKSFNRGEC

SEQ ID NO: 19
GAGATCCAGCTGCAGCAGTCTGGAGCTGAGCTGGTGAGGCCTGGGGCTTCAGTGACGCTGTC

CTGCAAGGCTTCGGGCTACACATTTACTGACTATGAAATGCACTGGGTGAAGCAGACACCTG

TTCATGGCCTGGAATGGATTGGAGCTATTGATCCTGAAACTGGTGGTACTGCCTACAATCAG

AAGTTCAAGGGCAAGGCCACACTGACTGCAGACAAATCCTCCAGCACAGCCTACATGGAGCT

CAGCAGCCTGACATCTGAGGACTCTGCCGTCTATTACTGTACAAGTTTCTACTATACTTACT

ATAATTACGACGTGGGGTTTGCTTACTGGGGCCAAGGGACTCTGGTCACTGTCTCTGCAGCC

TCAACTGGGGCGTCTTATTACTATGCTATGGACCACTGGGGTCAAGGAACCTCAGTCACCGT

CTCCTCAGCCTCAACGAAGGGCCCATCGGTCTTCCCCCTGGCGCCCTGCTCCAGGAGCACCT

CCGAGAGCACAGCCGCCCTGGGCTGCCTGGTCAAGGACTACTTCCCCGAACCGGTGACGGTG

TCGTGGAACTCAGGCGCTCTGACCAGCGGCGTGCACACCTTCCCAGCTGTCCTACAGTCCTC

```
AGGACTCTACTCCCTCAGCAGCGTGGTGACCGTGCCCTCCAGCAACTTCGGCACCCAGACCT

ACACCTGCAACGTAGATCACAAGCCCAGCAACACCAAGGTGGACAAGACAGTTGAGCGCAAA

TGTTGTGTCGAGTGCCCACCGTGCCCAGCACCACCTGTGGCAGGACCGTCAGTCTTCCGCTT

CCCCCCAAAACCCAAGGACACCCGCATGATCTCCCGGACCCCTGAGGTCACGTGCGTGGTGG

TGGATGTGAGCCACGAAGACCCCGAGGTCCAGTTCAACTGGTACGTGGACGGCGTGGAGGTG

CATAATGCCAAGACAAAGCCACGGGAGGAGCAGTTCAACAGCACGTTCCGTGTGGTCAGCGT

CCTCACCGTTGTGCACCAGGACTGGCTGAACGGCAAGGAGTACAAGTGCAAGGTCTCCAACA

AAGGCCTCCCAGCCCCCATCGAGAAAACCATCTCCAAAACCAAAGGGCAGCCCCGAGAACCA

CAGGTGTACACCCTGCCCCCATCCCGGGAGGAGATGACCAAGAACCAGGTCAGCCTGACCTG

CCTGGTCAAAGGCTTCTACCCCAGCGACATCGCCGTGGAGTGGGAGAGCAATGGGCAGCCGG

AGAACAACTACAAGACCACACCTCCCATGCTGGACTCCGACGGCTCCTTCTTCCTCTACAGC

AAGCTCACCGTGGACAAGAGCAGGTGGCAGCAGGGGAACGTCTTCTCATGCTCCGTGATGCA

TGAGGCTCTGCACAACCACTACACGCAGAAGAGCCTCTCCCTGTCTCCGGGTAAATGA

SEQ ID NO: 20
EIQLQQSGAELVRPGASVTLSCKASGYTFTDYEMHWVKQTPVHGLEWIGAIDPETGGTAYNQ

KFKGKATLTADKSSSTAYMELSSLTSEDSAVYYCTSFYYTYNYDVGFAYWGQGTLVTVSAA

STKGPSVFPLAPCSRSTSESTAALGCLVKDYFPEPVTVSWNSGALTSGVHTFPAVLQSSGLY

SLSSVVTVPSSNFGTQTYTCNVDHKPSNTKVDKTVERKCCVECPPCPAPPVAGPSVFLFPPK

PKDTLMISRTPEVTCVVVDVSHEDPEVQFNWYVDGVEVHNAKTKPREEQFNSTFRVVSVLTV

VHQDWLNGKEYKCKVSNKGLPAPIEKTISKTKGQPREPQVYTLPPSREEMTKNQVSLTCLVK

GFYPSDIAVEWESNGQPENNYKTTPPMLDSDGSFFLYSKLTVDKSRWQQGNVFSCSVMHEAL

HNHYTQKSLSLSPGK

SEQ ID NO: 21
GATATTGTGATGACCCAGGCTGCATTCTCCAATCCAGTCACTCTTGGAACATCAGCTTCCAT

CTCCTGCAGGTCTAGTAAGAGTCTCCTACATAGTAATGGCATCACTTATTTGTATTGGTATC

TGCAGAAGCCAGGCCAGTCTCCTCAGCTCCTGATTTATCAGATGTCCAACCTTGCCTCAGGA

GTCCCAGACAGGTTCAGTAGCAGTGGGTCAGGAACTGATTTCACACTGAGAATCAGCAGAGT

GGAGGCTGAGGATGTGGGTGTTTATTACTGTGCTCAAAATCTAGAACTTCCGTACACGTTCG

GAGGGGGGACCAAGCTGGAAATAAAACGGGCTGTGGCTGCACCATCTGTCTTCATCTTCCCG

CCATCTGATGAGCAGTTGAAATCTGGAACTGCCTCTGTTGTGTGCCTGCTGAATAACTTCTA

TCCCAGAGAGGCCAAAGTACAGTGGAAGGTGGATAACGCCCTCCAATCGGGTAACTCCCAGG

AGAGTGTCACAGAGCAGGACAGCAAGGACAGCACCTACAGCCTCAGCAGCACCCTGACGCTG

AGCAAAGCAGACTACGAGAAACACAAAGTCTACGCCTGCGAAGTCACCCATCAGGGCCTGAG

CTCGCCCGTCACAAAGAGCTTCAACAGGGGAGAGTGTTAG

SEQ ID NO: 22
DIVMTQAAFSNPVTLGTSASISCRSSKSLLHSNGITYLYWYLQKPGQSPQLLIYQMSNLASG

VPDRFSSSGSGTDFTLRISRVEAEDVGVYYCAQNLELPYTFGGGTKLEIKVAAPSVFIFPPS

DEQLKSGTASVVCLLNNFYPREAKVQWKVDNALQSGNSQESVTEQDSKDSTYSLSSTLTLSK

ADYEKHKVYACEVTHQGLSSPVTKSFNRGEC
```

SEQ ID NO: 23
CAGGTCCAAGTGCAGCAGCCTGGGGCTGAGCTTGTGAAGCCTGGGGCTTCGGTGAAGCTGTC

CTGCAAGGCTTCTGGCTACACCTTCACCAGCTACTGGATGCACTGGGTGAAGCAGAGGCCTG

GACAAGGCCTTGAGTGGATTGGACTGATTAATCCTAGCAACGCTCGTACTAACTACAATGAG

AAGTTCAATACCAAGGCCACACTGACTGTAGACAAATCCTCCAGCACAGCCTACATGCAACT

CAGCAGCCTGACATCTGAGGACTCTGCGGTCTATTACTGTGCAAGAGGGGGGGACGGGGACT

ACTTTGACTACTGGGGCCAAGGCACCACTCTCACAGTCTCCTCAGCCTCAACGAAGGGCCCA

TCGGTCTTCCCCCTGGCGCCCTGCTCCAGGAGCACCTCCGAGAGCACAGCCGCCCTGGGCTG

CCTGGTCAAGGACTACTTCCCCGAACCGGTGACGGTGTCGTGGAACTCAGGCGCTCTGACCA

GCGGCGTGCACACCTTCCCAGCTGTCCTACAGTCCTCAGGACTCTACTCCCTCAGCAGCGTG

GTGACCGTGCCCTCCAGCAACTTCGGCACCCAGACCTACACCTGCAACGTAGATCACAAGCC

CAGCAACACCAAGGTGGACAAGACAGTTGAGCGCAAATGTTGTGTCGAGTGCCCACCGTGCC

CAGCACCACCTGTGGCAGGACCGTCAGTCTTCCGCTTCCCCCCAAAACCCAAGGACACCCGC

ATGATCTCCCGGACCCCTGAGGTCACGTGCGTGGTGGTGGATGTGAGCCACGAAGACCCCGA

GGTCCAGTTCAACTGGTACGTGGACGGCGTGGAGGTGCATAATGCCAAGACAAAGCCACGGG

AGGAGCAGTTCAACAGCACGTTCCGTGTGGTCAGCGTCCTCACCGTTGTGCACCAGGACTGG

CTGAACGGCAAGGAGTACAAGTGCAAGGTCTCCAACAAAGGCCTCCCAGCCCCCATCGAGAA

AACCATCTCCAAAACCAAAGGGCAGCCCCGAGAACCACAGGTGTACACCCTGCCCCCATCCC

GGGAGGAGATGACCAAGAACCAGGTCAGCCTGACCTGCCTGGTCAAAGGCTTCTACCCCAGC

GACATCGCCGTGGAGTGGGAGAGCAATGGGCAGCCGGAGAACAACTACAAGACCACACCTCC

CATGCTGGACTCCGACGGCTCCTTCTTCCTCTACAGCAAGCTCACCGTGGACAAGAGCAGGT

GGCAGCAGGGGAACGTCTTCTCATGCTCCGTGATGCATGAGGCTCTGCACAACCACTACACG

CAGAAGAGCCTCTCCCTGTCTCCGGGTAAATGA

SEQ ID NO: 24
QVQVQQPGAELVKPGASVKLSCKASGYTFTSYWMHWVKQRPGQGLEWIGLINPSNARTNYNE

KFNTKATLTVDKSSSTAYMQLSSLTSEDSAVYYCARGGDGDYFDYWGQGTTLTVSSASTKGP

SVFPLAPCSRSTSESTAALGCLVKDYFPEPVTVSWNSGALTSGVHTFPAVLQSSGLYSLSSV

VTVPSSNFGTQTYTCNVDHKPSNTKVDKTVERKCCVECPPCPAPPVAGPSVFLFPPKPKDTL

MISRTPEVTCVVVDVSHEDPEVQFNWYVDGVEVHNAKTKPREEQFNSTFRVVSVLTVVHQDW

LNGKEYKCKVSNKGLPAPIEKTISKTKGQPREPQVYTLPPSREEMTKNQVSLTCLVKGFYPS

DIAVEWESNGQPENNYKTTPPMLDSDGSFFLYSKLTVDKSRWQQGNVFSCSVMHEALHNHYT

QKSLSLSPGK

SEQ ID NO: 25
CAAATTGTTCTCACCCAGTCTCCAACACTCATGTCTGCATCTCCAGGGGAGAAGGTCACCAT

GACCTGCAGTGCCAGCTCAAGTGTAAGTTACATGTACTGGTACCAGCAGAAGCCAAGATCCT

CCCCCAAACCCTGGATTTATCGCACATCCAACCTGGTTTCTGGAGTCCCTGTACGCTTCAGT

GGCAGTGGGTCTGGGACCTCTTACTCTCTCACAATCAGCAGCATGGAGGCTGAAGATGCTGC

CACTTATTACTGCCAGCAGTGGAGTAGTAACCCACCCACGTTCGGTGCTGGGACCAAGCTGG

AGCTGAAACGGGCTGTGGCTGCACCATCTGTCTTCATCTTCCCGCCATCTGATGAGCAGTTG

AAATCTGGAACTGCCTCTGTTGTGTGCCTGCTGAATAACTTCTATCCCAGAGAGGCCAAAGT

```
ACAGTGGAAGGTGGATAACGCCCTCCAATCGGGTAACTCCCAGGAGAGTGTCACAGAGCAGG

ACAGCAAGGACAGCACCTACAGCCTCAGCAGCACCCTGACGCTGAGCAAAGCAGACTACGAG

AAACACAAAGTCTACGCCTGCGAAGTCACCCATCAGGGCCTGAGCTCGCCCGTCACAAAGAG

CTTCAACAGGGGAGAGTGTTAG

SEQ ID NO: 26
QIVLTQSPTLMSASPGEKVTMTCSASSSVSYMYWYQQKPRSSPKPWIYRTSNLVSGVPVRFS

GSGSGTSYSLTISSMEAEDAATYYCQQWSSNPPTFGAGTKLELKVAAPSVFIFPPSDEQLKS

GTASVVCLLNNFYPREAKVQWKVDNALQSGNSQESVTEQDSKDSTYSLSSTLTLSKADYEKH

KVYACEVTHQGLSSPVTKSFNRGEC

SEQ ID NO: 27
GAAGTGAAGCTTGAGGAGTCTGGAGGTGGCCTGGTGCAGCCTGGAGGATCCCTGAAACTCTC

CTGTGCAGCCTCAGGATTCGATTTTAGTAAAGACTGGATGAGTTGGGTCCGGCAGGCTCCAG

GGAAAGGGCTAGAATGGATTGGAGAAATTAATCCAGATAGCAGTACGATAAACTATGCACCA

TCTCTTAAGGATAAATTCATCATCTCCAGAGAGAACGCCAAAAATACGCTGTACCTGCAAAT

GAGCAAAGTGAGATCTGAGGACACAGCCCTTTATTACTGTTCAAGACTAGAGGACTACGAAG

ACTGGTACTTCGATGTCTGGGGCGCAGGGACCACGGTCACCGTCTCCTCAGCCTCAACGAAG

GGCCCATCGGTCTTCCCCCTGGCGCCCTGCTCCAGGAGCACCTCCGAGAGCACAGCCGCCCT

GGGCTGCCTGGTCAAGGACTACTTCCCCGAACCGGTGACGGTGTCGTGGAACTCAGGCGCTC

TGACCAGCGGCGTGCACACCTTCCCAGCTGTCCTACAGTCCTCAGGACTCTACTCCCTCAGC

AGCGTGGTGACCGTGCCCTCCAGCAACTTCGGCACCCAGACCTACACCTGCAACGTAGATCA

CAAGCCCAGCAACACCAAGGTGGACAAGACAGTTGAGCGCAAATGTTGTGTCGAGTGCCCAC

CGTGCCCAGCACCACCTGTGGCAGGACCGTCAGTCTTCCTGCTTCCCCCCAAAACCCAAGGAC

ACCCTCATGATCTCCCGGACCCCTGAGGTCACGTGCGTGGTGGTGGATGTGAGCCACGAAGA

CCCCGAGGTCCAGTTCAACTGGTACGTGGACGGCGTGGAGGTGCATAATGCCAAGACAAAGC

CACGGGAGGAGCAGTTCAACAGCACGTTCCGTGTGGTCAGCGTCCTCACCGTTGTGCACCAG

GACTGGCTGAACGGCAAGGAGTACAAGTGCAAGGTCTCCAACAAAGGCCTCCCAGCCCCCAT

CGAGAAAACCATCTCCAAAACCAAAGGGCAGCCCCGAGAACCACAGGTGTACACCCTGCCCC

CATCCCGGGAGGAGATGACCAAGAACCAGGTCAGCCTGACCTGCCTGGTCAAAGGCTTCTAC

CCCAGCGACATCGCCGTGGAGTGGGAGAGCAATGGGCAGCCGGAGAACAACTACAAGACCAC

ACCTCCCATGCTGGACTCCGACGGCTCCTTCTTCCTCTACAGCAAGCTCACCGTGGACAAGA

GCAGGTGGCAGCAGGGGAACGTCTTCTCATGCTCCGTGATGCATGAGGCTCTGCACAACCAC

TACACGCAGAAGAGCCTCTCCCTGTCTCCGGGTAAATGA

SEQ ID NO: 28
EVKLEESGGGLVQPGGSLKLSCAASGFDFSKDWMSWVRQAPGKGLEWIGEINPDSSTINYAP

SLKDKFIISRENAKNTLYLQMSKVRSEDTALYYCSRLEDYEDWYFDVWGAGTTVTVSSASTK

GPSVFPLAPCSRSTSESTAALGCLVKDYFPEPVTVSWNSGALTSGVHTFPAVLQSSGLYSLS

SVVTVPSSNFGTQTYTCNVDHKPSNTKVDKTVERKCCVECPPCPAPPVAGPSVFLFPPKPKD

TLMISRTPEVTCVVVDVSHEDPEVQFNWYVDGVEVHNAKTKPREEQFNSTFRVVSVLTVVHQ

DWLNGKEYKCKVSNKGLPAPIEKTISKTKGQPREPQVYTLPPSREEMTKNQVSLTCLVKGFY

PSDIAVEWESNGQPENNYKTTPPMLDSDGSFFLYSKLTVDKSRWQQGNVFSCSVMHEALHNH

YTQKSLSLSPGK
```

SEQUENCE LISTINGS

SEQ ID NO: 29
AGTATTGTGATGACCCAGACTCCCAAATTCCTGCTTGTATCAGCAGGAGACAGGGTTACCAT

AACCTGCAAGGCCAGTCAGAGTGTGAGTAATGCTGTAGCTTGGTACCAACAGAAGCCAGGGC

AGTCTCCTAAACTGCTGATATACTATACATCCAATCGCTACACTGGAGTCCCTGATCGCTTC

ACTGGCAGTGGATATGGGACGGATTTCACTTTCACCATCACCACTGTGCAGGCTGAAGACCT

GGCAGTTTATTTCTGTCAGCAGGATTATACCTCTCCGTGGACGTTCGGTGGAGGCACCAAGC

TGGAAATCAAACGGGCTGTGGCTGCACCATCTGTCTTCATCTTCCCGCCATCTGATGAGCAG

TTGAAATCTGGAACTGCCTCTGTTGTGTGCCTGCTGAATAACTTCTATCCCAGAGAGGCCAA

AGTACAGTGGAAGGTGGATAACGCCCTCCAATCGGGTAACTCCCAGGAGAGTGTCACAGAGC

AGGACAGCAAGGACAGCACCTACAGCCTCAGCAGCACCCTGACGCTGAGCAAAGCAGACTAC

GAGAAACACAAAGTCTACGCCTGCGAAGTCACCCATCAGGGCCTGAGCTCGCCCGTCACAAA

GAGCTTCAACAGGGGAGAGTGTTAG

SEQ ID NO: 30
SIVMTQTPKFLLVSAGDRVTITCKASQSVSNAVAWYQQKPGQSPKLLIYYTSNRYTGVPDRF

TGSGYGTDFTFTITTVQAEDLAVYFCQQDYTSPWTFGGGTKLEIKVAAPSVFIFPPSDEQLK

SGTASVVCLLNNFYPREAKVQWKVDNALQSGNSQESVTEQDSKDSTYSLSSTLTLSKADYEK

HKVYACEVTHQGLSSPVTKSFNRGEC

SEQ ID NO: 31
CAGGTCCAACTGCAGCAGCCTGGGGCTGAACTGGCGAAGCCTGGGGCTTCAGTGAAGTTGTC

CTGCAAGGCTTCTGGCTACACCTTCAACACCTATAATATGTACTGGTTGAAACAGAGGCCTG

GGCAAGGCCTTGAGTGGATTGGGGGGATTGATCCTAGCAATGGTGATACTAAAATCAATGAG

AAGTTCAAGAACAAGGCCACACTGACTGTTGACAAATCCTCCAGTACAGCCTATATGCAACT

CAGCGGCCTGACATCTGAGGACTCTGCGGTCTATTACTGTACAAGCCATACGTACTGGGGCC

AAGGGACTCTGGTCACTGTCTCTGCAGCCTCAACGAAGGGCCCATCGGTCTTCCCCCTGGCG

CCCTGCTCCAGGAGCACCTCCGAGAGCACAGCCGCCCTGGGCTGCCTGGTCAAGGACTACTT

CCCCGAACCGGTGACGGTGTCGTGGAACTCAGGCGCTCTGACCAGCGGCGTGCACACCTTCC

CAGCTGTCCTACAGTCCTCAGGACTCTACTCCCTCAGCAGCGTGGTGACCGTGCCCTCCAGC

AACTTCGGCACCCAGACCTACACCTGCAACGTAGATCACAAGCCCAGCAACACCAAGGTGGA

CAAGACAGTTGAGCGCAAATGTTGTGTCGAGTGCCCACCGTGCCCAGCACCACCTGTGGCAG

GACCGTCAGTCTTCCGCTTCCCCCCAAAACCCAAGGACACCCGCATGATCTCCCGGACCCCT

GAGGTCACGTGCGTGGTGGTGGATGTGAGCCACGAAGACCCCGAGGTCCAGTTCAACTGGTA

CGTGGACGGCGTGGAGGTGCATAATGCCAAGACAAAGCCACGGGAGGAGCAGTTCAACAGCA

CGTTCCGTGTGGTCAGCGTCCTCACCGTTGTGCACCAGGACTGGCTGAACGGCAAGGAGTAC

AAGTGCAAGGTCTCCAACAAAGGCCTCCCAGCCCCCATCGAGAAAACCATCTCCAAAACCAA

AGGGCAGCCCCGAGAACCACAGGTGTACACCCTGCCCCCATCCCGGGAGGAGATGACCAAGA

ACCAGGTCAGCCTGACCTGCCTGGTCAAAGGCTTCTACCCCAGCGACATCGCCGTGGAGTGG

GAGAGCAATGGGCAGCCGGAGAACAACTACAAGACCACACCTCCCATGCTGGACTCCGACGG

CTCCTTCTTCCTCTACAGCAAGCTCACCGTGGACAAGAGCAGGTGGCAGCAGGGGAACGTCT

TCTCATGCTCCGTGATGCATGAGGCTCTGCACAACCACTACACGCAGAAGAGCCTCTCCCTG

TCTCCGGGTAAATGA

SEQ ID NO: 32
QVQLQQPGAELAKPGASVKLSCKASGYTFNTYNMYWLKQRPGQGLEWIGGIDPSNGDTKINE

KFKNKATLTVDKSSSTAYMQLSGLTSEDSAVYYCTSHTYWGQGTLVTVSAASTKGPSVFPLA

PCSRSTSESTAALGCLVKDYFPEPVTVSWNSGALTSGVHTFPAVLQSSGLYSLSSVVTVPSS

NFGTQTYTCNVDHKPSNTKVDKTVERKCCVECPPCPAPPVAGPSVFLFPPKPKDTLMISRTP

EVTCVVVDVSHEDPEVQFNWYVDGVEVHNAKTKPREEQFNSTFRVVSVLTVVHQDWLNGKEY

KCKVSNKGLPAPIEKTISKTKGQPREPQVYTLPPSREEMTKNQVSLTCLVKGFYPSDIAVEW

ESNGQPENNYKTTPPMLDSDGSFFLYSKLTVDKSRWQQGNVFSCSVMHEALHNHYTQKSLSL

SPGK

SEQ ID NO: 33
GATATTGTGATGACCCAGGCTGCACCCTCTGTACCTGTCACTCCTGGAGAGTCAGTATCCAT

CTCCTGCAGGTCTACTAAGAGTCTCCTGCATAGTAATGGCAACACTTACTTGTATTGGTTCC

TGCAGAGGCCAGGCCAGTCTCCTCAGCTCCTGATATATCGGATGTCCAACCTTGCCTCAGGA

GTCCCAGACAGGTTCAGTGGCAGTGGGTCAGGAACTGCTTTCACACTGAGAATCAGTAGAGT

GGAGGCTGAGGATGTGGGTGTTTATTACTGTATGCAACATCTAGAATATCCTTTCACGTTCG

GAGGGGGGACCAAGCTGGAAATAAAACGGGCTGTGGCTGCACCATCTGTCTTCATCTTCCCG

CCATCTGATGAGCAGTTGAAATCTGGAACTGCCTCTGTTGTGTGCCTGCTGAATAACTTCTA

TCCCAGAGAGGCCAAAGTACAGTGGAAGGTGGATAACGCCCTCCAATCGGGTAACTCCCAGG

AGAGTGTCACAGAGCAGGACAGCAAGGACAGCACCTACAGCCTCAGCAGCACCCTGACGCTG

AGCAAAGCAGACTACGAGAAACACAAAGTCTACGCCTGCGAAGTCACCCATCAGGGCCTGAG

CTCGCCCGTCACAAAGAGCTTCAACAGGGGAGAGTGTTAG

SEQ ID NO: 34
DIVMTQAAPSVPVTPGESVSISCRSTKSLLHSNGNTYLYWFLQRPGQSPQLLIYRMSNLASG

VPDRFSGSGSGTAFTLRISRVEAEDVGVYYCMQHLEYPFTFGGGTKLEIKVAAPSVFIFPPS

DEQLKSGTASVVCLLNNFYPREAKVQWKVDNALQSGNSQESVTEQDSKDSTYSLSSTLTLSK

ADYEKHKVYACEVTHQGLSSPVTKSFNRGEC

SEQ ID NO: 35
GAGATCCAGCTGCAGCAGTCTGGAGTTGAGCTGGTGAGGCCTGGGGCTTCAGTGACGCTGTC

CTGCAAGGCTTCGGGCTACACATTTACTGACTATGACATGCACTGGGTGAAGCAGACACCTG

TTCATGGCCTGGAATGGATTGGAACTATTGATCCTGAAACTGGTGGTACTGCCTACAATCAG

AAGTTCAAGGGCAAGGCCACACTGACTGCGGACAGATCCTCCACCACAGCCTACATGGAGCT

CAGCAGCCTGACATCTGAGGACTCTGCCGTCTATTACTGTACAAGTTTCTACTATACTTACT

CTAATTACGACGTGGGGTTTGCTTACTGGGGCCAAGGGACTCTGGTCACTGTCTCTGCAGCC

TCAACTGGGGCGTCTTATTACTATGCTATGGACCACTGGGGTCAAGGAACCTCAGTCACCGT

CTCCTCAGCCTCAACGAAGGGCCCATCGGTCTTCCCCCTGGCGCCCTGCTCCAGGAGCACCT

CCGAGAGCACAGCCGCCCTGGGCTGCCTGGTCAAGGACTACTTCCCCGAACCGGTGACGGTG

TCGTGGAACTCAGGCGCTCTGACCAGCGGCGTGCACACCTTCCCAGCTGTCCTACAGTCCTC

AGGACTCTACTCCCTCAGCAGCGTGGTGACCGTGCCCTCCAGCAACTTCGGCACCCAGACCT

ACACCTGCAACGTAGATCACAAGCCCAGCAACACCAAGGTGGACAAGACAGTTGAGCGCAAA

TGTTGTGTCGAGTGCCCACCGTGCCCAGCACCACCTGTGGCAGGACCGTCAGTCTTCCTCTT

CCCCCCAAAACCCAAGGACACCCGCATGATCTCCCGGACCCCTGAGGTCACGTGCGTGGTGG

-continued

SEQUENCE LISTINGS

TGGATGTGAGCCACGAAGACCCCGAGGTCCAGTTCAACTGGTACGTGGACGGCGTGGAGGTG

CATAATGCCAAGACAAAGCCACGGGAGGAGCAGTTCAACAGCACGTTCCGTGTGGTCAGCGT

CCTCACCGTTGTGCACCAGGACTGGCTGAACGGCAAGGAGTACAAGTGCAAGGTCTCCAACA

AAGGCCTCCCAGCCCCCATCGAGAAAACCATCTCCAAAACCAAAGGGCAGCCCCGAGAACCA

CAGGTGTACACCCTGCCCCCATCCCGGGAGGAGATGACCAAGAACCAGGTCAGCCTGACCTG

CCTGGTCAAAGGCTTCTACCCCAGCGACATCGCCGTGGAGTGGGAGAGCAATGGGCAGCCGG

AGAACAACTACAAGACCACACCTCCCATGCTGGACTCCGACGGCTCCTTCTTCCTCTACAGC

AAGCTCACCGTGGACAAGAGCAGGTGGCAGCAGGGGAACGTCTTCTCATGCTCCGTGATGCA

TGAGGCTCTGCACAACCACTACACGCAGAAGAGCCTCTCCCTGTCTCCGGGTAAATGA

SEQ ID NO: 36
EIQLQQSGVELVRPGASVTLSCKASGYTFTDYDMHWVKQTPVHGLEWIGTIDPETGGTAYNQ

KFKGKATLTADRSSTTAYMELSSLTSEDSAVYYCTSFYYTYSNYDVGFAYWGQGTLVTVSAA

STKGPSVFPLAPCSRSTSESTAALGCLVKDYFPEPVTVSWNSGALTSGVHTFPAVLQSSGLY

SLSSVVTVPSSNFGTQTYTCNVDHKPSNTKVDKTVERKCCVECPPCPAPPVAGPSVFLFPPK

PKDTLMISRTPEVTCVVVDVSHEDPEVQFNWYVDGVEVHNAKTKPREEQFNSTFRVVSVLTV

VHQDWLNGKEYKCKVSNKGLPAPIEKTISKTKGQPREPQVYTLPPSREEMTKNQVSLTCLVK

GFYPSDIAVEWESNGQPENNYKTTPPMLDSDGSFFLYSKLTVDKSRWQQGNVFSCSVMHEAL

HNHYTQKSLSLSPGK

SEQ ID NO: 37
GAAAATGTGCTCACCCAGTCTCCAGCAATCATGTCTGCATCTCCAGGGGAGAAGGTCACCAT

ATCCTGCAGTGCCAGCTCAAGTGTAAGTTACATGTACTGGTACCAGCAGAAGCCAGGATCCT

CCCCCAAACCCTGGATTTATCGCACATCCAACCTGGCTTCTGGAGTCCCTGCTCGCTTCAGT

GGCAGTGGGTCTGGGACCTCTTACTCTCTCACAATCAGCAGCATGGAGGCTGAAGATGCTGC

CACTTATTACTGCCAGCAGTGGAGTAGTAACCCACTCACGTTCGGTGCTGGGACCAAGCTGG

AGCTGAAA

SEQ ID NO: 38
ENVLTQSPAIMSASPGEKVTISCSASSSVSYMYWYQQKPGSSPKPWIYRTSNLASGVPARFS

GSGSGTSYSLTISSMEAEDAATYYCQQWSSNPLTFGAGTKLELK

SEQ ID NO: 39
GAGGTCCAGCTGCAACAATCTGGGACTGAGCTGGTGAGGCCTGGGTCCTCAGTGAAGATTTC

CTGCAAGGCTTCTGGCTACACCTTCACCAGGTACTGGATGGACTGGGTGAAGCAGAGGCCTG

GACAAGGCCTTGAGTGGATCGGAGAGATTGATCCTTCTGATAGTTATACTAACTACAATCAA

AAGTTCAAGGGCAAGGCCACATTGACTGTAGATAAATTCTCCAGAACAGCCTATATGGAACT

CAGCAGCCTGACATCTGAGGACTCTGCGGTCTATTACTGTGCAAGATCGGGGGCCTACTCTA

GTGACTATAGTTACGACGGGTTTGCTTACTGGGGCCAAGGGACTCTGGTCACTGTCTCTGCA

SEQ ID NO: 40
EVQLQQSGTELVRPGSSVKISCKASGYTFTRYWMDWVKQRPGQGLEWIGEIDPSDSYTNYNQ

KFKGKATLTVDKFSRTAYMELSSLTSEDSAVYYCARSGAYSSDYSYDGFAYWGQGTLVTVSA

SEQ ID NO: 41
GATATTGTGATGACCCAGGCTGCATTCTCCAATCCAGTCACTCTTGGAACATCAGCTTCCAT

CTCCTGCAGGTCTAGTAAGAGTCTCCTACATAGTAATGGCATCACTTATTTGTATTGGTATC

TGCAGAAGCCAGGCCAGTCTCCTCAGCTCCTGATTTATCAGATGTCCAACCTTGCCTCAGGA

```
GTCCCAGACAGGTTCAGTGGCAGTGGGTCAGGAACTGCTTTCACACTGAGAATCAGTAGAGT

GGAGGCTGAGGATGTGGGTGTTTATTACTGTATGCAACATCTAGAATATCCGTACACGTTCG

GAGGGGGGACCAAGCTGGAAATAAAA

SEQ ID NO: 42
DIVMTQAAFSNPVTLGTSASISCRSSKSLLHSNGITYLYWYLQKPGQSPQLLIYQMSNLASG

VPDRFSGSGSGTAFTLRISRVEAEDVGVYYCMQHLEYPYTFGGGTKLEIK

SEQ ID NO: 43
CAGGTCCAAGTGCAGCAGCCTGGGGCTGAAATTGTGAGGCCTGGGGCTTCAGTGAAGCTGTC

CTGCAAGGCTTCTGGCTACACCTTCACCAGCTACTGGATGCACTGGGTGAAGCAGAGGCCTG

GACAAGGCCTTGAGTGGATTGGACTGATTAATCCTACCAACGGTCGTACTAACTACAATGAG

AAGTTCAAGAGCAAGGCCACACTGACTGTAGACAAATCCTCCAGCACAGCCTACATGCAACT

CAGCAGCCTGACATCTGAGGACTCTGCGGTCTATTACTGTGCAAGAGGGGGGGACGGGGACT

ACTTTGACTACGGGGCCAAGGCACCACTCTCACAGTCTCCTCA

SEQ ID NO: 44
QVQVQQPGAEIVRPGASVKLSCKASGYTFTSYWMHWVKQRPGQGLEWIGLINPTNGRTNYNE

KFKSKATLTVDKSSSTAYMQLSSLTSEDSAVYYCARGGDGDYFDYWGQGTTLTVSS

SEQ ID NO: 45
GATATTGTGATGACCCAGGCTGCACCCTCTGTACCTGTCACTCCTGGAGAGTCAGTATCCAT

CTCCTGCAGGTCTACTAAGAGTCTCCTGCATAGTAATGGCAACACTTACTTGTATTGGTTCC

TGCAGAGGCCAGGCCAGTCTCCTCAGCTCCTGATATATCGGATGTCCAACCTTGCCTCAGGA

GTCCCAGACAGGTTCAGTGGCAGTGGGTCAGGAACTGCTTTCACACTGAGAATCAGTAGAGT

GGAGGCTGAGGATGTGGGTGTTTATTACTGTATGCAACATCTAGAATATCCTTTCACGTTCG

GAGGGGGGACCAAGCTGGAAATAAAA

SEQ ID NO: 46
DIVMTQAAPSVPVTPGESVSISCRSTKSLLHSNGNTYLYWFLQRPGQSPQLLIYRMSNLASG

VPDRFSGSGSGTAFTLRISRVEAEDVGVYYCMQHLEYPFTFGGGTKLEIK

SEQ ID NO: 47
GAGATCCAGCTGCAGCAGTCTGGAGTTGAGCTGGTGAGGCCTGGGGCTTCAGTGACGCTGTC

CTGCAAGGCTTCGGGCTACACATTTACTGACTATGACATGCACTGGGTGAAGCAGACACCTG

TTCATGGCCTGGAATGGATTGGAACTATTGATCCTGAAACTGGTGGTACTGCCTACAATCAG

AAGTTCAAGGGCAAGGCCACACTGACTGCGGACAGATCCTCCACCACAGCCTACATGGAGCT

CAGCAGCCTGACATCTGAGGACTCTGCCGTCTATTACTGTACAACTTTCTACTATAGTCACT

ATAATTACGACGTGGGGTTTGCTTACTGGGGCCAAGGGACTCTGGTCACTGTCTCTGCA

SEQ ID NO: 48
EIQLQQSGVELVRPGASVTLSCKASGYTFTDYDMHWVKQTPVHGLEWIGTIDPETGGTAYNQ

KFKGKATLTADRSSTTAYMELSSLTSEDSAVYYCTTFYYSHYNYDVGFAYWGQGTLVTVSA

SEQ ID NO: 49
GATATTGTGATGACCCAGGCTGCACCCTCTGTACCTGTCACTCCTGGAGAGTCAGTATCCAT

CTCCTGCAGGTCTAGTAAGAGTCTCCTGCATAGTAATGGCAACACTTACTTGTATTGGTTCC

TGCAGAGGCCAGGCCAGTCCCCTCAGCTCCTGATATATCGGATGTCCAACCTTGCCTCAGGA

GTCCCAGACAGGTTCAGTGGCAGTGGGTCAGGAACTGCTTTCACACTGAGAATCAGTAGAGT

GGAGGCTGAGGATGTGGGTGTTTATTACTGTATGCAACATCTAGAATATCCTTTCACGTTCG

GAGGGGGGACCAAGCTGGAAATAAAA
```

SEQUENCE LISTINGS

SEQ ID NO: 50
DIVMTQAAPSVPVTPGESVSISCRSSKSLLHSNGNTYLYWFLQRPGQSPQLLIYRMSNLASG

VPDRFSGSGSGTAFTLRISRVEAEDVGVYYCMQHLEYPFTFGGGTKLEIK

SEQ ID NO: 51
GAGATCCAGCTGCAGCAGTCTGGAGCTGAGCTGGTGAGGCCTGGGGCTTCAGTGACGCTGTC

CTGCAAGGCTTCGGGCTACACATTTACTGACTATGAAATGCACTGGGTGAAGCAGACACCTG

TTCATGGCCTGGAATGGATTGGAGCTATTGATCCTGAAACTGGTGGTACTGCCTACAATCAG

AAGTTCAAGGGCAAGGCCACACTGACTGCAGACAAATCCTCCAGCACAGCCTACATGGAGCT

CAGCAGCCTGACATCTGAGGACTCTGCCGTCTATTACTGTACAAGTTTCTACTATACTTACT

ATAATTACGACGTGGGGTTTGCTTACTGGGGCCAAGGGACTCTGGTCACTGTCTCTGCA

SEQ ID NO: 52
EIQLQQSGAELVRPGASVTLSCKASGYTFTDYEMHWVKQTPVHGLEWIGAIDPETGGTAYNQ

KFKGKATLTADKSSSTAYMELSSLTSEDSAVYYCTSFYYTYYNYDVGFAYWGQGTLVTVSA

SEQ ID NO: 53
GATATTGTGATGACCCAGGCTGCATTCTCCAATCCAGTCACTCTTGGAACATCAGCTTCCAT

CTCCTGCAGGTCTAGTAAGAGTCTCCTACATAGTAATGGCATCACTTATTTGTATTGGTATC

TGCAGAAGCCAGGCCAGTCTCCTCAGCTCCTGATTTATCAGATGTCCAACCTTGCCTCAGGA

GTCCCAGACAGGTTCAGTAGCAGTGGGTCAGGAACTGATTTCACACTGAGAATCAGCAGAGT

GGAGGCTGAGGATGTGGGTGTTTATTACTGTGCTCAAAATCTAGAACTTCCGTACACGTTCG

GAGGGGGGACCAAGCTGGAAATAAAA

SEQ ID NO: 54
DIVMTQAAFSNPVTLGTSASISCRSSKSLLHSNGITYLYWYLQKPGQSPQLLIYQMSNLASG

VPDRFSSSGSGTDFTLRISRVEAEDVGVYYCAQNLELPYTFGGGTKLEIK

SEQ ID NO: 55
CAGGTCCAAGTGCAGCAGCCTGGGGCTGAGCTTGTGAAGCCTGGGGCTTCGGTGAAGCTGTC

CTGCAAGGCTTCTGGCTACACCTTCACCAGCTACTGGATGCACTGGGTGAAGCAGAGGCCTG

GACAAGGCCTTGAGTGGATTGGACTGATTAATCCTAGCAACGCTCGTACTAACTACAATGAG

AAGTTCAATACCAAGGCCACACTGACTGTAGACAAATCCTCCAGCACAGCCTACATGCAACT

CAGCAGCCTGACATCTGAGGACTCTGCGGTCTATTACTGTGCAAGAGGGGGGGACGGGGACT

ACTTTGACTACTGGGGCCAAGGCACCACTCTCACAGTCTCCTCA

SEQ ID NO: 56
QVQVQQPGAELVKPGASVKLSCKASGYTFTSYWMHWVKQRPGQGLEWIGLINPSNARTNYNE

KFNTKATLTVDKSSSTAYMQLSSLTSEDSAVYYCARGGDGDYFDYWGQGTTLTVSS

SEQ ID NO: 57
CAAATTGTTCTCACCCAGTCTCCAACACTCATGTCTGCATCTCCAGGGGAGAAGGTCACCAT

GACCTGCAGTGCCAGCTCAAGTGTAAGTTACATGTACTGGTACCAGCAGAAGCCAAGATCCT

CCCCCAAACCCTGGATTTATCGCACATCCAACCTGGTTTCTGGAGTCCCTGTACGCTTCAGT

GGCAGTGGGTCTGGGACCTCTTACTCTCTCACAATCAGCAGCATGGAGGCTGAAGATGCTGC

CACTTATTACTGCCAGCAGTGGAGTAGTAACCCACCCACGTTCGGTGCTGGGACCAAGCTGG

AGCTGAAA

SEQ ID NO: 58
QIVLTQSPTLMSASPGEKVTMTCSASSSVSYMYWYQQKPRSSPKPWIYRTSNLVSGVPVRFS

GSGSGTSYSLTISSMEAEDAATYYCQQWSSNPPTFGAGTKLELK

-continued

SEQUENCE LISTINGS

SEQ ID NO: 59
GAAGTGAAGCTTGAGGAGTCTGGAGGTGGCCTGGTGCAGCCTGGAGGATCCCTGAAACTCTC

CTGTGCAGCCTCAGGATTCGATTTTAGTAAAGACTGGATGAGTTGGGTCCGGCAGGCTCCAG

GGAAAGGGCTAGAATGGATTGGAGAAATTAATCCAGATAGCAGTACGATAAACTATGCACCA

TCTCTTAAGGATAAATTCATCATCTCCAGAGAGAACGCCAAAAATACGCTGTACCTGCAAAT

GAGCAAAGTGAGATCTGAGGACACAGCCCTTTATTACTGTTCAAGACTAGAGGACTACGAAG

ACTGGTACTTCGATGTCTGGGGCGCAGGGACCACGGTCACCGTCTCCTCA

SEQ ID NO: 60
EVKLEESGGGLVQPGGSLKLSCAASGFDFSKDWMSWVRQAPGKGLEWIGEINPDSSTINYAP

SLKDKFIISRENAKNTLYLQMSKVRSEDTALYYCSRLEDYEDWYFDVWGAGTTVTVSS

SEQ ID NO: 61
AGTATTGTGATGACCCAGACTCCCAAATTCCTGCTTGTATCAGCAGGAGACAGGGTTACCAT

AACCTGCAAGGCCAGTCAGAGTGTGAGTAATGCTGTAGCTTGGTACCAACAGAAGCCAGGGC

AGTCTCCTAAACTGCTGATATACTATACATCCAATCGCTACACTGGAGTCCCTGATCGCTTC

ACTGGCAGTGGATATGGGACGGATTTCACTTTCACCATCACCACTGTGCAGGCTGAAGACCT

GGCAGTTTATTTCTGTCAGCAGGATTATACCTCTCCGTGGACGTTCGGTGGAGGCACCAAGC

TGGAAATCAAA

SEQ ID NO: 62
SIVMTQTPKFLLVSAGDRVTITCKASQSVSNAVAWYQQKPGQSPKLLIYYTSNRYTGVPDRF

TGSGYGTDFTFTITTVQAEDLAVYFCQQDYTSPWTFGGGTKLEIK

SEQ ID NO: 63
CAGGTCCAACTGCAGCAGCCTGGGGCTGAACTGGCGAAGCCTGGGGCTTCAGTGAAGTTGTC

CTGCAAGGCTTCTGGCTACACCTTCAACACCTATAATATGTACTGGTTGAAACAGAGGCCTG

GGCAAGGCCTTGAGTGGATTGGGGGGATTGATCCTAGCAATGGTGATACTAAAATCAATGAG

AAGTTCAAGAACAAGGCCACACTGACTGTTGACAAATCCTCCAGTACAGCCTATATGCAACT

CAGCGGCCTGACATCTGAGGACTCTGCGGTCTATTACTGTACAAGCCATACGTACTGGGGCC

AAGGGACTCTGGTCACTGTCTCTGCA

SEQ ID NO: 64
QVQLQQPGAELAKPGASVKLSCKASGYTFNTYNMYWLKQRPGQGLEWIGGIDPSNGDTKINE

KFKNKATLTVDKSSSTAYMQLSGLTSEDSAVYYCTSHTYWGQGTLVTVSA

SEQ ID NO: 65
GATATTGTGATGACCCAGGCTGCACCCTCTGTACCTGTCACTCCTGGAGAGTCAGTATCCAT

CTCCTGCAGGTCTACTAAGAGTCTCCTGCATAGTAATGGCAACACTTACTTGTATTGGTTCC

TGCAGAGGCCAGGCCAGTCTCCTCAGCTCCTGATATATCGGATGTCCAACCTTGCCTCAGGA

GTCCCAGACAGGTTCAGTGGCAGTGGGTCAGGAACTGCTTTCACACTGAGAATCAGTAGAGT

GGAGGCTGAGGATGTGGGTGTTTATTACTGTATGCAACATCTAGAATATCCTTTCACGTTCG

GAGGGGGGACCAAGCTGGAAATAAAA

SEQ ID NO: 66
DIVMTQAAPSVPVTPGESVSISCRSTKSLLHSNGNTYLYWFLQRPGQSPQLLIYRMSNLASG

VPDRFSGSGSGTAFTLRISRVEAEDVGVYYCMQHLEYPFTFGGGTKLEIK

SEQ ID NO: 67
GAGATCCAGCTGCAGCAGTCTGGAGTTGAGCTGGTGAGGCCTGGGGCTTCAGTGACGCTGTC

CTGCAAGGCTTCGGGCTACACATTTACTGACTATGACATGCACTGGGTGAAGCAGACACCTG

-continued

SEQUENCE LISTINGS

TTCATGGCCTGGAATGGATTGGAACTATTGATCCTGAAACTGGTGGTACTGCCTACAATCAG

AAGTTCAAGGGCAAGGCCACACTGACTGCGGACAGATCCTCCACCACAGCCTACATGGAGCT

CAGCAGCCTGACATCTGAGGACTCTGCCGTCTATTACTGTACAAGTTTCTACTATACTTACT

CTAATTACGACGTGGGGTTTGCTTACTGGGGCCAAGGGACTCTGGTCACTGTCTCTGCA

SEQ ID NO: 68
EIQLQQSGVELVRPGASVTLSCKASGYTFTDYDMHWVKQTPVHGLEWIGTIDPETGGTAYNQ
KFKGKATLTADRSSTTAYMELSSLTSEDSAVYYCTSFYYTYSNYDVGFAYWGQGTLVTVSA

SEQ ID NO: 69
SASSSVSYMY

SEQ ID NO: 70
RTSNLAS

SEQ ID NO: 71
QQWSSNPLT

SEQ ID NO: 72
GYTFTRYWMD

SEQ ID NO: 73
EIDPSDSYTN

SEQ ID NO: 74
ARSGAYSSDYSYDGFAY

SEQ ID NO: 75
RSSKSLLHSNGITYLY

SEQ ID NO: 76
QMSNLAS

SEQ ID NO: 77
MQHLEYPYT

SEQ ID NO: 78
GYTFTSYWMH

SEQ ID NO: 79
LINPTNGRTN

SEQ ID NO: 80
ARGGDGDYFDY

SEQ ID NO: 81
RSTKSLLHSNGNTYLY

SEQ ID NO: 82
RMSNLAS

SEQ ID NO: 83
MQHLEYPFT

SEQ ID NO: 84
GYTFTDYDMH

SEQ ID NO: 85
TIDPETGGTA

SEQ ID NO: 86
TTFYYSHYNYDVGFAY

SEQ ID NO: 87
RSSKSLLHSNGNTYLY

SEQ ID NO: 88
RMSNLAS

SEQ ID NO: 89
MQHLEYPFT

SEQ ID NO: 90
GYTFTDYEMH

-continued

SEQUENCE LISTINGS

SEQ ID NO: 91
AIDPETGGTA

SEQ ID NO: 92
TSFYYTYYNYDVGFAY

SEQ ID NO: 93
RSSKSLLHSNGITYLY

SEQ ID NO: 94
QMSNLAS

SEQ ID NO: 95
AQNLELPYT

SEQ ID NO: 96
GYTFTSYWMH

SEQ ID NO: 97
LINPSNARTN

SEQ ID NO: 98
ARGGDGDYFDY

SEQ ID NO: 99
SASSSVSYMY

SEQ ID NO: 100
RTSNLVS

SEQ ID NO: 101
QQWSSNPPT

SEQ ID NO: 102
GFDFSKDWMS

SEQ ID NO: 103
EINPDSSTIN

SEQ ID NO: 104
SRLEDYEDWYFDV

SEQ ID NO: 105
KASQSVSNAVA

SEQ ID NO: 106
YTSNRYT

SEQ ID NO: 107
QQDYTSPWT

SEQ ID NO: 108
GYTFNTYNMY

SEQ ID NO: 109
GIDPSNGDTK

SEQ ID NO: 110
TSHTY

SEQ ID NO: 111
RSTKSLLHSNGNTYLY

SEQ ID NO: 112
RMSNLAS

SEQ ID NO: 113
MQHLEYPFT

SEQ ID NO: 114
GYTFTDYDMH

SEQ ID NO: 115
TIDPETGGTA

SEQ ID NO: 116
TSFYYTYSNYDVGFAY

SEQUENCE LISTINGS

SEQ ID NO: 117
GTAAGCAAGCTTGCTCACGCCTTCCGCGCGCTC

SEQ ID NO: 118
GTAAGCAGATCTCTGGCGCCATGGAAGCGGAACAG

SEQ ID NO: 119
CACTGGGAGCTATGGAAGAAGAC

SEQ ID NO: 120
CAAAAGTGCAAAGAAGGGAAGACA

SEQ ID NO: 121
TGAAGGTCGGAGTCAACGGATTTGGT

SEQ ID NO: 122
CATGTGGGCCATGAGGTCCACCAC

SEQ ID NO: 123
VRTKIDTTENLLNTEVHSSPAQRWSMQVPPEVSAEAGDAAVLPCTFTHPHRHYDGPLTAIWR

AGEPYAGPQVFRCAAARGSELCQTALSLHGRFRLLGNPRRNDLSLRVERLALADDRRYFCRV

EFAGDVHDRYESRHGVRLHVTAAPRIVNISVLPSPAHAFRALCTAEGEPPPALAWSGPALGN

SLAAVRSPREGHGHLVTAELPALTHDGRYTCTAANSLGRSEASVYLFRFHGASGAS

SEQ ID NO: 124
GTAAGCGGATCCGTGAGAACTAAAATAGATACTA

SEQ ID NO: 125:
GTAAGCGCGGCCGCGCTGGCGCCATGGAAGCGGAACAGGTA

SEQ ID NO: 126
GTACATTTATATTGGCTCATGTCCAATATGACCGCCATGTTGACATTGATTATTGACTAGTTA

TTAATAGTAATCAATTACGGGGTCATTAGTTCATAGCCCATATATGGAGTTCCGCGTTACATA

ACTTACGGTAAATGGCCCGCCTGGCTGACCGCCCAACGACCCCCGCCCATTGACGTCAATAAT

GACGTATGTTCCCATAGTAACGCCAATAGGGACTTTCCATTGACGTCAATGGGTGGAGTATTT

ACGGTAAACTGCCCACTTGGCAGTACATCAAGTGTATCATATGCCAAGTCCGCCCCCTATTGA

CGTCAATGACGGTAAATGGCCCGCCTGGCATTATGCCCAGTACATGACCTTACGGGACTTTCC

TACTTGGCAGTACATCTACGTATTAGTCATCGCTATTACCATGGTGATGCGGTTTTGGCAGTA

CACCAATGGGCGTGGATAGCGGTTTGACTCACGGGGATTTCCAAGTCTCCACCCCATTGACGT

CAATGGGAGTTTGTTTTGGCACCAAAATCAACGGGACTTTCCAAAATGTCGTAATAACCCCGC

CCCGTTGACGCAAATGGGCGGTAGGCGTGTACGGTGGGAGGTCTATATAAGCAGAGCTCGTTT

AGTGAACCGTCAGATCCTCACTCTCTTCCGCATCGCTGTCTGCGAGGGCCAGCTGTTGGGCTC

GCGGTTGAGGACAAACTCTTCGCGGTCTTTCCAGTACTCTTGGATCGGAAACCCGTCGGCCTC

CGAACGGTACTCCGCCACCGAGGGACCTGAGCCAGTCCGCATCGACCGGATCGGAAAACCTCT

CGAGAAAGGCGTCTAACCAGTCACAGTCGCAAGGTAGGCTGAGCACCGTGGCGGGCGGCAGCG

GGTGGCGGTCGGGGTTGTTTCTGGCGGAGGTGCTGCTGATGATGTAATTAAAGTAGGCGGTCT

TGAGCCGGCGGATGGTCGAGGTGAGGTGTGGCAGGCTTGAGATCCAGCTGTTGGGGTGAGTAC

TCCCTCTCAAAAGCGGGCATGACTTCTGCGCTAAGATTGTCAGTTTCCAAAAACGAGGAGGAT

TTGATATTCACCTGGCCCGATCTGGCCATACACTTGAGTGACAATGACATCCACTTTGCCTTT

CTCTCCACAGGTGTCCACTCCCAGGTCCAAGTTTGCCGCCACCATGGAGACAGACACACTCCT

GCTATGGGTACTGCTGCTCTGGGTTCCAGGTTCCACTGGCGCCGGATCAACTCACACATGCCC

ACCGTGCCCAGCACCTGAACTCCTGGGGGGACCGTCAGTCTTCCTCTTCCCCCCAAAACCCAA

GGACACCCTCATGATCTCCCGGACCCCTGAGGTCACATGCGTGGTGGTGGACGTGAGCCACGA

-continued

SEQUENCE LISTINGS

AGACCCTGAGGTCAAGTTCAACTGGTACGTGGACGGCGTGGAGGTGCATAATGCCAAGACAAA

GCCGCGGGAGGAGCAGTACAACAGCACGTACCGTGTGGTCAGCGTCCTCACCGTCCTGCACCA

GGACTGGCTGAATGGCAAGGAGTACAAGTGCAAGGTCTCCAACAAAGCCCTCCCAGCCCCCAT

CGAGAAAACCATCTCCAAAGCCAAAGGGCAGCCCCGAGAACCACAGGTGTACACCCTGCCCCC

ATCCCGGGATGAGCTGACCAAGAACCAGGTCAGCCTGACCTGCCTGGTCAAAGGCTTCTATCC

CAGCGACATCGCCGTGGAGTGGGAGAGCAATGGGCAGCCGGAGAACAACTACAAGACCACGCC

TCCCGTGTTGGACTCCGACGGCTCCTTCTTCCTCTACAGCAAGCTCACCGTGGACAAGAGCAG

GTGGCAGCAGGGGAACGTCTTCTCATGCTCCGTGATGCATGAGGCTCTGCACAACCACTACAC

GCAGAAGAGCCTCTCCCTGTCTCCCGGGAAAGCTAGCGGAGCCGGAAGCACAACCGAAAACCT

GTATTTTCAGGGCGGATCCGAATTCAAGCTTGATATCTGATCCCCCGACCTCGACCTCTGGCT

AATAAAGGAAATTTATTTTCATTGCAATAGTGTGTTGGAATTTTTTGTGTCTCTCACTCGGAA

GGACATATGGGAGGGCAAATCATTTGGTCGAGATCCCTCGGAGATCTCTAGCTAGAGCCCCGC

CGCCGGACGAACTAAACCTGACTACGGCATCTCTGCCCCTTCTTCGCGGGGCAGTGCATGTAA

TCCCTTCAGTTGGTTGGTACAACTTGCCAACTGAACCCTAAACGGGTAGCATATGCTTCCCGG

GTAGTAGTATATACTATCCAGACTAACCCTAATTCAATAGCATATGTTACCCAACGGGAAGCA

TATGCTATCGAATTAGGGTTAGTAAAAGGGTCCTAAGGAACAGCGATGTAGGTGGGCGGGCCA

AGATAGGGGCGCGATTGCTGCGATCTGGAGGACAAATTACACACACTTGCGCCTGAGCGCCAA

GCACAGGGTTGTTGGTCCTCATATTCACGAGGTCGCTGAGAGCACGGTGGGCTAATGTTGCCA

TGGGTAGCATATACTACCCAAATATCTGGATAGCATATGCTATCCTAATCTATATCTGGGTAG

CATAGGCTATCCTAATCTATATCTGGGTAGCATATGCTATCCTAATCTATATCTGGGTAGTAT

ATGCTATCCTAATTTATATCTGGGTAGCATAGGCTATCCTAATCTATATCTGGGTAGCATATG

CTATCCTAATCTATATCTGGGTAGTATATGCTATCCTAATCTGTATCCGGGTAGCATATGCTA

TCCTAATAGAGATTAGGGTAGTATATGCTATCCTAATTTATATCTGGGTAGCATATACTACCC

AAATATCTGGATAGCATATGCTATCCTAATCTATATCTGGGTAGCATATGCTATCCTAATCTA

TATCTGGGTAGCATAGGCTATCCTAATCTATATCTGGGTAGCATATGCTATCCTAATCTATAT

CTGGGTAGTATATGCTATCCTAATTTATATCTGGGTAGCATAGGCTATCCTAATCTATATCTG

GGTAGCATATGCTATCCTAATCTATATCTGGGTAGTATATGCTATCCTAATCTGTATCCGGGT

AGCATATGCTATCCTCACGATGATAAGCTGTCAAACATGAGAATTAATTCTTGAAGACGAAAG

GGCCTCGTGATACGCCTATTTTTATAGGTTAATGTCATGATAATAATGGTTTCTTAGACGTCA

GGTGGCACTTTTCGGGGAAATGTGCGCGGAACCCCTATTTGTTTATTTTTCTAAATACATTCA

AATATGTATCCGCTCATGAGACAATAACCCTGATAAATGCTTCAATAATATTGAAAAGGAAG

AGTATGAGTATTCAACATTTCCGTGTCGCCCTTATTCCCTTTTTTGCGGCATTTTGCCTTCCT

GTTTTTGCTCACCCAGAAACGCTGGTGAAAGTAAAAGATGCTGAAGATCAGTTGGGTGCACGA

GTGGGTTACATCGAACTGGATCTCAACAGCGGTAAGATCCTTGAGAGTTTTCGCCCCGAAGAA

CGTTTTCCAATGATGAGCACTTTTAAAGTTCTGCTATGTGGCGCGGTATTATCCCGTGTTGAC

GCCGGGCAAGAGCAACTCGGTCGCCGCATACACTATTCTCAGAATGACTTGGTTGAGTACTCA

CCAGTCACAGAAAAGCATCTTACGGATGGCATGACAGTAAGAGAATTATGCAGTGCTGCCATA

ACCATGAGTGATAACACTGCGGCCAACTTACTTCTGACAACGATCGGAGGACCGAAGGAGCTA

ACCGCTTTTTTGCACAACATGGGGGATCATGTAACTCGCCTTGATCGTTGGGAACCGGAGCTG

-continued

SEQUENCE LISTINGS

AATGAAGCCATACCAAACGACGAGCGTGACACCACGATGCCTGCAGCAATGGCAACAACGTTG

CGCAAACTATTAACTGGCGAACTACTTACTCTAGCTTCCCGGCAACAATTAATAGACTGGATG

GAGGCGGATAAAGTTGCAGGACCACTTCTGCGCTCGGCCCTTCCGGCTGGCTGGTTTATTGCT

GATAAATCTGGAGCCGGTGAGCGTGGGTCTCGCGGTATCATTGCAGCACTGGGGCCAGATGGT

AAGCCCTCCCGTATCGTAGTTATCTACACGACGGGGAGTCAGGCAACTATGGATGAACGAAAT

AGACAGATCGCTGAGATAGGTGCCTCACTGATTAAGCATTGGTAACTGTCAGACCAAGTTTAC

TCATATATACTTTAGATTGATTTAAAACTTCATTTTTAATTTAAAAGGATCTAGGTGAAGATC

CTTTTTGATAATCTCATGACCAAAATCCCTTAACGTGAGTTTTCGTTCCACTGAGCGTCAGAC

CCCGTAGAAAAGATCAAAGGATCTTCTTGAGATCCTTTTTTTCTGCGCGTAATCTGCTGCTTG

CAAACAAAAAAACCACCGCTACCAGCGGTGGTTTGTTTGCCGGATCAAGAGCTACCAACTCTT

TTTCCGAAGGTAACTGGCTTCAGCAGAGCGCAGATACCAAATACTGTCCTTCTAGTGTAGCCG

TAGTTAGGCCACCACTTCAAGAACTCTGTAGCACCGCCTACATACCTCGCTCTGCTAATCCTG

TTACCAGTGGCTGCTGCCAGTGGCGATAAGTCGTGTCTTACCGGGTTGGACTCAAGACGATAG

TTACCGGATAAGGCGCAGCGGTCGGGCTGAACGGGGGGTTCGTGCACACAGCCCAGCTTGGAG

CGAACGACCTACACCGAACTGAGATACCTACAGCGTGAGCATTGAGAAAGCGCCACGCTTCCC

GAAGGGAGAAAGGCGGACAGGTATCCGGTAAGCGGCAGGGTCGGAACAGGAGAGCGCACGAGG

GAGCTTCCAGGGGGAAACGCCTGGTATCTTTATAGTCCTGTCGGGTTTCGCCACCTCTGACTT

GAGCGTCGATTTTTGTGATGCTCGTCAGGGGGCGGAGCCTATGGAAAAACGCCAGCAACGCG

GCCTTTTTACGGTTCCTGGCCTTTTGCTGGCCTTTTGCTCACATGTTCTTTCCTGCGTTATCC

CCTGATTCTGTGGATAACCGTATTACCGCCTTTGAGTGAGCTGATACCGCTCGCCGCAGCCGA

ACGACCGAGCGCAGCGAGTCAGTGAGCGAGGAAGC

SEQ ID NO: 127
GTAAGCGCTAGCGCCTCAACGAAGGGCCCATCTGTCTTTCCCCTGGCCCC

SEQ ID NO: 128
GTAAGCGAATTCACAAGATTTGGGCTCAACTTTCTTG

SEQ ID NO: 129
GCTGTGGCTGCACCATCTGTCTTCATCTTCCCGCCATCTGATGAGCAGTTGAAATCTGGAAC

TGCCTCTGTTGTGTGCCTGCTGAATAACTTCTATCCCAGAGAGGCCAAAGTACAGTGGAAGG

TGGATAACGCCCTCCAATCGGGTAACTCCCAGGAGAGTGTCACAGAGCAGGACAGCAAGGAC

AGCACCTACAGCCTCAGCAGCACCCTGACGCTGAGCAAAGCAGACTACGAGAAACACAAAGT

CTACGCCTGCGAAGTCACCCATCAGGGCCTGAGCTCGCCCGTCACAAAGAGCTTCAACAGGG

GAGAGTGTTAG

SEQ ID NO: 130
AVAAPSVFIFPPSDEQLKSGTASVVCLLNNFYPREAKVQWKVDNALQSGNSQESVTEQDSKD

STYSLSSTLTLSKADYEKHKVYACEVTHQGLSSPVTKSFNRGEC

SEQ ID NO: 131
CTTGAGCCGGCGGATGGTCGAGGTGAGGTGTGGCAGGCTTGAGATCCAGCTGTTGGGGTGAG

TACTCCCTCTCAAAAGCGGGCATTACTTCTGCGCTAAGATTGTCAGTTTCCAAAAACGAGGA

GGATTTGATATTCACCTGGCCCGATCTGGCCATACACTTGAGTGACAATGACATCCACTTTG

CCTTTCTCTCCACAGGTGTCCACTCCCAGGTCCAAGTTTAAACGGATCTCTAGCGAATTCAT

GAACTTTCTGCTGTCTTGGGTGCATTGGAGCCTTGCCTTGCTGCTCTACCTCCACCATGCCA

-continued

SEQUENCE LISTINGS

AGTGGTCCCAGGCTTGAGACGGAGCTTACAGCGCTGTGGCTGCACCATCTGTCTTCATCTTC

CCGCCATCTGATGAGCAGTTGAAATCTGGAACTGCCTCTGTTGTGTGCCTGCTGAATAACTT

CTATCCCAGAGAGGCCAAAGTACAGTGGAAGGTGGATAACGCCCTCCAATCGGGTAACTCCC

AGGAGAGTGTCACAGAGCAGGACAGCAAGGACAGCACCTACAGCCTCAGCAGCACCCTGACG

CTGAGCAAAGCAGACTACGAGAAACACAAAGTCTACGCCTGCGAAGTCACCCATCAGGGCCT

GAGCTCGCCCGTCACAAAGAGCTTCAACAGGGGAGAGTGTTAGGGTACCGCGGCCGCTTCGA

ATGAGATCCCCCGACCTCGACCTCTGGCTAATAAAGGAAATTTATTTTCATTGCAATAGTGT

GTTGGAATTTTTTGTGTCTCTCACTCGGAAGGACATATGGGAGGGCAAATCATTTGGTCGAG

ATCCCTCGGAGATCTCTAGCTAGAGCCCCGCCGCCGGACGAACTAAACCTGACTACGGCATC

TCTGCCCCTTCTTCGCGGGGCAGTGCATGTAATCCCTTCAGTTGGTTGGTACAACTTGCCAA

CTGGGCCCTGTTCCACATGTGACACGGGGGGGACCAAACACAAAGGGGTTCTCTGACTGTA

GTTGACATCCTTATAAATGGATGTGCACATTTGCCAACACTGAGTGGCTTTCATCCTGGAGC

AGACTTTGCAGTCTGTGGACTGCAACACAACATTGCCTTTATGTGTAACTCTTGGCTGAAGC

TCTTACACCAATGCTGGGGACATGTACCTCCCAGGGGCCCAGGAAGACTACGGGAGGCTAC

ACCAACGTCAATCAGAGGGGCCTGTGTAGCTACCGATAAGCGGACCCTCAAGAGGGCATTAG

CAATAGTGTTTATAAGGCCCCCTTGTTAACCCTAAACGGGTAGCATATGCTTCCCGGGTAGT

AGTATATACTATCCAGACTAACCCTAATTCAATAGCATATGTTACCCAACGGGAAGCATATG

CTATCGAATTAGGGTTAGTAAAAGGGTCCTAAGGAACAGCGATATCTCCCACCCCATGAGCT

GTCACGGTTTTATTTACATGGGGTCAGGATTCCACGAGGGTAGTGAACCATTTTAGTCACAA

GGGCAGTGGCTGAAGATCAAGGAGCGGGCAGTGAACTCTCCTGAATCTTCGCCTGCTTCTTC

ATTCTCCTTCGTTTAGCTAATAGAATAACTGCTGAGTTGTGAACAGTAAGGTGTATGTGAGG

TGCTCGAAAACAAGGTTTCAGGTGACGCCCCCAGAATAAAATTTGGACGGGGGGTTCAGTGG

TGGCATTGTGCTATGACACCAATATAACCCTCACAAACCCCTTGGGCAATAAATACTAGTGT

AGGAATGAAACATTCTGAATATCTTTAACAATAGAAATCCATGGGGTGGGGACAAGCCGTAA

AGACTGGATGTCCATCTCACACGAATTTATGGCTATGGGCAACACATAATCCTAGTGCAATA

TGATACTGGGGTTATTAAGATGTGTCCCAGGCAGGGACCAAGACAGGTGAACCATGTTGTTA

CACTCTATTTGTAACAAGGGGAAAGAGAGTGGACGCCGACAGCAGCGGACTCCACTGGTTGT

CTCTAACACCCCCGAAAATTAAACGGGGCTCCACGCCAATGGGGCCCATAAACAAAGACAAG

TGGCCACTCTTTTTTTTGAAATTGTGGAGTGGGGGCACGCGTCAGCCCCCACACGCCGCCCT

GCGGTTTTGGACTGTAAAATAAGGGTGTAATAACTTGGCTGATTGTAACCCCGCTAACCACT

GCGGTCAAACCACTTGCCCACAAAACCACTAATGGCACCCCGGGGAATACCTGCATAAGTAG

GTGGGCGGGCCAAGATAGGGCGCGATTGCTGCGATCTGGAGGACAAATTACACACACTTGC

GCCTGAGCGCCAAGCACAGGGTTGTTGGTCCTCATATTCACGAGGTCGCTGAGAGCACGGTG

GGCTAATGTTGCCATGGGTAGCATATACTACCCAAATATCTGGATAGCATATGCTATCCTAA

TCTATATCTGGGTAGCATAGGCTATCCTAATCTATATCTGGGTAGCATATGCTATCCTAATC

TATATCTGGGTAGTATATGCTATCCTAATTTATATCTGGGTAGCATAGGCTATCCTAATCTA

TATCTGGGTAGCATATGCTATCCTAATCTATATCTGGGTAGTATATGCTATCCTAATCTGTA

TCCGGGTAGCATATGCTATCCTAATAGAGATTAGGGTAGTATATGCTATCCTAATTTATATC

TGGGTAGCATATACTACCCAAATATCTGGATAGCATATGCTATCCTAATCTATATCTGGGTA

SEQUENCE LISTINGS

```
GCATATGCTATCCTAATCTATATCTGGGTAGCATAGGCTATCCTAATCTATATCTGGGTAGC
ATATGCTATCCTAATCTATATCTGGGTAGTATATGCTATCCTAATTTATATCTGGGTAGCAT
AGGCTATCCTAATCTATATCTGGGTAGCATATGCTATCCTAATCTATATCTGGGTAGTATAT
GCTATCCTAATCTGTATCCGGGTAGCATATGCTATCCTCACGATGATAAGCTGTCAAACATG
AGAATTAATTCTTGAAGACGAAAGGGCCTCGTGATACGCCTATTTTTATAGGTTAATGTCAT
GATAATAATGGTTTCTTAGACGTCAGGTGGCACTTTTCGGGGAAATGTGCGCGGAACCCCTA
TTTGTTTATTTTTCTAAATACATTCAAATATGTATCCGCTCATGAGACAATAACCCTGATAA
ATGCTTCAATAATATTGAAAAAGGAAGAGTATGAGTATTCAACATTTCCGTGTCGCCCTTAT
TCCCTTTTTTGCGGCATTTTGCCTTCCTGTTTTTGCTCACCCAGAAACGCTGGTGAAAGTAA
AAGATGCTGAAGATCAGTTGGGTGCACGAGTGGGTTACATCGAACTGGATCTCAACAGCGGT
AAGATCCTTGAGAGTTTTCGCCCCGAAGAACGTTTTCCAATGATGAGCACTTTTAAAGTTCT
GCTATGTGGCGCGGTATTATCCCGTGTTGACGCCGGGCAAGAGCAACTCGGTCGCCGCATAC
ACTATTCTCAGAATGACTTGGTTGAGTACTCACCAGTCACAGAAAAGCATCTTACGGATGGC
ATGACAGTAAGAGAATTATGCAGTGCTGCCATAACCATGAGTGATAACACTGCGGCCAACTT
ACTTCTGACAACGATCGGAGGACCGAAGGAGCTAACCGCTTTTTTGCACAACATGGGGGATC
ATGTAACTCGCCTTGATCGTTGGGAACCGGAGCTGAATGAAGCCATACCAAACGACGAGCGT
GACACCACGATGCCTGCAGCAATGGCAACAACGTTGCGCAAACTATTAACTGGCGAACTACT
TACTCTAGCTTCCCGGCAACAATTAATAGACTGGATGGAGGCGGATAAAGTTGCAGGACCAC
TTCTGCGCTCGGCCCTTCCGGCTGGCTGGTTTATTGCTGATAAATCTGGAGCCGGTGAGCGT
GGGTCTCGCGGTATCATTGCAGCACTGGGGCCAGATGGTAAGCCCTCCCGTATCGTAGTTAT
CTACACGACGGGGAGTCAGGCAACTATGGATGAACGAAATAGACAGATCGCTGAGATAGGTG
CCTCACTGATTAAGCATTGGTAACTGTCAGACCAAGTTTACTCATATATACTTTAGATTGAT
TTAAAACTTCATTTTTAATTTAAAAGGATCTAGGTGAAGATCCTTTTTGATAATCTCATGAC
CAAAATCCCTTAACGTGAGTTTTCGTTCCACTGAGCGTCAGACCCCGTAGAAAAGATCAAAG
GATCTTCTTGAGATCCTTTTTTTCTGCGCGTAATCTGCTGCTTGCAAACAAAAAAACCACCG
CTACCAGCGGTGGTTTGTTTGCCGGATCAAGAGCTACCAACTCTTTTTCCGAAGGTAACTGG
CTTCAGCAGAGCGCAGATACCAAATACTGTCCTTCTAGTGTAGCCGTAGTTAGGCCACCACT
TCAAGAACTCTGTAGCACCGCCTACATACCTCGCTCTGCTAATCCTGTTACCAGTGGCTGCT
GCCAGTGGCGATAAGTCGTGTCTTACCGGGTTGGACTCAAGACGATAGTTACCGGATAAGGC
GCAGCGGTCGGGCTGAACGGGGGGTTCGTGCACACAGCCCAGCTTGGAGCGAACGACCTACA
CCGAACTGAGATACCTACAGCGTGAGCATTGAGAAAGCGCCACGCTTCCCGAAGGGAGAAAG
GCGGACAGGTATCCGGTAAGCGGCAGGGTCGGAACAGGAGAGCGCACGAGGGAGCTTCCAGG
GGGAAACGCCTGGTATCTTTATAGTCCTGTCGGGTTTCGCCACCTCTGACTTGAGCGTCGAT
TTTTGTGATGCTCGTCAGGGGGCGGAGCCTATGGAAAAACGCCAGCAACGCGGCCTTTTTA
CGGTTCCTGGCCTTTTGCTGGCCTTTTGCTCACATGTTCTTTCCTGCGTTATCCCCTGATTC
TGTGGATAACCGTATTACCGCCTTTGAGTGAGCTGATACCGCTCGCCGCAGCCGAACGACCG
AGCGCAGCGAGTCAGTGAGCGAGGAAGCGGAAGAGCGCCCAATACGCAAACCGCCTCTCCCC
GCGCGTTGGCCGATTCATTAATGCAGCTGGCACGACAGGTTTCCCGACTGGAAAGCGGGCAG
TGAGCGCAACGCAATTAATGTGAGTTAGCTCACTCATTAGGCACCCCAGGCTTTACACTTTA
```

TGCTTCCGGCTCGTATGTTGTGTGGAATTGTGAGCGGATAACAATTTCACACAGGAAACAGC

TATGACCATGATTACGCCAAGCTCTAGCTAGAGGTCGACCAATTCTCATGTTTGACAGCTTA

TCATCGCAGATCCGGGCAACGTTGTTGCATTGCTGCAGGCGCAGAACTGGTAGGTATGGCAG

ATCTATACATTGAATCAATATTGGCAATTAGCCATATTAGTCATTGGTTATATAGCATAAAT

CAATATTGGCTATTGGCCATTGCATACGTTGTATCTATATCATAATATGTACATTTATATTG

GCTCATGTCCAATATGACCGCCATGTTGACATTGATTATTGACTAGTTATTAATAGTAATCA

ATTACGGGGTCATTAGTTCATAGCCCATATATGGAGTTCCGCGTTACATAACTTACGGTAAA

TGGCCCGCCTGGCTGACCGCCCAACGACCCCCGCCCATTGACGTCAATAATGACGTATGTTC

CCATAGTAACGCCAATAGGGACTTTCCATTGACGTCAATGGGTGGAGTATTTACGGTAAACT

GCCCACTTGGCAGTACATCAAGTGTATCATATGCCAAGTCCGCCCCCTATTGACGTCAATGA

CGGTAAATGGCCCGCCTGGCATTATGCCCAGTACATGACCTTACGGGACTTTCCTACTTGGC

AGTACATCTACGTATTAGTCATCGCTATTACCATGGTGATGCGGTTTTGGCAGTACACCAAT

GGGCGTGGATAGCGGTTTGACTCACGGGGATTTCCAAGTCTCCACCCCATTGACGTCAATGG

GAGTTTGTTTTGGCACCAAAATCAACGGGACTTTCCAAAATGTCGTAATAACCCCGCCCCGT

TGACGCAAATGGGCGGTAGGCGTGTACGGTGGGAGGTCTATATAAGCAGAGCTCGTTTAGTG

AACCGTCAGATCCTCACTCTCTTCCGCATCGCTGTCTGCGAGGGCCAGCTGTTGGGCTCGCG

GTTGAGGACAAACTCTTCGCGGTCTTTCCAGTACTCTTGGATCGGAAACCCGTCGGCCTCCG

AACGGTACTCCGCCACCGAGGGACCTGAGCGAGTCCGCATCGACCGGATCGGAAAACCTCTC

GAGAAAGGCGTCTAACCAGTCACAGTCGCAAGGTAGGCTGAGCACCGTGGCGGGCGGCAGCG

GGTGGCGGTCGGGGTTGTTTCTGGCGGAGGTGCTGCTGATGATGTAATTAAAGTAGGCGGT

SEQ ID NO: 132
ATGCCAAGTGGTCCCAGGCTGAAAATGTGCTCACCCAGTCTCC

SEQ ID NO: 133
ATGCCAAGTGGTCCCAGGCTGATATTGTGATGACCCAGGCTGC

SEQ ID NO: 134
ATGCCAAGTGGTCCCAGGCTCAAATTGTTCTCACCCAGTCTCC

SEQ ID NO: 135
ATGCCAAGTGGTCCCAGGCTAGTATTGTGATGACCCAGACTCC

SEQ ID NO: 136
GGGAAGATGAAGACAGATGGTGCAGCCACAGC

SEQ ID NO: 137
GTAAGCGCTAGCGCCTCAACGAAGGGCCCATCTGTCTTTCCCCTGGCCCC

SEQ ID NO: 138
GTAAGCGAATTCACAAGATTTGGGCTCAACTTTCTTG

SEQ ID NO: 139
GCCTCCACCAAGGGCCCATCGGTCTTCCCCCTGGCACCCTCCTCCAAGAGCACCTCTGGGGG

CACAGCAGCCCTGGGCTGCCTGGTCAAGGACTACTTCCCCGAACCGGTGACGGTGTCGTGGA

ACTCAGGCGCCCTGACCAGCGGCGTGCACACCTTCCCGGCTGTCCTACAGTCCTCAGGACTC

TACTCCCTCAGCAGCGTGGTGACCGTGCCCTCCAGCAGCTTGGGCACCCAGACCTACATCTG

CAACGTGAATCACAAGCCCAGCAACACCAAGGTGGACAAGAAAGTTGAGCCCAAATCTTGT

SEQ ID NO: 140
ASTKGPSVFPLAPSSKSTSGGTAALGCLVKDYFPEPVTVSWNSGALTSGVHTFPAVLQSSGL

YSLSSVVTVPSSSLGTQTYICNVNHKPSNTKVDKKVEPKSC

-continued

SEQUENCE LISTINGS

SEQ ID NO: 141
CTTGAGCCGGCGGATGGTCGAGGTGAGGTGTGGCAGGCTTGAGATCCAGCTGTTGGGGTGAG

TACTCCCTCTCAAAAGCGGGCATTACTTCTGCGCTAAGATTGTCAGTTTCCAAAAACGAGGA

GGATTTGATATTCACCTGGCCCGATCTGGCCATACACTTGAGTGACAATGACATCCACTTTG

CCTTTCTCTCCACAGGTGTCCACTCCCAGGTCCAAGTTTGCCGCCACCATGGAGACAGACAC

ACTCCTGCTATGGGTACTGCTGCTCTGGGTTCCAGGTTCCACTGGCGGAGACGGAGCTTACG

GGCCCATCGGTCTTCCCCCTGGCGCCCTGCTCCAGGAGCACCTCCGAGAGCACAGCGGCCCT

GGGCTGCCTGGTCAAGGACTACTTCCCCGAACCGGTGACGGTGTCGTGGAACTCAGGCGCTC

TGACCAGCGGCGTGCACACCTTCCCAGCTGTCCTACAGTCCTCAGGACTCTACTCCCTCAGC

AGCGTGGTGACCGTGCCCTCCAGCAACTTCGGCACCCAGACCTACACCTGCAACGTAGATCA

CAAGCCCAGCAACACCAAGGTGGACAAGACAGTTGAGCGCAAATGTTGTGTCGAGTGCCCAC

CGTGCCCAGCACCACCTGTGGCAGGACCGTCAGTCTTCCTCTTCCCCCCAAAACCCAAGGAC

ACCCTCATGATCTCCCGGACCCCTGAGGTCACGTGCGTGGTGGTGGACGTGAGCCACGAAGA

CCCCGAGGTCCAGTTCAACTGGTACGTGGACGGCGTGGAGGTGCATAATGCCAAGACAAAGC

CACGGGAGGAGCAGTTCAACAGCACGTTCCGTGTGGTCAGCGTCCTCACCGTTGTGCACCAG

GACTGGCTGAACGGCAAGGAGTACAAGTGCAAGGTCTCCAACAAAGGCCTCCCAGCCCCCAT

CGAGAAAACCATCTCCAAAACCAAAGGGCAGCCCCGAGAACCACAGGTGTACACCCTGCCCC

CATCCCGGGAGGAGATGACCAAGAACCAGGTCAGCCTGACCTGCCTGGTCAAAGGCTTCTAC

CCCAGCGACATCGCCGTGGAGTGGGAGAGCAATGGGCAGCCGGAGAACAACTACAAGACCAC

ACCTCCCATGCTGGACTCCGACGGCTCCTTCTTCCTCTACAGCAAGCTCACCGTGGACAAGA

GCAGGTGGCAGCAGGGGAACGTCTTCTCATGCTCCGTGATGCATGAGGCTCTGCACAACCAC

TACACGCAGAAGAGCCTCTCCCTGTCTCCCGGGAAATGATCCCCCGACCTCGACCTCTGGCT

AATAAAGGAAATTTATTTTCATTGCAATAGTGTGTTGGAATTTTTTGTGTCTCTCACTCGGA

AGGACATATGGGAGGGCAAATCATTTGGTCGAGATCCCTCGGAGATCTCTAGCTAGAGCCCC

GCCGCCGGACGAACTAAACCTGACTACGGCATCTCTGCCCCTTCTTCGCGGGGCAGTGCATG

TAATCCCTTCAGTTGGTTGGTACAACTTGCCAACTGAACCCTAAACGGGTAGCATATGCTTC

CCGGGTAGTAGTATATACTATCCAGACTAACCCTAATTCAATAGCATATGTTACCCAACGGG

AAGCATATGCTATCGAATTAGGGTTAGTAAAAGGGTCCTAAGGAACAGCGATGTAGGTGGGC

GGGCCAAGATAGGGGCGCGATTGCTGCGATCTGGAGGACAAATTACACACACTTGCGCCTGA

GCGCCAAGCACAGGGTTGTTGGTCCTCATATTCACGAGGTCGCTGAGAGCACGGTGGGCTAA

TGTTGCCATGGGTAGCATATACTACCCAAATATCTGGATAGCATATGCTATCCTAATCTATA

TCTGGGTAGCATAGGCTATCCTAATCTATATCTGGGTAGCATATGCTATCCTAATCTATATC

TGGGTAGTATATGCTATCCTAATTTATATCTGGGTAGCATAGGCTATCCTAATCTATATCTG

GGTAGCATATGCTATCCTAATCTATATCTGGGTAGTATATGCTATCCTAATCTGTATCCGGG

TAGCATATGCTATCCTAATAGAGATTAGGGTAGTATATGCTATCCTAATTTATATCTGGGTA

GCATATACTACCCAAATATCTGGATAGCATATGCTATCCTAATCTATATCTGGGTAGCATAT

GCTATCCTAATCTATATCTGGGTAGCATAGGCTATCCTAATCTATATCTGGGTAGCATATGC

TATCCTAATCTATATCTGGGTAGTATATGCTATCCTAATTTATATCTGGGTAGCATAGGCTA

TCCTAATCTATATCTGGGTAGCATATGCTATCCTAATCTATATCTGGGTAGTATATGCTATC

-continued

SEQUENCE LISTINGS

CTAATCTGTATCCGGGTAGCATATGCTATCCTCACGATGATAAGCTGTCAAACATGAGAATT

AATTCTTGAAGACGAAAGGGCCTCGTGATACGCCTATTTTTATAGGTTAATGTCATGATAAT

AATGGTTTCTTAGACGTCAGGTGGCACTTTTCGGGGAAATGTGCGCGGAACCCCTATTTGTT

TATTTTTCTAAATACATTCAAATATGTATCCGCTCATGAGACAATAACCCTGATAAATGCTT

CAATAATATTGAAAAAGGAAGAGTATGAGTATTCAACATTTCCGTGTCGCCCTTATTCCCTT

TTTTGCGGCATTTTGCCTTCCTGTTTTTGCTCACCCAGAAACGCTGGTGAAAGTAAAAGATG

CTGAAGATCAGTTGGGTGCACGAGTGGGTTACATCGAACTGGATCTCAACAGCGGTAAGATC

CTTGAGAGTTTTCGCCCCGAAGAACGTTTTCCAATGATGAGCACTTTTAAAGTTCTGCTATG

TGGCGCGGTATTATCCCGTGTTGACGCCGGGCAAGAGCAACTCGGTCGCCGCATACACTATT

CTCAGAATGACTTGGTTGAGTACTCACCAGTCACAGAAAAGCATCTTACGGATGGCATGACA

GTAAGAGAATTATGCAGTGCTGCCATAACCATGAGTGATAACACTGCGGCCAACTTACTTCT

GACAACGATCGGAGGACCGAAGGAGCTAACCGCTTTTTTGCACAACATGGGGGATCATGTAA

CTCGCCTTGATCGTTGGGAACCGGAGCTGAATGAAGCCATACCAAACGACGAGCGTGACACC

ACGATGCCTGCAGCAATGGCAACAACGTTGCGCAAACTATTAACTGGCGAACTACTTACTCT

AGCTTCCCGGCAACAATTAATAGACTGGATGGAGGCGGATAAAGTTGCAGGACCACTTCTGC

GCTCGGCCCTTCCGGCTGGCTGGTTTATTGCTGATAAATCTGGAGCCGGTGAGCGTGGGTCT

CGCGGTATCATTGCAGCACTGGGGCCAGATGGTAAGCCCTCCCGTATCGTAGTTATCTACAC

GACGGGGAGTCAGGCAACTATGGATGAACGAAATAGACAGATCGCTGAGATAGGTGCCTCAC

TGATTAAGCATTGGTAACTGTCAGACCAAGTTTACTCATATATACTTTAGATTGATTTAAAA

CTTCATTTTTAATTTAAAAGGATCTAGGTGAAGATCCTTTTTGATAATCTCATGACCAAAAT

CCCTTAACGTGAGTTTTCGTTCCACTGAGCGTCAGACCCCGTAGAAAAGATCAAAGGATCTT

CTTGAGATCCTTTTTTTCTGCGCGTAATCTGCTGCTTGCAAACAAAAAAACCACCGCTACCA

GCGGTGGTTTGTTTGCCGGATCAAGAGCTACCAACTCTTTTTCCGAAGGTAACTGGCTTCAG

CAGAGCGCAGATACCAAATACTGTCCTTCTAGTGTAGCCGTAGTTAGGCCACCACTTCAAGA

ACTCTGTAGCACCGCCTACATACCTCGCTCTGCTAATCCTGTTACCAGTGGCTGCTGCCAGT

GGCGATAAGTCGTGTCTTACCGGGTTGGACTCAAGACGATAGTTACCGGATAAGGCGCAGCG

GTCGGGCTGAACGGGGGGTTCGTGCACACAGCCCAGCTTGGAGCGAACGACCTACACCGAAC

TGAGATACCTACAGCGTGAGCATTGAGAAAGCGCCACGCTTCCCGAAGGGAGAAAGGCGGAC

AGGTATCCGGTAAGCGGCAGGGTCGGAACAGGAGAGCGCACGAGGGAGCTTCCAGGGGGAAA

CGCCTGGTATCTTTATAGTCCTGTCGGGTTTCGCCACCTCTGACTTGAGCGTCGATTTTTGT

GATGCTCGTCAGGGGGCGGAGCCTATGGAAAAACGCCAGCAACGCGGCCTTTTTACGGTTC

CTGGCCTTTTGCTGGCCTTTTGCTCACATGTTCTTTCCTGCGTTATCCCCTGATTCTGTGGA

TAACCGTATTACCGCCTTTGAGTGAGCTGATACCGCTCGCCGCAGCCGAACGACCGAGCGCA

GCGAGTCAGTGAGCGAGGAAGCGTACATTTATATTGGCTCATGTCCAATATGACCGCCATGT

TGACATTGATTATTGACTAGTTATTAATAGTAATCAATTACGGGGTCATTAGTTCATAGCCC

ATATATGGAGTTCCGCGTTACATAACTTACGGTAAATGGCCCGCCTGGCTGACCGCCCAACG

ACCCCCGCCCATTGACGTCAATAATGACGTATGTTCCCATAGTAACGCCAATAGGGACTTTC

CATTGACGTCAATGGGTGGAGTATTTACGGTAAACTGCCCACTTGGCAGTACATCAAGTGTA

TCATATGCCAAGTCCGCCCCCTATTGACGTCAATGACGGTAAATGGCCCGCCTGGCATTATG

| SEQUENCE LISTINGS |
| --- |
| CCCAGTACATGACCTTACGGGACTTTCCTACTTGGCAGTACATCTACGTATTAGTCATCGCT |
| ATTACCATGGTGATGCGGTTTTGGCAGTACACCAATGGGCGTGGATAGCGGTTTGACTCACG |
| GGGATTTCCAAGTCTCCACCCCATTGACGTCAATGGGAGTTTGTTTTGGCACCAAAATCAAC |
| GGGACTTTCCAAAATGTCGTAATAACCCCGCCCCGTTGACGCAAATGGGCGGTAGGCGTGTA |
| CGGTGGGAGGTCTATATAAGCAGAGCTCGTTTAGTGAACCGTCAGATCCTCACTCTCTTCCG |
| CATCGCTGTCTGCGAGGGCCAGCTGTTGGGCTCGCGGTTGAGGACAAACTCTTCGCGGTCTT |
| TCCAGTACTCTTGGATCGGAAACCCGTCGGCCTCCGAACGGTACTCCGCCACCGAGGGACCT |
| GAGCGAGTCCGCATCGACCGGATCGGAAAACCTCTCGAGAAAGGCGTCTAACCAGTCACAGT |
| CGCAAGGTAGGCTGAGCACCGTGGCGGGCGGCAGCGGGTGGCGGTCGGGGTTGTTTCTGGCG |
| GAGGTGCTGCTGATGATGTAATTAAAGTAGGCGGT |

SEQ ID NO: 142
GGGTTCCAGGTTCCACTGGCGAGGTCCAGCTGCAACAATCTGG

SEQ ID NO: 143
GGGTTCCAGGTTCCACTGGCCAGGTCCAAGTGCAGCAGCCTGG

SEQ ID NO: 144
GGGTTCCAGGTTCCACTGGCGAGATCCAGCTGCAGCAGTCTGG

SEQ ID NO: 145
GGGTTCCAGGTTCCACTGGCGAAGTGAAGCTTGAGGAGTCTGG

SEQ ID NO: 146
GGGTTCCAGGTTCCACTGGCCAGGTCCAACTGCAGCAGCCTGG

SEQ ID NO: 147
GGGGCCAGGGGAAAGACAGATGGGCCCTTCGTTGAGGC

SEQ ID NO.: 148
RSX$_{1a}$X$_{2a}$SLLHSNGX$_{3a}$TYLY
X$_{1a}$ is a neutral hydrophilic amino acid
X$_{3a}$ is an hydrophobic amino acid or asparagine.
X$_{2a}$ is lysine or glutamic acid SEQ ID NO.: 149
X$_{1b}$MSNLAS
wherein X$_{1b}$ is a basic amino acid.

SEQ ID NO.: 150
RX$_{1c}$SNLX$_{2c}$S
wherein X$_{1c}$ is methionine or threonine
wherein X$_{2c}$ is an hydrophobic amino acid.

SEQ ID NO.: 151
X$_{1d}$QX$_{2d}$LEX$_{3d}$PX$_{4d}$T
wherein X$_{1d}$ is an hydrophobic amino acid;
wherein X$_{2d}$ is a basic amino acid;
wherein X$_{3d}$ is tyrosine or leucine, and;
wherein X$_{4d}$ is an aromatic amino acid.

SEQ ID NO.: 152
QQWSSNPX$_{1e}$T
Wherein X$_{1e}$ is proline or leucine.

SEQ ID NO.: 153
GYTFX$_{1f}$X$_{2f}$YX$_{3f}$MX
wherein X$_{1f}$ is threonine or asparagine;
wherein X$_{2f}$ is threonine, arginine, serine or aspartic acid;
wherein X$_{3f}$ is tryptophan, asparagine, aspartic acid or glutamic acid, and;
wherein X$_{4f}$ is tyrosine, histidine or aspartic acid.

SEQ ID NO.: 154
GYTFTDYX$_{5f}$MH
Wherein X$_{5f}$ is an acidic amino acid.

SEQ ID NO.: 155
LINPX$_{1g}$NX$_{2g}$RX$_{3g}$N

-continued

SEQUENCE LISTINGS

Wherein $X_{1g}$ is a neutral hydrophilic amino acid;
Wherein $X_{2g}$ is alanine or glycine, and;
Wherein $X_{3g}$ is proline ot threonine.

SEQ ID NO.: 156
$X_{1h}$IDPETGGTA
Wherein $X_{1h}$ is alanine or threonine.

SEQ ID NO.: 157
EI$X_{1i}$P$X_{2i}$$X_{3i}$S$X_{4i}$$X_{5i}$N
Wherein $X_{1i}$ is aspartic acid or asparagine;
Wherein $X_{2i}$ is aspartic acid or serine;
Wherein $X_{3i}$ is aspartic acid or serine;
Wherein $X_{4i}$ is tyrosine or threonine, and;
Wherein $X_{5i}$ is threonine or isoleucine.

SEQ ID NO.: 158
T$X_{1j}$FYY$X_{2j}$$X_{3j}$$X_{4j}$NYDVGFAY
Wherein $X_{1j}$ is a neutral hydrophilic amino acid;
Wherein $X_{2j}$ is a neutral hydrophilic amino acid;
Wherein $X_{3j}$ is tyrosine or histidine, and;
Wherein $X_{4j}$ is tyrosine or serine.

SEQ ID NO.: 159
GTAAGCGAATTCATGGTGAAAACTAGAAGAGACGC

SEQ ID NO.: 160
GTAAGCAAGCTTTTAGCCGTGGAAGCGGAACAGG

SEQ ID NO.: 161 (25B02 variable light chain DNA)
AACATCCAGATGACCCAGTCTCCAGCCTCCCTATCTGCATCTGTGGGAGAAACTGTC

ACCATCACATGTCGAGCAAGTGAGAATATTTACAGTTATTTAGCATGGTATCAACAG

AAGCAGGGAAAATCTCCTCAGCTCCTGGTCTATAATGCAAAAACCTTACCAGAAGGT

GTGTCAGTAAGGTTCAGTGGCAGTGGATCAGGCACACAGTTTTCTCTGAAGATCAAC

AACCTGCAGCCTGAAGATTTTGGGAGTTATCACTGTCAACATCATTATGGTGTTCCT

CTTACGTTCGGTTCTGGGACCAAGCTGGAGTTGAAA

SEQ ID NO.: 162 (25B02 variable light chain amino acids)
NIQMTQSPASLSASVGETVTITCRASENIYSYLAWYQQKQGKSPQLLVYNAKTLPEG

VSVRFSGSGSGTQFSLKINNLQPEDFGSYHCQHHYGVPLTFGSGTKLELK

SEQ ID NO.: 163 (25B02 variable heavy chain DNA)
CAGGTGAAGCTTCAGCAGTCCGGGGCTGAGCTGGCAAGACCTGGGGCTTCAGTGAAG

TTTTCCTGCAAGGCTTCTGGCTACACCTTCACTAGGAACTGGATACAGTGGGTAAAA

CAGAGGCCTGGACAGGGTCTGGAATGGATTGGGGCTATTTATCCTGGAAATGGTGAT

AGTAGGTATACTCAGAAGTTCAAGGGCAAGGCCACATTGACTGCAGATAAATCCTCG

AACACAGCCTACATGCAACTCAGCGGTTTGGCATCTGAGGACTCTGCGGTCTATTAC

TGTGCAAGATTGGCTGGTAACTACGCTTACTACTTTGACTACTGGGGCCAAGGCACC

GCTCTCACAGTCTCCTCA

SEQ ID NO.: 164 (25B02 variable heavy chain amino acids)
QVKLQQSGAELARPGASVKFSCKASGYTFTRNWIQWVKQRPGQGLEWIGAIYPGNGD

SRYTQKFKGKATLTADKSSNTAYMQLSGLASEDSAVYYCARLAGNYAYYFDYWGQT

ALTVSS

SEQ ID NO.: 165 (25D11 variable light chain DNA)
GACATCCAGATGACCCAGTCTCCAGCCTCCCTATCTGCATCTGTGGGAGAAACTGTC

ACCATCACATGTCGAGCAAGTGGGAATATTCACAATTATTTAGCATGGTATCAACAG

AAGCAGGGAAAATCTCCTCAGCTCCTGGTCTATAATGCAAAAACCTTACCAGAAGGT

GTGTCAGTAAGGTTCAGTGGCAGTGGATCAGGCACACAGTTTTCTCTGAAGATCAAC

AACCTGCAGCCTGAAGATTTTGGGAGTTATCACTGTCAACATCATTATGGTGTTCCT

CTTACGTTCGGTTCTGGGACCAAGCTGGAGTTGAAA

SEQ ID NO.: 166 (25D11 variable light chain amino acids)
DIQMTQSPASLSASVGETVTITCRASGNIHNYLAWYQQKQGKSPQLLVYNAKTLPEG

VSVRFSGSGSGTQFSLKINNLQPEDFGSYHCQHHYGVPLTFGSGTKLELK

SEQ ID NO.: 167 (25D11 variable heavy chain DNA)
CAGGTGAAGCTTCAGCAGTCCGGGGCTGAGCTGGCAAGACCTGGGGCTTCAGTGAAG

TTTTCCTGCAAGGCTTCTGGCTACACCTTCACTAGGAACTGGATACAGTGGGTAAAA

CAGAGGCCTGGACAGGGTCTGGAATGGATTGGGCTATTTATCCTGGAAATGGTGAT

AGTAGGTATACTCAGAAGTTCAAGGGCAAGGCCACATTGACTGCAGATAAATCCTCG

AACACAGCCTACATGCAACTCAGCGGTTTGGCATCTGAGGACTCTGCGGTCTATTAC

TGTGCAAGATTGGCTGGTAACTACGCTTACTACTTTGACTACTGGGGCCAAGGCACC

GCTCTCACAGTCTCCTCA

SEQ ID NO.: 168 (25D11 variable heavy chain amino acids)
QVKLQQSGAELARPGASVKFSCKASGYTFTRNWIQWVKQRPGQGLEWIGAIYPGNGD

SRYTQKFKGKATLTADKSSNTAYMQLSGLASEDSAVYYCARLAGNYAYYFDYWGQGT

ALTVSS

SEQ ID NO.: 169 (25E10 variable light chain DNA)
GACATCCAGATGACCCAGTCTCCAGCCTCCCTATCTGCATCTGTGGGAGAAACTGTC

ACCATCACATGTCGAGCAAGTGGGAATATTCACAATTATTTAGCATGGTATCAGCAG

AAACAGGGAAAATCTCCTCAGCTCCTGGTCTATAATGCAAAAACCCTAGCAGATGGT

GTGCCATCAAGGTTCAGTGGCAGTGGATCAGGAACACAATATTCTCTCAAGATCAAC

AGCCTGCAGCCTGAAGATTTTGGGAGTTATTACTGTCAACATCATTACGGTGCTCCT

CTTACGTTCGGTGCTGGGACCAAGGTGGAGCTGAAA

SEQ ID NO.: 170 (25E10 variable light chain amino acids)
DIQMTQSPASLSASVGETVTITCRASGNIHNYLAWYQQKQGKSPQLLVYNAKTLADG

VPSRFSGSGSGTQYSLKINSLQPEDFGSYYCQHHYGAPLTFGAGTKVELK

SEQ ID NO.: 171 (25E10 variable heavy chain DNA)
GATGTGCAGCTGCAACAATCTGGGGCTGAGCTGGCAAGACCTGGGGCTTCAGTGAAG

TTTTCCTGCAAGGCTTCTGGCTACACCTTTACTAGGAACTGGATACAGTGGGTTAAA

CAGAGGCCTGGACAGGGTCTGGAATGGATTGGGCTGTTTATCCTGGAAATGGTGAT

AGTAGGTATACTCAGAAGTTCAAGGGCAAGGCCACATTGACTGCAGATAAATCCTCC

AGCACAGCCTACATGCAACTCAACAGTTTGTCATCTGAGGACTCTGCGGTCTATTAC

TGCGCAAGATTGGCTGGTAACTACGCTTACTACTTTGACTACTGGGGCCAAGGCACC

GCTCTCACAGTCTCCTCA

SEQ ID NO.: 172 (25E10 variable heavy chain amino acids)
DVQLQQSGAELARPGASVKFSCKASGYTFTRNWIQWVKQRPGQGLEWIGAVYPGNGD

SRYTQKFKGKATLTADKSSSTAYMQLNSLSSEDSAVYYCARLAGNYAYYFDYWGQGT

ALTVSS

SEQ ID NO.: 173
RASENIYSYLA

-continued

SEQUENCE LISTINGS

SEQ ID NO.: 174
NAKTLPE

SEQ ID NO.: 175
QHHYGVPLT

SEQ ID NO.: 176
GYTFTRNWIQ

SEQ ID NO.: 177
AIYPGNGDSR

SEQ ID NO.: 178
ARLAGNYAYYFDY

SEQ ID NO.: 179
RASGNIHNYLA

SEQ ID NO.: 180
NAKTLPE

SEQ ID NO.: 181
QHHYGVPLT

SEQ ID NO.: 182
GYTFTRNWIQ

SEQ ID NO.: 183
AIYPGNGDSR

SEQ ID NO.: 184
ARLAGNYAYYFDY

SEQ ID NO.: 185
RASGNIHNYLA

SEQ ID NO.: 186
NAKTLAD

SEQ ID NO.: 187
QHHYGAPLT

SEQ ID NO.: 188
GYTFTRNWIQ

SEQ ID NO.: 189
AVYPGNGDSR

SEQ ID NO.: 190
ARLAGNYAYYFDY

TABLE 5A

Anti-siglec-15 heavy chain variable sequences.

| ID | FR1 | CDR-H1 | FR2 | CDR-H2 | FR3 | CDR-H3 | FR4 |
|---|---|---|---|---|---|---|---|
| 25E6 | QVQLQQPGAELAKPGASVKLSCKAS | GYTFNTYNMY | WLKQRPGQGLEWIG | GIDPSNGDTK | INEKFKNKATLTVDKSSSTAYMQLSGLTSEDSAVYYC | TSH---------TY | WGQGTLVTVSA |
| 25H10 | QVQLQQPGAELAKPGASVKLSCKAS | GYTFNTYNMY | WLKQRPGQGLEWIG | GIDPSNGDTK | INEKFKNKATLTVDKSSSTAYMQLSGLTSEDSAVYYC | TSH---------TY | WGQGTLVTVSA |
| 25H11 | QVQLQQPGAELAKPGASVKLSCKAS | GYTFNTYNMY | WLKQRPGQGLEWIG | GIDPSNGDTK | INEKFKNKATLTVDKSSSTAYMQLSGLTSEDSAVYYC | TSH---------TY | WGQGTLVTVSA |
| 25A3 | QVQLQQSRAELVKPGASVKLSCKAS | GYTFTSYWMH | WVKQRPGQGLEWIG | LINPSNARTN | YNEKFKNKATLTVDKSSSTAYMQLSSLTSEDSAVYYC | ARGGDGDYF----DY | WGQGTTLTVSS |
| 25A5 | QVQVQQPGAELVKPGASVKLSCKAS | GYTFTSYWMH | WVKQRPGQGLEWIG | LINPSNARTN | YNEKFKSKATLTVDKSSSTAYMQLSSLTSEDSAVYYC | ARGGDGDYF----DY | WGQGTTLTVSS |
| 25A11 | QVQVQQPGAEIVRPGASVKLSCKAS | GYTFTSYWMH | WVKQRPGQGLEWIG | LINPTNGRTN | YNEKFKSKATLTVDKSSSTAYMQLSSLTSEDSAVYYC | ARGGDGDYF----DY | WGQGTTLTVSS |
| 25B4 | QVQLQQSRAELVKPGASVKLSCKAS | GYTFTSYWMH | WVKQRPGQGLEWIG | LINPTNGRTN | YNEKFKNKATLTVDKSSSTAYMQLSSLTSEDSAVYYC | ARGGDGDYF----DY | WGQGTTLTVSS |
| 25B12 | QVQVQQPGAEIVRPGASVKLSCKAS | GYTFTSYWMH | WVKQRPGQGLEWIG | LINPTNGRTN | YNEKFKSKATLTVDKSSSTAYMQLSSLTSEDSAVYYC | ARGGDGDYF----DY | WGQGTTLTVSS |
| 25C9 | QVQVQQPGAELVKPGASVKLSCKAS | GYTFTSYWMH | WVKQRPGQGLEWIG | LINPTNGRTN | YNEKFNTKATLTVDKSSSTAYMQLSSLTSEDSAVYYC | ARGGDGDYF----DY | WGQGTTLTVSS |
| 25C10 | QVQVQQPGAEIVRPGASVKLSCKAS | GYTFTSYWMH | WVKQRPGQGLEWIG | LINPTNGRTN | YNEKFKNKATLTVDKSSSTAYMQLSSLTSEDSAVYYC | ARGGDGDYF----DY | WGQGTTLTVSS |
| 25D3 | QVQVQQPGAEIVRPGASVKLSCKAS | GYTFTSYWMH | WVKQRPGQGLEWIG | LINPTNGRTN | YNEKFKSKATLTVDKSSSTAYMQLSSLTSEDSAVYYC | ARGGDGDYF----DY | WGQGTTLTVSS |
| 25D4 | QVQVQQPGAELVKPGASVKLSCKAS | GYTFTSYWMH | WVKQRPGQGLEWIG | LINPTNGRTN | YNEKFKSKATLTVDKSSSTAYMQLSSLTSEDSAVYYC | ARGGDGDYF----DY | WGQGTTLTVSS |
| 25D5 | QVQVQQPGAEIVRPGASVKLSCKAS | GYTFTSYWMH | WVKQRPGQGLEWIG | LINPTNGRTN | YNEKFNTKATLTVDKSSSTAYMQLSSLTSEDSAVYYC | ARGGDGDYF----DY | WGQGTTLTVSS |
| 25D6 | QVQVQQPGAELVKPGASVKLSCKAS | GYTFTSYWMH | WVKQRPGQGLEWIG | LINPTNGRTN | YNEKFKSKATLTVDKSSSTAYMQLSSLTSEDSAVYYC | ARGGDGDYF----DY | WGQGTTLTVSS |
| 25D8 | QVQVQQPGAEIVRPGASVKLSCKAS | GYTFTSYWMH | WVKQRPGQGLEWIG | LINPTNGRTN | YNEKFKSKATLTVDKSSSTAYMQLSSLTSEDSAVYYC | ARGGDGDYF----DY | WGQGTTLTVSS |
| 25D10 | QVQVQQPGAEIVRPGASVKLSCKAS | GYTFTSYWMH | WVKQRPGQGLEWIG | LINPSNARTN | YNEKFKSKATLTVDKSSSTAYMQLSSLTSEDSAVYYC | ARGGDGDYF----DY | WGQGTTLTVSS |
| 25E7 | QVQLQQPGTELVKPGASVKLSCKAS | GYTFTTYWMH | WVKQRPGQGLEWIG | LINPTNGRTN | YNEKFKSKATLTVDKSSSTAYMQLSSLTSEDSAVYYC | ARGGDGDYF----DY | WGQGTTLTVSS |
| 25E8 | QVQVQQPGAELVKPGASVKLSCKAS | GYTFTSYWMH | WVKQRPGQGLEWIG | LINPTNGRTN | YNEKFKSKATLTVDKSSSTAYMQLSSLTSEDSAVYYC | ARGGDGDYF----DY | WGQGTTLTVSS |
| 25E12 | QVQVQQPGAEIVRPGASVKLSCKAS | GYTFTSYWMH | WVKQRPGQGLEWIG | LINPTNGRTN | YNEKFNTKATLTVDKSSSTAYMHLSSLTSEDSAVYYC | ARGGDGDYF----DY | WGQGTTLTVSS |
| 25F2 | QVQVQQPGAELVKPGASVKLSCKAS | GYTFTSYWMH | WVKQRPGQGLEWIG | LINPTNGRTN | YNEKFKSKATLTVDKSSSTAYMQLSSLTSEDSAVYYC | ARGGDGDYF----DY | WGQGTTLTVSS |
| 25F3 | QVQVQQPGAEIVRPGASVKLSCKAS | GYTFTSYWMH | WVKQRPGQGLEWIG | LINPTNGRTN | YNEKFKNKATLTVDKSSSTAYMQLSSLTSEDSAVYYC | ARGGDGDYF----DY | WGQGTTLTVSS |
| 25F5 | QVQVQQPGTELVKPGASVKLSCKAS | GYTFTTYWMH | WVKQRPGQGLEWIG | LINPTNGRTN | YNEKFKSKATLTVDKSSSTAYMQLSSLTSEDSAVYYC | ARGGDGDYF----DY | WGQGTTLTVSS |
| 25F6 | QVQVQQPGAELVKPGASVKLSCKAS | GYTFTSYWMH | WVKQRPGQGLEWIG | LINPTNGRTN | YNEKFNTKATLTVDKSSSTAYMQLSSLTSEDSAVYYC | ARGGDGDYF----DY | WGQGTTLTVSS |
| 25F7 | EIQLQQSGTELVKPGASVKLSCKAS | GYTFTTYWMH | WVKQRPGQGLEWIG | LINPTNGRTN | YNEKFNTKATLTVDKSSSTAYMQLSSLTSEDSAVYYC | ARGGDGDYF----DY | WGQGTTLTVSS |

TABLE 5A-continued

Anti-siglec-15 heavy chain variable sequences.

| ID | FR1 | CDR-H1 | FR2 | CDR-H2 | FR3 | CDR-H3 | FR4 |
|---|---|---|---|---|---|---|---|
| 25F9 | QVQVQQPGAEIVRPGASVKLSCKAS | GYTFTSYWMH | WVKQRPGQGLEWIG | LINPTNGRTN | YNEKFKSKATLTVDKSSSTAYMQLSSLTSEDSAVYYC | ARGGDGDYF-----DY | WGQGTTLTVSS |
| 25F10 | QVQVQQPGTELVKPGASVKLSCKAS | GYTFTTYWMH | WVKQRPGQGLEWIG | LINPTNGRTN | YNEKFKSKATLTVDKSSSTAYMQLSSLTSEDSAVYYC | ARGGDGDYF-----DY | WGQGTTLTVSS |
| 25F11 | QVQVQQPGAEIVRPGASVKLKPGAS | GYTFTSYWMH | WVKQRPGQGLEWIG | LINPTNGRTN | YNEKFKSKATLTVDKSSSTAYMQLSSLTSEDSAVYYC | ARGGDGDYF-----DY | WGQGTTLTVSS |
| 25E12 | QVQVQQPGAEIVRPGASVKLSCKAS | GYTFTSYWMH | WVKQRPGQGLEWIG | LINPTNGRTN | YNEKFKNKATLTVDKSSSTAYMQLSSLTSEDSAVYYC | ARGGDGDYF-----DY | WGQGTTLTVSS |
| 25G3 | QVQVQQPGAEIVRPGASVKLSCKAS | GYTFTSYWMH | WVKQRPGQGLEWIG | LINPTNGRTN | YNEKFKSKATLTVDKSSSTAYMQLSSLTSEDSAVYYC | ARGGDGDYF-----DY | WGQGTTLTVSS |
| 25G4 | QVQVQQPGAEIVRPGASVKLSCKAS | GYTFTSYWMH | WVKQRPGQGLEWIG | LINPTNGRTN | YNEKFKSKATLTVDKSSSTAYMQLSSLTSEDSAVYYC | ARGGDGDYF-----DY | WGQGTTLTVSS |
| 25G7 | QVQVQQPGTELVKPGASVKLSCKAS | GYTFTTYWMH | WVKQRPGQGLEWIG | LINPTNGRTN | YNEKFKSKATLTVDKSSSTAYMQLSSLTSEDSAVYYC | ARGGDGDYF-----DY | WGQGTTLTVSS |
| 25G8 | QVQVQQPGAEIVRPGASVKLSCKAS | GYTFTTYWMH | WVKQRPGQGLEWIG | LINPTNGRTN | YNEKFKSKATLTVDKSSSTAYMQLSSLTSEDSAVYYC | ARGGDGDYF-----DY | WGQGTTLTVSS |
| 25H1 | QVQLQQSRAELVKPGASVKLSCKAS | GYTFTSYWMH | WVKQRPGQGLEWIG | LINPTNGRTN | YNEKFKSKATLTVDKSSSTAYMQLSSLTSEDSAVYYC | ARGGDGDYF-----DY | WGQGTTLTVSS |
| 25H2 | QVQLQQSGAELVKPGASVKLSCKAS | GYTFTSYWMH | WVKQRPGQGLEWIG | LINPTNGRTN | YNEKFKSKATLTVDKSSSTAYMQLSSLTSEDSAVYYC | ARGGDGDYF-----DY | WGQGTTLTVSS |
| 25H5 | QVQVQQPGAEIVRPGASVKLSCKAS | GYTFTSYWMH | WVKQRPGQGLEWIG | LINPTNGRTN | YNERFKTKATLTVDKSSSTAYMHLSSLTSEDSAVYYC | ARGGDGDYF-----DY | WGQGTTLTVSS |
| 25H6 | QVQVQQPGAEIVRPGASVKLSCKAS | GYTFTSYWMH | WVKQRPGQGLEWIG | LINPSNGRPN | YNEKFNTKATLTVDKSSSTAYMQLSSLTSEDSAVYYC | ARGGDGDYF-----DY | WGQGTTLTVSS |
| 25H7 | QVQVQQPGAEIVRPGASVKLSCKAS | GYTFTSYWMH | WVKQRPGQGLEWIG | LINPSNARTN | YNEKFKSKATLTVDKSSSTAYMQLSSLTSEDSAVYYC | ARGGDGDYF-----DY | WGQGTTLTVSS |
| 25H8 | QVQVQQPGAEIVRPGASVKLSCKAS | GYTFTSYWMH | WVKQRPGQGLEWIG | LINPTNGRTN | YNEKFKSKATLTVDKSSSTAYMQLSSLTSEDSAVYYC | ARGGDGDYF-----DY | WGQGTTLTVSS |
| 25B2 | QVKLQQSGAELARPGASVKFSCKAS | GYTFTRNWIQ | WVKQRPGQGLEWIG | AIYPGNGDSR | YTQKFKGKATLTADKSSNTAYMQLSGLASEDSAVYYC | ARLAGNYAYF----DY | WGQGTALTVSS |
| 25D11 | QVKLQQSGAELARPGASVKFSCKAS | GYTFTRNWIQ | WVKQRPGQGLEWIG | AIYPGNGDSR | YTQKFKGKATLTADKSSNTAYMQLSGLASEDSAVYYC | ARLAGNYAYF----DY | WGQGTALTVSS |
| 25E10 | DVQLQQSGAELARPGASVKFSCKAS | GYTFTRNWIQ | WVKQRPGQGLEWIG | AVYPGNGDSR | YTQKFKGKATLTADKSSSTAYMQLNSLSSEDSAVYYC | ARLAGNYAYF----DY | WGQGTALTVSS |
| 25E5 | EVKLEESGGGLVQPGGSLKLSCAAS | GFDFSKDWMS | WVRQAPGKGLEWIG | EINPDSSTIN | YAPSLKDKFIISRENAKNT LYLQMSKVRSEDTALYYC | SRLEDYEDWYF----DV | WGAGTTVTVSS |
| 25B6 | QAYLQQSGVELVRPGASVTLSCKAS | GTFTDYDMH | WVKQTPVHGLEWIG | TIDDETGGTA | YNQKFKGKATLTADRSSTTAYMELSSLTSEDSAVYYC | TSFYYTYSNYDVGF-AY | WGQGTLVTVSA |
| 25B11 | EIQLQQSGVELVRPGASVTLSCKAS | GTFTDYDMH | WVKQTPVHGLEWIG | TIDDETGGTA | YNQKFKGKATLTADRSSTTAYMELSSLTSEDSAVYYC | TSFYYTYSNYDVGF-AY | WGQGTLVTVSA |
| 25E9 | EIQLQQSGVELVRPGASVTLSCKAS | GTFTDYDMH | WVKQTPVHGLEWIG | TIDDETGGTA | YNQKFKGKATLTADRSSTTAYMELSSLTSEDSAVYYC | TSFYYTYSNYDVGF-AY | WGQGTLVTVSA |
| 25C1 | EIQLQQSGAELVRPGASVTLSCKAS | GYTFTDYEMH | WVKQTPVHGLEWIG | AIDPETGGTA | YNQKFKGKATLTADKSSSTAYMELSSLTSEDSAVYYC | TSFYYTYNYDVGF-AY | WGQGTLVTVSA |
| 25B8 | EIQLQQSGVELVRPGASVTLSCKAS | GYTFTDYDMH | WVKQTPVHGLEWIG | TIDDETGGTA | YNQKFKGKATLTADRSSTTAYMELSSLTSEDSAVYYC | TTFYYSHYNYDVGF-AY | WGQGTLVTVSA |
| 25A1 | EVQLQQSGTELVRPGSVKISCKAS | GYTFTRYWMD | WVKQPGQGLEWIG | EIDPSDSYTN | YNQKFKGKATLTVDKFSRTAYMELSSLTSEDSAVYYC | ARSGAYSSDYISYDGFAY | WGQGTLVTVSA |

TABLE 5B

Anti-siglec-15 light chain variable sequences.

| ID | FR1 | CDR-L1 | FR2 | CDR-L2 |
|---|---|---|---|---|
| 25E6 | SIVMTQTPKFLLVSAGDRVTITC | KASQSVS-----NAVA | WYQQKPGQSPKLLIY | YTSNRYT |
| 25H10 | SIVMTQTPKFLLVSAGDRVTITC | KASQSVS-----NAVA | WYQQKPGQSPKLLIY | YTSNRYT |
| 25H11 | SIVMTQTPKFLLVSAGDRVTITC | KASQSVS-----NAVA | WYQQKPGQSPKLLIY | YTSNRYT |
| 25A3 | DIVMTQAAFSNPVTLGTSASISC | RSSKSLLHSNGITYLY | WYLQKPGQSPQLLIY | QMSNLAS |
| 25A5 | DIVMTQAAFSNPVTLGTSASISC | RSSKSLLHSNGITYLY | WYLQKPGQSPQLLIY | QMSNLAS |
| 25A11 | DIVMTQAAFSNPVTLGTSASISC | RSSKSLLHSNGITYLY | WYLQKPGQSPQLLIY | QMSNLAS |
| 25B4 | DIVMTQAAFSNPVTLGTSASISC | RSSKSLLHSNGITYLY | WYLQKPGQSPQLLIY | QMSNLAS |
| 25B12 | DIVMTQAAFSNPVTLGTSASISC | RSSKSLLHSNGITYLY | WYLQKPGQSPQLLIY | QMSNLAS |
| 25C9 | DIVMTQAAFSNPVTLGTSASISC | RSSKSLLHSNGITYLY | WYLQKPGQSPQLLIY | QMSNLAS |
| 25C10 | DIVMTQAAFSNPVTLGTSASISC | RSSKSLLHSNGITYLY | WYLQKPGQSPQLLIY | QMSNLAS |
| 25D3 | DIVMTQAAFSNPVTLGTSASISC | RSSKSLLHSNGITYLY | WYLQKPGQSPQLLIY | QMSNLAS |
| 25D4 | DIVMTQAAFSNPVTLGTSASISC | RSSKSLLHSNGITYLY | WYLQKPGQSPQLLIY | QMSNLAS |
| 25D5 | DIVMTQAAFSNPVTLGTSASISC | RSSKSLLHSNGITYLY | WYLQKPGQSPQLLIY | QMSNLAS |
| 25D6 | DIVMTQAAFSNPVTLGTSASISC | RSSKSLLHSNGITYLY | WYLQKPGQSPQLLIY | QMSNLAS |
| 25D8 | DIVMTQAAFSNPVTLGTSASISC | RSSKSLLHSNGITYLY | WYLQKPGQSPQLLIY | QMSNLAS |
| 25D10 | DIVMTQAAFSNPVTLGTSASISC | RSSKSLLHSNGITYLY | WYLQKPGQSPQLLIY | QMSNLAS |
| 25E7 | DIVMTQAVFSNPVILGTPASISC | RSSKSLLHSNGVTYLY | WYLQKPGQSPQLLIY | QMSNLAS |
| 25E8 | DIVMTQAAFSNPVTLGTSASISC | RSSKSLLHSNGITYLY | WYLQKPGQSPQLLIY | QMSNLAS |
| 25E12 | DIVMTQAAFSNPVTLGTSASISC | RSSESLLHSNGITYLY | WYLQKPGQSPQLLIY | QMSNLAS |
| 25F2 | DIVMTQAAFSNPVTLGTSASISC | RSSKSLLHSNGITYLY | WYLQKPGQSPQLLIY | QMSNLAS |
| 25F3 | DIVMTHAAFSNPVTLGTSASISC | RSSKSLLHSNGITYLY | WYLQKPGQSPQLLIY | QMSNLAS |
| 25F5 | DIVMTQAVFSNPVILGTPASISC | RSSKSLLHSNGVTYLY | WYLQKPGQSPQLLIY | QMSNLAS |
| 25F6 | DIVMTQAAFSNPVTLGTSASISC | RSSKSLLHSNGITYLY | WYLQKPGQSPQLLIY | QMSNLAS |
| 25F7 | DIVMTQAAFSNPVTLGTSASISC | RSSKSLLHSNGITYLY | WYLQKPGQSPQLLIY | QMSNLAS |
| 25F9 | DIVMTQAAFSNPVTLGTSASISC | RSSKSLLHSNGITYLY | WYLQKPGQSPQLLIY | QMSNLAS |
| 25F10 | DIVMTQAVFSNPVILGTPASISC | RSSKSLLHSNGVTYLY | WYLQKPGQSPQLLIY | QMSNLAS |
| 25F11 | DIVMTQAAFSNPVTLGTSASISC | RSSKSLLHSNGITYLY | WYLQKPGQSPQLLIY | QMSNLAS |
| 25F12 | DIVMTQAAFSNPVTLGTSASISC | RSSKSLLHSNGITYLY | WYLQKPGQSPQLLIY | QMSNLAS |
| 25G3 | DIVMTQAAFSNPVTLGTSASISC | RSSKSLLHSNGITYLY | WYLQKPGQSPQLLIY | QMSNLAS |
| 25G4 | DIVMTQAAFSNPVTLGTSASISC | RSSKSLLHSNGITYLY | WYLQKPGQSPQLLIY | QMSNLAS |
| 25G7 | DIVMTQAAFSNPVTLGTSASISC | RSSKSLLHSNGITYLY | WYLQKPGQSPQLLIY | QMSNLAS |
| 25G8 | DIVMTQAAFSNPVTLGTSASISC | RSSKSLLHSNGITYLY | WYLQKPGQSPQLLIY | QMSNLAS |
| 25H1 | DIVMTQAAFSNPVTLGTSASISC | RSSKSLLHSNGITYLY | WYLQKPGQSPQLLIY | QMSNLAS |
| 25H2 | DIVMTQAAFSNPVTLGTSASISC | RSSKSLLHSNGITYLY | WYLQKPGQSPQLLIY | QMSNLAS |
| 25H5 | DIVMTQAAFSNPVTLGTSASISC | RSSKSLLHSNGITYLY | WYLQKPGQSPQLLIY | QMSNLAS |
| 25H6 | DIVMTQAAFSNPVTLGTSASISC | RSSKSLLHSNGITYLY | WYLQKPGQSPQLLIY | QMSNLAS |
| 25H7 | DIVMTQAAFSNPVTLGTSASISC | RSSKSLLHSNGITYLY | WYLQKPGQSPQLLIY | QMSNLAS |
| 25H8 | DIVMTQAAFSNPVTLGTSASISC | RSSKSLLHSNGITYLY | WYLQKPGQSPQLLIY | QMSNLAS |

TABLE 5B-continued

Anti-siglec-15 light chain variable sequences.

| ID | | | |
|---|---|---|---|
| 25B2 | NIQMTQSPASLSASVGETVTITC | RASENIY-----SYLA WYQQKQGKSPQLLVY | NAKTLPE |
| 25D11 | DIQMTQSPASLSASVGETVTITC | RASGNIH-----NYLA WYQQKQGKSPQLLVY | NAKTLPE |
| 25E10 | DIQMTQSPASLSASVGETVTITC | RASGNIH-----NYLA WYQQKQGKSPQLLVY | NAKTLAD |
| 25E5 | QIVLTQSPTLMSASPGEKVTMTC | SASSSV------SYMY WYQQKPRSSPKPWIY | RTSNLVS |
| 25B6 | DIVMTQAAPSVPVTPGESVSISC | RSSKSLLHSNGNTYLY WFLQRPGQSPQLLIY | RMSNLAS |
| 25B11 | DIVMTQAAPSVPVTPGESVSISC | RSTKSLLHSNGNTYLY WFLQRPGQSPQLLIY | RMSNLAS |
| 25E9 | DIVMTQAAPSVPVTPGESVSISC | RSTKSLLHSNGNTYLY WFLQRPGQSPQLLIY | RMSNLAS |
| 25C1 | DIVMTQAAPSVPVTPGESVSISC | RSSKSLLHSNGNTYLY WFLQRPGQSPQLLIY | RMSNLAS |
| 25B8 | DIVMTQAAPSVPVTPGESVSISC | RSTKSLLHSNGNTYLY WFLQRPGQSPQLLIY | RMSNLAS |
| 25A1 | ENVLTQSPAIMSASPGEKVTISC | SASSSV------SYMY WYQQKPGSSPKPWIY | RTSNLAS |

| ID | FR3 | CDR-L3 | FR4 |
|---|---|---|---|
| 25E6 | GVPDRFTGSGYGTDFTFTITTVQAEDLAVYFC | QQDYTSPWT | FGGGTKLEIK |
| 25H10 | GVPDRFTGSGYGTDFTFTITTVQAEDLAVYFC | QQDYTSPWT | FGGGTKLEIK |
| 25H11 | GVPDRFTGSGYGTDFTFTITTVQAEDLAVYFC | QQDYTSPWT | FGGGTKLEIK |
| 25A3 | GVPDRFSSSGSGTDFTLRISRVEAEDVGVYYC | AQNLELPYT | FGGGTKLEIK |
| 25A5 | GVPDRFSSSGSGTDFTLRISRVEAEDVGVYYC | AQNLELPYT | FGGGTKLEIK |
| 25A11 | GVPDRFSGSGSGTAFTLRISRVEAEDVGVYYC | MQHLEYPYT | FGGGTKLEIK |
| 25B4 | GVPDRFSGSGSGTAFTLRISRVEAEDVGVYYC | MQHLEYPYT | FGGGTKLEIK |
| 25B12 | GVPDRFSSSGSGTDFTLRISRVEAEDVGVYYC | AQNLELPYT | FGGGTKLEIK |
| 25C9 | GVPDRFSSSGSGTDFTLRISRVEAEDVGVYYC | AQNLELPYT | FGGGTKLEIK |
| 25C10 | GVPDRFSSSGSGTDFTLRISRVEAEDVGVYYC | AQNLELPYT | FGGGTKLEIK |
| 25D3 | GVPDRFSSSGSGTDFTLRISRVEAEDVGVYYC | AQNLELPYT | FGGGTKLEIK |
| 25D4 | GVPDRFSGSGSGTAFTLRISRVEAEDVGVYYC | MQHLEYPYT | FGGGTKLEIK |
| 25D5 | GVPDRFSGSGSGTAFTLRISRVEAEDVGVYYC | MQHLEYPYT | FGGGTKLEIK |
| 25D6 | GVPDRFSGSGSGTAFTLRISRVEAEDVGVYYC | MQHLEYPYT | FGGGTKLEIK |
| 25D8 | GVPDRFSSSGSGTDFTLRISRVEAEDVGVYYC | AQNLELPYT | FGGGTKLEIK |
| 25D10 | GVPDRFSGSGSGTAFTLRISRVEAEDVGVYYC | MQHLEYPYT | FGGGTKLEIK |
| 25E7 | GVPDRFSSSGSGTDFTLRISRVEAEDVGVYYC | MQHLEYPYT | FGGGTKLEIK |
| 25E8 | GVPDRFSSSGSGTDFTLRISRVEAEDVGVYYC | AQNLELPYT | FGGGTKLEIK |
| 25E12 | GVPDRFSGSGSGTAFTLRISRVEAEDVGVYYC | MQHLEYPYT | FGGGTKLEIK |
| 25F2 | GVPDRFSGSGSGTAFTLRISRVEAEDVGVYYC | MQHLEYPYT | FGGGTKLEIK |
| 25F3 | GVPDRFSSSGSGTDFTLRISRVEAEDVGVYYC | AQNLELPYT | FGGGTKLEIK |
| 25F5 | GVPDRFSSSGSGTDFTLRISRVEAEDVGVYYC | MQHLEYPYT | FGGGTKLEIK |
| 25F6 | GVPDRFSGSGSGTAFTLRISRVEAEDVGVYYC | MQHLEYPYT | FGGGTKLEIK |
| 25F7 | GVPDRFSGSGSGTAFTLRISRVEAEDVGVYYC | MQHLEYPYT | FGGGTKLEIK |
| 25F9 | GVPDRFSGSGSGTAFTLRISRVEAEDVGVYYC | MQHLEYPYT | FGGGTKLEIK |
| 25F10 | GVPDRFSSSGSGTDFTLRISRVEAEDVGVYYC | MQHLEYPYT | FGGGTKLEIK |
| 25F11 | GVPDRFSGSGSGTAFTLRISRVEAEDVGVYYC | MQHLEYPYT | FGGGTKLEIK |
| 25F12 | GVPDRFSGSGSGTAFTLRISRVEAEDVGVYYC | MQHLEYPYT | FGGGTKLEIK |

TABLE 5B-continued

Anti-siglec-15 light chain variable sequences.

| | | |
|---|---|---|
| 25G3 | GVPDRFSGSGSGTAFTLRISRVEAEDVGVYYC | MQHLEYPYT FGGGTKLEIK |
| 25G4 | GVPDRFSGSGSGTAFTLRISRVEAEDVGVYYC | MQHLEYPYT FGGGTKLEIK |
| 25G7 | GVPDRFSGSGSGTAFTLRISRVEAEDVGVYYC | MQHLEYPYT FGGGTKLEIK |
| 25G8 | GVPDRFSGSGSGTAFTLRISRVEAEDVGVYYC | MQHLEYPYT FGGGTKLEIK |
| 25H1 | GVPDRFSSSGSGTDFTLRISRVEAEDVGVYYC | AQNLELPYT FGGGTKLEIK |
| 25H2 | GVPDRFSGSGSGTAFTLRISRVEAEDVGVYYC | MQHLEYPYT FGGGTKLEIK |
| 25H5 | GVPDRFSSSGSGTDFTLRISRVEAEDVGVYYC | AQNLELPYT FGGGTKLEIK |
| 25H6 | GVPDRFSSSGSGTDFTLRISRVEAEDVGVYYC | AQNLEYPYT FGSGTKLEIK |
| 25H7 | GVPDRFSSSGSGTDFTLRISRVEAEDVGVYYC | AQNLELPYT FGGGTKLEIK |
| 25H8 | GVPDRFSGSGSGTAFTLRISRVEAEDVGVYYC | MQHLEYPYT FGGGTKLEIK |
| 25B2 | GVSVRFSGSGSGTQFSLKINNLQPEDFGSYHC | QHHYGVPLT FGSGTKLELK |
| 25D11 | GVSVRFSGSGSGTQFSLKINNLQPEDFGSYHC | QHHYGVPLT FGSGTKLELK |
| 25E10 | GVPSRFSGSGSGTQYSLKINSLQPEDFGSYYC | QHHYGAPLT FGAGTKVELK |
| 25E5 | GVPVRFSGSGSGTSYSLTISSMEAEDAATYYC | QQWSSNPPT FGAGTKLELK |
| 25B6 | GVPDRFSGSGSGTAFTLRLSRVEAEDVGVYYC | MQHLEYPFT FGGGTKLEIK |
| 25B11 | GVPDRFSGSGSGTAFTLRISRVEAEDVGVYYC | MQHLEYPFT FGGGTKLEIK |
| 25E9 | GVPDRFSGSGSGTAFTLRISRVEAEDVGVYYC | MQHLEYPFT FGGGTKLEIK |
| 25C1 | GVPDRFSGSGSGTAFTLRISRVEAEDVGVYYC | MQHLEYPFT FGGGTKLEIK |
| 25B8 | GVPDRFSGSGSGTAFTLRISRVEAEDVGVYYC | MQHLEYPFT FGGGTKLEIK |
| 25A1 | GVPARFSGSGSGTSYSLTISSMEAEDAATYYC | QQWSSNPLT FGAGTKLELK |

We claim:

1. An isolated antibody or an antigen binding fragment thereof having a light chain variable domain comprising the amino acid sequence set forth in SEQ ID NO:111, the amino acid sequence set forth in SEQ ID NO:112 and the amino acid sequence set forth in SEQ ID NO:113 and a heavy chain variable domain comprising the amino acid sequence set forth in SEQ ID NO:114, the amino acid sequence set forth in SEQ ID NO:115 and the amino acid sequence set forth in SEQ ID NO:116, wherein said antibody or antigen binding fragment specifically binds Siglec-15.

2. The isolated antibody or antigen binding fragment of claim 1, wherein the antibody or antigen binding fragment thereof is a monoclonal antibody, a chimeric antibody, a humanized antibody or a human antibody.

3. The isolated antibody or antigen binding fragment of claim 1, wherein the antigen binding fragment is selected from the group consisting of scFv, a Fab, a Fab' or a (Fab')$_2$.

4. The isolated antibody or antigen binding fragment of claim 1, comprising a human constant region or a fragment thereof.

5. The isolated antibody or antigen binding fragment of claim 4, wherein the constant region is from a human IgG2 immunoglobulin.

6. The isolated antibody or antigen binding fragment of claim 4, wherein the constant region is from a human IgG1 immunoglobulin.

7. The isolated antibody or antigen binding fragment of claim 5, wherein the antibody or antigen binding fragment thereof is a humanized antibody or a human antibody.

8. The isolated antibody or antigen binding fragment of claim 6, wherein the antibody or antigen binding fragment thereof is a humanized antibody or a human antibody.

9. The isolated antibody or antigen binding fragment of claim 1, conjugated with a cytotoxic moiety.

10. The isolated antibody or antigen binding fragment of claim 1, conjugated with a detectable moiety.

11. The isolated antibody or an antigen binding fragment thereof of claim 1, wherein the light chain variable region comprises the amino acid sequence of SEQ ID NO:66 and the heavy chain variable region comprises the amino acid sequence of SEQ ID NO:68.

12. A pharmaceutical composition comprising an antibody or antigen binding fragment having a light chain variable domain comprising the amino acid sequence set for forth in SEQ ID NO:111, the amino acid sequence set forth in SEQ ID NO:112 and the amino acid sequence set forth in SEQ ID NO:113 and a heavy chain variable domain comprising the amino acid sequence set forth in SEQ ID NO:114, the amino acid sequence set forth in SEQ ID NO:115 and the amino acid sequence set forth in SEQ ID NO:116 and a pharmaceutically acceptable carrier, wherein said antibody or antigen binding fragment specifically binds Siglec-15.

13. The pharmaceutical composition of claim 12, wherein the light chain variable region comprises the amino acid sequence of SEQ ID NO.:66 and the heavy chain variable region comprises the amino acid sequence of SEQ ID NO.:68.

14. The pharmaceutical composition of claim 12, wherein the antibody or antigen binding fragment is conjugated with a cytotoxic moiety or a detectable moiety.

15. The pharmaceutical composition of claim 13, wherein the antibody or antigen binding fragment is conjugated with a cytotoxic moiety or a detectable moiety.

16. The pharmaceutical composition of claim 12, wherein the antibody or antigen binding fragment thereof is a monoclonal antibody, a chimeric antibody, a humanized antibody or a human antibody.

17. The pharmaceutical composition of claim 12, wherein the antibody or antigen binding fragment thereof comprises a constant region from a human IgG2 immunoglobulin.

18. The pharmaceutical composition of claim 12, wherein the antibody or antigen binding fragment thereof comprises a constant region from a human IgG1 immunoglobulin.

19. The pharmaceutical composition of claim 13, wherein the antibody or antigen binding fragment thereof is a monoclonal antibody, a chimeric antibody, a humanized antibody or a human antibody.

20. The pharmaceutical composition of claim 13, wherein the antibody or antigen binding fragment thereof comprises a constant region from a human IgG2 immunoglobulin.

21. The pharmaceutical composition of claim 13, wherein the antibody or antigen binding fragment thereof comprises a constant region from a human IgG1 immunoglobulin.

* * * * *

UNITED STATES PATENT AND TRADEMARK OFFICE
CERTIFICATE OF CORRECTION

PATENT NO.       : 8,741,289 B2                                     Page 1 of 1
APPLICATION NO.  : 13/499792
DATED            : June 3, 2014
INVENTOR(S)      : Matthew Stuible et al.

It is certified that error appears in the above-identified patent and that said Letters Patent is hereby corrected as shown below:

In the Claims:

Claim 11, at col 300, ll. 30-34 includes the phrase, "light chain variable region." Please correct this to read, "light chain variable domain." Claim 11, at col 300, ll. 30-34 also includes the phrase, "heavy chain variable region." Please correct this to read, "heavy chain variable domain."

Claim 13, at col 300, ll. 46-49 includes the phrase, "light chain variable region." Please correct this to read, "light chain variable domain." Claim 13, at col 300, ll. 46-49 also includes the phrase, "heavy chain variable region." Please correct this to read, "heavy chain variable domain."

Signed and Sealed this
Nineteenth Day of January, 2016

Michelle K. Lee
*Director of the United States Patent and Trademark Office*